(12) United States Patent
Fava et al.

(10) Patent No.: US 9,546,401 B2
(45) Date of Patent: Jan. 17, 2017

(54) ASSAYS AND METHODS FOR SELECTING A TREATMENT REGIMEN FOR A SUBJECT WITH DEPRESSION

(71) Applicants: The General Hospital Corporation, Boston, MA (US); NESTLE HEALTH SCIENCE—PAMLAB, INC., Covington, LA (US)

(72) Inventors: Maurizio Fava, Newton, MA (US); George Papakostas, Brookline, MA (US); Harold O. Koch, Jr., Mandeville, LA (US); David Kronlage, Slidell, LA (US)

(73) Assignee: NESTEC S.A., Vevey (CH)

(*) Notice: Subject to any disclaimer, the term of this patent is extended or adjusted under 35 U.S.C. 154(b) by 222 days.

(21) Appl. No.: 13/796,362

(22) Filed: Mar. 12, 2013

(65) Prior Publication Data
US 2013/0267523 A1    Oct. 10, 2013

Related U.S. Application Data

(63) Continuation-in-part of application No. PCT/US2012/065084, filed on Nov. 14, 2012.

(60) Provisional application No. 61/559,541, filed on Nov. 14, 2011.

(51) Int. Cl.
C12Q 1/68 (2006.01)
C12P 19/34 (2006.01)
A61K 31/714 (2006.01)

(52) U.S. Cl.
CPC ....... *C12Q 1/6883* (2013.01); *C12Q 2600/106* (2013.01); *C12Q 2600/156* (2013.01); *C12Q 2600/158* (2013.01); *G01N 2800/52* (2013.01)

(58) Field of Classification Search
CPC ............ C12Q 1/6883; C12Q 2600/106; C12Q 2600/156; C12Q 2600/172; C12Q 1/34; C12Q 2600/112; C12Q 2600/136; G01N 2800/52; G01N 2800/28
See application file for complete search history.

(56) References Cited

U.S. PATENT DOCUMENTS

| | | |
|---|---|---|
| 6,218,120 B1 | 4/2001 | Rozen et al. |
| 6,528,259 B1 | 3/2003 | Rozen et al. |
| 2003/0100476 A1 | 5/2003 | Weinberger et al. |
| 2003/0148323 A1 | 8/2003 | Rozen |
| 2005/0069936 A1 | 3/2005 | Diamond et al. |
| 2006/0234223 A1 | 10/2006 | Darvasi et al. |
| 2007/0254288 A1* | 11/2007 | Woolf et al. ............. 435/6 |
| 2009/0075827 A1 | 3/2009 | Young et al. |
| 2009/0307180 A1 | 12/2009 | Colby et al. |
| 2010/0112589 A1 | 5/2010 | Xie |
| 2010/0304391 A1 | 12/2010 | Lombard |
| 2011/0086763 A1 | 4/2011 | Bodeau et al. |
| 2011/0189161 A1 | 8/2011 | Blum et al. |
| 2012/0277180 A1 | 11/2012 | Marini et al. |
| 2012/0329749 A1 | 12/2012 | Smith et al. |
| 2013/0172361 A1 | 7/2013 | Fava et al. |
| 2016/0058766 A1* | 3/2016 | Fava .................... A61K 31/519 |
| | | 514/249 |

FOREIGN PATENT DOCUMENTS

| | | |
|---|---|---|
| WO | 2012/128799 A2 | 9/2012 |
| WO | 2010/138796 A2 | 12/2012 |

OTHER PUBLICATIONS

Rivenes A.C. et al. Journal of Psychosomatic Research 66 (2009) 269-275.*
Combination Deplin® and Antidepressant Therapy for a Major Depressive Episode (MDE)—a Retrospective Analysis (Dec. 3, 2009), NCT01001559, from clinicaltrials.gov, pp. 1-3.*
Levomefolic acid—from Wikipedia, the free encyclopedia—3 printed pages from May 12, 2015, en.wikipedia.org.*
Alpert et al., "Folinic Acid (Leucovorin) as an Adjunctive Treatment for SSRI-Refractory Depression," Annals of Clinical Psychiatry, Mar. 2002, vol. 14(1), pp. 33-38.
Coppen et al., Enhancement of the antidepressant action of fluoxetine by folic acid: a randomized, placebo controlled trial. Journal of Affective Disorders 60 (2000) 121-130.
Jacques et al., Relation between folate status, a common mutation in methylenetetrahydrofolate reductase, and plasma homocysteine concentactions. Circulation, 1996; 93: 7-9.
Tong et al., The effects of polymorphisms in methylenetetrahydrofolate reductase (MTHFR), methionine synthase (MTR), and methionine synthase reductase (MTRR) on the risk of cervical intraepithelial neoplasia and cervical cancer in Korean women. Cancer Causes Control (2010) 21:23-30.

(Continued)

*Primary Examiner* — Stephen Kapushoc
(74) *Attorney, Agent, or Firm* — Kilpatrick Townsend & Stockton LLP

(57) ABSTRACT

Disclosed herein are novel assays, systems and kits for selecting a treatment regimen for a subject with depression by identifying at least one nucleic acid polymorphism, e.g., but not limited to, at the MTHFR, MTR, or MTRR locus, and/or determining expression levels of peripheral biomarkers (e.g., SAM, SAH, 4-HNE, and/or hsCRP) in a test sample from a human subject. These biomarkers can be used to determine the effectiveness of treating a depressed subject with a folate-containing compound (alone or as an adjunct to an antidepressant). Additionally, these biomarkers can be used to select an appropriate treatment regimen for subjects with treatment-resistant depression (e.g., resistant to at least one selective serotonin reuptake inhibitor). Methods and compositions for treating at least one symptom (e.g., at least one core symptom) of depression in a subject and/or determining or improving the effectiveness of an antidepressant drug taken by a subject are also provided herein.

18 Claims, 34 Drawing Sheets

(56) References Cited

OTHER PUBLICATIONS

Aberg et al., Journal of Affective Disorders, 129:158-166 (2011). "The functional VAL158Met polymorphism in catechol-O-methyltransferase (COMT) is associated with depression and motivation in men from a Swedish population-based study."
Agurs-Collins et al., Appetite, 57:339-348 (2011). "Dopamine polymorphisms and depressive symptoms predict foods intake. Results from a nationally representative sample."
Baune et al., Neuropsychopharmacology, 33:924-932 (2008). "Association of the COMT val158met Variant with Antidepressant Treatment Response in Major Depression."
Bhat et al., Progress in Neurobiology, 99:1-14 (2012). "CACNA1C (Cav1.2) in the pathophysiology of psychiatric disease."
Bi et al., Neurobiology of Aging, 30:1601-1607 (2009). "Association of RFC1 A80G and MTHFR C677T polymorphisms with Alzheimer's disease."
Bigos et al., Arch Gen Psychiatry, 67(9):939-945 (2010). "Genetic Variation in CACNA1C Affects Brain Circuitries Related to Mental Illness."
Bjelland et al., Arch Gen Psychiatry, 60:618-626 (2003). "Folate, Vitamin B12, Homocysteine, and the MTHFR 677C-T Polymorphism in Anxiety and Depression."
Bosco et al., J Neurol Neurosurg Psychiatry, 75:1036-1038 (2004). "Assocation of IL-1 RN*2 allele and methionine synthase 2756 AA genotype with dementia severity of sporadic Alzheimer's disease."
Casamassima et al., Am J Med Genet Part B, 153B:1373-1390 (2010). "L-Type Calcium Channels and Psychiatric Disorders: A Brief Review."
Coppen et al., Journal of Psychopharmacology, 19(1):59-65 (2005). "Treatment of depression: time to consider folic acid and vitamin B12."
Dao et al., Biol Psychiatry, 68:801-810 (2010). "Mood Disorder Susceptibility Gene CACNA1C Modifies Mood-Related Behaviors in Mice and Interacts with Sex to Influence Behavior in Mice and Diagnosis in Humans."
De Wit et al., Psychiatry Research, 178:230-235 (2010). "Depression and obesity: a meta-analysis of community-based studies."
Domschke et al., NeuroImage, 60:2222-2229 (2012). "Catechol-O-methyltransferase gene variation: Impact on amygdala response to aversive stimuli."
Evinova et al., Gen. Physiol. Biophys., 31:415-422 (2012). "Analysis of genetic polymorphisms of brain-derived neurotrophic factor and methylenetetrahydrofolate reductase in depressed patients in a Slovak (Caucasian) population."
Elovainio et al., Psychosomatic Medicine, 69:391-395 (2007). "Genetic Variants in the DRD2 Gene Moderate the Relationship Between Stressful Life Events and Depressive Symptoms in Adults: Cardiovascular Risk in Young Finns Study."
Fava et al., J Clin Psychiatry, 70(suppl 5):12-17 (2009). "Folate in Depression: Efficacy, Safety, Differences in Formulations, and Clinical Issues."
Feng et al., International Review of Neurobiology, 89:67-84 (2009). "The Role of DNA Methylation in the Central Nervous System and Neuropsychiatric Disorders."
Fernandez-De-Las-Penas et al., The Journal of Pain, 13(11):1068-1074 (2012). "Catechol-O-Methyltransferase Val158Met Polymorphism Influences Anxiety, Depression, and Disability, but not Pressure Pain Sensitivity, in Women with Fibromyalgia Syndrome."
Gilbody et al., Am J Epidemiol, 165:1-13 (2007). "Methylenetetrahydrofolate Reductase (MTHFR) Genetic Polymorphisms and Psychiatric Disorders: A HuGE Review."
Green et al., Molecular Psychiatry, 15:1016-1022 (2010). "The bipolar disorder risk allele at CACNA1C also confers risk of recurrent major depression and of schizophrenia."
Guilarte et al., Schizophrenia Research, 99:324-332 (2008). "Dysregulation of glutamate carboxypeptidase II in psychiatric disease."
Hahn et al., Arch Neurol, 58:749-755 (2001). "Neurologic and Psychiatric Manifestations in a Family With a Mutation in Exon 2 of the Guanosine Triphosphate-Cyclohydrolase Gene."
Halsted et al., Am J Clin Nutr, 86:514-521 (2007). "Relations of glutamate carboxypeptidase II (GCPII) polymorphisms to folate and homocysteine concentrations and to scores of cognition, anxiety, and depression in a homogenous Norwegian population: the Hordaland Homocysteine Study."
Hatzimanolis et al., Journal of Affective Disorders, http://dx.doi.org/10.1016/j.jad.2012.12.018 (2013). "Potential role of membrane-bound COMT gene polymorphisms in female depression vulnerability."
Higuchi et al., Journal of Psychiatric Research, 45:1295-1300 (2011). "State-dependent changes in the expression of DNA methyltransferases in mood disorder patients."
Kempisty et al., Psychiatric Genetics, 17:177-181 (2007). "MTHFD 1958G>A and MTR 2756A>G polymorphisms are associated with bipolar disorder and schizophrenia."
Kishi et al., Journal of Affective Disorders, 142:315-322 (2012). "GTP cyclohydrolase 1 gene haplotypes as predictors of SSRI response in Japanese patients with major depressive disorder."
Kloiber et al., Biol Psychiatry, 62:321-326 (2007). "Overweight and Obesity Affect Treatment Response in Major Depression."
Lewis et al., Molecular Psychiatry, 11:352-360 (2006). "The thermolabile variant of MTHFR is associated with depression in the British Women's Heart and Health Study and a meta-analysis."
Lewis et al., European Journal of Clinical Nutrition, 66:97-103 (2012). "Folic acid supplementation during pregnancy may protect against depression 21 months after pregnancy, an effect modified by MTHFR C677T genotype."
Liu et al., Human Gene Therapy, 13:1777-1782 (2002). "The Murine-Reduced Folate Carrier Gene Can Act as a Selectable Marker and a Suicide Gene in Hematopoietic Cells In Vivo."
Lucock, Molecular Genetics and Metabolism, 71:121-138 (2000). "Folic Acid: Nutritional Biochemistry, Molecular Biology, and Role in Disease Processes."
McHugh et al., The Pharmacogenomics Journal, 11:207-213 (2011). "A polymorphism of the GTP-cyclohydrolase I feedback regulator gene alters transcriptional activity and may affect response to SSRI antidepressants."
McHugh, Pharmacogenomics, 12(12): 1625-1627 (2011). "The tetrahydrobiopterin pathway: a novel target for the treatment of depression."
Mischoulon et al., CNS Spectrums, 17:76-86 (2012). "Prevalence of MTHFR C677T and MS A2756G polymorphisms in major depressive disorder, and their impact on response to fluoxetine treatment."
Murphy et al., Genes, Brain and Behavior, 12:125-132 (2013). "Genetic variation in DNMT3B and increased global DNA methylation is associated with suicide attempts in psychiatric patients."
Nelson et al., The Journal of Neuroscience, 28(2):395-406 (2008). "Activity-Dependent Suppression of Miniature Neurotransmission through the Regulation of DNA Methylation."
Pan et al., BMJ Case Reports, doi:10.1136/bcr.03.2011.3927 (2011). "GTP-cyclohydrolase deficiency responsive to sapropterin and 5-HTP supplementation: relief of treatment-refractory depression and suicidal behaviour."
Peerbooms et al., Brain Behavior, and Immunity, 25:1530-1543 (2011). "Meta-analysis of MTHFR gene variants in schizophrenia, bipolar disorder and unipolar depressive disorder: Evidence for a common genetic vulnerability?"
Roberts et al., BMC Psychiatry, 7:65 doi.10.1186/1471-244X-7-65 (2007). "Folate Augmentation of Treatment—Evaluation for Depression (FolATED): protocol of a randomised controlled trial."
Roetker et al., BMJ Open, 2:e000944 (2012). "Multigene interactions and the prediction of depression in the Wisconsin Longitudinal Study."
Roffman et al., Schizophrenia Bulletin, 39(2):330-338 (2013). "Genetic Variation Throughout the Folate Metabolic Pathway Influences Negative Symptom Severity in Schizophrenia."
Schaevitz et al., Develop Neurobiol, 72:891-905 (2012). "Glutamate Carboxypeptidase II and Folate Deficiencies Result in Reciprocal Protection Against Cognitive and Social Deficits in Mice: Implications for Neurodevelopmental Disorders."

(56) References Cited

OTHER PUBLICATIONS

Shelton et al., Progress in Neurobiology, 91:275-299 (2010). "Eating ourselves to death (and despair): The contribution of adiposity and inflammation to depression."

Slopien et al., Maturitas, 61:252-255 (2008). "Polymorphic variants of genes encoding MTHFR, MTR, and MTHFD1 and the risk of depression in postmenopausal women in Poland."

Stanislawska-Sachadyn et al., Annals of Human Genetics, 73:484-491 (2009). "The Reduced Folate Carrier (SLC19A1) c.80G>A Polymorphism is Associated with Red Cell Folate Concentrations Among Women."

Stapleton et al., Pharmacogenetics and Genomics, 21:447-453 (2011). "Association between DRD2/ANKK1 Taq1A genotypes, depression and smoking cessation with nicotine replacement therapy."

Uher et al., Journal of Affective Disorders, 118:147-154 (2009). "Body weight as a predictor of antidepressant efficacy in the GENDEP project."

Villanueva et al., Alcohol Clin Exp Res, 25(3):415-420 (2001). "Reduced Folate Carrier: Tissue Distribution and Effects of Chronic Ethanol Intake in the Micropig."

Wang et al., Psychiatry Research, 200:1047-1050 (2012). "The role of single nucleotide polymorphism of D2 dopamine receptor gene on major depressive disorder and response to antidepressant treatment."

Wray et al., Molecular Psychiatry, 17:36-48 (2012). "Genome-wide association study of major depressive disorder: new results, meta-analysis, and lessons learned."

Ye et al., Psychosomatic Medicine, 73:385-392 (2011). "The Folate Hydrolase 1561C>T Polymorphism is Associated With Depressive Symptoms in Puerto Rican Adults."

Zhang et al., Neuroscience Letters, 462:308-311 (2009). "DNA methyltransferase 3B gene increases risk of early onset schizophrenia."

Zhao et al., Brain Research, 1204:118-122 (2008). "Association analysis of methionine synthase gene 2756 A>G polymorphism and Alzheimer disease in a Chinese population."

Zimmermann et al., Biochem J., 448:93-102 (2012). "Antidepressants inhibit DNA methyltransferase 1 through reducing G9a levels."

Zintzaras, Psychiatric Genetics, 16:105-115 (2006). "C677T and A1298C methylenetetrahydrofolate reductase gene polymorphisms in schizophrenia, biopolar disorder and depression: a meta-analysis of genetic association studies."

Kocabas et al., International Clinical Psychopharmacology, 25:218-227 (2010). "The impact of catechol-O-methyltransferase SNPs and haplotypes on treatment response phenotypes in major depressive disorder: a case-control association study."

Casamassima et al., Am J Med Genet Part B, 153B:303-309 (2009). "Phenotypic Effects of a Bipolar Liability Gene Among Individuals With Major Depressive Disorder."

Jain et al., "Personalized therapy of adjunctive L-methylfolate to selective serotonin reuptake inhibitor-resistant major depressive disorder," Poster presentation at the College of Psychiatric and Neurologic Pharmacists Annual Meeting, Tampa, Florida, May 2, 2012.

Bedson, E. et al., "Folate Augmentation of Treatment—Evaluation for Depression (FolATED): randomized trial and economic evaluation," Health Technology Assessment, National Institute for Health Research, published by the NIHR Journals Library, Jul. 2014, 18(48):vii-viii, 1-159.

Taylor, Matthew J. et al.; Folate for depressive disorders: systematic review and meta-analysis of randomized controlled trials; Journal of Psychopharmacology; 18(2) (2004) 251-256.

Deplin 15 Capsules package insert, Mar. 2004, from Nestle Health Science—Pamlab, Inc. Covington, LA 70433, 2 printed pages, Mar. 2014.

\* cited by examiner

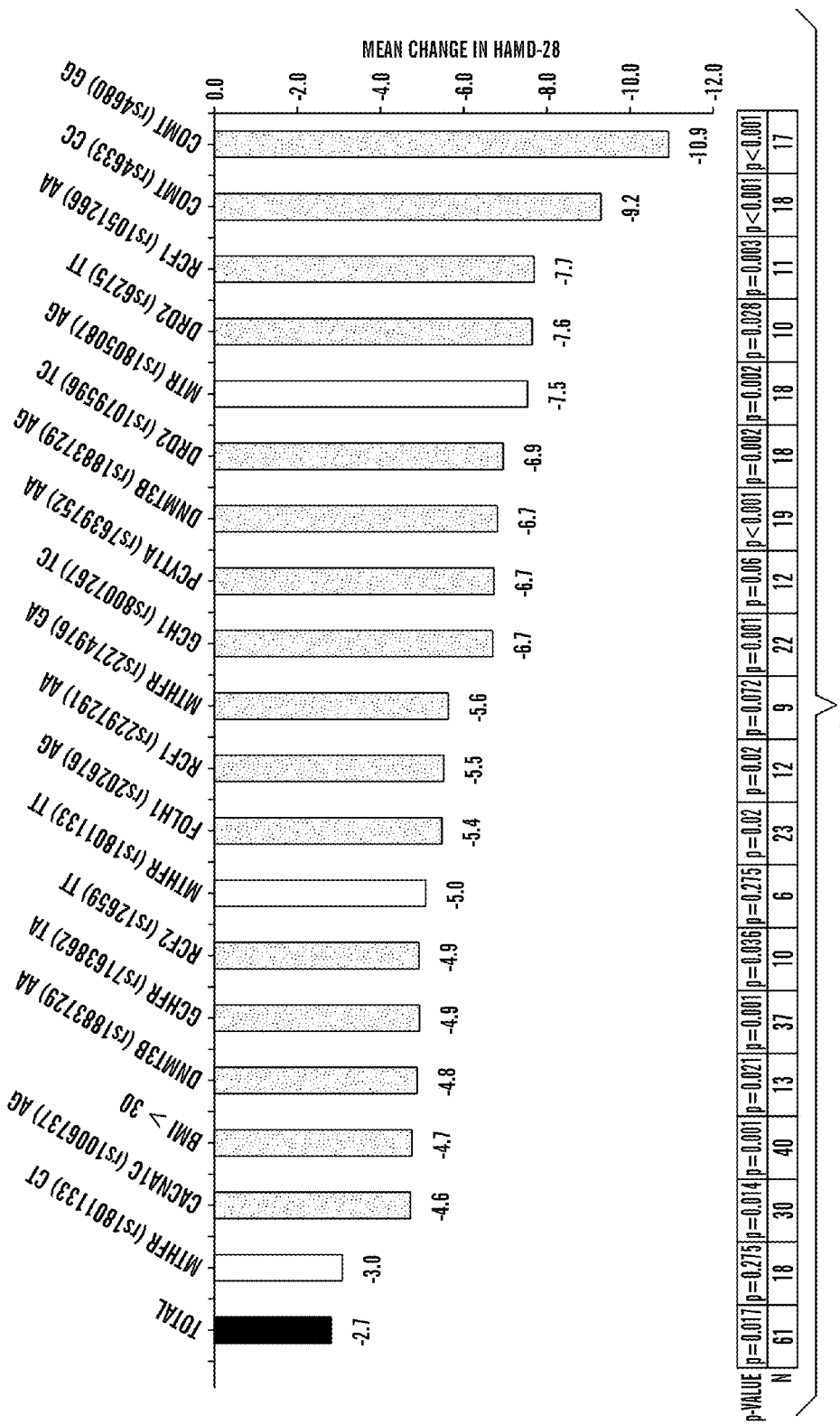

| | TOTAL | MTHFR 677 (CT) | CACNA1C (AG) [Ca ION] | BMI>30 | DNMT3B (AA) | GCHFR (TA) [BH4] | RCF2 815 (TT) | MTHFR 677 (TT) | FOLH1 (GCPII) (AG) | RCF1 (AA) |
|---|---|---|---|---|---|---|---|---|---|---|
| MEAN CHANGE IN HAMD-28 | -2.7 | -3 | -4.6 | -4.7 | -4.8 | -4.9 | -4.9 | -5 | -5.4 | -5.5 |
| p-VALUE | p=0.017 | p=0.275 | p=0.014 | p=0.001 | p=0.021 | p=0.001 | p=0.036 | p=0.275 | p=0.02 | p=0.02 |
| N | 61 | 18 | 30 | 40 | 13 | 37 | 10 | 6 | 23 | 12 |
| PREVALENCE | | 30% | 49% | 66% | 21% | 61% | 16% | 10% | 38% | 20% |
| GENE | | CT | AG | | AA | TA | TT | TT | AG | AA |
| RS# | | rs1801133 | rs1006737 | | rs1883729 | rs7163862 | rs12659 | rs1801133 | rs202676 | rs2297291 |
| LOCUS | | 1p36.3 | 12p13.33 | | 20q11.2 | 15q15.1 | 21q22.3 | 1p36.3 | 11p11.2 | 21q22.3 |

| | MTHFR 1793 (GA) | GCH1 (TC) [BH4] | PCYT1A (AA) | DNMT3B (AG) | DRD2 (TC) | MTR (AG) | DRD2 129 (TT) | RCF1 80 (AA) | COMT (rs4633) (CC) | COMT (rs4680) (GG) |
|---|---|---|---|---|---|---|---|---|---|---|
| MEAN CHANGE IN HAMD-28 | -5.6 | -6.7 | -6.7 | -6.7 | -6.9 | -7.5 | -7.6 | -7.7 | -9.2 | -10.9 |
| p-VALUE | p=0.072 | p=0.001 | p=0.06 | p<0.001 | p=0.002 | p=0.002 | p=0.028 | p=0.003 | p<0.001 | p<0.001 |
| N | 9 | 22 | 12 | 19 | 18 | 18 | 10 | 11 | 18 | 17 |
| PREVALENCE | 15% | 36% | 20% | 31% | 30% | 30% | 16% | 18% | 30% | 28% |
| GENE | GA | TC | AA | AG | TC | AG | TT | AA | CC | GG |
| RS# | rs2274976 | rs8007267 | rs7639752 | rs1883729 | rs1079596 | rs1805087 | rs6275 | rs1051266 | rs4633 | rs4680 |
| LOCUS | 1p36.3 | 14q22.1-q22.2 | 3q29 | 20q11.2 | 11q23.2 | 1q43 | 11q23.2 | 21q22.3 | 22q11.21-q11.23 | 22q11.21 | 22q11.21-q11.23 | 22q11.21 |

FIG. 8B

Analyses on full sample

*denotes sample size in (phase I, phase II)

|  | Phase I | | Phase II | | Pooled phases | | |
| --- | --- | --- | --- | --- | --- | --- | --- |
|  | Effect | p-value | Effect | p-value | Effect | 95% CI | p-value |
| SFQ (70,34)* | -0.066 | 0.850 | 0.111 | 0.779 | 0.092 | (-0.412, 0.596) | 0.720 |
| VAS (65,30) | -0.257 | 0.736 | 0.589 | 0.432 | -0.061 | (-1.015, 0.893) | 0.900 |
| CPFQ (74,38) | -2.565 | 0.045 | -0.394 | 0.775 | -1.510 | (-3.130, 0.110) | 0.068 |

Analyses in biomarker subgroups
*denotes sample size in (phase I, phase II)

|  | Phase I | | Phase II | | Pooled phases | | |
| --- | --- | --- | --- | --- | --- | --- | --- |
|  | Effect | p-value | Effect | p-value | Effect | 95% CI | p-value |
| SFQ | | | | | | | |
| SAM/SAH >=med (34,16)* | -0.567 | 0.387 | 0.571 | 0.464 | 0.215 | (-0.701, 1.130) | 0.646 |
| SAM/SAH < med (35,18) | 0.383 | 0.261 | -0.182 | 0.594 | 0.094 | (-0.466, 0.655) | 0.741 |
| hsCRP >=med (33,16) | 0.024 | 0.954 | 0 | 1 | -0.033 | (-0.540, 0.474) | 0.898 |
| hsCRP < med (36,18) | -0.399 | 0.513 | 0.250 | 0.742 | -0.032 | (-0.915, 0.851) | 0.944 |
| HNE-his >=med (34,16) | 0.213 | 0.710 | -0.333 | 0.447 | -0.051 | (-0.856, 0.755) | 0.902 |
| HNE-his < med (35,18) | -0.300 | 0.474 | 0.610 | 0.365 | 0.146 | (-0.534, 0.827) | 0.673 |
| 5-MTHF >=med (35,15) | -0.421 | 0.395 | 0 | 1 | -0.184 | (-0.686, 0.318) | 0.472 |
| 5-MTHF < med (34,19) | 0.462 | 0.363 | 0.222 | 0.755 | 0.504 | (-0.339, 1.347) | 0.241 |
| Female (48,21) | -0.349 | 0.407 | -0.083 | 0.878 | -0.053 | (-0.735, 0.629) | 0.879 |
| Male (22,13) | 0.529 | 0.392 | 0.262 | 0.640 | 0.280 | (-0.572, 1.132) | 0.519 |
| BMI < 25 (14,7) | -0.300 | 0.630 | -0.700 | 0.672 | 0.740 | (-0.949, 2.429) | 0.390 |
| 25 =< BMI < 30 (17,9) | 0.095 | 0.924 | 0.050 | 0.879 | 0.222 | (-0.671, 1.114) | 0.627 |
| BMI >= 30 (37,17) | -0.140 | 0.767 | 0.097 | 0.841 | -0.068 | (-0.794, 0.658) | 0.854 |
| VAS | | | | | | | |
| SAM/SAH >=med (32,16) | 0.417 | 0.739 | -0.175 | 0.817 | -0.112 | (-1.444, 1.221) | 0.869 |
| SAM/SAH < med (33,14) | -0.861 | 0.364 | 1.289 | 0.383 | 0.014 | (-1.494, 1.522) | 0.985 |
| hsCRP >=med (33,15) | 0.455 | 0.638 | 0.333 | 0.717 | 0.292 | (-0.939, 1.524) | 0.642 |
| hsCRP < med (32,15) | -1.011 | 0.419 | 0.804 | 0.531 | -0.581 | (-2.217, 1.055) | 0.487 |
| HNE-his >=med (30,11) | -1.365 | 0.108 | -0.893 | 0.241 | -1.045 | (-1.943, -0.148) | 0.022 |
| HNE-his < med (35,19) | 0.692 | 0.571 | 1.321 | 0.254 | 0.549 | (-1.021, 2.118) | 0.493 |
| 5-MTHF >=med (32,13) | 0.147 | 0.886 | 0.548 | 0.565 | 0.697 | (-0.649, 2.043) | 0.310 |
| 5-MTHF < med (33,17) | -0.725 | 0.549 | 0.611 | 0.596 | -0.850 | (-2.400, 0.701) | 0.283 |

| | | | | | | | |
|---|---|---|---|---|---|---|---|
| Female (45,21) | -0.743 | 0.422 | 0.436 | 0.652 | -0.203 | (-1.395, 0.989) | 0.738 |
| Male (20,9) | 0.867 | 0.534 | 1.050 | 0.329 | 0.414 | (-1.444, 2.272) | 0.662 |
| | | | | | | | |
| BMI < 25 (14,6) | -4.200 | 0.013 | 1.000 | 0.720 | -1.212 | (-3.924, 1.500) | 0.381 |
| 25 =< BMI < 30 (17,8) | 0.952 | 0.318 | -0.250 | 0.809 | 0.366 | (-0.920, 1.651) | 0.577 |
| BMI >= 30 (32,15) | 1.009 | 0.415 | 0.571 | 0.574 | 0.124 | (-1.356, 1.604) | 0.870 |
| | | | | | | | |
| CPFQ | | | | | | | |
| | | | | | | | |
| SAM/SAH >=med (36,20) | -2.250 | 0.314 | 1.828 | 0.371 | -0.150 | (-2.812, 2.512) | 0.912 |
| SAM/SAH < med (37,18) | -2.634 | 0.076 | -2.377 | 0.202 | -2.661 | (-4.607, -0.715) | 0.007 |
| | | | | | | | |
| hsCRP >=med (36,18) | -1.931 | 0.169 | -0.844 | 0.669 | -1.594 | (-3.791, 0.603) | 0.155 |
| hsCRP < med (37,20) | -2.429 | 0.289 | 0.374 | 0.855 | -0.807 | (-3.457, 1.844) | 0.551 |
| | | | | | | | |
| HNE-his >=med (36,19) | -3.556 | 0.064 | 0.886 | 0.644 | -1.548 | (-3.994, 0.898) | 0.215 |
| HNE-his < med (37,19) | -1.533 | 0.388 | -0.869 | 0.677 | -0.904 | (-3.117, 1.308) | 0.423 |
| | | | | | | | |
| 5-MTHF >=med (37,17) | -2.812 | 0.148 | 0.871 | 0.654 | -1.531 | (-3.868, 0.806) | 0.199 |
| 5-MTHF < med (36,21) | -2.125 | 0.220 | -1.109 | 0.581 | -1.271 | (-3.834, 1.291) | 0.331 |
| | | | | | | | |
| Female (52,25) | -2.822 | 0.078 | 1.110 | 0.537 | -0.958 | (-3.068, 1.152) | 0.374 |
| Male (22,13) | -1.859 | 0.385 | -3.048 | 0.170 | -2.574 | (-5.435, 0.288) | 0.078 |
| | | | | | | | |
| BMI < 25 (15,7) | -4.818 | 0.107 | 1.200 | 0.442 | -1.520 | (-4.055, 1.016) | 0.240 |
| 25 =< BMI < 30 (18,10) | -0.267 | 0.905 | 2.200 | 0.213 | 1.605 | (-1.021, 4.232) | 0.231 |
| BMI >= 30 (39,20) | -3.645 | 0.036 | -1.600 | 0.506 | -3.043 | (-5.820, -0.265) | 0.032 |

*FIG. 9B (cont.)*

Analyses in genetic subgroups
*denotes sample size in (phase I, phase II);

|  | Phase I | | Phase II | | Pooled phases | | |
| --- | --- | --- | --- | --- | --- | --- | --- |
|  | Effect | p-value | Effect | p-value | Effect | 95% CI | p-value |
| SFQ | | | | | | | |
| MTHFR 677 CC (37,15)* | 0.444 | 0.383 | 0.661 | 0.411 | 0.293 | (-0.603, 1.190) | 0.521 |
| MTHFR 677 CT (18,9) | -0.250 | 0.673 | -0.550 | 0.456 | -0.503 | (-1.401, 0.395) | 0.272 |
| MTHFR 677 TT (6,3) | -0.250 | 0.541 | - | - | - | - | - |
| MTHFR 677 CT/TT (24,12) | -0.314 | 0.502 | -0.333 | 0.541 | -0.326 | (-1.018, 0.365) | 0.355 |
|  | | | | | | | |
| MTR 2756 AA (42,18) | -0.183 | 0.688 | 0.475 | 0.529 | 0.099 | (-0.701, 0.900) | 0.808 |
| MTR 2756 AG (17,7) | 0.429 | 0.297 | -0.333 | 0.286 | 0.039 | (-0.363, 0.441) | 0.848 |
| MTR 2756 GG (2,2) | - | - | - | - | - | - | - |
| MTR 2756 AG/GG (19,9) | 0.179 | 0.719 | -0.250 | 0.292 | -0.125 | (-0.773, 0.523) | 0.705 |
|  | | | | | | | |
| MTRR 66 AA (16,8) | 0.000 | 1.000 | 0.733 | 0.582 | 0.509 | (-0.763, 1.781) | 0.433 |
| MTRR 66 AG (30,13) | 0.105 | 0.860 | 0.350 | 0.579 | -0.086 | (-0.865, 0.694) | 0.829 |
| MTRR 66 GG (15,6) | -0.500 | 0.526 | 0.500 | 0.178 | 0.087 | (-1.027, 1.200) | 0.879 |
| MTRR 66 AG/GG (45,19) | -0.014 | 0.976 | 0.233 | 0.595 | -0.045 | (-0.652, 0.562) | 0.884 |
|  | | | | | | | |
| VAS | | | | | | | |
| MTHFR 677 CC (36,15) | -0.607 | 0.636 | 0.696 | 0.573 | -0.510 | (-2.147, 1.127) | 0.541 |
| MTHFR 677 CT (17,8) | -0.028 | 0.978 | 0.250 | 0.823 | 0.036 | (-1.123, 1.194) | 0.952 |
| MTHFR 677 TT (5,3) | 1.167 | 0.630 | 0.500 | 0.667 | - | - | - |
| MTHFR 677 CT/TT (22,11) | 0.283 | 0.749 | 0.300 | 0.703 | 0.311 | (-0.723, 1.346) | 0.555 |
|  | | | | | | | |
| MTR 2756 AA (39,18) | -0.166 | 0.875 | 0.778 | 0.496 | -0.357 | (-1.845, 1.130) | 0.638 |
| MTR 2756 AG (17,7) | -0.286 | 0.804 | 0.250 | 0.677 | 0.131 | (-0.564, 0.826) | 0.712 |
| MTR 2756 GG (2,1) | - | - | - | - | - | - | - |
| MTR 2756 AG/GG (19,8) | -0.786 | 0.529 | 0.250 | 0.620 | -0.046 | (-0.861, 0.769) | 0.912 |
|  | | | | | | | |
| MTRR 66 AA (16,9) | -0.346 | 0.655 | -0.833 | 0.375 | -0.189 | (-1.363, 0.984) | 0.752 |
| MTRR 66 AG (28,10) | -0.200 | 0.871 | 1.375 | 0.318 | 0.236 | (-1.741, 2.214) | 0.815 |
| MTRR 66 GG (14,7) | -2.394 | 0.287 | 4.900 | 0.021 | 0.224 | (-2.523, 2.971) | 0.873 |
| MTRR 66 AG/GG (42,17) | -0.358 | 0.736 | 1.514 | 0.184 | -0.084 | (-1.489, 1.321) | 0.907 |

*FIG. 9C*

| CPFQ | | | | | | | |
|---|---|---|---|---|---|---|---|
| MTHFR 677 CC (41,19) | -0.460 | 0.824 | -0.811 | 0.747 | -0.955 | (-3.802, 1.891) | 0.511 |
| MTHFR 677 CT (18,9) | -5.775 | 0.001 | 1.600 | 0.424 | -2.220 | (-4.159, -0.280) | 0.025 |
| MTHFR 677 TT (6,3) | -2.500 | 0.662 | -4.500 | 0.593 | - | - | - |
| MTHFR 677 CT/TT (24,12) | -5.214 | 0.004 | 0.000 | 1.000 | -2.212 | (-4.072, -0.352) | 0.020 |
| | | | | | | | |
| MTR 2756 AA (45,21) | -1.260 | 0.462 | -0.436 | 0.849 | -0.626 | (-3.103, 1.850) | 0.620 |
| MTR 2756 AG (18,8) | -4.442 | 0.078 | 0.000 | 1.000 | -2.846 | (-5.960, 0.268) | 0.073 |
| MTR 2756 GG (2,2) | - | - | - | - | - | - | - |
| MTR 2756 AG/GG (20,10) | -5.022 | 0.036 | -0.600 | 0.782 | -3.005 | (-6.107, 0.097) | 0.058 |
| | | | | | | | |
| MTRR 66 AA (17,9) | -3.000 | 0.103 | 3.833 | 0.025 | 0.685 | (-1.715, 3.086) | 0.576 |
| MTRR 66 AG (33,15) | -1.697 | 0.424 | -4.900 | 0.135 | -3.981 | (-7.370, -0.591) | 0.021 |
| MTRR 66 GG (15,7) | -5.333 | 0.145 | 1.700 | 0.530 | -1.995 | (-6.715, 2.725) | 0.407 |
| MTRR 66 AG/GG (48,22) | -2.497 | 0.160 | -2.267 | 0.309 | -2.846 | (-5.345, -0.347) | 0.026 |

*FIG. 9C (cont.)*

Maier SPCD

| | Phase I | | Phase II | | Pooled phases | | |
|---|---|---|---|---|---|---|---|
| | Effect | p-value | Effect | p-value | Effect | 95% CI | p-value |
| MAIER | | | | | | | |
| HAMD7 | -1.802 | 0.041 | -1.786 | 0.130 | -1.616 | (-2.936, -0.296) | 0.016 |
| HAMD7 >= median | -2.198 | 0.058 | -3.000 | 0.037 | -2.691 | (-4.203, -1.180) | <0.001 |
| HAMD7 < median | -1.405 | 0.303 | -1.186 | 0.929 | -0.083 | (-2.481, 2.315) | 0.946 |

*FIG. 10A*

Maier means

| | | Phase I | | | Phase II | | | Pooled | |
|---|---|---|---|---|---|---|---|---|---|
| | Med=12.5 | N | Mean | Std | N | Mean | Std | Mean | Std |
| MAIER | | | | | | | | | |
| Treatment | All | 18 | -4.4 | 3.4 | 18 | -2.2 | 4.0 | -3.3 | 3.7 |
| | maier>=med | 9 | -4.6 | 3.6 | 11 | -2.7 | 3.2 | -3.6 | 3.4 |
| | maier<med | 9 | -4.3 | 3.4 | 7 | -1.3 | 5.2 | -2.8 | 4.3 |
| Placebo | All | 56 | -2.6 | 3.1 | 21 | -0.4 | 3.2 | -1.5 | 3.2 |
| | maier>=med | 28 | -2.4 | 2.7 | 11 | 0.3 | 3.1 | -1.0 | 2.9 |
| | maier<med | 28 | -2.9 | 3.5 | 10 | -1.1 | 3.3 | -2.0 | 3.4 |

*FIG. 10B*

HAMD 7 SPCD

| | Phase I | | Phase II | | Pooled phases | | |
|---|---|---|---|---|---|---|---|
| | Effect | p-value | Effect | p-value | Effect | 95% CI | p-value |
| HAMD-7 | | | | | | | |
| HAMD7 | -1.998 | 0.032 | -1.325 | 0.245 | -1.494 | (-2.737, -0.251) | 0.018 |
| HAMD7 > median | -3.860 | 0.003 | -3.022 | 0.065 | -3.437 | (-5.043, -1.830) | <0.001 |
| HAMD7 =< median | 0.194 | 0.887 | 0.333 | 0.838 | 0.322 | (-1.596, 2.240) | 0.742 |

*FIG. 10C*

HAMD7 means

| | | Phase I | | | Phase II | | | Pooled | |
|---|---|---|---|---|---|---|---|---|---|
| | Med=12 | N | Mean | Std | N | Mean | Std | Mean | Std |
| HAMD7 | | | | | | | | | |
| Treatment | All | 18 | -4.9 | 3.7 | 18 | -1.9 | 3.7 | -3.4 | 3.7 |
| | HAMD7 >med | 10 | -6.5 | 3.6 | 9 | -3.2 | 3.8 | -4.9 | 3.7 |
| | HAMD7=<med | 8 | -3.0 | 3.0 | 9 | -0.7 | 3.4 | -1.8 | 3.2 |
| Placebo | All | 56 | -2.9 | 3.3 | 21 | -0.6 | 3.3 | -1.8 | 3.3 |
| | HAMD7 >med | 25 | -2.6 | 3.0 | 10 | -0.2 | 2.9 | -1.4 | 2.9 |
| | HAMD7=<med | 31 | -3.2 | 3.5 | 11 | -1.0 | 3.7 | -2.1 | 3.6 |

*FIG. 10D*

TRD2 Biomarker and genetic analyses on Maier scale

| | Phase I | | Phase II | | Pooled phases | | |
|---|---|---|---|---|---|---|---|
| | Effect | p-value | Effect | p-value | Effect | 95% CI | p-value |
| Maier | | | | | | | |
| SAM/SAH >=med (36,21)* | -0.695 | 0.572 | 0.009 | 0.995 | -0.380 | (-2.239, 1.479) | 0.689 |
| SAM/SAH < med (37,18) | -2.311 | 0.072 | -4.130 | 0.027 | -2.398 | (-4.312, -0.485) | 0.014 |
| | | | | | | | |
| HNE-his >=med (37,20) | -2.198 | 0.126 | -2.727 | 0.127 | -2.471 | (-4.483, -0.459) | 0.016 |
| HNE-his < med (36,19) | -1.296 | 0.225 | -0.619 | 0.714 | -0.796 | (-2.579, 0.988) | 0.382 |
| | | | | | | | |
| hsCRP >=med (37,19) | -1.823 | 0.169 | -2.131 | 0.270 | -1.668 | (-3.843, 0.507) | 0.133 |
| hsCRP < med (36,20) | -1.533 | 0.214 | -1.707 | 0.281 | -1.918 | (-3.637, -0.199) | 0.029 |
| | | | | | | | |
| BMI < 25 (14,7) | -0.849 | 0.663 | -2.000 | 0.475 | -1.812 | (-6.195, 2.570) | 0.418 |
| 25 =< BMI < 30 (18,10) | 1.600 | 0.417 | 0.200 | 0.927 | 1.597 | (-0.904, 4.098) | 0.211 |
| BMI >= 30 (40,21) | -3.477 | 0.001 | -1.773 | 0.304 | -2.637 | (-4.410, -0.864) | 0.004 |
| BMI < 30 (32,17) | 0.308 | 0.823 | -0.857 | 0.586 | 0.320 | (-1.729, 2.370) | 0.760 |
| | | | | | | | |
| MTHFR 677 CC (41,20) | -0.807 | 0.518 | -1.300 | 0.447 | -0.948 | (-2.611, 0.715) | 0.264 |
| MTHFR 677 CT (18,9) | -2.750 | 0.074 | -0.550 | 0.843 | -1.621 | (-4.650, 1.409) | 0.294 |
| MTHFR 677 TT(6,3) | -0.750 | 0.765 | -3.000 | 0.667 | - | - | - |
| MTHFR 677 CT/TT(24,12) | -2.457 | 0.061 | -1.500 | 0.509 | -2.004 | (-4.315, 0.308) | 0.089 |
| | | | | | | | |
| MTR 2756 AA (45,21) | -0.250 | 0.795 | -0.746 | 0.678 | -0.632 | (-2.484, 1.221) | 0.504 |
| MTR 2756 AG (18,9) | -4.333 | 0.021 | -2.750 | 0.256 | -3.582 | (-6.257, -0.904) | 0.009 |
| MTR 2756 GG (2,2) | - | - | - | - | - | - | - |
| MTR 2756 GG (20,11) | -4.619 | 0.009 | -2.767 | 0.155 | -3.686 | (-5.881, -1.491) | 0.001 |

*FIG. 10E*

|  |  | PLACEBO Beta | p-value | DRUG Beta | p-value |
|---|---|---|---|---|---|
| A: m677=CT or m677=TT | Unadjusted | 2.018 | 0.392 | -4.083 | 0.116 |
|  | Baseline | 1.937 | 0.409 | -1.126 | 0.64 |
|  | Base,race,age,sex | 4.279 | 0.089 | 0.24 | 0.926 |
|  | Base,race,age,sex,BMI | 4.68 | 0.038 | -0.22 | 0.94 |
| B: rs1006737=1,3 | Unadjusted | 0.191 | 0.935 | -3.55 | 0.212 |
|  | Baseline | 0.244 | 0.917 | -2.237 | 0.35 |
|  | Base,race,age,sex | 0.696 | 0.772 | -1.789 | 0.479 |
|  | Base,race,age,sex,BMI | 0.012 | 0.995 | -2.213 | 0.422 |
| C: BslBMI>=30 | Unadjusted | 4.359 | 0.028 | -4.611 | 0.061 |
|  | Baseline | 5.43 | 0.006 | -2.377 | 0.292 |
|  | Base,race,age,sex | 6.596 | 0.001 | -2.835 | 0.233 |
|  | Base,race,age,sex,BMI | 6.596 | 0.001 | -2.835 | 0.233 |
| D: rs1883729=1,1 | Unadjusted | 7.756 | 0.008 | -1.636 | 0.678 |
|  | Baseline | 7.935 | 0.007 | 0.897 | 0.792 |
|  | Base,race,age,sex | 6.627 | 0.142 | 2.016 | 0.623 |
|  | Base,race,age,sex,BMI | 7.367 | 0.039 | 1.607 | 0.714 |
| E: rs7163862=4,1 | Unadjusted | 1.206 | 0.626 | -5.098 | 0.093 |
|  | Baseline | 0.947 | 0.702 | -3.742 | 0.143 |
|  | Base,race,age,sex | 1.737 | 0.495 | -2.643 | 0.327 |
|  | Base,race,age,sex,BMI | 3.334 | 0.126 | -2.3 | 0.405 |
| F: rs12659=1,1 | Unadjusted | -0.786 | 0.801 | -3.732 | 0.273 |
|  | Baseline | 0.23 | 0.943 | -1.511 | 0.603 |
|  | Base,race,age,sex | -0.498 | 0.883 | -1.868 | 0.521 |
|  | Base,race,age,sex,BMI | -0.569 | 0.844 | -1.749 | 0.586 |

FIG. 12A

| | | | | |
|---|---|---|---|---|
| G: rs2202676=3 1 | Unadjusted | -0.664 | 0.789 | -2.3 | 0.422 |
| | Baseline | 0.206 | 0.936 | -1.331 | 0.578 |
| | Base,race,age,sex | -0.358 | 0.889 | -1.809 | 0.48 |
| | Base,race,age,sex,BMI | -0.159 | 0.942 | -1.164 | 0.664 |
| H: rs1883729=1 3 or rs1883729=1 1 | Unadjusted | 7.882 | 0 | -3.494 | 0.228 |
| | Baseline | 8.055 | 0 | 0 | 1 |
| | Base,race,age,sex | 8.268 | 0 | -1.006 | 0.73 |
| | Base,race,age,sex,BMI | 7.776 | 0 | -1.735 | 0.565 |
| I: rs2297291=1 1 | Unadjusted | -0.786 | 0.801 | -3.732 | 0.273 |
| | Baseline | 0.23 | 0.943 | -1.511 | 0.603 |
| | Base,race,age,sex | -0.498 | 0.883 | -1.868 | 0.521 |
| | Base,race,age,sex,BMI | -0.569 | 0.844 | -1.749 | 0.586 |
| J: rs2274976=4 2 | Unadjusted | 0.352 | 0.916 | -2.933 | 0.442 |
| | Baseline | -0.043 | 0.99 | -2.341 | 0.46 |
| | Base,race,age,sex | -0.701 | 0.83 | -3.144 | 0.322 |
| | Base,race,age,sex,BMI | -1.029 | 0.712 | -2.315 | 0.511 |
| K: rs8007267=4 2 | Unadjusted | 5.31 | 0.025 | -5.407 | 0.094 |
| | Baseline | 5.418 | 0.021 | -2.943 | 0.292 |
| | Base,race,age,sex | 4.465 | 0.114 | -5.491 | 0.067 |
| | Base,race,age,sex,BMI | 3.398 | 0.163 | -5.82 | 0.055 |
| L: rs1079596=4 2 | Unadjusted | 4.651 | 0.055 | -4.327 | 0.157 |
| | Baseline | 4.932 | 0.041 | -0.863 | 0.753 |
| | Base,race,age,sex | 4.282 | 0.084 | -0.198 | 0.943 |
| | Base,race,age,sex,BMI | 4.499 | 0.031 | 0.441 | 0.878 |

| | | | | |
|---|---|---|---|---|
| Unadjusted | -0.167 | 0.964 | 1.667 | 0.729 |
| Baseline | 1.762 | 0.646 | -1.415 | 0.732 |
| Base,race,age,sex | 0.319 | 0.933 | -1.827 | 0.634 |
| Base,race,age,sex,BMI | 1.393 | 0.652 | -1.394 | 0.74 |

N: rs1051266=4 4

| | | | | |
|---|---|---|---|---|
| Unadjusted | 1.798 | 0.564 | -5.133 | 0.149 |
| Baseline | 3.204 | 0.324 | -2.364 | 0.442 |
| Base,race,age,sex | 1.364 | 0.7 | -3.14 | 0.305 |
| Base,race,age,sex,BMI | -0.836 | 0.786 | -3.174 | 0.353 |

O: m2756=AG or m2756=GG

| | | | | |
|---|---|---|---|---|
| Unadjusted | 2.329 | 0.322 | -7.905 | 0.003 |
| Baseline | 2.447 | 0.296 | -5.845 | 0.015 |
| Base,race,age,sex | 0.786 | 0.746 | -6.239 | 0.01 |
| Base,race,age,sex,BMI | 1.672 | 0.431 | -6.951 | 0.005 |

P: rs4633=2 2

| | | | | |
|---|---|---|---|---|
| Unadjusted | 7.259 | 0.003 | -7.084 | 0.043 |
| Baseline | 8.295 | 0.001 | -3.985 | 0.196 |
| Base,race,age,sex | 7.938 | 0.002 | -4.764 | 0.12 |
| Base,race,age,sex,BMI | 6.157 | 0.007 | -4.981 | 0.116 |

Q: rs4680=3 3

| | | | | |
|---|---|---|---|---|
| Unadjusted | 7.259 | 0.003 | -7.933 | 0.032 |
| Baseline | 8.295 | 0.001 | -5.199 | 0.105 |
| Base,race,age,sex | 7.938 | 0.002 | -5.609 | 0.081 |
| Base,race,age,sex,BMI | 6.157 | 0.007 | -5.877 | 0.073 |

*FIG. 12A (cont.)*

|   |   | PLACEBO Beta | P-value | DRUG Beta | P-value |
|---|---|---|---|---|---|
| A: m677=CT or m677=TT | Unadjusted | 2.187 | 0.388 | -2.611 | 0.34 |
|   | Baseline | 2.115 | 0.408 | -1.476 | 0.544 |
|   | Base,race,age,sex | 4.793 | 0.079 | -0.216 | 0.935 |
|   | Base,race,age,sex,BMI | 5.285 | 0.035 | -0.672 | 0.822 |
| B: rs10006737=1 3 | Unadjusted | -0.372 | 0.881 | -4.516 | 0.143 |
|   | Baseline | -0.196 | 0.942 | -3.605 | 0.146 |
|   | Base,race,age,sex | 0.41 | 0.872 | -3.289 | 0.225 |
|   | Base,race,age,sex,BMI | -0.283 | 0.898 | -3.769 | 0.211 |
| C: BslBMI>=30 | Unadjusted | 4.818 | 0.026 | -2.985 | 0.274 |
|   | Baseline | 5.38 | 0.013 | -2.919 | 0.213 |
|   | Base,race,age,sex | 6.308 | 0.003 | -3.525 | 0.166 |
|   | Base,race,age,sex,BMI | 6.308 | 0.003 | -3.525 | 0.166 |
| D: rs1883729=1 1 | Unadjusted | 8.588 | 0.006 | 0 | 1 |
|   | Baseline | 8.799 | 0.005 | 0.146 | 0.964 |
|   | Base,race,age,sex | 6.632 | 0.165 | 2.488 | 0.545 |
|   | Base,race,age,sex,BMI | 7.611 | 0.046 | 1.859 | 0.677 |
| E: rs7163862=4 1 | Unadjusted | 0.72 | 0.78 | -6.977 | 0.039 |
|   | Baseline | 0.797 | 0.76 | -7.39 | 0.005 |
|   | Base,race,age,sex | 1.919 | 0.482 | -7.47 | 0.015 |
|   | Base,race,age,sex,BMI | 3.305 | 0.159 | -7.085 | 0.024 |
| F: rs12659=1 1 | Unadjusted | -0.382 | 0.905 | -2.398 | 0.494 |
|   | Baseline | 0.119 | 0.972 | -2.34 | 0.404 |
|   | Base,race,age,sex | -1.05 | 0.77 | -2.372 | 0.411 |
|   | Base,race,age,sex,BMI | -0.905 | 0.77 | -2.798 | 0.385 |

| | | | | | |
|---|---|---|---|---|---|
| | Unadjusted | -0.155 | 0.952 | -4.443 | 0.149 |
| | Baseline | 0.202 | 0.94 | -1.663 | 0.525 |
| | Base,race,age,sex | -0.503 | 0.849 | -2.433 | 0.405 |
| | Base,race,age,sex,BMI | -0.224 | 0.922 | -1.451 | 0.641 |

H: rs1883729=1 3 or rs1883729=1 1

| | | | | | |
|---|---|---|---|---|---|
| | Unadjusted | 8.35 | 0 | -1.857 | 0.55 |
| | Baseline | 8.532 | 0 | -0.598 | 0.812 |
| | Base,race,age,sex | 8.24 | 0.001 | -1.089 | 0.709 |
| | Base,race,age,sex,BMI | 7.931 | 0 | -1.696 | 0.573 |

I: rs2297291=1 1

| | | | | | |
|---|---|---|---|---|---|
| | Unadjusted | -0.382 | 0.905 | -2.398 | 0.494 |
| | Baseline | 0.119 | 0.972 | -2.34 | 0.404 |
| | Base,race,age,sex | -1.05 | 0.77 | -2.372 | 0.411 |
| | Base,race,age,sex,BMI | -0.905 | 0.77 | -2.798 | 0.385 |

J: rs2274976=4 2

| | | | | | |
|---|---|---|---|---|---|
| | Unadjusted | -0.952 | 0.796 | -1.625 | 0.676 |
| | Baseline | -0.997 | 0.789 | -4.593 | 0.142 |
| | Base,race,age,sex | -2.484 | 0.501 | -4.875 | 0.13 |
| | Base,race,age,sex,BMI | -2.265 | 0.475 | -4.856 | 0.183 |

K: rs8007267=4 2

| | | | | | |
|---|---|---|---|---|---|
| | Unadjusted | 5.806 | 0.022 | -4.159 | 0.214 |
| | Baseline | 6.434 | 0.013 | -3.604 | 0.179 |
| | Base,race,age,sex | 5.416 | 0.078 | -5.606 | 0.062 |
| | Base,race,age,sex,BMI | 3.901 | 0.149 | -5.811 | 0.056 |

L: rs1079596=4 2

| | | | | | |
|---|---|---|---|---|---|
| | Unadjusted | 4.712 | 0.072 | -2.938 | 0.359 |
| | Baseline | 5.43 | 0.045 | -0.958 | 0.716 |
| | Base,race,age,sex | 4.468 | 0.103 | -0.364 | 0.895 |
| | Base,race,age,sex,BMI | 4.632 | 0.047 | 0.277 | 0.923 |

| | | | | |
|---|---|---|---|---|
| Unadjusted | 0.214 | 0.955 | 2.417 | 0.668 |
| Baseline | 1.846 | 0.639 | 0.939 | 0.839 |
| Base,race,age,sex | 0.514 | 0.894 | -1.469 | 0.768 |
| Base,race,age,sex,BMI | 1.436 | 0.652 | -0.648 | 0.916 |

N: rs1051266=4 4

| | | | | |
|---|---|---|---|---|
| Unadjusted | 2.244 | 0.484 | -3.901 | 0.284 |
| Baseline | 3.091 | 0.361 | -2.578 | 0.382 |
| Base,race,age,sex | 0.914 | 0.807 | -3.142 | 0.3 |
| Base,race,age,sex,BMI | -1.129 | 0.73 | -3.579 | 0.29 |

O: m2756=AG or m2756=GG

| | | | | |
|---|---|---|---|---|
| Unadjusted | 2.863 | 0.256 | -7.217 | 0.01 |
| Baseline | 2.923 | 0.25 | -5.553 | 0.029 |
| Base,race,age,sex | 1.044 | 0.689 | -6.343 | 0.015 |
| Base,race,age,sex,BMI | 1.961 | 0.397 | -6.945 | 0.008 |

P: rs4633=2 2

| | | | | |
|---|---|---|---|---|
| Unadjusted | 8 | 0.001 | -5.95 | 0.097 |
| Baseline | 8.369 | 0.001 | -3.79 | 0.2 |
| Base,race,age,sex | 8.257 | 0.002 | -4.453 | 0.144 |
| Base,race,age,sex,BMI | 6.522 | 0.007 | -4.453 | 0.162 |

Q: rs4680=3 3

| | | | | |
|---|---|---|---|---|
| Unadjusted | 8 | 0.001 | -6.833 | 0.071 |
| Baseline | 8.369 | 0.001 | -5.236 | 0.087 |
| Base,race,age,sex | 8.257 | 0.002 | -5.577 | 0.079 |
| Base,race,age,sex,BMI | 6.522 | 0.007 | -5.695 | 0.079 |

*FIG. 12B (cont.)*

|  | | PHASE 1 | | | | PHASE 2 | | | | | POOLED | | |
| --- | --- | --- | --- | --- | --- | --- | --- | --- | --- | --- | --- | --- | --- |
|  | Sample Size Drug | Sample Size Placebo | Resp Rate Drug | Resp Rate Placebo | Difference | Sample Size Drug | Sample Size Placebo | Resp Rate Drug | Resp Rate Placebo | Difference | Resp Rate Difference | Z-score | P-value |
| A: m677=CT or m677=TT | 10 | 14 | 0.2 | 0.071 | 0.129 | 6 | 6 | 0.5 | 0.167 | 0.333 | 0.231 | 1.579 | 0.114 |
| B: rs1006737=1 3 | 7 | 23 | 0.571 | 0.217 | 0.354 | 10 | 6 | 0.4 | 0.167 | 0.233 | 0.294 | 1.967 | 0.049 |
| C: BslBMI>=30 | 11 | 29 | 0.364 | 0.069 | 0.295 | 10 | 11 | 0.4 | 0.091 | 0.309 | 0.302 | 2.61 | 0.009 |
| D: rs1883729=1 1 | 2 | 11 | 0.5 | 0.091 | 0.409 | 3 | 5 | 0 | 0 | 0 | 0.205 | 1.124 | 0.261 |
| E: rs7163862=4 1 | 10 | 27 | 0.5 | 0.222 | 0.278 | 12 | 8 | 0.333 | 0 | 0.333 | 0.306 | 2.729 | 0.006 |
| F: rs12659=1 1 | 3 | 7 | 0.667 | 0 | 0.667 | 5 | 2 | 0.2 | 0 | 0.2 | 0.433 | 2.661 | 0.008 |
| G: rs202676=3 1 | 8 | 15 | 0.375 | 0.2 | 0.175 | 5 | 4 | 0.4 | 0 | 0.4 | 0.288 | 2.033 | 0.042 |
| H: rs1883729=1 3 or rs1883729=1 1 | 7 | 25 | 0.429 | 0.08 | 0.349 | 7 | 11 | 0.286 | 0 | 0.286 | 0.317 | 2.464 | 0.014 |
| I: rs2297291=1 1 | 3 | 9 | 0.667 | 0 | 0.667 | 5 | 2 | 0.2 | 0 | 0.2 | 0.433 | 2.553 | 0.011 |
| J: rs2274976=4 2 | 3 | 6 | 0.667 | 0.167 | 0.5 | 3 | 2 | 0.333 | 0.5 | -0.167 | 0.167 | 0.623 | 0.533 |
| K: rs8007267=4 2 | 5 | 17 | 0.6 | 0.118 | 0.482 | 4 | 6 | 0.5 | 0 | 0.5 | 0.491 | 2.899 | 0.004 |
| L: rs1079596=4 2 | 4 | 14 | 0.75 | 0.143 | 0.607 | 7 | 4 | 0.286 | 0 | 0.286 | 0.446 | 3.008 | 0.003 |
| N: rs1051266=4 4 | 3 | 8 | 0.667 | 0 | 0.667 | 4 | 2 | 0.25 | 0 | 0.25 | 0.458 | 2.602 | 0.009 |
| O: m2756=AG or m2756=GG | 6 | 14 | 0.667 | 0.143 | 0.524 | 5 | 6 | 0.4 | 0.167 | 0.233 | 0.379 | 2.236 | 0.025 |
| P: rs4633=2 2 | 4 | 14 | 0.5 | 0 | 0.5 | 3 | 6 | 0.667 | 0 | 0.667 | 0.583 | 3.366 | 0.001 |
| Q: rs4680=3 3 | 3 | 14 | 0.667 | 0 | 0.667 | 3 | 6 | 0.667 | 0 | 0.667 | 0.667 | 3.674 | 0 |

FIG. 13A

| | PHASE 1 | | | | | PHASE 2 | | | | | POOLED | | |
|---|---|---|---|---|---|---|---|---|---|---|---|---|---|
| | Sample Size | | Resp Rate | | | Sample Size | | Resp Rate | | | Resp Rate | | |
| | Drug | Placebo | Drug | Placebo | Difference | Drug | Placebo | Drug | Placebo | Difference | Difference | Z-score | P-value |
| H+O 4 | 4 | 9 | 0.75 | 0 | 0.75 | 3 | 5 | 0.667 | 0 | 0.667 | 0.708 | 4.284 | 0 |
| C+Q 2 | 2 | 12 | 0.5 | 0 | 0.5 | 3 | 4 | 0.667 | 0 | 0.667 | 0.583 | 2.687 | 0.007 |
| E+Q 3 | 3 | 7 | 0.667 | 0 | 0.667 | 3 | 3 | 0.667 | 0 | 0.667 | 0.667 | 3.578 | 0 |
| B+K 3 | 3 | 8 | 1 | 0.125 | 0.875 | 3 | 2 | 0.667 | 0 | 0.667 | 0.771 | 4.814 | 0 |
| K+O 4 | 4 | 5 | 0.75 | 0 | 0.75 | 2 | 2 | 0.5 | 0 | 0.5 | 0.625 | 3.216 | 0.001 |
| B+M 5 | 5 | 11 | 0.6 | 0.273 | 0.327 | 4 | 4 | 0.25 | 0 | 0.25 | 0.289 | 1.749 | 0.08 |
| A+C 6 | 6 | 7 | 0.333 | 0 | 0.333 | 3 | 3 | 0.667 | 0 | 0.667 | 0.5 | 3.133 | 0.002 |
| C+L 2 | 2 | 8 | 1 | 0.125 | 0.875 | 4 | 2 | 0.5 | 0 | 0.5 | 0.688 | 4.851 | 0 |
| L+O 3 | 3 | 5 | 0.667 | 0 | 0.667 | 3 | 2 | 0.667 | 0 | 0.667 | 0.667 | 3.464 | 0.001 |
| E+P 4 | 4 | 7 | 0.5 | 0 | 0.5 | 3 | 3 | 0.667 | 0 | 0.667 | 0.583 | 3.27 | 0.001 |
| C+P 3 | 3 | 12 | 0.333 | 0 | 0.333 | 3 | 4 | 0.667 | 0 | 0.667 | 0.5 | 2.696 | 0.007 |
| A+B 4 | 4 | 6 | 0.5 | 0.167 | 0.333 | 2 | 2 | 0.5 | 0 | 0.5 | 0.5 | 2.394 | 0.017 |
| G+K 2 | 2 | 7 | 0.5 | 0 | 0.5 | 4 | 3 | 0.5 | 0 | 0.5 | 0.5 | 2.066 | 0.039 |
| E+O 5 | 5 | 7 | 0.8 | 0 | 0.8 | 7 | 2 | 0.286 | 0 | 0.286 | 0.65 | 4.229 | 0 |
| E+L 3 | 3 | 12 | 1 | 0.167 | 0.833 | 3 | 3 | 0.667 | 0 | 0.667 | 0.56 | 5.186 | 0 |
| G+O 3 | 3 | 5 | 0.667 | 0 | 0.667 | 3 | 2 | 0.667 | 0 | 0.667 | 0.667 | 3.464 | 0.001 |
| B+H 4 | 4 | 13 | 0.75 | 0.077 | 0.673 | 5 | 5 | 0.4 | 0 | 0.4 | 0.537 | 3.322 | 0.001 |

FIG. 13B

| | | | | | | | | | | |
|---|---|---|---|---|---|---|---|---|---|---|
| B+H | 4 | 13 | 0.75 | 0.077 | 0.673 | 5 | 5 | 0.4 | 0.4 | 0.537 | 3.322 | 0.001 |
| G+H | 3 | 10 | 0.333 | 0 | 0.333 | 3 | 4 | 0.667 | 0.667 | 0.5 | 2.696 | 0.007 |
| C+B | 4 | 16 | 0.75 | 0.125 | 0.625 | 7 | 5 | 0.571 | 0.371 | 0.498 | 2.871 | 0.004 |
| K+H | 3 | 13 | 0.667 | 0.077 | 0.59 | 2 | 5 | 0.5 | 0.5 | 0.545 | 2.625 | 0.009 |
| E+K | 4 | 8 | 0.75 | 0.25 | 0.5 | 3 | 2 | 0.667 | 0.667 | 0.583 | 2.924 | 0.003 |
| I+N | 3 | 7 | 0.667 | 0 | 0.667 | 4 | 2 | 0.25 | 0.25 | 0.458 | 2.555 | 0.011 |
| F+N | 3 | 6 | 0.667 | 0 | 0.667 | 4 | 2 | 0.25 | 0.25 | 0.458 | 2.636 | 0.008 |
| C+E | 6 | 13 | 0.5 | 0.077 | 0.423 | 7 | 4 | 0.571 | 0.571 | 0.497 | 3.446 | 0.001 |
| E+H | 4 | 15 | 0.75 | 0.133 | 0.617 | 6 | 6 | 0.333 | 0.333 | 0.475 | 3.094 | 0.002 |
| H+L | 2 | 12 | 0.5 | 0.167 | 0.333 | 5 | 4 | 0.4 | 0.4 | 0.367 | 1.683 | 0.092 |
| C+G | 5 | 8 | 0.4 | 0 | 0.4 | 3 | 2 | 0.667 | 0.667 | 0.533 | 3.091 | 0.002 |
| F+I | 3 | 7 | 0.667 | 0 | 0.667 | 5 | 2 | 0.2 | 0.2 | 0.433 | 2.661 | 0.008 |
| P+Q | 3 | 14 | 0.667 | 0 | 0.667 | 3 | 6 | 0.667 | 0.667 | 0.667 | 3.674 | 0 |
| B+E | 6 | 16 | 0.667 | 0.25 | 0.417 | 8 | 3 | 0.5 | 0.5 | 0.458 | 3.205 | 0.001 |
| A+H | 2 | 7 | 0.5 | 0 | 0.5 | 3 | 3 | 0.333 | 0.333 | 0.417 | 1.913 | 0.056 |
| E+G | 6 | 10 | 0.5 | 0.3 | 0.2 | 4 | 2 | 0.5 | 0.5 | 0.35 | 2.066 | 0.039 |
| A+H | 2 | 7 | 0.5 | 0 | 0.5 | 3 | 3 | 0.333 | 0.333 | 0.417 | 1.913 | 0.056 |
| A+E | 5 | 10 | 0.4 | 0.1 | 0.3 | 5 | 4 | 0.4 | 0.4 | 0.35 | 2.107 | 0.035 |

FIG. 13B (cont.)

```
                        SEQUENCE LISTING

<160> NUMBER OF SEQ ID NOS: 28

<210> SEQ ID NO 1
<211> LENGTH: 1983
<212> TYPE: DNA
<213> ORGANISM: Homo sapiens

<400> SEQUENCE: 1
aggaacccag  ccatggtgaa  cgaagccaga  ggaaacagca  gcctcaaccc  ctgcttggag      60
ggcagtgcca  gcagtggcag  tgagagctcc  aaagatagtt  cgagatgttc  caccccgggc     120
ctggaccccg  agcggcatga  gagactccgg  gagaagatga  ggcggcgatt  ggaatctggt     180
gacaagtggt  tctccctgga  attcttccct  cctcgaactg  ctgagggagc  tgtcaatctc     240
```

| | |
|---|---:|
| atctcaaggt tgaccggat ggcagcaggt ggcccctct acatagacgt gacctggcac | 300 |
| ccagcaggtg accctggctc agacaaggag acctcctcca tgatgatcgc cagcaccgcc | 360 |
| gtgaactact gtggcctgga gaccatcctg cacatgacct gctgccgtca gcgcctggag | 420 |
| gagatcacgg ccatctgca caaagctaag cagctgggcc tgaagaacat catggcgctg | 480 |
| cggggagacc aataggtga ccagtgggaa gaggaggagg gaggcttcaa ctacgcagtg | 540 |
| gacctggtga agcacatccg aagtgagttt ggtgactact ttgacatctg tgtggcaggt | 600 |
| taccccaaag gccaccccga agcagggagc tttgaggctg acctgaagca cttgaaggag | 660 |
| aaggtgtctg cggagccga tttcatcatc acgcagcttt tctttgaggc tgacacattc | 720 |
| ttccgctttg tgaaggcatg caccgacatg ggcatcactt gccccatcgt ccccgggatc | 780 |
| tttcccatcc agggctacca ctcccttcgg cagcttgtga agctgtccaa gctgaggtg | 840 |
| ccacaggaga tcaaggacgt gattgagcca atcaaagaca cgatgctgc catccgcaac | 900 |
| tatggcatcg agctgccgt gagcctgtgc caggagcttc tggccagtgg cttggtgcca | 960 |
| ggcctccact tctacaccct caaccgcgag atggctacca cagaggtgct gaagcgcctg | 1020 |
| gggatgtgga ctgaggaccc caggcgtccc ctaccctggg ctctcagcgc ccaccccaag | 1080 |
| cgccgagagg aagatgtacg tcccatcttc tgggcctcca gaccaaagag ttacatctac | 1140 |
| cgtacccagg agtgggacga gttccctaac ggccgctggg gcaattcctc ttcccctgcc | 1200 |
| tttggggagc tgaaggacta ctacctcttc tacctgaaga gcaagtcccc caaggaggag | 1260 |
| ctgctgaaga tgtgggggga ggagctgacc agtgaagaaa gtgtctttga agtcttcgtt | 1320 |
| ctttacctct cggagaacc aaaccggaat ggtcacaaag tgacttgcct gccctggaac | 1380 |
| gatgagcccc tggcggctga gaccagcctg ctgaaggagg agctgctgcg ggtgaaccgc | 1440 |
| cagggcatcc tcaccatcaa ctcacagccc aacatcaacg ggaagccgtc ctccgacccc | 1500 |
| atcgtgggct ggggccccag cggggctat gtcttccaga aggcctactt agagttttc | 1560 |
| acttccgcg agacagcgga agcacttctg caagtgctga gaagtacga gctccgggtt | 1620 |
| aattaccacc ttgtcaatgt gaagggtgaa acatcacca tgccctga actgcagccg | 1680 |
| aatgctgtca cttggggcat cttccctggg cgagagatca tccagcccac cgtagtggat | 1740 |
| cccgtcagct tcatgttctg gaaggacgag gcctttgccc tgtggattga gcggtgggga | 1800 |
| aagctgtatg aggaggagtc cccgtcccgc accatcatcc agtacatcca cgacaactac | 1860 |
| ttcctggtca acctggtgga caatgacttc ccactggaca actgcctctg gcaggtggtg | 1920 |
| gaagacacat ggagcttcct caacaggccc acccagaatg cgagagaaac ggaggctcca | 1980 |
| tga | 1983 |

```
<210> SEQ ID NO 2
<211> LENGTH: 3798
<212> TYPE: DNA
<213> ORGANISM: Homo sapiens

<400> SEQUENCE: 2
```

| | |
|---|---:|
| atgtcacccg cgctccaaga cctgtcgcaa cccgaaggtc tgaagaaaac cctgcgggat | 60 |
| gagatcaatg ccattctgca gaagaggatt atggtgctgg atggagggat ggggaccatg | 120 |
| atccagcggg agaagctaaa cgaagaacac ttccgaggtc aggaatttaa agatcatgcc | 180 |
| aggccgctga aagcaacaa tgacatttta agtataactc agcctgatgt catttaccaa | 240 |
| atccataagg aatacttgct ggctgggca gatatcattg aaacaaatac ttttagcagc | 300 |
| actagtattg cccaagctga ctatggcctt gaacacttgg cctaccggat gaacatgtgc | 360 |

```
tctgcaggag tggccagaaa agctgccgag gaggtaactc tccagacagg aattaagagg    420
tttgtggcag gggctctggg tccgactaat aagacactct ctgtgtcccc atctgtggaa    480
aggccggatt ataggaacat cacatttgat gagcttgttg aagcatacca agagcaggcc    540
aaaggacttc tggatggcgg ggttgatatc ttactcattg aaactatttt tgatactgcc    600
aatgccaagg cagccttgtt tgcactccaa atcttttttg aggagaaata tgctccccgg    660
cctatcttta tttcagggac gatcgttgat aaaagtgggc ggactctttc cggacagaca    720
ggagagggat ttgtcatcag cgtgtctcat ggagaaccac tctgcattgg attaaattgt    780
gctttgggtg cagctgaaat gagacctttt attgaaataa ttggaaaatg tacaacagcc    840
tatgtcctct gttatcccaa tgcaggtctt cccaacacct tggtgactat gatgaaacg    900 ccttctatga tggccaagca cctaaaggat tttgctatgg atggcttggt caatatagtt    960
ggaggatgct gtgggtcaac accagatcat atcagggaaa ttgctgaagc tgtgaaaaat    1020
tgtaagccta gagttccacc tgccactgct tttgaaggac atatgttact gtctggtcta    1080
gagcccttca ggattggacc gtacaccaac tttgttaaca ttggagagcg ctgtaatgtt    1140
gcaggatcaa ggaagtttgc taaactcatc atggcaggaa actatgaaga agccttgtgt    1200
gttgccaaag tgcaggtgga atgggagcc caggtgttgg atgtcaacat ggatgatggc    1260
atgctagatg gtccaagtgc aatgaccaga ttttgcaact taattgcttc cgagccagac    1320
atcgcaaagg tacctttgtg catcgactcc tccaattttg ctgtgattga agctgggtta    1380
aagtgctgcc aagggaagtg cattgtcaat agcattagtc tgaaggaagg agaggacgac    1440
ttcttggaga aggccaggaa gattaaaaag tatggagctg ctatggtggt catggctttt    1500
gatgaagaag acaggcaac agaaacagac acaaaaatca gagtgtgcac ccgggcctac    1560
catctgcttg tgaaaaaact gggctttaat ccaaatgaca ttatttttga ccctaatatc    1620
ctaaccattg ggactggaat ggaggaacac aacttgtatg ccattaattt tatccatgca    1680
acaaaagtca ttaaagaaac attacctgga gccagaataa gtggaggtct ttccaacttg    1740
tccttctcct tccgaggaat ggaagccatt cgagaagcaa tgcatgggt tttcctttac    1800 catgcaatca agtctggcat ggacatgggg atagtgaatg ctggaaaccct ccctgtgtat    1860 gatgatatcc ataaggaact tctgcagctc tgtgaagatc tcatctggaa taaagacctt    1920
gaggccactg agaagctctt acgttatgcc cagactcaag gcacaggagg gaagaaagtc    1980
attcagactg atgagtggag aaatggccct gtcgaagaac gccttgagta tgcccttgtg    2040
aagggcattg aaaaacatat tattgaggat actgaggaag ccaggttaaa ccaaaaaaaa    2100
tatccccgac ctctcaatat aattgaagga ccctgatga atggaatgaa aattgttggt    2160
gatctttttg gagctggaaa aatgtttcta cctcaggtta taaagtcagc ccgggttatg    2220
aagaaggctg ttggccacct tatcccttc atggaaaaag aaagagaaga accagagtg    2280 cttaacggca cagtagaaga agaggaccct taccagggca ccatcgtgct ggccactgtt    2340
aaaggcgacg tgcacgacat aggcaagaac atagttggag tagtccttgg ctgcaataat    2400
ttccgagtta ttgatttagg agtcatgact ccatgtgata agatactgaa agctgctctt    2460
gaccacaaag cagatataat tggcctgtca ggactcatcc ctccttccct ggatgaaatg    2520 attttttgttg ccaaggaaat ggagagatta gctataagga ttccattgtt gattggagga    2580
gcaaccactt caaaaaccca cacagcagtt aaaatagctc cgagatacag tgcacctgta    2640
atccatgtcc tggacgcgtc caagagtgtg gtggtgtgtt cccagctgtt agatgaaaat    2700
```

-continued

| | |
|---|---|
| ctaaaggatg aatactttga ggaaatcatg aagaatatg aagatattag acaggaccat | 2760 |
| tatgagtctc tcaaggagag gagatactta cccttaagtc aagccagaaa aagtggtttc | 2820 |
| caaatggatt ggctgtctga acctcaccca gtgaagccca cgtttattgg acccaggtc | 2880 |
| tttgaagact atgacctgca gaagctggtg gactacattg actggaagcc tttctttgat | 2940 |
| gtctggcagc tccggggcaa gtacccgaat cgaggctttc ccaagatatt taacgacaaa | 3000 |
| acagtaggtg gagaggccag gaaggtctac gatgatgccc acaatatgct gaacacactg | 3060 |
| attagtcaaa agaaactccg ggcccggggt gtggttgggt tctggccagc acagagtatc | 3120 |
| caagacgaca ttcacctgta cgcagaggct gctgtgcccc aggctgcaga gcccatagcc | 3180 |
| accttctatg ggttaaggca acaggctgag aaggactctg ccagcacgga gccatactac | 3240 |
| tgcctctcag acttcatcgc tcccttgcat tctggcatcc gtgactacct gggcctgttt | 3300 |
| gccgttgcct gctttggggt agaagagctg agcaaggcct atgaggatga tggtgacgac | 3360 |
| tacagcagca tcatggtcaa ggcgctgggg gaccggctgg cagaggcctt tgcagaagag | 3420 |
| ctccatgaaa gagttcgccg agaactgtgg gcctactgtg gcagtgagca gctggacgtc | 3480 |
| gcagacctgc gcaggctgcg gtacaagggc atccgcccgg ctcctggcta ccccagccag | 3540 |
| cccgaccaca ccgagaagct caccatgtgg agactcgcag acatcgagca gtctacaggc | 3600 |
| attaggttaa cagaatcatt agcaatggca cctgcttcag cagtctcagg cctctacttc | 3660 |
| tccaatttga agtccaaata ttttgctgtg gggaagattt ccaaggatca ggttgaggat | 3720 |
| tatgcattga ggaagaacat atctgtggct gaggttgaga aatggcttgg acccattttg | 3780 |
| ggatatgata cagactaa | 3798 |

<210> SEQ ID NO 3
<211> LENGTH: 2097
<212> TYPE: DNA
<213> ORGANISM: Homo sapiens

<400> SEQUENCE: 3

| | |
|---|---|
| atgaggaggt ttctgttact atatgctaca cagcagggac aggcaaaggc catcgcagaa | 60 |
| gaaatatgtg agcaagctgt ggtacatgga ttttctgcag atcttcactg tattagtgaa | 120 |
| tccgataagt atgacctaaa aaccgaaaca gctcctcttg ttgttgtggt ttctaccacg | 180 |
| ggcaccggag acccacccga cacagcccgc aagtttgtta aggaaataca gaaccaaaca | 240 |
| ctgccggttg atttctttgc tcacctgcgg tatgggttac tgggtctcgg tgattcagaa | 300 |
| tacacctact tttgcaatgg ggggaagata attgataaac gacttcaaga gcttggagcc | 360 |
| cggcatttct atgacactgg acatgcagat gactgtgtag gtttagaact tgtggttgag | 420 |
| ccgtggattg ctggactctg gccagccctc agaaagcatt ttaggtcaag cagaggacaa | 480 |
| gaggagataa gtggcgcact cccggtggca tcacctgcat cctcgaggac agaccttgtg | 540 |
| aagtcagagc tgctacacat tgaatctcaa gtcgagcttc tgagattcga tgattcagga | 600 |
| agaaaggatt ctgaggtttt gaagcaaaat gcagtgaaca gcaaccaatc caatgttgta | 660 |
| attgaagact ttgagtcctc acttacccgt tcggtacccc cactctcaca gcctctctg | 720 |
| aatattcctg gttacccccc agaatattta caggtacatc tgcaggagtc tcttggccag | 780 |
| gaggaaagcc aagtatctgt gacttcagca gatccagttt tcaagtgcc aatttcaaag | 840 |
| gcagttcaac ttactacgaa tgatgccata aaaaccactc tgctggtaga attggacatt | 900 |
| tcaaatacag acttttccta tcagcctgga gatgccttca gcgtgatctg ccctaacagt | 960 |
| gattctgagg tacaaagcct actccaaaga ctgcagcttg aagataaaag agagcactgc | 1020 |

-continued

```
gtccttttga aaataaaggc agacacaaag aagaaggag ctaccttacc ccagcatata    1080
cctgcgggat gttctctcca gttcattttt acctggtgtc ttgaaatccg agcaattcct    1140
aaaaaggcat ttttgcgagc ccttgtggac tataccagtg acagtgctga aaagcgcagg    1200
ctacaggagc tgtgcagtaa acaaggggca gccgattata gccgctttgt acgagatgcc    1260
tgtgcctgct tgttggatct cctcctcgct ttcccttctt gccagccacc actcagtctc    1320
ctgctcgaac atcttcctaa acttcaaccc agaccatatt cgtgtgcaag ctcaagttta    1380
tttcacccag gaaagctcca ttttgtcttc aacattgtgg aatttctgtc tactgccaca    1440
acagaggttc tgcggaaggg agtatgtaca ggctggctgg ccttgttggt tgcttcagtt    1500
cttcagccaa acatacatgc atcccatgaa gacagcggga aagccctggc tcctaagata    1560
tccatctctc ctcgaacaac aaattctttc cacttaccag atgacccctc aatccccatc    1620
ataatggtgg gtccaggaac cggcatagcc ccgtttattg ggttcctaca acatagagag    1680
aaactccaag aacaacaccc agatggaaat tttggagcaa tgtggttgtt ttttggctgc    1740
aggcataagg atagggatta tctattcaga aaagagctca gacatttcct taagcatggg    1800
atcttaactc atctaaaggt ttccttctca agagatgctc ctgttgggga ggaggaagcc    1860
ccagcaaagt atgtgcaaga caacatccag cttcatggcc agcaggtggc gagaatcctc    1920
ctccaggaga acggccatat ttatgtgtgt ggagatgcaa agaatatggc caaggatgta    1980
catgatgccc ttgtgcaaat aataagcaaa gaggttggag ttgaaaaact agaagcaatg    2040
aaaaccctgg ccactttaaa agaagaaaaa cgctaccttc aggatatttg gtcataa      2097
```

<210> SEQ ID NO 4
<211> LENGTH: 656
<212> TYPE: PRT
<213> ORGANISM: Homo sapiens

<400> SEQUENCE: 4

```
Met Val Asn Glu Ala Arg Gly Asn Ser Ser Leu Asn Pro Cys Leu Glu
1               5                   10                  15

Gly Ser Ala Ser Ser Gly Ser Glu Ser Ser Lys Asp Ser Ser Arg Cys
            20                  25                  30

Ser Thr Pro Gly Leu Asp Pro Glu Arg His Glu Arg Leu Arg Glu Lys
        35                  40                  45

Met Arg Arg Arg Leu Glu Ser Gly Asp Lys Trp Phe Ser Leu Glu Phe
    50                  55                  60

Phe Pro Pro Arg Thr Ala Glu Gly Ala Val Asn Leu Ile Ser Arg Phe
65                  70                  75                  80

Asp Arg Met Ala Ala Gly Gly Pro Leu Tyr Ile Asp Val Thr Trp His
                85                  90                  95

Pro Ala Gly Asp Pro Gly Ser Asp Lys Glu Thr Ser Ser Met Met Ile
            100                 105                 110

Ala Ser Thr Ala Val Asn Tyr Cys Gly Leu Glu Thr Ile Leu His Met
        115                 120                 125

Thr Cys Cys Arg Gln Arg Leu Glu Glu Ile Thr Gly His Leu His Lys
    130                 135                 140

Ala Lys Gln Leu Gly Leu Lys Asn Ile Met Ala Leu Arg Gly Asp Pro
145                 150                 155                 160

Ile Gly Asp Gln Trp Glu Glu Glu Gly Gly Phe Asn Tyr Ala Val
                165                 170                 175

Asp Leu Val Lys His Ile Arg Ser Glu Phe Gly Asp Tyr Phe Asp Ile
```

```
            180                 185                 190
Cys Val Ala Gly Tyr Pro Lys Gly His Pro Glu Ala Gly Ser Phe Glu
            195                 200                 205

Ala Asp Leu Lys His Leu Lys Glu Lys Val Ser Ala Gly Ala Asp Phe
        210                 215                 220

Ile Ile Thr Gln Leu Phe Phe Glu Ala Asp Thr Phe Phe Arg Phe Val
225                 230                 235                 240

Lys Ala Cys Thr Asp Met Gly Ile Thr Cys Pro Ile Val Pro Gly Ile
                245                 250                 255

Phe Pro Ile Gln Gly Tyr His Ser Leu Arg Gln Leu Val Lys Leu Ser
            260                 265                 270

Lys Leu Glu Val Pro Gln Glu Ile Lys Asp Val Ile Glu Pro Ile Lys
        275                 280                 285

Asp Asn Asp Ala Ala Ile Arg Asn Tyr Gly Ile Glu Leu Ala Val Ser
    290                 295                 300

Leu Cys Gln Glu Leu Leu Ala Ser Gly Leu Val Pro Gly Leu His Phe
305                 310                 315                 320

Tyr Thr Leu Asn Arg Glu Met Ala Thr Thr Glu Val Leu Lys Arg Leu
                325                 330                 335

Gly Met Trp Thr Glu Asp Pro Arg Arg Pro Leu Pro Trp Ala Leu Ser
            340                 345                 350

Ala His Pro Lys Arg Arg Glu Glu Asp Val Arg Pro Ile Phe Trp Ala
        355                 360                 365

Ser Arg Pro Lys Ser Tyr Ile Tyr Arg Thr Gln Glu Trp Asp Glu Phe
    370                 375                 380

Pro Asn Gly Arg Trp Gly Asn Ser Ser Ser Pro Ala Phe Gly Glu Leu
385                 390                 395                 400

Lys Asp Tyr Tyr Leu Phe Tyr Leu Lys Ser Lys Ser Pro Lys Glu Glu
                405                 410                 415

Leu Leu Lys Met Trp Gly Glu Glu Leu Thr Ser Glu Glu Ser Val Phe
            420                 425                 430

Glu Val Phe Val Leu Tyr Leu Ser Gly Glu Pro Asn Arg Asn Gly His
        435                 440                 445

Lys Val Thr Cys Leu Pro Trp Asn Asp Glu Pro Leu Ala Ala Glu Thr
    450                 455                 460

Ser Leu Leu Lys Glu Glu Leu Leu Arg Val Asn Arg Gln Gly Ile Leu
465                 470                 475                 480

Thr Ile Asn Ser Gln Pro Asn Ile Asn Gly Lys Pro Ser Ser Asp Pro
                485                 490                 495

Ile Val Gly Trp Gly Pro Ser Gly Gly Tyr Val Phe Gln Lys Ala Tyr
            500                 505                 510

Leu Glu Phe Phe Thr Ser Arg Glu Thr Ala Glu Ala Leu Leu Gln Val
        515                 520                 525

Leu Lys Lys Tyr Glu Leu Arg Val Asn Tyr His Leu Val Asn Val Lys
    530                 535                 540

Gly Glu Asn Ile Thr Asn Ala Pro Glu Leu Gln Pro Asn Ala Val Thr
545                 550                 555                 560

Trp Gly Ile Phe Pro Gly Arg Glu Ile Ile Gln Pro Thr Val Val Asp
                565                 570                 575

Pro Val Ser Phe Met Phe Trp Lys Asp Glu Ala Phe Ala Leu Trp Ile
            580                 585                 590

Glu Arg Trp Gly Lys Leu Tyr Glu Glu Ser Pro Ser Arg Thr Ile
        595                 600                 605
```

```
Ile Gln Tyr Ile His Asp Asn Tyr Phe Leu Val Asn Leu Val Asp Asn
        610                 615                 620

Asp Phe Pro Leu Asp Asn Cys Leu Trp Gln Val Val Glu Asp Thr Leu
625                 630                 635                 640

Glu Leu Leu Asn Arg Pro Thr Gln Asn Ala Arg Glu Thr Glu Ala Pro
                645                 650                 655

<210> SEQ ID NO 5
<211> LENGTH: 1265
<212> TYPE: PRT
<213> ORGANISM: Homo sapiens

<400> SEQUENCE: 5

Met Ser Pro Ala Leu Gln Asp Leu Ser Gln Pro Glu Gly Leu Lys Lys
1               5                   10                  15

Thr Leu Arg Asp Glu Ile Asn Ala Ile Leu Gln Lys Arg Ile Met Val
            20                  25                  30

Leu Asp Gly Gly Met Gly Thr Met Ile Gln Arg Glu Lys Leu Asn Glu
        35                  40                  45

Glu His Phe Arg Gly Gln Glu Phe Lys Asp His Ala Arg Pro Leu Lys
    50                  55                  60

Gly Asn Asn Asp Ile Leu Ser Ile Thr Gln Pro Asp Val Ile Tyr Gln
65                  70                  75                  80

Ile His Lys Glu Tyr Leu Leu Ala Gly Ala Asp Ile Ile Glu Thr Asn
                85                  90                  95

Thr Phe Ser Ser Thr Ser Ile Ala Gln Ala Asp Tyr Gly Leu Glu His
            100                 105                 110

Leu Ala Tyr Arg Met Asn Met Cys Ser Ala Gly Val Ala Arg Lys Ala
        115                 120                 125

Ala Glu Glu Val Thr Leu Gln Thr Gly Ile Lys Arg Phe Val Ala Gly
    130                 135                 140

Ala Leu Gly Pro Thr Asn Lys Thr Leu Ser Val Ser Pro Ser Val Glu
145                 150                 155                 160

Arg Pro Asp Tyr Arg Asn Ile Thr Phe Asp Glu Leu Val Glu Ala Tyr
                165                 170                 175

Gln Glu Gln Ala Lys Gly Leu Leu Asp Gly Gly Val Asp Ile Leu Leu
            180                 185                 190

Ile Glu Thr Ile Phe Asp Thr Ala Asn Ala Lys Ala Ala Leu Phe Ala
        195                 200                 205

Leu Gln Asn Leu Phe Glu Glu Lys Tyr Ala Pro Arg Pro Ile Phe Ile
    210                 215                 220

Ser Gly Thr Ile Val Asp Lys Ser Gly Arg Thr Leu Ser Gly Gln Thr
225                 230                 235                 240

Gly Glu Gly Phe Val Ile Ser Val Ser His Gly Glu Pro Leu Cys Ile
                245                 250                 255

Gly Leu Asn Cys Ala Leu Gly Ala Ala Glu Met Arg Pro Phe Ile Glu
            260                 265                 270

Ile Ile Gly Lys Cys Thr Thr Ala Tyr Val Leu Cys Tyr Pro Asn Ala
        275                 280                 285

Gly Leu Pro Asn Thr Phe Gly Asp Tyr Asp Glu Thr Pro Ser Met Met
    290                 295                 300

Ala Lys His Leu Lys Asp Phe Ala Met Asp Gly Leu Val Asn Ile Val
305                 310                 315                 320

Gly Gly Cys Cys Gly Ser Thr Pro Asp His Ile Arg Glu Ile Ala Glu
```

-continued

```
                325                 330                 335
Ala Val Lys Asn Cys Lys Pro Arg Val Pro Pro Ala Thr Ala Phe Glu
                340                 345                 350

Gly His Met Leu Leu Ser Gly Leu Glu Pro Phe Arg Ile Gly Pro Tyr
                355                 360                 365

Thr Asn Phe Val Asn Ile Gly Glu Arg Cys Asn Val Ala Gly Ser Arg
                370                 375                 380

Lys Phe Ala Lys Leu Ile Met Ala Gly Asn Tyr Glu Ala Leu Cys
385                 390                 395                 400

Val Ala Lys Val Gln Val Glu Met Gly Ala Gln Val Leu Asp Val Asn
                405                 410                 415

Met Asp Asp Gly Met Leu Asp Gly Pro Ser Ala Met Thr Arg Phe Cys
                420                 425                 430

Asn Leu Ile Ala Ser Glu Pro Asp Ile Ala Lys Val Pro Leu Cys Ile
                435                 440                 445

Asp Ser Ser Asn Phe Ala Val Ile Glu Ala Gly Leu Lys Cys Cys Gln
                450                 455                 460

Gly Lys Cys Ile Val Asn Ser Ile Ser Leu Lys Glu Gly Glu Asp Asp
465                 470                 475                 480

Phe Leu Glu Lys Ala Arg Lys Ile Lys Lys Tyr Gly Ala Ala Met Val
                485                 490                 495

Val Met Ala Phe Asp Glu Glu Gly Gln Ala Thr Glu Thr Asp Thr Lys
                500                 505                 510

Ile Arg Val Cys Thr Arg Ala Tyr His Leu Leu Val Lys Lys Leu Gly
                515                 520                 525

Phe Asn Pro Asn Asp Ile Ile Phe Asp Pro Asn Ile Leu Thr Ile Gly
                530                 535                 540

Thr Gly Met Glu Glu His Asn Leu Tyr Ala Ile Asn Phe Ile His Ala
545                 550                 555                 560

Thr Lys Val Ile Lys Glu Thr Leu Pro Gly Ala Arg Ile Ser Gly Gly
                565                 570                 575

Leu Ser Asn Leu Ser Phe Ser Phe Arg Gly Met Glu Ala Ile Arg Glu
                580                 585                 590

Ala Met His Gly Val Phe Leu Tyr His Ala Ile Lys Ser Gly Met Asp
                595                 600                 605

Met Gly Ile Val Asn Ala Gly Asn Leu Pro Val Tyr Asp Asp Ile His
                610                 615                 620

Lys Glu Leu Leu Gln Leu Cys Glu Asp Leu Ile Trp Asn Lys Asp Pro
625                 630                 635                 640

Glu Ala Thr Glu Lys Leu Leu Arg Tyr Ala Gln Thr Gln Gly Thr Gly
                645                 650                 655

Gly Lys Lys Val Ile Gln Thr Asp Glu Trp Arg Asn Gly Pro Val Glu
                660                 665                 670

Glu Arg Leu Glu Tyr Ala Leu Val Lys Gly Ile Glu Lys His Ile Ile
                675                 680                 685

Glu Asp Thr Glu Glu Ala Arg Leu Asn Gln Lys Lys Tyr Pro Arg Pro
                690                 695                 700

Leu Asn Ile Ile Glu Gly Pro Leu Met Asn Gly Met Lys Ile Val Gly
705                 710                 715                 720

Asp Leu Phe Gly Ala Gly Lys Met Phe Leu Pro Gln Val Ile Lys Ser
                725                 730                 735

Ala Arg Val Met Lys Lys Ala Val Gly His Leu Ile Pro Phe Met Glu
                740                 745                 750
```

-continued

Lys Glu Arg Glu Glu Thr Arg Val Leu Asn Gly Thr Val Glu Glu Glu
            755                 760                 765

Asp Pro Tyr Gln Gly Thr Ile Val Leu Ala Thr Val Lys Gly Asp Val
        770                 775                 780

His Asp Ile Gly Lys Asn Ile Val Gly Val Leu Gly Cys Asn Asn
785                 790                 795                 800

Phe Arg Val Ile Asp Leu Gly Val Met Thr Pro Cys Asp Lys Ile Leu
                805                 810                 815

Lys Ala Ala Leu Asp His Lys Ala Asp Ile Ile Gly Leu Ser Gly Leu
                820                 825                 830

Ile Thr Pro Ser Leu Asp Glu Met Ile Phe Val Ala Lys Glu Met Glu
                835                 840                 845

Arg Leu Ala Ile Arg Ile Pro Leu Leu Ile Gly Gly Ala Thr Thr Ser
850                 855                 860

Lys Thr His Thr Ala Val Lys Ile Ala Pro Arg Tyr Ser Ala Pro Val
865                 870                 875                 880

Ile His Val Leu Asp Ala Ser Lys Ser Val Val Cys Ser Gln Leu
                885                 890                 895

Leu Asp Glu Asn Leu Lys Asp Glu Tyr Phe Glu Glu Ile Met Glu Glu
                900                 905                 910

Tyr Glu Asp Ile Arg Gln Asp His Tyr Glu Ser Leu Lys Glu Arg Arg
            915                 920                 925

Tyr Leu Pro Leu Ser Gln Ala Arg Lys Ser Gly Phe Gln Met Asp Trp
        930                 935                 940

Leu Ser Glu Pro His Pro Val Lys Pro Thr Phe Ile Gly Thr Gln Val
945                 950                 955                 960

Phe Glu Asp Tyr Asp Leu Gln Lys Leu Val Asp Tyr Ile Asp Trp Lys
                965                 970                 975

Pro Phe Phe Asp Val Trp Gln Leu Arg Gly Lys Tyr Pro Asn Arg Gly
                980                 985                 990

Phe Pro Lys Ile Phe Asn Asp Lys Thr Val Gly Gly Glu Ala Arg Lys
        995                 1000                1005

Val Tyr Asp Asp Ala His Asn Met Leu Asn Thr Leu Ile Ser Gln
    1010                1015                1020

Lys Lys Leu Arg Ala Arg Gly Val Val Gly Phe Trp Pro Ala Gln
    1025                1030                1035

Ser Ile Gln Asp Asp Ile His Leu Tyr Ala Glu Ala Ala Val Pro
    1040                1045                1050

Gln Ala Ala Glu Pro Ile Ala Thr Phe Tyr Gly Leu Arg Gln Gln
    1055                1060                1065

Ala Glu Lys Asp Ser Ala Ser Thr Glu Pro Tyr Tyr Cys Leu Ser
    1070                1075                1080

Asp Phe Ile Ala Pro Leu His Ser Gly Ile Arg Asp Tyr Leu Gly
    1085                1090                1095

Leu Phe Ala Val Ala Cys Phe Gly Val Glu Glu Leu Ser Lys Ala
    1100                1105                1110

Tyr Glu Asp Asp Gly Asp Asp Tyr Ser Ser Ile Met Val Lys Ala
    1115                1120                1125

Leu Gly Asp Arg Leu Ala Glu Ala Phe Ala Glu Glu Leu His Glu
    1130                1135                1140

Arg Val Arg Arg Glu Leu Trp Ala Tyr Cys Gly Ser Glu Gln Leu
    1145                1150                1155

```
Asp Val Ala Asp Leu Arg Arg Leu Arg Tyr Lys Gly Ile Arg Pro
    1160                1165                1170

Ala Pro Gly Tyr Pro Ser Gln Pro Asp His Thr Glu Lys Leu Thr
    1175                1180                1185

Met Trp Arg Leu Ala Asp Ile Glu Gln Ser Thr Gly Ile Arg Leu
    1190                1195                1200

Thr Glu Ser Leu Ala Met Ala Pro Ala Ser Ala Val Ser Gly Leu
    1205                1210                1215

Tyr Phe Ser Asn Leu Lys Ser Lys Tyr Phe Ala Val Gly Lys Ile
    1220                1225                1230

Ser Lys Asp Gln Val Glu Asp Tyr Ala Leu Arg Lys Asn Ile Ser
    1235                1240                1245

Val Ala Glu Val Glu Lys Trp Leu Gly Pro Ile Leu Gly Tyr Asp
    1250                1255                1260

Thr Asp
    1265

<210> SEQ ID NO 6
<211> LENGTH: 698
<212> TYPE: PRT
<213> ORGANISM: Homo sapiens

<400> SEQUENCE: 6

Met Arg Arg Phe Leu Leu Leu Tyr Ala Thr Gln Gln Gly Gln Ala Lys
1               5                   10                  15

Ala Ile Ala Glu Glu Ile Cys Glu Gln Ala Val Val His Gly Phe Ser
            20                  25                  30

Ala Asp Leu His Cys Ile Ser Glu Ser Asp Lys Tyr Asp Leu Lys Thr
        35                  40                  45

Glu Thr Ala Pro Leu Val Val Val Ser Thr Thr Gly Thr Gly Asp
    50                  55                  60

Pro Pro Asp Thr Ala Arg Lys Phe Val Lys Glu Ile Gln Asn Gln Thr
65                  70                  75                  80

Leu Pro Val Asp Phe Phe Ala His Leu Arg Tyr Gly Leu Leu Gly Leu
                85                  90                  95

Gly Asp Ser Glu Tyr Thr Tyr Phe Cys Asn Gly Gly Lys Ile Ile Asp
            100                 105                 110

Lys Arg Leu Gln Glu Leu Gly Ala Arg His Phe Tyr Asp Thr Gly His
        115                 120                 125

Ala Asp Asp Cys Val Gly Leu Glu Leu Val Val Glu Pro Trp Ile Ala
    130                 135                 140

Gly Leu Trp Pro Ala Leu Arg Lys His Phe Arg Ser Ser Arg Gly Gln
145                 150                 155                 160

Glu Glu Ile Ser Gly Ala Leu Pro Val Ala Ser Pro Ala Ser Ser Arg
                165                 170                 175

Thr Asp Leu Val Lys Ser Glu Leu Leu His Ile Glu Ser Gln Val Glu
            180                 185                 190

Leu Leu Arg Phe Asp Asp Ser Gly Arg Lys Asp Ser Glu Val Leu Lys
        195                 200                 205

Gln Asn Ala Val Asn Ser Asn Gln Ser Asn Val Ile Glu Asp Phe
    210                 215                 220

Glu Ser Ser Leu Thr Arg Ser Val Pro Leu Ser Gln Ala Ser Leu
225                 230                 235                 240

Asn Ile Pro Gly Leu Pro Pro Glu Tyr Leu Gln Val His Leu Gln Glu
                245                 250                 255
```

```
Ser Leu Gly Gln Glu Glu Ser Gln Val Ser Val Thr Ser Ala Asp Pro
            260                 265                 270

Val Phe Gln Val Pro Ile Ser Lys Ala Val Gln Leu Thr Asn Asp
            275                 280                 285

Ala Ile Lys Thr Thr Leu Leu Val Glu Leu Asp Ile Ser Asn Thr Asp
290                 295                 300

Phe Ser Tyr Gln Pro Gly Asp Ala Phe Ser Val Ile Cys Pro Asn Ser
305                 310                 315                 320

Asp Ser Glu Val Gln Ser Leu Gln Arg Leu Gln Leu Glu Asp Lys
            325                 330                 335

Arg Glu His Cys Val Leu Leu Lys Ile Lys Ala Asp Thr Lys Lys Lys
            340                 345                 350

Gly Ala Thr Leu Pro Gln His Ile Pro Ala Gly Cys Ser Leu Gln Phe
            355                 360                 365

Ile Phe Thr Trp Cys Leu Glu Ile Arg Ala Ile Pro Lys Lys Ala Phe
            370                 375                 380

Leu Arg Ala Leu Val Asp Tyr Thr Ser Asp Ser Ala Glu Lys Arg Arg
385                 390                 395                 400

Leu Gln Glu Leu Cys Ser Lys Gln Gly Ala Ala Asp Tyr Ser Arg Phe
                405                 410                 415

Val Arg Asp Ala Cys Ala Cys Leu Leu Asp Leu Leu Leu Ala Phe Pro
            420                 425                 430

Ser Cys Gln Pro Pro Leu Ser Leu Leu Leu Glu His Leu Pro Lys Leu
            435                 440                 445

Gln Pro Arg Pro Tyr Ser Cys Ala Ser Ser Ser Leu Phe His Pro Gly
            450                 455                 460

Lys Leu His Phe Val Phe Asn Ile Val Glu Phe Leu Ser Thr Ala Thr
465                 470                 475                 480

Thr Glu Val Leu Arg Lys Gly Val Cys Thr Gly Trp Leu Ala Leu Leu
                485                 490                 495

Val Ala Ser Val Leu Gln Pro Asn Ile His Ala Ser His Glu Asp Ser
            500                 505                 510

Gly Lys Ala Leu Ala Pro Lys Ile Ser Ile Ser Pro Arg Thr Thr Asn
            515                 520                 525

Ser Phe His Leu Pro Asp Asp Pro Ser Ile Pro Ile Ile Met Val Gly
            530                 535                 540

Pro Gly Thr Gly Ile Ala Pro Phe Ile Gly Phe Leu Gln His Arg Glu
545                 550                 555                 560

Lys Leu Gln Glu Gln His Pro Asp Gly Asn Phe Gly Ala Met Trp Leu
                565                 570                 575

Phe Phe Gly Cys Arg His Lys Asp Arg Asp Tyr Leu Phe Arg Lys Glu
            580                 585                 590

Leu Arg His Phe Leu Lys His Gly Ile Leu Thr His Leu Lys Val Ser
            595                 600                 605

Phe Ser Arg Asp Ala Pro Val Gly Glu Glu Ala Pro Ala Lys Tyr
            610                 615                 620

Val Gln Asp Asn Ile Gln Leu His Gly Gln Gln Val Ala Arg Ile Leu
625                 630                 635                 640

Leu Gln Glu Asn Gly His Ile Tyr Val Cys Gly Asp Ala Lys Asn Met
                645                 650                 655

Ala Lys Asp Val His Asp Ala Leu Val Gln Ile Ile Ser Lys Glu Val
            660                 665                 670
```

```
Gly Val Glu Lys Leu Glu Ala Met Lys Thr Leu Ala Thr Leu Lys Glu
            675                 680                 685

Glu Lys Arg Tyr Leu Gln Asp Ile Trp Ser
    690                 695

<210> SEQ ID NO 7
<211> LENGTH: 52
<212> TYPE: DNA
<213> ORGANISM: Homo sapiens

<400> SEQUENCE: 7
cttgaaggag aaggtgtctg cgggagycga tttcatcatc acgcagcttt tc          52

<210> SEQ ID NO 8
<211> LENGTH: 52
<212> TYPE: DNA
<213> ORGANISM: Homo sapiens

<400> SEQUENCE: 8
cgaggccttt gccctgtgga ttgagcrgtg gggaaagctg tatgaggagg ag          52

<210> SEQ ID NO 9
<211> LENGTH: 52
<212> TYPE: DNA
<213> ORGANISM: Homo sapiens

<400> SEQUENCE: 9
ggaagaatat gaagatatta gacaggrcca ttatgagtct ctcaaggtaa gt          52

<210> SEQ ID NO 10
<211> LENGTH: 52
<212> TYPE: DNA
<213> ORGANISM: Homo sapiens

<400> SEQUENCE: 10
caggcaaagg ccatcgcaga agaaatrtgt gagcaagctg tggtacatgg at          52

<210> SEQ ID NO 11
<211> LENGTH: 52
<212> TYPE: DNA
<213> ORGANISM: Homo sapiens

<400> SEQUENCE: 11
taagttccat tccatctcag cccgaartgt tttcagagcc ggagacctca ca          52

<210> SEQ ID NO 12
<211> LENGTH: 52
<212> TYPE: DNA
<213> ORGANISM: Homo sapiens

<400> SEQUENCE: 12
ctgctgctgg tatcagcctg gaggaartga gtgacatcag ttctcagcat ta          52

<210> SEQ ID NO 13
<211> LENGTH: 52
<212> TYPE: DNA
<213> ORGANISM: Homo sapiens

<400> SEQUENCE: 13
aaccaatcac aacaaggcag ataaagwagg atgagttgtc agattttgat aa          52

<210> SEQ ID NO 14
<211> LENGTH: 52
```

<212> TYPE: DNA
<213> ORGANISM: Homo sapiens

<400> SEQUENCE: 14
gcttcggagc tggagcgcat gaatccyggc ccaggcggga agctgggaca cg                52

<210> SEQ ID NO 15
<211> LENGTH: 52
<212> TYPE: DNA
<213> ORGANISM: Homo sapiens

<400> SEQUENCE: 15
aagctgagaa catcaagaag ttcttayagt aagtacatcc tcgaaagttt at                52

<210> SEQ ID NO 16
<211> LENGTH: 52
<212> TYPE: DNA
<213> ORGANISM: Homo sapiens

<400> SEQUENCE: 16
gggagggcac ccgcagaggc ctgcgcrctg acactgctga gtggctctgc tc                52

<210> SEQ ID NO 17
<211> LENGTH: 52
<212> TYPE: DNA
<213> ORGANISM: Homo sapiens

<400> SEQUENCE: 17
tgaccccgag ctccggtcct ggcggcrcct cgtgtgctac ctttgcttct ac                52

<210> SEQ ID NO 18
<211> LENGTH: 52
<212> TYPE: DNA
<213> ORGANISM: Homo sapiens

<400> SEQUENCE: 18
caataggagc gtgtgtttga acagtayacg ccaaacttca gtcattcaag ta                52

<210> SEQ ID NO 19
<211> LENGTH: 52
<212> TYPE: DNA
<213> ORGANISM: Homo sapiens

<400> SEQUENCE: 19
ggcctaatca atccttctca tcttttrtac ccacctttg caggaaacct gt                 52

<210> SEQ ID NO 20
<211> LENGTH: 52
<212> TYPE: DNA
<213> ORGANISM: Homo sapiens

<400> SEQUENCE: 20
ctgactctcc ccgacccgtc ccaccayggt ctccacagca ctcccgacag cc                52

<210> SEQ ID NO 21
<211> LENGTH: 52
<212> TYPE: DNA
<213> ORGANISM: Homo sapiens

<400> SEQUENCE: 21
gtccctgcag tttaattatc ctcaacrtta ctgccatacc ctacattttt gg                52

<210> SEQ ID NO 22

<210> SEQ ID NO 22
<211> LENGTH: 52
<212> TYPE: DNA
<213> ORGANISM: Homo sapiens

<400> SEQUENCE: 22
ctcacagttt gtggttgaga ctaagtrtga caacagtggc actttgtggt cc    52

<210> SEQ ID NO 23
<211> LENGTH: 52
<212> TYPE: DNA
<213> ORGANISM: Homo sapiens

<400> SEQUENCE: 23
accaaggagc agcgcatcct gaaccaygtg ctgcagcatg cggagcccgg ga    52

<210> SEQ ID NO 24
<211> LENGTH: 52
<212> TYPE: DNA
<213> ORGANISM: Homo sapiens

<400> SEQUENCE: 24
cccagcggat ggtggatttc gctggcrtga aggacaaggt gtgcatgcct ga    52

<210> SEQ ID NO 25
<211> LENGTH: 52
<212> TYPE: DNA
<213> ORGANISM: Homo sapiens

<400> SEQUENCE: 25
taatatggcc accccaactt tcgtatsatt actgtttgtg tggtattatc tt    52

<210> SEQ ID NO 26
<211> LENGTH: 52
<212> TYPE: DNA
<213> ORGANISM: Homo sapiens

<400> SEQUENCE: 26
atcagcccta gatgcttgac cagctcytcg ggcctcacct cctggttctt cc    52

<210> SEQ ID NO 27
<211> LENGTH: 52
<212> TYPE: DNA
<213> ORGANISM: Homo sapiens

<400> SEQUENCE: 27
ctgggccaac aagcttgagt gcgatcyggt ctgcaatgat ggaggaattg cc    52

<210> SEQ ID NO 28
<211> LENGTH: 271
<212> TYPE: PRT
<213> ORGANISM: Homo sapiens

<400> SEQUENCE: 28

Met Pro Glu Ala Pro Pro Leu Leu Leu Ala Ala Val Leu Leu Gly Leu
1               5                   10                  15

Val Leu Leu Val Val Leu Leu Leu Leu Arg His Trp Gly Trp Gly
            20                  25                  30

Leu Cys Leu Ile Gly Trp Asn Glu Phe Ile Leu Gln Pro Ile His Asn
        35                  40                  45

Leu Leu Met Gly Asp Thr Lys Glu Gln Arg Ile Leu Asn His Val Leu
    50                  55                  60

Gln His Ala Glu Pro Gly Asn Ala Gln Ser Val Leu Glu Ala Ile Asp

-continued

```
                65                  70                  75                  80
Thr Tyr Cys Glu Gln Lys Glu Trp Ala Met Asn Val Gly Asp Lys Lys
                    85                  90                  95

Gly Lys Ile Val Asp Ala Val Ile Gln Glu His Gln Pro Ser Val Leu
                    100                 105                 110

Leu Glu Leu Gly Ala Tyr Cys Gly Tyr Ser Ala Val Arg Met Ala Arg
                115                 120                 125

Leu Leu Ser Pro Gly Ala Arg Leu Ile Thr Ile Glu Ile Asn Pro Asp
            130                 135                 140

Cys Ala Ala Ile Thr Gln Arg Met Val Asp Phe Ala Gly Val Lys Asp
145                 150                 155                 160

Lys Val Thr Leu Val Val Gly Ala Ser Gln Asp Ile Ile Pro Gln Leu
                    165                 170                 175

Lys Lys Lys Tyr Asp Val Asp Thr Leu Asp Met Val Phe Leu Asp His
                180                 185                 190

Trp Lys Asp Arg Tyr Leu Pro Asp Thr Leu Leu Leu Glu Glu Cys Gly
                195                 200                 205

Leu Leu Arg Lys Gly Thr Val Leu Leu Ala Asp Asn Val Ile Cys Pro
            210                 215                 220

Gly Ala Pro Asp Phe Leu Ala His Val Arg Gly Ser Ser Cys Phe Glu
225                 230                 235                 240

Cys Thr His Tyr Gln Ser Phe Leu Glu Tyr Arg Glu Val Val Asp Gly
                    245                 250                 255

Leu Glu Lys Ala Ile Tyr Lys Gly Pro Gly Ser Glu Ala Gly Pro
                260                 265                 270
```

ASSAYS AND METHODS FOR SELECTING A TREATMENT REGIMEN FOR A SUBJECT WITH DEPRESSION

CROSS REFERENCE TO RELATED APPLICATIONS

This application is a Continuation-In-Part of PCT application Ser. No. PCT/US12/65084 filed Nov. 14, 2012, which claims the benefit under 35 U.S.C. §119(e) of U.S. Provisional Patent Application No. 61/559,541 filed Nov. 14, 2011, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Mar. 6, 2013, is named 341471PC.txt and is 38,877 bytes in size.

TECHNICAL FIELD OF THE DISCLOSURE

Embodiments of the inventions generally relate to assays, methods and systems for selecting a treatment regimen for a subject with depression, e.g., major depressive disorder. The inventions further relate to methods for treating a subject with depression, e.g., major depressive disorder.

BACKGROUND

Recent estimates indicate that more than 19 million Americans over the age of 18 years experience a depressive illness each year. It has been generally believed that there is some form of association between folate-deficiency states and depression [1, 2 and 3], which in turn helps to explain prior observations on the myriad neuropsychiatric presentations of megaloblastic anemia [4]. Recently, the relevance of folate in other medical conditions, in particular neural tube defects [5] and cardiovascular disease, [6] and potential antidepressant efficacy of agents marketed as dietary supplements or "nutraceuticals," [7 and 8] such as S-adenosylmethionine (SAMe), hypericum perforatum (St. John's wort), and omega-3-fatty acids, has been increasingly recognized. The field has gradually moved toward researching the impact of folate deficiency, replacement, and supplementation on the course and management of depressive disorders, in particular major depressive disorder, [9] and putative roles of folate in central-nervous-system function. [10, 11 and 12]. While significant advances in the treatment of depression have been made in the past decade, as many as 29% to 46% of patients with depression taking an anti-depressant are still partially or totally resistant to the treatment. Those who suffer from treatment-resistant depression have almost no alternatives. As not every treatment regimen is effective for each individual, there is a strong need to identify markers that can facilitate selection of an appropriate treatment regimen for a subject with depression.

SUMMARY

A significant portion of patients with depression, such as major depressive disorders, show only partial or no response to conventional antidepressant drugs, e.g., selective serotonin reuptake inhibitors. Thus, there is a strong need to develop effective antidepressant therapies and/or to stratify patients with depression such that they can receive appropriate antidepressant therapies. Aspects of various embodiments described herein stem from the discovery of single nucleotide polymorphisms (SNPs), peripheral biomarkers and/or clinical features that are associated with an efficacy response to the use of a folate-containing compound for treatment of depression, e.g., major depressive disorders, as a monotherapy or as an adjunct to an antidepressant drug. In some embodiments, the inventors have also shown that these markers or conditions described herein can also be used to select a more effective treatment for subjects with treatment-resistant depression (TRD), e.g., resistant to at least one selective serotonin reuptake inhibitor (SSRI).

Particularly, one or a combination of biomarkers that can be indicative of a patient (e.g., with major depressive disorders and/or TRD) suitable for a treatment regimen comprising a folate-containing compound include, but are not limited to, at least one or more SNPs identified by rs numbers as follows: rs1801133 present in methylenetetrahydrofolate reductase (MTHFR); rs2274976 present in MTHFR; rs1805087 present in methionine synthase (MTR); rs1801394 present in methionine synthase reductase (MTRR); rs1006737 present in calcium channel, voltage-dependent, L-type, alpha 1C subunit (CACNA1C); rs1883729 present in DNA (cytosine-5)-methyltransferase 3 beta (DNMT3B); rs7163862 present in GTP cyclohydrolase 1 feedback regulatory protein (GCHFR); rs12659 present in reduced folate carrier protein (RCF2); rs202676 present in folate hydrolase (prostate-specific membrane antigen) (FOLH1); rs2297291 present in reduced folate carrier protein (RCF1); rs1051266 present in reduced folate carrier protein 1 (RCF1); rs8007267 present in GTP cyclohydrolase 1 (GCH1); rs7639752 present in choline-phosphate cytidylytransferase A (PCYT1A); rs6275 present in dopamine receptor D2 (DRD2); rs1079596 present in DRD2; rs11240594 present in DRD2; rs4633 present in catechol-β-methyltransferase (COMT); rs4680 present in COMT; rs250682 present in dopamine active transporter (DAT, or SLC6A3); rs2277820 present in formiminotransferase cyclodeaminase (FTCD); rs2236225 present in methylenetetrahydrofolate dehydrogenase (NADP+ dependent) 1 (MTHFD1); and any combinations thereof and/or expression of at least one of s-adenosyl methionine (SAM), s-adenosyl homocysteine (SAH), 4-hydroxynonenal (4-HNE), high sensitivity c-reactive protein (hsCRP), and any combinations thereof. Additionally or alternatively, determination of whether a human subject is obese or not (e.g., by measurement of a BMI value) can also be used as a biomarker to select an appropriate treatment regimen (e.g., comprising a folate-containing compound or not) for a patient with depression or a risk for depression. Any individual or combinations of such biomarkers disclosed herein can be used to identify patients, who are diagnosed as having depression or having a risk for depression, for receiving a treatment regimen comprising a folate-containing compound. In some embodiments, a folate-containing compound can be used in the absence of an anti-depressant drug for treatment of depression (e.g., major depressive disorders) in subjects selected for carrying at least one or more biomarkers described herein. In alternative embodiments, a folate-containing compound can be used alone or in combination (e.g., as an adjunct) with an anti-depressant drug for treatment of depression (e.g., major depressive disorders) in subjects selected for carrying at least one or more biomarkers described herein. In one embodiment, the anti-depressant drug can include a selective serotonin reuptake inhibitor (SSRI). Examples of the SSRI include, but are not limited to, fluoxetine, citalopram, paroxetine, escitalopram, sertraline, and any combinations thereof.

Accordingly, provided herein generally relate to assays, methods, systems, and kits for selecting a treatment regimen for a subject with depression or a risk for depression, treating a subject with depression or a risk for depression, and/or improving the effectiveness of a treatment regimen recommended for or administered to a subject with depression or a risk for depression. Provided herein also relate to folate-comprising compositions for use in treatment of depression in a subject (e.g., a human subject) selected to carry at least one (e.g., at least two or more) or any combinations of the biomarkers or conditions described herein.

In one aspect, provided herein is an assay for selecting a treatment regimen for a human subject having depression or having a risk for depression. The assay comprises:
(a) subjecting a test sample of a human subject, who is diagnosed as having depression or having a risk for depression, to at least one analysis to determine parameters of at least two biomarkers from the following:
  (i) genotype of a SNP locus at position 677 of SEQ ID NO. 1 or position 27 of SEQ ID NO. 7 (identified by rs1801133), wherein the SEQ ID NO. 1 and SEQ ID NO. 7 are each independently a portion of a genomic nucleic acid sequence of methylenetetrahydrofolate reductase (MTHFR);
  (ii) genotype of a SNP locus at position 1793 of SEQ ID NO. 1 or position 27 of SEQ ID NO. 8 (identified by rs2274976), wherein the SEQ ID NO. 1 and SEQ ID NO. 8 are each independently a portion of a genomic nucleic acid sequence of MTHFR;
  (iii) genotype of a SNP locus at position 2756 of SEQ ID NO. 2 or position 27 of SEQ ID NO. 9 (identified by rs1805087), wherein the SEQ ID NO. 2 and SEQ ID NO. 9 are each independently a portion of a genomic nucleic acid sequence of methionine synthase (MTR);
  (iv) genotype of a SNP locus at position 66 of SEQ ID NO. 3 or position 27 of SEQ ID NO. 10 (identified by rs1801394), wherein the SEQ ID NO. 3 and SEQ ID NO. 10 are each independently a portion of a genomic nucleic acid sequence of methionine synthase reductase (MTRR);
  (v) genotype of a SNP locus at position 27 of SEQ ID NO. 11 (identified by rs1006737), wherein the SEQ ID NO. 11 is a portion of a genomic nucleic acid sequence of calcium channel, voltage-dependent, L type, alpha 1C subunit (CACNA1C);
  (vi) genotype of a SNP locus at position 27 of SEQ ID NO. 12 (identified by rs1883729), wherein the SEQ ID NO. 12 is a portion of a genomic nucleic acid sequence of DNA (cytosine-5)-methyltransferase 3 beta (DNMT3B);
  (vii) genotype of a SNP locus at position 27 of SEQ ID NO. 13 (identified by rs7163862), wherein the SEQ ID NO. 13 is a portion of a genomic nucleic acid sequence of GTP cyclohydrolase 1 feedback regulatory protein (GCHFR);
  (viii) genotype of a SNP locus at position 27 of SEQ ID NO. 14 (identified by rs12659), wherein the SEQ ID NO. 14 is a portion of a genomic nucleic acid sequence of reduced folate carrier protein (RCF2);
  (ix) genotype of a SNP locus at position 27 of SEQ ID NO. 15 (identified by rs202676), wherein the SEQ ID NO. 15 is a portion of a genomic nucleic acid sequence of folate hydrolase (prostate-specific membrane antigen) 1 (FOLH1);
  (x) genotype of a SNP locus at position 27 of SEQ ID NO. 16 (identified by rs2297291), wherein the SEQ ID NO. 16 is a portion of a genomic nucleic acid sequence of reduced folate carrier protein (RCF1);
  (xi) genotype of a SNP locus at position 27 of SEQ ID NO. 17 (identified by rs1051266), wherein the SEQ ID NO. 17 is a portion of a genomic nucleic acid sequence of reduced folate carrier protein (RCF1);
  (xii) genotype of a SNP locus at position 27 of SEQ ID NO. 18 (identified by rs8007267), wherein the SEQ ID NO. 18 is a portion of a genomic nucleic acid sequence of GTP cyclohydrolase 1 (GCH1);
  (xiii) genotype of a SNP locus at position 27 of SEQ ID NO. 19 (identified by rs7639752), wherein the SEQ ID NO. 19 is a portion of a genomic nucleic acid sequence of choline-phosphate cytidylyltransferase A (PCYT1A);
  (xiv) genotype of a SNP locus at position 27 of SEQ ID NO. 20 (identified by rs6275), wherein the SEQ ID NO. 20 is a portion of a genomic nucleic acid sequence of dopamine receptor D2 (DRD2);
  (xv) genotype of a SNP locus at position 27 of SEQ ID NO. 21 (identified by rs1079596), wherein the SEQ ID NO. 21 is a portion of a genomic nucleic acid sequence of dopamine receptor D2 (DRD2);
  (xvi) genotype of a SNP locus at position 27 of SEQ ID NO. 22 (identified by rs11240594), wherein the SEQ ID NO. 22 is a portion of a genomic nucleic acid sequence of dopamine receptor D2 (DRD2);
  (xvii) genotype of a SNP locus at position 27 of SEQ ID NO. 23 (identified by rs4633), wherein the SEQ ID NO. 23 is a portion of a genomic nucleic acid sequence of catechol-β-methyltransferase (COMT);
  (xviii) genotype of a SNP locus at position 27 of SEQ ID NO. 24 (identified by rs4680), wherein the SEQ ID NO. 24 is a portion of a genomic nucleic acid sequence of catechol-β-methyltransferase (COMT);
  (xix) genotype of a SNP locus at position 27 of SEQ ID NO. 25 (identified by rs250682), wherein the SEQ ID NO. 25 is a portion of a genomic nucleic acid sequence of solute carrier family 6 (neurotransmitted transported, dopamine), member 3 (SLC6A3);
  (xx) genotype of a SNP locus at position 27 of SEQ ID NO. 26 (identified by rs2277820), wherein the SEQ ID NO. 26 is a portion of a genomic nucleic acid sequence of formiminotransferase cyclodeaminase (FTCD);
  (xxi) genotype of a SNP locus at position 27 of SEQ ID NO. 27 (identified by rs2236225), wherein the SEQ ID NO. 27 is a portion of a genomic nucleic acid sequence of methylenetetrahydrofolate dehydrogenase (NADP+ dependent) 1 (MTHFD1));
  (xxii) level of expression of SAM and SAH;
  (xxiii) level of expression of 4-HNE;
  (xxiv) level of expression of hsCRP; and any combinations thereof; and
(b) detecting, optionally with a non-human machine, from the determined parameters of at least two biomarkers, the presence of at least one condition selected from the following:
  (A) a SNP at position 677 of SEQ ID NO. 1 or position 27 of SEQ ID NO. 7 (identified by rs1801133) comprising at least one thymine "T" allele;
  (B) a SNP at position 1793 of SEQ ID NO. 1 or position 27 of SEQ ID NO. 8 (identified by rs2274976) comprising at least one adenine "A" allele;

(C) a SNP at position 2756 of SEQ ID NO. 2 or position 27 of SEQ ID NO. 9 (identified by rs1805087) comprising at least one guanine "G" allele;
(D) a SNP at position 66 of SEQ ID NO. 3 or position 27 of SEQ ID NO. 10 (identified by rs1801394) comprising at least one guanine "G" allele;
(E) a SNP at position 27 of SEQ ID NO. 11 (identified by rs1006737) comprising at least one adenine "A" allele;
(F) a SNP at position 27 of SEQ ID NO. 12 (identified by rs1883729) comprising at least one adenine "A" allele;
(G) a SNP at position 27 of SEQ ID NO. 13 (identified by rs7163862) comprising at least one thymine "T" allele;
(H) a SNP at position 27 of SEQ ID NO. 14 (identified by rs12659) comprising at least one thymine "T" allele;
(I) a SNP at position 27 of SEQ ID NO. 15 (identified by rs202676) comprising at least one guanine "G" allele;
(J) a SNP at position 27 of SEQ ID NO. 16 (identified by rs2297291) comprising at least one adenine "A" allele;
(K) a SNP at position 27 of SEQ ID NO. 17 (identified by at rs1051266) comprising at least one adenine "A" allele;
(L) a SNP at position 27 of SEQ ID NO. 18 (identified by rs8007267) comprising at least one thymine "T" allele;
(M) a SNP at position 27 of SEQ ID NO. 19 (identified by rs7639752) comprising at least one adenine "A" allele;
(N) a SNP at position 27 of SEQ ID NO. 20 (identified by rs6275) comprising at least one thymine "T" allele;
(O) a SNP at position 27 of SEQ ID NO. 21 (identified by rs1079596) comprising at least one thymine "T" allele;
(P) a SNP at position 27 of SEQ ID NO. 22 (identified by rs11240594) comprising at least one adenine "A" allele;
(Q) a SNP at position 27 of SEQ ID NO. 23 (identified by rs4633) comprising at least one cytosine "C" allele;
(R) a SNP at position 27 of SEQ ID NO. 24 (identified by rs4680) comprising at least one guanine "G" allele;
(S) a SNP at position 27 of SEQ ID NO. 25 (identified by rs250682) comprising at least one cytosine "C" allele;
(T) a SNP at position 27 of SEQ ID NO. 26 (identified by rs2277820) comprising at least one thymine "T" allele;
(U) a SNP at position 1958 of SEQ ID NO. 27 (identified by rs2236225) comprising at least one adenine "A" allele;
(V) an expression level ratio of SAM to SAH smaller than a pre-determined reference ratio;
(W) an expression level of 4-HNE greater than a first pre-determined reference value;
(X) an expression of hsCRP greater than a second pre-determined reference value; and any combinations thereof.

Based on the analysis results from step (b), if at least one of the conditions described above is detected, the assay can further comprise selecting for the human subject and optionally administering to the human subject a treatment regimen comprising an effective amount of a folate-containing compound.

In some embodiments of this aspect and all other aspects described herein, any of the SNPs described herein can comprise one or two folate-responsive alleles. By way of example only, a SNP at position 677 of SEQ ID NO. 1 or position 27 of SEQ ID NO. 7 (identified by rs1801133) can comprise one thymine "T" allele, or two thymine "T" alleles.

Any combinations of at least two biomarkers (i) to (xxiv) described herein can be determined in a test sample for the assays described herein. Exemplary combinations of at least two biomarkers described herein can comprise genotypes of at least two SNP loci; or genotype of at least one SNP loci and expression level of at least one indicated biomarker (e.g., 4-HNE); or expression level of at least two indicated biomarkers (e.g., SAM, SAH). Depending upon selected combinations of at least two biomarkers described herein, the test sample can be subjected to one or more analyses, e.g., including, but not limited to, genotyping assays, expression assays (e.g., protein and/or transcript levels), or any combinations thereof.

Accordingly, in some embodiments, the assay can comprise subjecting a test sample from a human subject, who is diagnosed as having depression or having a risk for depression to at least one genotyping assay adapted to determine genotypes of at least two loci, wherein said at least two loci are: (i) position 677 of SEQ ID NO. 1 or position 27 of SEQ ID NO. 7 (identified by rs1801133) and (ii) position 2756 of SEQ ID NO. 2 or position 27 of SEQ ID NO. 9 (identified by rs1805087). In such embodiment, detection of at least one SNP at either position 677 of SEQ ID NO. 1 (or position 27 of SEQ ID NO. 7) comprising at least one thymine "T" allele or position 2756 of SEQ ID NO. 2 (or position 27 of SEQ ID NO. 9) comprising at least one guanine "G" allele, or detection of both aforementioned SNPs indicates selection and optional administration of a treatment regimen comprising an effective amount of a folate-containing compound to the human subject.

In some embodiments, the genotyping assay can comprise the step of amplifying the test sample with a set of primers flanking any one of the SNPs described herein. In some embodiments, at least two (e.g., at least three, at least four, at least five or more) sets of primers amplifying at least two (e.g., at least three, at least four, at least five or more) of the SNPs can be used in a multiplex amplification assay.

In some embodiments, the test sample can be subjected to determine parameters of at least three, at least four, at least five or more biomarkers (i) to (xxiv) described herein. For example, in some embodiments, the assay can comprise: (a) subjecting a test sample of a subject to one or more than one analyses (e.g., genotyping and/or expression analyses) to determine the presence or absence of at least one of the following conditions:
  i. an expression ratio of s-adenosyl methionine (SAM) to s-adenosyl homocysteine (SAH) smaller than a pre-determined reference ratio;
  ii. expression of 4-hydroxynonenal (4-HNE) greater than a first pre-determined reference value;
  iii. a single nucleotide polymorphism (SNP) at position 677 of SEQ ID NO: 1 comprising at least one thymine "T" allele, wherein the SEQ ID NO: 1 is a portion of a genomic nucleic acid sequence of methylenetetrahydrofolate reductase (MTHFR);
  iv. a SNP at position 2756 of SEQ ID NO: 2 comprising at least one guanine "G" allele, wherein the SEQ ID NO: 2 is a portion of a genomic nucleic acid sequence of methionine synthase (MTR); and
  v. a SNP at position 66 of SEQ ID NO: 3 comprising at least one guanine "G" allele, wherein the SEQ ID NO: 3 is a portion of a genomic nucleic acid sequence of methionine synthase reductase (MTRR); and
if at least one of these conditions is determined to be present, the assay can further comprise selecting for the human subject and optionally administering to the human subject a treatment regimen comprising an effective amount of a folate-containing compound.

In some embodiments of this aspect and all other aspects described herein, when the expression ratio of SAM to SAH is smaller than the pre-determined reference ratio, e.g., smaller than a control ratio of SAM/SAH as measured in a biological sample of normal healthy subjects, the subject can be recommended for and/or optionally administered with a treatment regimen comprising a folate-containing compound. In one embodiment, the control ratio of SAM to SAH as measured in a serum sample of normal healthy subjects can range from about 4 to about 12. In one embodiment, the control ratio of SAM to SAH as measured in a serum sample of normal healthy subjects can be about 7. In one embodiment, the expression ratio of SAM to SAH being smaller than 3.0, or smaller than about 2.8, as measured in a plasma sample, is indicative of a subject recommended for and/or optionally administered with a treatment regimen comprising a folate-containing compound. In one embodiment, the expression ratio of SAM to SAH being smaller than 2.71, as measured in a plasma sample, is indicative of a subject recommended for and/or optionally administered with a treatment regimen comprising a folate-containing compound. In some embodiments, if the expression ratio of SAM to SAH is at least or greater than the pre-determined reference ratio (e.g., at least or greater than 2.71 as measured in a plasma sample), the subject is not recommended for nor administered with a treatment regimen comprising a folate-containing compound. Depending on the test sample source, e.g., a blood sample vs. a cerebrospinal fluid sample, the pre-determined reference ratio for a blood plasma sample can be different from that for, e.g., a cerebrospinal fluid sample.

In some embodiments of this aspect and all other aspects described herein, when the expression of 4-HNE in the subject is greater than the first pre-determined reference value, e.g., greater than a control value of 4-HNE as measured in a biological sample of normal healthy subjects, the subject can be recommended for and/or optionally administered with a treatment regimen comprising a folate-containing compound. In one embodiment, the control value of 4-HNE as measured in a serum sample of the normal healthy subjects can be about 0.24 µmol per liter of serum, or about 0.04 mg per liter of serum. In some embodiments, when the expression of 4-HNE in the subject is greater than about 3 mg per liter, or greater than about 3.2 mg per liter of plasma or higher as measured in a plasma sample, the subject can be recommended for and/or optionally administered with a treatment regimen comprising a folate-containing compound. In one embodiment, if the expression of 4-HNE is at least 3.28 mg per liter of plasma as measured in a plasma sample or higher, a subject can be recommended for and/or optionally administered with a treatment regimen comprising a folate-containing compound. In some embodiments, if the expression of 4-HNE is less than the first pre-determined reference value (e.g., less than 3.28 mg per liter of plasma as measured in a plasma sample or lower), the subject is not recommended for nor administered with a treatment regimen comprising a folate-containing compound. Depending on the test sample source, e.g., a blood sample vs. a cerebrospinal fluid sample, the pre-determined reference value for a plasma sample can be different from that for, e.g., a cerebrospinal fluid sample.

In some embodiments of this aspect and all other aspects described herein, the assay can further comprise determining if the human subject is obese or not. If the human subject is determined to be obese, then selecting for the human subject and optionally administering to the human subject a treatment regimen comprising an effective amount of a folate-containing compound. Methods of determining obesity in a human subject are known in the art and can include, but are not limited to, body mass index (BMI) measurement, measurement of abdominal fat (e.g., by waist circumference or waist-hip ratio), measurement of body fat, skinfold thickness, underwater weighing (densitometry), air-displacement plethysmography, computerized tomography (CT) and magnetic resonance imaging (MRI), and dual energy X-ray absorptiometry (DEXA), and any combinations thereof. For example, in one embodiment, the assay can further comprise measuring body mass index (BMI) of the human subject to determine if the human subject is obese or not, and if the BMI value of at least 30 kg/m$^2$ or greater is measured in the subject, then selecting for the human subject and optionally administering to the human subject a treatment regimen comprising an effective amount of a folate-containing compound. In some embodiments, if the human subject has a BMI value of less than 30 kg/m$^2$, it may not be desirable to recommend or administer to the human subject a treatment regimen comprising a folate-containing compound.

In some embodiments, the assay can further comprise determining the presence or absence of a SNP at position 1298 of the SEQ ID NO. 1 comprising at least one cytosine "C" allele, wherein the presence of the SNP at position 1298 of the SEQ ID NO: 1 comprising at least one cytosine "C" is indicative of the subject recommended for and optionally administered with a treatment regimen comprising a folate-containing compound.

In some embodiments, the assay can further comprise determining expression of high-sensitivity c-reactive protein (hsCRP), wherein the hsCRP expression greater than a second pre-determined reference value, e.g., greater than a control value of hsCRP as measured in a biological sample of normal healthy subjects, is indicative of the subject recommended for and optionally administered with a treatment regimen comprising a folate-containing compound. In one embodiment, the control value of hsCRP as measured in a serum sample of normal healthy subjects can range from about 0.5 mg per liter of serum to about 4.5 mg per liter of serum. In some embodiments, if the expression of hsCRP is greater than about 2.3 mg per liter of plasma, as measured in a plasma sample, the subject is recommended for and optionally administered with a treatment regimen comprising a folate-containing compound. In some embodiments, if the expression of hsCRP is lower than the second pre-determined reference value (e.g., lower than 2.3 mg per liter of plasma, as measured in a plasma sample), then the subject is not recommended for nor administered with a treatment regimen comprising a folate-containing compound. Depending on the test sample source, e.g., a blood sample vs. a cerebrospinal fluid sample, the hsCRP expression a plasma sample can be different from that in, e.g., a cerebrospinal fluid sample.

While detection of the presence of at least one condition (A)-(X) described herein in a test sample of a human subject with depression is generally sufficient to indicate the human subject be amenable to a treatment regimen comprising an effective amount of a folate-containing compound, in some embodiments, it can be desirable to detect the presence of at least two conditions, three conditions, four conditions or more corresponding to the selected biomarkers in order to select for or administer to the human subject a treatment regimen comprising an effective amount of a folate-containing compound. In some embodiments, if none of these conditions (A)-(X) described herein occurs in the human subject, the subject is not recommended for a treatment regimen comprising a folate-containing compound.

Accordingly, in some embodiments of this aspect and all other aspects described herein, the test sample can be analyzed to determine at least one or at least two, at least three, at least four, at least five or six of the conditions (A)-(X) provided herein. For example, in some embodiments, the test sample can be analyzed to determine if the subject has at least the SNPs located at the positions 677 and 2756 of the MTHFR and MTR loci, respectively. In some embodiments, the test sample can be analyzed to determine if the subject is obese (e.g., whether the subject has at least the BMI value of at least 30 kg/m$^2$), and at least one or both of the SNPs located at the positions 2756 and 66 of the MTR and MTRR loci, respectively. In some embodiments, the test sample can be analyzed to determine if the subject is obese (e.g., whether the subject has at least the BMI value of at least 30 kg/m$^2$), and at least one or both of the SNPs located at the positions 677 and 2756 of the MTHFR and MTR loci, respectively. In other embodiments, the test sample can be analyzed to determine if the subject has at least the BMI value of at least 30 kg/m$^2$ and the SNP located at the position 2756 of the MTR locus. In some embodiments, the test sample can be analyzed to determine if the subject has at least the SAM/SAH ratio smaller than the pre-determined reference ratio and the SNP located at the position 2756 of the MTR locus. In some embodiments, the test sample can be analyzed to determine if the subject has at least the 4-HNE expression greater than the first pre-determined reference value and the SNPs located at the positions 2756 and 66 of the MTR and MTRR loci, respectively. It is envisioned that any combinations of all the conditions (A)-(X) can be analyzed in the assay as described herein.

In some embodiments, if at least one or at least two, including at least three or more, of the conditions (A)-(X) provided herein are determined to be present in the test sample, a treatment regimen comprising a folate-containing compound is recommended or selected and optionally administered to the human subject.

In some embodiments, if the human subject satisfies at least one, including at least two, at least three or more, of the conditions (A)-(X) described herein (and an indicator of a human subject being obese, e.g., a BMI value of at least 30 kg/m$^2$ or greater), the subject can be administered or prescribed with a folate-containing compound.

Some embodiments of the assays described herein can be included as part of a treatment strategy, e.g., to select an appropriate treatment regimen for a human subject diagnosed as having or having a risk for depression. Accordingly, another aspect provided herein relates to methods of treating a human subject diagnosed as having, or having a risk, for depression. In some embodiments, a method for treating a human subject with depression can comprise performing one or more embodiments of the assay provided herein. In some embodiments, if the subject satisfies at least one of the conditions described in the assay provided herein, the treatment method can further comprise administering or prescribing the subject with a treatment regimen comprising an effective amount of a folate-containing compound.

Accordingly, in one embodiment, the method can comprise determining in a test sample of a human subject parameters of at least two or more (including at least three, at least four, at least five or more) biomarkers (i) to (xxiv) described herein; and administering to the human subject a treatment regimen comprising an effective amount of a folate-containing compound, if the presence of at least one or more (including at least two, at least three, at least four, at least five or more), or any combinations of the conditions (A)-(X) described herein is detected in the test sample.

In particular embodiments, the method can comprise determining in a test sample of human subject genotypes of at least two loci at position 677 of SEQ ID NO. 1 (or position 27 of SEQ ID NO. 7) and at position 2756 of SEQ ID NO. 2 (or position 27 of SEQ ID NO. 9); and administering to the human subject a treatment regimen comprising an effective amount of a folate-containing compound if either at least one or both of the following conditions is/are detected: (i) at least one thymine "T" allele present at position 677 of SEQ ID NO. 1 (or position 27 of SEQ ID NO. 7); and (ii) at least one guanine "G" allele present at position 2756 of SEQ ID NO. 2 (or position 27 of SEQ ID NO. 9). In these embodiments, the method can further comprise determining the presence or absence of any of the conditions (A)-(X) described herein.

In some embodiments, a method for treating a human subject with depression (e.g., treating at least one symptom of depression in a human subject) can comprise administering a composition comprising an effective amount of a folate-containing compound to the human subject, who is diagnosed as having, or having a risk for, depression, and is further determined to carry at least one or more (including at least two, at least three, at least four or more), or any combinations of the conditions (A)-(X) described herein. In some embodiments, the method for treating a human subject with depression (e.g., treating at least one symptom of depression in a human subject) can comprise administering a composition comprising an effective amount of a folate-containing compound to the human subject, who is diagnosed as having, or having a risk for, depression, and is further determined to be obese and carry at least one or more (including at least two, at least three, at least four or more), or any combinations of the conditions (A)-(X) described herein. In some embodiments, the method can further comprise selecting for the human subject a treatment comprising the folate-comprising compound, optionally administered in combination with an anti-depressant drug, based on the recognition that the presence of at least one or any combinations of the folate-responsive conditions described herein is associated with positive-symptom-reducing response to the folate-containing compound. In some embodiments, the method can further comprise administering to the human subject an anti-depressant drug.

In certain embodiments, the method for treating a human subject with depression (e.g., treating at least one symptom of depression in a human subject) can comprise administering a composition comprising an effective amount of a folate-containing compound to the human subject, who is diagnosed as having, or having a risk for, depression, and is further determined to carry at least one or a combination of the SNP biomarkers as follows: (i) a SNP at position 677 of SEQ ID NO. 1 or position 27 of SEQ ID NO. 7 (identified by rs1801133) comprising at least one thymine "T" allele, and (ii) a SNP at position 2756 of SEQ ID NO. 2 or position 27 of SEQ ID NO. 9 comprising at least one guanine "G" allele. In one embodiment, the subject can be determined to carry at least a combination of both SNP biomarkers as follows: (i) a SNP at position 677 of SEQ ID NO. 1 or position 27 of SEQ ID NO. 7 (identified by rs1801133) comprising at least one thymine "T" allele, and (ii) a SNP at position 2756 of SEQ ID NO. 2 or position 27 of SEQ ID NO. 9 (identified by rs1805087) comprising at least one guanine "G" allele. In these embodiments, the method can further comprise determining the presence or absence of any of the conditions (A)-(X) described herein.

In some embodiments, the subject administered with a treatment regimen comprising a folate-containing compound can be further determined to be obese (e.g., with a BMI value of at least about 30 kg/m$^2$ or higher).

In some embodiments of this aspect and all other aspects described herein, a folate-containing compound can be administered in an amount effective to reduce at least one symptom (e.g., but not limited to, low mood, insomnia, agitation, anxiety and/or weight loss) associated with depression, e.g., major depressive disorders. In some embodiments, the effective amount of a folate-containing compound can provide at least about 0.1 to about 1 mg/kg body weight per day administration to the human subject. In some embodiments, the effective amount of a folate-containing compound can provide at least about 7.5 mg/day to about 50 mg/day administration to the human subject. In one embodiment, the effective amount of a folate-containing compound can provide at least about 15 mg/day of folate administration to the human subject.

The effective amount of the folate-containing compound can be administered to a selected human subject as a single daily dose, or alternatively, in more than one divided doses per day via any suitable administration route, e.g., oral administration.

The effective amount of folate administered to a selected human subject for treatment of depression as described herein is significantly higher than the typical amount taken as a dietary supplement (between 50-600 μg/day). In some embodiments, the effective amount of folate administered to a selected human subject is at least about 2-fold, at least about 5-fold, at least about 10-fold, at least about 25-fold, at least about 50-fold, at least about 100-fold, at least about 250-fold, at least about 500-fold, at least about 1000-fold or more than the typical amount taken as a dietary supplement. Accordingly, in some embodiments, the folate-containing compound is desirable to be formulated in slow-release or sustained release composition. For example, in one embodiment, the composition comprising a folate-containing compound can be formulated to release the effective amount of the folate-containing compound over a period between 3-6 hours or 4-5 hours post-administration.

Any art-recognized folate-containing compound can be selected and/or optionally administered to a human subject selected to carry at least one or more conditions (A)-(X) described herein. In some embodiments, the folate-containing compound can comprise a L-methylfolate compound. In one embodiment, the folate-containing compound can comprise 6(S)-5-methyltetrahydrofolate or a derivative thereof.

In some embodiments of this aspect and all other aspects described herein, the treatment regimen can further comprise selecting and optionally administering an antidepressant drug. In some embodiments, the anti-depressant drug can include a selective serotonin reuptake inhibitor, including, but not limited to, fluoxetine, citalopram, paroxetine, escitalopram, sertraline, and any combinations thereof.

In these embodiments, an antidepressant drug can be administered in the same composition as the folate-containing compound. In alternative embodiments, the antidepressant drug and the folate-containing compound can be administered in separate compositions at the same time (e.g., concurrently) or sequentially (e.g., one after the other), or in any temporal administration regimen, where the adjuvant effect of the folate-containing compound increases the efficacy of the antidepressant drug as compared to the efficacy without the folate-containing compound. In some embodiments, the anti-depressant drug and/or the folate-containing compound can be administered in a single dose or in divided doses. The number of dosages administered over a period of time (e.g., per day) for the antidepressant drug and the folate-containing compound can be the same or different. The antidepressant drug and the folate-containing compound can be administered via the same or different routes.

In some embodiments of this aspect and all other aspects described herein, the adjuvant effect of the folate-containing compound administered in combination with an antidepressant drug can be additive.

In some embodiments of this aspect and all other aspects described herein, the adjuvant effect of the folate-containing compound administered in combination with an antidepressant drug can be synergistic.

A further aspect provided herein is a method of determining and/or improving the effectiveness of an anti-depressant drug administered to a human subject, e.g., by determining if the human subject is amenable to folate or a derivative thereof as an adjuvant, e.g., using the assay described herein. In some embodiments of this aspect, the method can further comprise administering or prescribing the subject with a compound containing an effective amount of folate as an adjuvant to the anti-depressant drug, if the subject satisfies at least one of the conditions (A)-(X) provided herein.

In some embodiments, a method of improving the effectiveness of an anti-depressant drug administered to a human subject can comprise administering a composition comprising an effective amount of a folate-containing compound, in combination with an anti-depressant drug, to the human subject, who is diagnosed to have depression, and is further determined to carry at least one or more (including at least two, at least three, at least four or more), or any combinations of the conditions (A)-(X) described herein. In some embodiments, the method of improving the effectiveness of an anti-depressant drug administered to a human subject can comprise administering a composition comprising an effective amount of a folate-containing compound to the human subject, who is diagnosed to have depression, and is further determined to be obese and carry at least one or more (including at least two, at least three, at least four or more), or any combinations of the conditions (A)-(X) described herein. In some embodiments, the method can further comprise selecting for the human subject a treatment comprising the folate-comprising compound, administered in combination with an anti-depressant drug, based on the recognition that the presence of at least one or any combinations of the folate-responsive conditions described herein is associated with increasing the effectiveness of the anti-depressant drug when administered in combination with the folate-containing compound.

In certain embodiments, the method of improving the effectiveness of an anti-depressant drug administered to a human subject can comprise administering a composition comprising an effective amount of a folate-containing compound, in combination with an anti-depressant drug to the human subject, who is diagnosed to have depression, and is further determined to carry at least one or a combination of the SNP biomarkers as follows: (i) a SNP at position 677 of SEQ ID NO. 1 or position 27 of SEQ ID NO. 7 (identified by rs1801133) comprising at least one thymine "T" allele, and (ii) a SNP at position 2756 of SEQ ID NO. 2 or position 27 of SEQ ID NO. 9 (identified by rs1805087) comprising at least one guanine "G" allele. In one embodiment, the subject can be determined to carry at least a combination of both SNP biomarkers as follows: (i) a SNP at position 677 of SEQ ID NO. 1 or position 27 of SEQ ID NO. 7 (identified by rs1801133) comprising at least one thymine "T" allele, and (ii) a SNP at position 2756 of SEQ ID NO. 2 or position 27 of SEQ ID NO. 9 (identified by rs1805087) comprising at least one guanine "G" allele. In these embodiments, the method can further comprise determining the presence or absence of any of the conditions (A)-(X) described herein.

An exemplary effective amount of folate is about 7.5 mg/day to about 50 my day, or in one embodiment, the effective amount is at least about 15 mg/day. In one embodiment, the anti-depressant drug is a selective serotonin reuptake inhibitor, for example, without limitations, fluoxetine, citalopram, paroxetine, escitalopram, sertraline, and any combinations thereof.

Yet another aspect provided herein is a method of improving the effectiveness or efficacy of an anti-depressant drug taken by a subject, e.g., by identifying the subject with at least one of the conditions as determined in the assay described herein. Accordingly, in some embodiments of this aspect, the method can further comprise administering or prescribing the subject with a compound containing an effective amount of folate as an adjuvant to the anti-depressant drug, if the subject satisfies at least one of the conditions determined in the assay provided herein. An exemplary effective amount of folate is at least about 15 mg/day. In one embodiment, the anti-depressant drug is a selective serotonin reuptake inhibitor, for example, without limitations, fluoxetine, citalopram, paroxetine, escitalopram, sertraline, and any combinations thereof.

In some embodiments of various aspects described herein, the therapeutic effect (e.g., reducing at least one of core symptoms associated with depression) can be synergistic when a human subject, who is determined to carry at least two of the folate-responsive biomarkers (i)-(xxv), is administered with a folate-comprising compound.

Computer systems for use in any aspects of the assays and/or methods described herein are also provided. For example, one embodiment provided herein is a computer system for obtaining data from at least one test sample obtained from at least one subject. The system comprises: (a) a determination module configured to receive at least one test sample and perform at least one analysis on at least one test sample to determine parameters of at least two biomarkers (i) to (xxiv) described herein; (b) a storage device configured to store output data from the determination module; (c) a computing module, e.g., a non-human machine, comprising specifically-programmed instructions to determine from the output data the presence of at least one condition (A) to (X) described herein; and (d) a display module for displaying a content based in part on the data output from the computing module, wherein the content comprises a signal indicative of the presence of at least one condition (A) to (X) described herein, and optionally the absence of any one of the conditions (A) to (X) described herein, or a signal indicative of the absence of all of the conditions (A) to (X) described herein.

In some embodiments, the determination module can be configured to perform at least one genotyping analysis on at least one test sample to determine the genotypes of at least two loci comprising position 677 of SEQ ID NO. 1 (or position 27 of SEQ ID NO. 7) and position 2756 of SEQ ID NO. 2 (or position 27 of SEQ ID NO. 9). In these embodiments, the computing module can be configured to determine the presence of at least one SNP located at position 677 of SEQ ID NO. 1 (or position 27 of SEQ ID NO. 7) comprising at least one thymine "T" allele, and/or at position 2756 of SEQ ID NO. 2 (or position 27 of SEQ ID NO. 9) comprising at least one guanine "G" allele.

In another embodiment, the determination module can be configured to perform at least one analysis on at least one test sample to determine the presence or absence of at least one of the following conditions:

i. an expression ratio of s-adenosyl methionine (SAM) to s-adenosyl homocysteine (SAH) smaller than a pre-determined reference ratio;
ii. expression of 4-hydroxynonenal (4-HNE) greater than a first pre-determined reference value;
iii. a single nucleotide polymorphism (SNP) at position 677 of SEQ ID NO. 1 (or at position 27 of SEQ ID NO. 7) comprising at least one thymine "T" allele, wherein the SEQ ID NO. 1 and SEQ ID NO. 7 are each independently a portion of a genomic nucleic acid sequence of methylenetetrahydrofolate reductase (MTHFR);
iv. a SNP at position 2756 of SEQ ID NO. 2 (or at position 27 of SEQ ID NO. 9) comprising at least one guanine "G" allele, wherein the SEQ ID NO. 2 and SEQ ID NO. 9 are each independently a portion of a genomic nucleic acid sequence of methionine synthase (MTR); and
v. a SNP at position 66 of SEQ ID NO. 3 (or at position 27 of SEQ ID NO. 10) comprising at least one guanine "G" allele, wherein the SEQ ID NO. 3 and SEQ ID NO. 10 are each independently a portion of a genomic nucleic acid sequence of methionine synthase reductase (MTRR).

In these embodiments, the determination module can be further configured to determine the presence or absence of at least one other condition (A)-(X) described herein. For example, in some embodiments, the determination module can be further configured to determine expression of high-sensitivity c-reactive protein (hsCRP). In some embodiments, the determination module can be further configured to determine the presence or absence of a SNP at position 1298 of the SEQ ID NO. 1 comprising at least one cytosine "C" allele.

In some embodiments, the determination module can be configured to analyze at least one test sample to determine the presence or absence of at least two of the conditions provided above.

In some embodiments, the determination module can further comprise a comparison module adapted to compare the data output from the determination module with reference data stored on the storage device.

In some embodiments, the storage device can be further configured to store physical information of at least one subject, for example, comprising indicators of whether a test subject is obese, e.g., BMI of at least one subject).

In some embodiments, the content displayed on the display module can further comprises the BMI value or a signal indicative of whether the BMI value is at least 30 kg/m$^2$ or not. In some embodiments, the content displayed on the display module can further comprise a signal indicative of the subject recommended to receive a treatment regimen comprising a folate-containing compound, or a signal indicative of the subject recommended to receive an alternative treatment regimen without a folate-containing compound.

A tangible and non-transitory (e.g., not transitory forms of signal transmission) computer readable medium having computer readable instructions recorded thereon to define software modules for implementing a method on a computer is also provided herein. In one embodiment, the computer readable storage medium comprises: (a) instructions for comparing the data stored on a storage device with reference data to provide a comparison result, wherein the comparison identifies the presence or absence of at least one condition (A)-(X) described herein; and (b) instructions for displaying a content based in part on the data output from the determination module, wherein the content comprises a signal indicative of the presence of at least one of the conditions (A)-(X) described herein, and optionally the absence of any one of these conditions (A)-(X) described herein. In other embodiments, the content can comprise a signal indicative of the absence of all of the conditions (A)-(X) described herein.

In some embodiments, the instructions can be specifically programmed to perform a comparison to identify the presence of at least one SNP located at position 677 of SEQ ID NO. 1 (or position 27 of SEQ ID NO. 7) comprising at least one thymine "T" allele, and/or at position 2756 of SEQ ID NO. 2 (or position 27 of SEQ ID NO. 9) comprising at least one guanine "G" allele.

In other embodiments, the instructions can be specifically programmed to perform a comparison to identify one of the following conditions:

i. an expression ratio of s-adenosyl methionine (SAM) to s-adenosyl homocysteine (SAH) smaller than a pre-determined reference ratio;

ii. expression of 4-hydroxynonenal (4-HNE) greater than a first pre-determined reference value;

iii. a single nucleotide polymorphism (SNP) at position 677 of SEQ ID NO: 1 comprising at least one thymine "T" allele, wherein the SEQ ID NO: 1 is a portion of a genomic nucleic acid sequence of methylenetetrahydrofolate reductase (MTHFR);

iv. a SNP at position 2756 of SEQ ID NO: 2 comprising at least one guanine "G" allele, wherein the SEQ ID NO: 2 is a portion of a genomic nucleic acid sequence of methionine synthase (MTR); and v. a SNP at position 66 of SEQ ID NO: 3 comprising at least one guanine "G" allele, wherein the SEQ ID NO: 3 is a portion of a genomic nucleic acid sequence of methionine synthase reductase (MTRR);

In these embodiments, the computer readable medium can further comprise instructions to identify the presence or absence of at least one other condition (A)-(X) described herein. For example, in one embodiment, the computer readable medium can further comprise instructions to identify the presence or absence of a SNP at position 1298 of the SEQ ID NO: 1 comprising at least one cytosine "C" allele. In some embodiments, the computer readable medium can further comprise instructions to compare expression of high-sensitivity c-reactive protein (hsCRP) with the reference data.

In some embodiments, the computer readable medium can further comprise instructions to determine or calculate if the subject is obese (e.g., whether the subject has BMI of at least 30 kg/m$^2$ or not), based on input data of the subject's physical features (e.g., weight and height).

In some embodiments, the computer readable medium can further comprise instructions to display a measurement to determine whether a subject is obese (e.g., a BMI value) or a signal indicative of whether the subject is obese (e.g., whether the BMI value is at least 30 kg/m$^2$ or not).

In some embodiments, the computer readable medium can further comprise instructions to display a signal indicative of the subject recommended to receive a treatment regimen comprising a folate-containing compound, or a signal indicative of the subject recommended to receive an alternative treatment regimen without a folate-containing compound.

Based on the identification of SNPs and/or peripheral markers associated with a response to the use of a folate-containing compound, one aspect described herein also provides for the design and preparation of detection reagents needed to identify the SNPs and/or peripheral markers disclosed herein in a test sample of a subject. For example, the detection reagents can be designed and prepared to identify SNPs in MTHFR locus and MTR locus and optionally MTRR locus involved in assays and methods described herein, and/or measure expression levels of SAM, SAH and 4-HNE in a test sample. Examples of detection reagents that can be used to identify the disclosed SNPs in a test sample can include a primer and a probe, wherein the probe can selectively hybridize the SNP-containing nucleic acid molecules, as compared to a nucleic acid molecule which does not contain the SNP at the same nucleotide position. Examples of detection regents that can be used to measure expression levels of serum or plasma proteins (e.g., SAM, SAH and/or 4-HNE) in a test sample can include antibodies against such proteins, or a primer and a probe, wherein the probe specifically hybridizes to a nucleic acid molecule corresponding to such proteins.

In one embodiment, a kit can comprise an oligonucleotide array affixed with a plurality of oligonucleotide probes that interrogate, e.g., no more than 30 SNPs, wherein the SNPs comprise at least two or any combinations of the conditions (A)-(U) described herein (e.g., but not limited to, a combination of conditions (A) and (C)); and an optional container containing a detectable label (e.g., comprising a fluorescent molecule) to be conjugated to a nucleotide molecule derived from a test sample of a human subject; and at least one reagent. Examples of a reagent that can be included in the kit can include, without limitations, a restriction enzyme, a universal adaptor to be conjugated to a nucleotide molecule, a primer complementary to the universal adaptor, a wash agent, and any combinations thereof.

In an alternative embodiment, a kit can comprise a plurality of oligonucleotide primers that bind to at least one allele of no more than 30 SNPs, wherein each subset of oligonucleotide primers that bind to a specific allele of a SNP is labeled with a distinct reporter, and wherein said SNPs comprise at least two or any combinations of the SNP conditions (A)-(U) described herein (e.g., but not limited to a combination of conditions (A) and (C)); and at least one reagent, e.g., but not limited to, free nucleotide bases, a polymerase, or both.

In some embodiments, the kit can further comprise at least one reagent to determine expression of at least one biomarker described herein (e.g., SAM, SAH, 4-HNE and hsCRP). For example, in one embodiment, the kit can further comprise a solid substrate support affixed with at least one protein-based binding moiety (e.g., an antibody) that specifically binds to one or more of the biomarkers described herein. Exemplary solid substrate support can include, but not limited to, a microtiter plate for ELISA, a dipstick, a magnetic bead, or any combinations thereof. In another embodiment, the kit can further comprise at least one primer designed to probe one or more biomarkers described herein.

The assays, methods, systems and/or kits described herein can be performed and/or used by a third-party service provider. For example, a third-party service provider can provide and charge for a service offered to determine the presence or absence of at least one condition (A)-(X) in a test sample of a human subject, e.g., to facilitate selection of a treatment regimen for a human subject with depression. Accordingly, methods for selecting a treatment regimen for a human subject are also provided herein. For example, the method comprises (a) obtaining a test sample from a human subject diagnosed as having, or having a risk, for depression; (b) subjecting the test sample to at least one analysis to determine parameters of at least two biomarkers (i)-(xxiv)

described herein (e.g., but not limited to, a combination of biomarkers (i) and (iii)); (c) determining, from the parameters of the selected biomarkers, the presence of at least one condition (A)-(X) (e.g., but not limited to, either one or both of conditions (A) and (C)); and (d) providing a result output setting forth whether at least one of the conditions (A)-(X) is detected in the test sample. If at least one condition is present, the method can further comprise selecting and optionally administering a treatment regimen comprising an effective amount of a folate-containing compound to the human subject.

In some embodiments, the step (b) of the method can further comprise optionally packing and shipping the test sample to a test facility, e.g., a third-party CLIA-certified service provider.

In some embodiments, the step (d) of the method is performed by a non-human machine.

The test sample for use in the assays, methods, systems or kits described herein can be derived from a biological sample of the subject, e.g., a blood sample or plasma or serum sample from the subject. In some embodiments, the test sample can comprise a urine sample. In some embodiments, the test sample can comprise a buccal sample. In some embodiments, the test sample can comprise a saliva sample. In some embodiments, the test sample can comprise a cerebrospinal fluid (CSF) sample.

If the test sample is a nucleic acid sample, the test sample can be subjected to at least one analysis selected from the group consisting of allele-specific probe hybridization, allele-specific primer extension, allele-specific amplification, sequencing, 5' nuclease digestion, molecular beacon assay, DNA chip analysis, oligonucleotide ligation assay, size analysis, single-stranded conformation polymorphism, polymerase chain reaction (PCR), real-time quantitative PCR, and any combinations thereof.

If the test sample is a protein sample, the test sample can be subjected to at least one analysis selected from the group consisting of western blot, enzyme linked absorbance assay, mass spectrometry, immunoassay, flow cytometry, immunohistochemical analysis, and any combinations thereof.

A still further aspect provided herein relates to uses of a folate-comprising composition in the treatment of depression in a human subject who carries at least one of the conditions (A)-(X) described herein (e.g., but not limited to, either one or both conditions (A) and (C)). Another aspect provided herein relates to a folate-comprising composition in combination with an anti-depressant for use in the treatment of depression in a human subject who carries at least one of the conditions (A)-(X) described herein (e.g., but not limited to, either one or both conditions (A) and (C)). In some embodiments of these aspects described herein, the folate-comprising composition can comprise at least about 5 mg of folate (e.g., about 7.5 mg to about 50 mg of folate). In some embodiments, the folate-comprising composition can be formulated for a pre-determined release profile (e.g., a sustained release). In some embodiments, the human subject is an adult.

Embodiments of various aspects described herein can be employed for use in a human subject diagnosed as having, or having a risk for, any form of depression. In one embodiment, various aspects described herein can be employed for use in a human subject diagnosed as having, or having a risk for, a major depressive disorder. In some embodiments, the human subject can be further determined to be resistant to at least one anti-depressant monotherapy. In some embodiments, the human subject is an adult.

In some embodiments, various aspects described herein can be employed for use in a human subject who is currently taking an antidepressant. In these embodiments, the human subject who is determined to satisfy at least one (including, e.g., at least two, at least three or more) of the conditions (A)-(X) can be selected and/or administered with a treatment regimen comprising a folate-containing compound. In some embodiments, the treatment regimen does not include an antidepressant. In some embodiments, the treatment regimen can include the same antidepressant that the human subject is currently taking or a different antidepressant.

BRIEF DESCRIPTION OF THE DRAWINGS

FIG. 1A shows an exemplary study design, in which 7.5 mg/day L-methylfolate (e.g., 6(S)-5-methyltetrahydrofolate, abbreviated as 6(S)-5-MTHF as described herein) is administered as an adjunct to an SSRI. FIG. 1B shows an exemplary study design, in which 15 mg/day L-methylfolate (e.g., 6(S)-5-MTHF) is administered as an adjunct to an SSRI.

FIG. 3A shows the response rates of MDD patients treated with either a folate-containing compound or a placebo, in conjunction with an SSRI, after 30-day treatment. A responder is a MDD patient with at least 50% reduction in HDAM-17 after treatment. FIG. 3B shows the mean change in scores of various neuropsychological tests (e.g., HDAM-17, QIDS-SR, and CGI-S) for MDD patients treated with either a folate-containing compound or a placebo, in conjunction with an SSRI, after 30-day treatment. FIG. 3C shows percents of MDD patients in remission, as measured by HDAM-17, after treated with either a folate-containing compound or a placebo, in conjunction with an SSRI, after 30-day treatment. FIG. 3D shows percents of MDD patients in remission, as measured by QIDS-SR, after treated with either a folate-containing compound or a placebo, in conjunction with an SSRI, after 30-day treatment. FIGS. 3C-3D show that remission rates after 30 days of adjuvant 15 mg/day L-methylfolate and an SSRI, compared to placebo and the SSRI, was not significant in depressed patients who inadequately respond to SSRI monotherapy. FIG. 3E shows percent of MDD patients discontinued from Trial 2, indicating no significant difference in discontinuation rates due to overall adverse events.

FIG. 4A shows efficacy results as measured by HDAM-28 (28-item Hamilton Depression Rating Scale). FIG. 4B shows efficacy results as measured by CGI-S (Clinical Global Impression-Severity).

FIG. 5A shows efficacy results as measured by HAMD-28 (28-item Hamilton Depression Rating Scale) with a chi-square of 3.94 for the treatment effect. FIG. 4B shows efficacy results as measured by CGI-S (Clinical Global Impression-Severity) with a chi-square of 10.03 for the treatment effect.

FIGS. 8A-8B show mean changes in HAMD-28 in MDD patients carrying at least one rare variant on the indicated gene, as opposed to fully normal on the respective gene, when they were treated with a folate-containing compound, e.g., as an adjunct to an SSRI. FIG. 8A is a bar graph showing the mean change in HAMD-28 with respect to various SNP biomarkers as indicated. FIG. 8B is a table showing the results as shown in FIG. 8A and the corresponding loci in chromosomes. The term "prevalence" as used in FIG. 8B refers to the total percentage of MDD patients who carry the SNP as indicated in this particular study.

FIGS. 9A-9C are result tables showing effects of the presence or absence of an indicated condition, in MDD patients on the degree of depression, when the patients were treated with a treatment regimen comprising a folate-containing compound. The degree of depression was measured by Social Functioning Questionnaire (SFQ), Visual Analogue Scale (VAS), and Cognitive and Physical Function Questionnaire (CPFQ). FIG. 9A shows analyses on all samples. FIG. 9B shows analyses in biomarker subgroups. FIG. 9C shows analyses in genetic subgroups.

FIGS. 10A-10E are result tables showing effects of the presence or absence of an indicated condition, in MDD patients on the degree of depression, when the patients were treated with a folate-containing compound (treatment group) or without a folate-containing compound (placebo group). The degree of depression was measured by Maier or HAMD-7 subscale of HAMD. FIG. 10A shows results of Maier SPCD. FIG. 10B shows Maier means. FIG. 10C shows HAMD-7 SPCD. FIG. 10D shows HAMD-7 means. FIG. 10E shows a summary of the biomarker and genetic analyses on Maier scale.

FIGS. 12A-12B is a set of result tables showing the statistical analysis on the effects of genetic moderators (e.g., race, age, sex, and BMI) comparing biomarker positive versus biomarker negative subjects within the placebo (an antidepressant administered without a folate-comprising compound) or folate-comprising treatment (a folate-comprising compound administered as an adjuvant to the antidepressant) arms of clinical studies. Results show statistically significant treatment effect within all of the indicated genetic modifiers (e.g., race, age, sex, and BMI) for subjects positive for the MTR 2756 AG or GG genotype [associated single-nucleotide polymorphism (SNP) rs1805087] compared to subjects negative for this SNP. Subjects positive for the COMT CC (rs4633) or GG (rs4680) SNP also show statistically significant treatment effect in at least one genetic moderator category.

FIGS. 13A-13B is a set of result tables showing the response rates of biomarker positive subjects within the placebo and folate-comprising treatment arms of clinical studies. A responder is indicated by a reduction of at least about 50% in HAMD-28 over the evaluation period.

DETAILED DESCRIPTION OF THE INVENTION

Figure 1A:
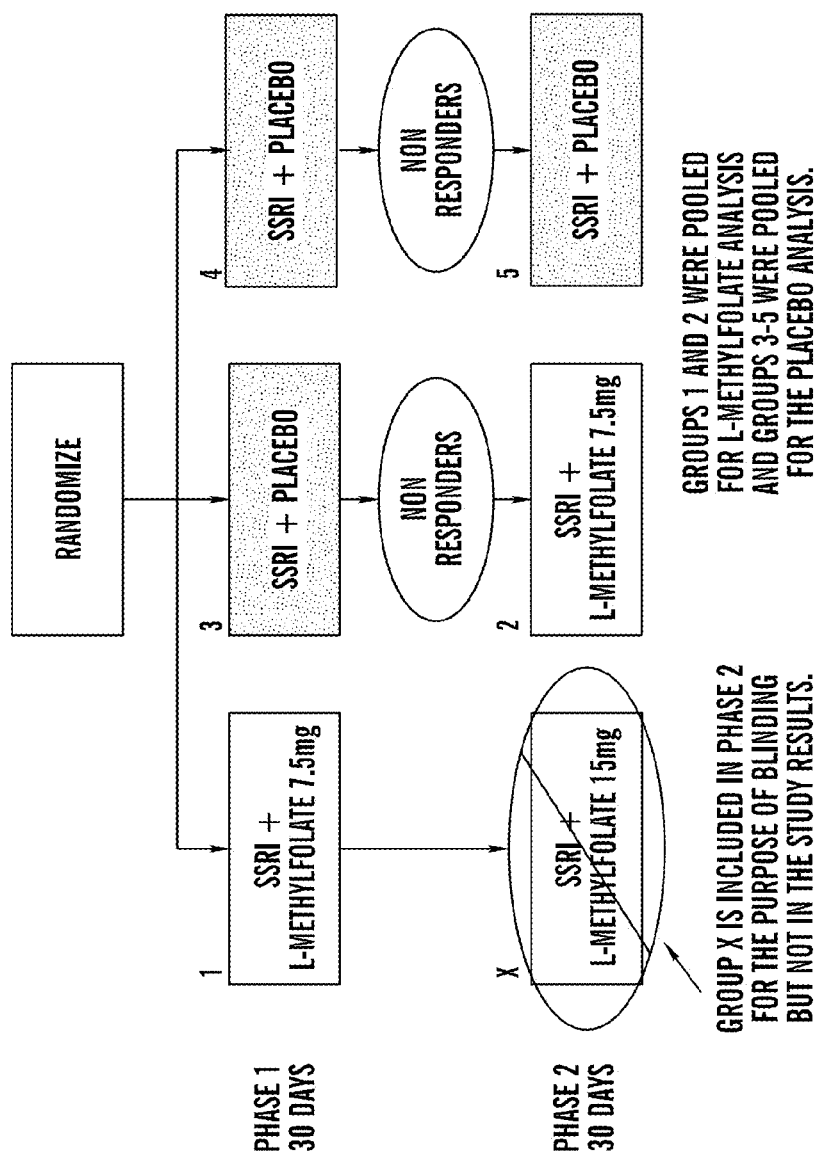
FIGS. 1A-1B show schematic diagrams of exemplary study designs of analyzing the efficacy of a folate-containing compound, e.g., as an adjunct to a selective serotonin reuptake inhibitor (SSRI) for treating a subject with depression or identifying biomarkers or conditions indicative of a subject with depression recommended for a treatment regimen comprising a folate-containing compound and an SSRI.

Recent estimates indicate that more than 19 million Americans over the age of 18 years experience a depressive illness each year. While significant advances in the treatment of depression have been made in the past decade, as many as 29% to 46% of patients with depression taking an anti-depressant are still partially or totally resistant to the treatment. Those who suffer from treatment-resistant depression have almost no alternatives. As not every treatment regimen is effective for each individual, there is a strong need to identify markers that can facilitate selection of an appropriate treatment regimen for a human subject with depression In accordance with aspects of various embodiments described herein, at least 21 single nucleotide polymorphisms (SNPs) and 4 peripheral biomarker parameters have been discovered for predicting the effectiveness or efficacy of a treatment regimen comprising a folate-containing compound. That is, these SNPs and serum/plasma/cerebrospinal fluid (CSF) biomarker parameters can be used to identify subjects with depression that would benefit from or respond to a treatment regimen comprising a folate-containing compound, as compared to a treatment without a folate-containing compound. In particular, these SNPs and serum/plasma/CSF biomarker parameters can be used to identify a subject with treatment-resistant depression (e.g., a subject resistant to at least one selective serotonin reuptake inhibitor (SSRI)) who would benefit from or respond to a treatment regimen comprising a folate-containing compound, as compared to a treatment without the folate-containing compound. The folate-containing compound can be administered in the absence of an anti-depressant drug, or it can be provided as an adjuvant to an antidepressant drug. In some embodiments, the adjuvant effect of the folate-containing compound administered in combination with an antidepressant drug can additive. In other embodiments, the adjuvant effect of the folate-containing compound administered in combination with an antidepressant drug can be synergistic.

Specifically, the SNPs that can predict efficacy of administering to a human subject a folate-containing compound (e.g., alone or in a combination therapy to increase the efficacy of an antidepressant) for treatment of depression include at least one or a combination of SNPs identified by rs numbers as follows: rs1801133 present in methylenetetrahydrofolate reductase (MTHFR); rs2274976 present in MTHFR; rs1805087 present in methionine synthase (MTR); rs1801394 present in methionine synthase reductase (MTRR); rs1006737 present in calcium channel, voltage-dependent, L-type, alpha 1C subunit (CACNA1C); rs1883729 present in DNA (cytosine-5)-methyltransferase 3 beta (DNMT3B); rs7163862 present in GTP cyclohydrolase 1 feedback regulatory protein (GCHFR); rs12659 present in reduced folate carrier protein (RCF2); rs202676 present in folate hydrolase (prostate-specific membrane antigen) (FOLH1); rs2297291 present in reduced folate carrier protein (RCF1); rs1051266 present in reduced folate carrier protein 1 (RCF1); rs8007267 present in GTP cyclohydrolase 1 (GCH1); rs7639752 present in choline-phosphate cytidylytransferase A (PCYT1A); rs6275 present in dopamine receptor D2 (DRD2); rs1079596 present in DRD2; rs11240594 present in DRD2; rs4633 present in catechol-β-methyltransferase (COMT); rs4680 present in COMT; rs250682 present in dopamine active transporter (DAT, or SLC6A3); rs2277820 present in formiminotransferase cyclodeaminase (FTCD); rs2236225 present in methylenetetrahydrofolate dehydrogenase (NADP+ dependent) 1 (MTHFD1); and any combinations thereof.

Further, peripheral biomarker parameters that can predict efficacy of administering to a human subject a folate-containing compound (e.g., alone or in a combination therapy to increase the efficacy of an antidepressant) for treatment of depression include relative expression levels between s-adenosyl methionine (SAM) and s-adenosyl homocysteine (SAH), expression of 4-hydroxynonenal (4-HNE), expression of high-sensitivity c-reactive protein (hsCRP), and any combinations thereof. Additionally, obesity has also been discovered to be predicative of effectiveness of a treatment regimen comprising a folate-containing compound (e.g., as a monotherapy or a combination therapy with an antidepressant). These genetic polymorphisms, peripheral biomarkers and clinical features have been assessed on a human cohort, who has major depressive disorder and has shown resistance to anti-depressant monotherapies, e.g., has treatment-resistant depression (TRD), in particular, selective serotonin reuptake inhibitor (SSRI)-resistant depression.

Accordingly, some embodiments described herein are generally related to assays, methods, systems or kits for selecting a treatment regimen for a subject with depression or identifying a subject with depression amenable for, or responsive to a treatment comprising a folate-containing compound. In some embodiments, the treatment can comprise a combination of a folate-containing compound and an antidepressant drug. In one embodiment, the assays, methods, systems and kits are directed to determining in a test sample from a human subject, e.g., a human subject diagnosed as having, or having a risk for depression (e.g., but not limited to, major depressive disorder) the presence or absence of at least one of single nucleotide polymorphisms (SNPs) and/or peripheral biomarker parameters to predict the response of a subject to a treatment comprising a folate-containing compound. If at least one of the conditions described herein is determined to be present in the test sample from the human subject, a treatment regimen comprising a folate-containing compound can be selected and optionally administered to the human subject. In some embodiments, the treatment regimen can further comprise an anti-depressant drug (e.g., an SSRI) to be administered, separately or concurrently, with a folate-containing compound.

Assays for Selecting a Treatment Regimen for a Human Subject with Depression

Accordingly, provided herein generally relate to assays, methods, systems, and kits for selecting a treatment regimen for a subject with depression or a risk for depression; for treating a subject with depression or a risk for depression, and/or for improving the effectiveness of a treatment regimen recommended for and/or administered to a subject with depression or a risk for depression. Provided herein also relate to folate-comprising compositions for use in treatment of depression in a subject (e.g., a human subject) selected to carry at least one (e.g., at least two or more) or any combinations of the biomarkers or conditions described herein.

One aspect described herein provides an assay for selecting a treatment regimen for a subject with depression, by identifying in a test sample from the subject genotypes of at least one of the SNPs and/or expression of at least one peripheral biomarker as described herein in order to determine the responsiveness of the human subject to a treatment regimen comprising a folate-containing compound. The assay comprises:

(a) subjecting a test sample of a human subject, who is diagnosed as having depression or having a risk for depression, to at least one analysis to determine parameters of at least two (including, e.g., at least three, at least four, at least five or more) of the biomarkers (i) to (xxiv):

(i) genotype of a SNP locus at position 677 of SEQ ID NO. 1 or position 27 of SEQ ID NO. 7 (identified by rs1801133), wherein the SEQ ID NO. 1 and SEQ ID NO. 7 are each independently a portion of a genomic nucleic acid sequence of methylenetetrahydrofolate reductase (MTHFR);

(ii) genotype of a SNP locus at position 1793 of SEQ ID NO. 1 or position 27 of SEQ ID NO. 8 (identified by rs2274976), wherein the SEQ ID NO. 1 and SEQ ID NO. 8 are each independently a portion of a genomic nucleic acid sequence of MTHFR;

(iii) genotype of a SNP locus at position 2756 of SEQ ID NO. 2 or position 27 of SEQ ID NO. 9 (identified by rs1805087), wherein the SEQ ID NO. 2 and SEQ ID NO. 9 are each independently a portion of a genomic nucleic acid sequence of methionine synthase (MTR);

(iv) genotype of a SNP locus at position 66 of SEQ ID NO. 3 or position 27 of SEQ ID NO. 10 (identified by rs1801394), wherein the SEQ ID NO. 3 and SEQ ID NO. 10 are each independently a portion of a genomic nucleic acid sequence of methionine synthase reductase (MTRR);

(v) genotype of a SNP locus at position 27 of SEQ ID NO. 11 (identified by rs1006737), wherein the SEQ ID NO. 11 is a portion of a genomic nucleic acid sequence of calcium channel, voltage-dependent, L type, alpha 1C subunit (CACNA1C);

(vi) genotype of a SNP locus at position 27 of SEQ ID NO. 12 (identified by rs1883729), wherein the SEQ ID NO. 12 is a portion of a genomic nucleic acid sequence of DNA (cytosine-5)-methyltransferase 3 beta (DNMT3B);

(vii) genotype of a SNP locus at position 27 of SEQ ID NO. 13 (identified by rs7163862), wherein the SEQ ID NO. 13 is a portion of a genomic nucleic acid sequence of GTP cyclohydrolase 1 feedback regulatory protein (GCHFR);

(viii) genotype of a SNP locus at position 27 of SEQ ID NO. 14 (identified by rs12659), wherein the SEQ ID NO. 14 is a portion of a genomic nucleic acid sequence of reduced folate carrier protein (RCF2);

(ix) genotype of a SNP locus at position 27 of SEQ ID NO. 15 (identified by rs202676), wherein the SEQ ID NO. 15 is a portion of a genomic nucleic acid sequence of folate hydrolase (prostate-specific membrane antigen) 1 (FOLH1);

(x) genotype of a SNP locus at position 27 of SEQ ID NO. 16 (identified by rs2297291), wherein the SEQ ID NO. 16 is a portion of a genomic nucleic acid sequence of reduced folate carrier protein (RCF1);

(xi) genotype of a SNP locus at position 27 of SEQ ID NO. 17 (identified by rs1051266), wherein the SEQ ID NO. 17 is a portion of a genomic nucleic acid sequence of reduced folate carrier protein (RCF1);

(xii) genotype of a SNP locus at position 27 of SEQ ID NO. 18 (identified by rs8007267), wherein the SEQ ID NO. 18 is a portion of a genomic nucleic acid sequence of GTP cyclohydrolase 1 (GCH1);

(xiii) genotype of a SNP locus at position 27 of SEQ ID NO. 19 (identified by rs7639752), wherein the SEQ ID NO. 19 is a portion of a genomic nucleic acid sequence of choline-phosphate cytidylyltransferase A (PCYT1A);

(xiv) genotype of a SNP locus at position 27 of SEQ ID NO. 20 (identified by rs6275), wherein the SEQ ID NO. 20 is a portion of a genomic nucleic acid sequence of dopamine receptor D2 (DRD2);

(xv) genotype of a SNP locus at position 27 of SEQ ID NO. 21 (identified by rs1079596), wherein the SEQ ID NO. 21 is a portion of a genomic nucleic acid sequence of dopamine receptor D2 (DRD2);

(xvi) genotype of a SNP locus at position 27 of SEQ ID NO. 22 (identified by rs11240594), wherein the SEQ ID NO. 22 is a portion of a genomic nucleic acid sequence of dopamine receptor D2 (DRD2);

(xvii) genotype of a SNP locus at position 27 of SEQ ID NO. 23 (identified by rs4633), wherein the SEQ ID NO. 23 is a portion of a genomic nucleic acid sequence of catechol-β-methyltransferase (COMT);

(xviii) genotype of a SNP locus at position 27 of SEQ ID NO. 24 (identified by rs4680), wherein the SEQ ID NO. 24 is a portion of a genomic nucleic acid sequence of catechol-β-methyltransferase (COMT);

(xix) genotype of a SNP locus at position 27 of SEQ ID NO. 25 (identified by rs250682), wherein the SEQ ID NO. 25 is a portion of a genomic nucleic acid sequence of solute carrier family 6 (neurotransmitted transported, dopamine), member 3 (SLC6A3);

(xx) genotype of a SNP locus at position 27 of SEQ ID NO. 26 (identified by rs2277820), wherein the SEQ ID NO. 26 is a portion of a genomic nucleic acid sequence of formiminotransferase cyclodeaminase (FTCD);

(xxi) genotype of a SNP locus at position 27 of SEQ ID NO. 27 (identified by rs2236225), wherein the SEQ ID NO. 27 is a portion of a genomic nucleic acid sequence of methylenetetrahydrofolate dehydrogenase (NADP+ dependent) 1 (MTHFD1));

(xxii) level of expression of SAM and SAH;

(xxiii) level of expression of 4-HNE;

(xxiv) level of expression of hsCRP; and any combinations thereof; and (b) detecting, optionally with a non-human machine, from the determined parameters of at least two biomarkers, the presence of at least one condition (including, e.g., at least two conditions, at least three conditions, at least four conditions or more) selected from the following conditions (A)-(X):

(A) a SNP at position 677 of SEQ ID NO. 1 or position 27 of SEQ ID NO. 7 (identified by rs1801133) comprising at least one thymine "T" allele;

(B) a SNP at position 1793 of SEQ ID NO. 1 or position 27 of SEQ ID NO. 8 (identified by rs2274976) comprising at least one adenine "A" allele;

(C) a SNP at position 2756 of SEQ ID NO. 2 or position 27 of SEQ ID NO. 9 (identified by rs1805087) comprising at least one guanine "G" allele;

(D) a SNP at position 66 of SEQ ID NO. 3 or position 27 of SEQ ID NO. 10 (identified by rs1801394) comprising at least one guanine "G" allele;

(E) a SNP at position 27 of SEQ ID NO. 11 (identified by rs1006737) comprising at least one adenine "A" allele;

(F) a SNP at position 27 of SEQ ID NO. 12 (identified by rs1883729) comprising at least one adenine "A" allele;

(G) a SNP at position 27 of SEQ ID NO. 13 (identified by rs7163862) comprising at least one thymine "T" allele;

(H) a SNP at position 27 of SEQ ID NO. 14 (identified by rs12659) comprising at least one thymine "T" allele;

(I) a SNP at position 27 of SEQ ID NO. 15 (identified by rs202676) comprising at least one guanine "G" allele;

(J) a SNP at position 27 of SEQ ID NO. 16 (identified by rs2297291) comprising at least one adenine "A" allele;

(K) a SNP at position 27 of SEQ ID NO. 17 (identified by at rs1051266) comprising at least one adenine "A" allele;

(L) a SNP at position 27 of SEQ ID NO. 18 (identified by rs8007267) comprising at least one thymine "T" allele;

(M) a SNP at position 27 of SEQ ID NO. 19 (identified by rs7639752) comprising at least one adenine "A" allele;

(N) a SNP at position 27 of SEQ ID NO. 20 (identified by rs6275) comprising at least one thymine "T" allele;

(O) a SNP at position 27 of SEQ ID NO. 21 (identified by rs1079596) comprising at least one thymine "T" allele;

(P) a SNP at position 27 of SEQ ID NO. 22 (identified by rs11240594) comprising at least one adenine "A" allele;

(Q) a SNP at position 27 of SEQ ID NO. 23 (identified by rs4633) comprising at least one cytosine "C" allele;

(R) a SNP at position 27 of SEQ ID NO. 24 (identified by rs4680) comprising at least one guanine "G" allele;

(S) a SNP at position 27 of SEQ ID NO. 25 (identified by rs250682) comprising at least one cytosine "C" allele;

(T) a SNP at position 27 of SEQ ID NO. 26 (identified by rs2277820) comprising at least one thymine "T" allele;

(U) a SNP at position 1958 of SEQ ID NO. 27 (identified by rs2236225) comprising at least one adenine "A" allele;

(V) an expression level ratio of SAM to SAH smaller than a pre-determined reference ratio;

(W) an expression level of 4-HNE greater than a first pre-determined reference value;

(X) an expression of hsCRP greater than a second pre-determined reference value (e.g., about 2.3 mg per liter as measured in a plasma sample); and any combinations thereof.

In some embodiments of this aspect and all other aspects described herein, any of the SNPs described herein can comprise one or two folate-responsive alleles. By way of example only, a SNP at position 677 of SEQ ID NO. 1 or position 27 of SEQ ID NO. 7 (identified by rs1801133) can comprise one thymine "T" allele, or two thymine "T" alleles. Without wishing to be bound by theory, a human subject determined to carry two folate-responsive alleles in a SNP locus described herein can show greater response to a treatment regimen comprising a folate-containing compound than a human subject with one folate-responsive allele in the same SNP locus.

Depending on the design of primers and probes, the SNP conditions (A)-(U) can be also represented by alleles complementary to the corresponding folate-responsive alleles described herein. For example, instead of detecting the presence of a SNP at position 677 of SEQ ID NO. 1 or position 27 of SEQ ID NO. 7 (identified by rs1801133) comprising at least one thymine "T" allele, one of skill in the art can readily design primers and/or probes for the complementary sequence of SEQ ID NO. 7 to probe for a SNP at the same location comprising at least one "A" allele instead. Accordingly, in some embodiments of this aspect and all other aspects described herein, the presence of at least one condition (including, e.g., at least two conditions, at least three conditions, at least four conditions or more) selected from the conditions (A)-(U) can be indicated by detecting the presence of the complementary allele of the folate-responsive allele as shown above and also in Table 42 below.

Based on the analysis results from step (b), if at least one of the conditions (A)-(X) described above is detected, the assay can further comprise selecting for the human subject and optionally administering to the human subject a treatment regimen comprising an effective amount of a folate-containing compound.

Any combinations of at least two biomarkers (i) to (xxiv) described herein can be determined in a test sample for the assays described herein. Exemplary combinations of at least two biomarkers described herein can comprise genotypes of at least two SNP loci or more (e.g., including at least three SNP loci, at least four SNP loci, at least five SNP loci or more); or genotype of at least one SNP loci or more (e.g., including at least two SNP loci or more) and expression level of at least one peripheral biomarker or more (e.g., 4-HNE, SAM, SAH); or expression level of at least two peripheral biomarkers (e.g., 4-HNE, SAM, SAH). Depending upon selected combinations of at least two biomarkers described herein, the test sample can be subjected to one or more analyses, e.g., including, but not limited to, genotyping assays, expression assays (e.g., protein and/or transcript levels), or any combinations thereof.

Accordingly, in some embodiments, the assay can comprise subjecting a test sample from a human subject, who is diagnosed as having depression or having a risk for depression to at least one genotyping assay adapted to determine genotypes of at least two loci, wherein said at least two loci are: (i) position 677 of SEQ ID NO. 1 or position 27 of SEQ ID NO. 7 (identified by rs1801133) and (ii) position 2756 of SEQ ID NO. 2 or position 27 of SEQ ID NO. 9 (identified by rs1805087). In such embodiment, detection of at least one SNP at either position 677 of SEQ ID NO. 1 (or position 27 of SEQ ID NO. 7) comprising at least one thymine "T" allele or position 2756 of SEQ ID NO. 2 (or position 27 of SEQ ID NO. 9) comprising at least one guanine "G" allele, or detection of both aforementioned SNPs indicates selection and optional administration of a treatment regimen comprising an effective amount of a folate-containing compound to the human subject.

In some embodiments, the test sample can be subjected to at least one genotyping assay adapted to determine genotypes of at least three loci, at least four loci, at least five loci, at least six loci, at least seven loci, at least eight loci, at least nine loci, at least ten loci or more. The additional loci to be interrogated can be selected from any combinations of the biomarkers (i)-(xxi).

In some embodiments, the genotyping assay can comprise the step of amplifying the test sample with a set of primers flanking any one of the SNPs described herein. In some embodiments, at least two (e.g., at least three, at least four, at least five or more) sets of primers amplifying at least two (e.g., at least three, at least four, at least five or more) of the SNPs can be used in a multiplex amplification assay.

In some embodiments, the test sample can be subjected to determine parameters of at least three, at least four, at least five or more biomarkers (i) to (xxiv) described herein. For example, in some embodiments, the assay can comprise: (a) subjecting a test sample of a subject to one or more than one analyses (e.g., genotyping and/or expression analyses) to determine the presence or absence of at least one of the following conditions:

i. an expression ratio of s-adenosyl methionine (SAM) to s-adenosyl homocysteine (SAH) smaller than a pre-determined reference ratio;

ii. expression of 4-hydroxynonenal (4-HNE) greater than a first pre-determined reference value;

iii. a single nucleotide polymorphism (SNP) at position 677 of SEQ ID NO: 1 (or at position 27 of SEQ ID NO. 7) comprising at least one thymine "T" allele, wherein the SEQ ID NO: 1 and SEQ ID NO. 7 are each independently a portion of a genomic nucleic acid sequence of methylenetetrahydrofolate reductase (MTHFR);

iv. a SNP at position 2756 of SEQ ID NO: 2 (or at position 27 of SEQ ID NO. 9) comprising at least one guanine "G" allele, wherein the SEQ ID NO. 2 and SEQ ID NO. 9 are each independently a portion of a genomic nucleic acid sequence of methionine synthase (MTR); and v. a SNP at position 66 of SEQ ID NO. 3 (or at position 27 of SEQ ID NO. 10) comprising at least one guanine "G" allele, wherein the SEQ ID NO. 3 and SEQ ID NO. 10 are each independently a portion of a genomic nucleic acid sequence of methionine synthase reductase (MTRR).

In these embodiments, detection of the presence of at least one of these conditions is indicative of the subject recommended for a treatment regimen comprising a folate-containing compound. In some embodiments, if none of the conditions described herein is present, the subject is not recommended for a treatment regimen comprising a folate-containing compound.

In some embodiments of this aspect and all other aspects described herein, when the expression ratio of SAM to SAH is smaller than the pre-determined reference ratio, e.g., smaller than a control ratio of SAM/SAH as measured in a biological sample of normal healthy subjects, the subject can be recommended for and/or optionally administered with a treatment regimen comprising a folate-containing compound. In one embodiment, the control ratio of SAM/SAH as measured in a serum sample of normal healthy subjects can range from about 4 to about 12. In one embodiment, the expression ratio of SAM to SAH being smaller than 3.0, or smaller than about 2.8, as measured in a plasma sample, is indicative of a subject recommended for and/or optionally administered with a treatment regimen comprising a folate-containing compound. In one embodiment, the expression ratio of SAM to SAH being smaller than 2.71, as measured in a plasma sample, is indicative of a subject recommended for and/or optionally administered with a treatment regimen comprising a folate-containing compound. In some embodiments, if the expression ratio of SAM to SAH is at least or greater than 2.71 as measured in a plasma sample, the subject is not recommended for nor administered with a treatment regimen comprising a folate-containing compound. Depending on the test sample source, e.g., a blood sample vs. a cerebrospinal fluid sample, the pre-determined reference ratio for a blood plasma sample can be different from that for, e.g., a cerebrospinal fluid sample.

In some embodiments of this aspect and all other aspects described herein, when the expression of 4-HNE in the subject is greater than the first pre-determined reference value, e.g., greater than a control value of 4-HNE as measured in a biological sample of normal healthy subjects, the subject can be recommended for and/or optionally administered with a treatment regimen comprising a folate-containing compound. In one embodiment, the control value of 4-HNE as measured in a serum sample of the normal healthy subjects can be about 0.24 µmol per liter of serum, or about 0.04 mg per liter of serum. In some embodiments, when the expression of 4-HNE in the subject is greater than about 3 mg per liter, or greater than about 3.2 mg per liter of plasma or higher as measured in a plasma sample, the subject can be recommended for and/or optionally administered with a treatment regimen comprising a folate-containing compound. In one embodiment, if the expression of 4-HNE is at least 3.28 mg per liter of plasma as measured in a plasma sample or higher, a subject can be recommended for and/or optionally administered with a treatment regimen comprising a folate-containing compound. In some embodiments, if the expression of 4-HNE is less than 3.28 mg per liter of plasma as measured in a plasma sample or lower, the subject is not recommended for nor administered with a treatment regimen comprising a folate-containing compound. Depending on the test sample source, e.g., a blood sample vs. a cerebrospinal fluid sample, the pre-determined reference value for a plasma sample can be different from that for, e.g., a cerebrospinal fluid sample.

In some embodiments of this aspect and all other aspects described herein, the assay can further comprise determining if the human subject is obese or not. If the human subject is determined to be obese, then the human subject is selected for and optionally administered with a treatment regimen comprising an effective amount of a folate-containing compound. Methods of determining obesity in a human subject are known in the art and can include, but are not limited to, body mass index (BMI) measurement, measurement of abdominal fat (e.g., by waist circumference or waist-hip ratio), measurement of body fat, skinfold thickness, underwater weighing (densitometry), air-displacement plethysmography, computerized tomography (CT) and magnetic resonance imaging (MRI), and dual energy X-ray absorptiometry (DEXA), and any combinations thereof.

Obesity can be defined clinically in different ways. For example, obesity can be defined by a body mass index (BMI) value of at least about 30 kg/m$^2$ or higher. In another embodiment, obesity can be defined by excessive abdominal fat (e.g., indicated by waist circumference and/or waist-hip ratio). For example, excess abdominal fat can be clinically defined as a waist circumference >40 inches (>102 cm) in men and >35 inches (>88 cm) in women. Alternatively, abdominal obesity can be defined as a waist-hip ratio above 0.95 for males and above 0.80 for females. In some embodiments, obesity can be defined by body fat percentage, e.g., obesity is defined as a body fat percentage of at least about 32% or more in women and at least about 25% or more in men.

In one embodiment, measurement of BMI can be used to determine whether a human subject is obese. In such embodiment, the assay can further comprise measuring body mass index (BMI) of the human subject to determine if the human subject is obese or not, and if the BMI value of at least 30 kg/m$^2$ or greater is measured in the subject, then selecting for the human subject and optionally administering to the human subject a treatment regimen comprising an effective amount of a folate-containing compound. In some embodiments, if the human subject has a BMI value of less than 30 kg/m$^2$, it may not be desirable to recommend or administer to the human subject a treatment regimen comprising a folate-containing compound.

In some embodiments, the assay can further comprise determining the presence or absence of a SNP at position 1298 of the SEQ ID NO: 1 comprising at least one cytosine "C" allele, wherein the presence of the SNP at position 1298 of the SEQ ID NO: 1 comprising at least one cytosine "C" is indicative of the subject recommended for and/or administered with a treatment regimen comprising a folate-containing compound.

In some embodiments, the assay can further comprise determining expression of high-sensitivity c-reactive protein (hsCRP), wherein the hsCRP expression greater than a second pre-determined reference value, e.g., greater than a control value of hsCRP as measured in a biological sample of normal healthy subjects, is indicative of the subject recommended for and optionally administered with a treatment regimen comprising a folate-containing compound. In one embodiment, the control value of hsCRP as measured in a serum sample of normal healthy subjects can range from about 0.5 mg per liter of serum to about 4.5 mg per liter of serum. In some embodiments, if the expression of hsCRP is greater than about 2.3 mg per liter of plasma, as measured in a plasma sample, the subject is recommended for and optionally administered with a treatment regimen comprising a folate-containing compound. In some embodiments, if the expression of hsCRP is lower than 2.3 mg per liter of plasma, as measured in a plasma sample, then the subject is not recommended for nor administered with a treatment regimen comprising a folate-containing compound. Depending on the test sample source, e.g., a blood sample vs. a cerebrospinal fluid sample, the hsCRP expression a plasma sample can be different from that in, e.g., a cerebrospinal fluid sample.

In some embodiments of the assay described herein, a test sample can be analyzed to determine at least one or at least two, at least three, at least four, at least five, at least six of the conditions provided herein. For example, in some embodiments, the test sample can be analyzed to determine if the subject has at least the SNPs located at the positions 677 and 2756 of the MTHFR and MTR loci, respectively. In some embodiments, the test sample can be analyzed to determine if the subject is obese (e.g., whether the subject has at least the BMI value of at least 30 kg/m$^2$), and the SNPs located at the positions 2756 and 66 of the MTR and MTRR loci, respectively. In other embodiments, the test sample can be analyzed to determine if the subject is obese (e.g., whether the subject has at least the BMI value of at least 30 kg/m$^2$) and the SNP located at the position 2756 of the MTR locus. In some embodiments, the test sample can be analyzed to determine if the subject has at least the SAM/SAH ratio smaller than the pre-determined reference ratio and the SNP located at the position 2756 of the MTR locus. In some embodiments, the test sample can be analyzed to determine if the subject has at least the 4-HNE expression greater than the first pre-determined reference value and the SNPs located at the positions 2756 and 66 of the MTR and MTRR loci, respectively. As discussed previously, any combinations of one or more of the conditions (A)-(X) described herein can be assayed at the same time or at different times.

In some embodiments, if at least one or at least two, including at least three or more, of the conditions provided herein are determined to be present in the test sample of a human subject, a treatment regimen comprising a folate-containing compound is selected and optionally administered to the human subject.

In some embodiments, if the human subject satisfies at least one, including at least two, at least three or more, of the conditions (A)-(X) described herein (and obesity, e.g., defined by a BMI value of at least 30 kg/m$^2$ or greater), the subject can be administered or prescribed with a treatment regimen comprising a folate-containing compound.

In some embodiments, the treatment regimen can further comprise an anti-depressant drug (e.g., an SSRI) to be administered in combination (e.g. concurrently or separately) with a folate-containing compound.

In some embodiments, the folate-containing compound can comprise a L-methylfolate compound. In one embodiment, the folate-containing compound can comprise 6(S)-5-methyltetrahydrofolate or a derivative thereof.

The assays, methods, systems and/or kits described herein can be performed and/or used by a third-party service provider. For example, a third-party service provider can provide and charge for a service offered to determine the presence or absence of at least one condition (A)-(X) in a test sample of a human subject, e.g., to facilitate selection of a treatment regimen for a human subject with depression. Accordingly, methods for selecting a treatment regimen for a human subject are also provided herein. For example, the method comprises (a) obtaining a test sample from a human subject diagnosed as having, or having a risk, for depression; (b) subjecting the test sample to at least one analysis to determine parameters of at least two biomarkers (i)-(xxiv) described herein (e.g., but not limited to, a combination of biomarkers (i) and (iii)); (c) determining, from the parameters of the selected biomarkers, the presence of at least one condition (A)-(X) (e.g., but not limited to, either one or both of conditions (A) and (C)); and (d) providing a result output setting forth whether at least one of the conditions (A)-(X) is detected in the test sample. If at least one condition is present, the method can further comprise selecting and optionally administering a treatment regimen comprising an effective amount of a folate-containing compound to the human subject.

In some embodiments, the step (b) of the method can further comprise optionally packing and shipping the test sample to a test facility, e.g., a third-party CLIA-certified service provider.

In some embodiments, the step (d) of the method is performed by a non-human machine.

Folate-Responsive Biomarkers (i)-(xxv) and Associated Conditions (A)-(X) Indicative of a Treatment Regimen Comprising a Folate-Containing Compound Table 41A-41B below indicates folate-responsive biomarkers (i)-(xxiv) and associated conditions (A)-(X), the presence of at least one of which in a test sample of a human subject diagnosed as having, or having a risk for, depression, indicates a treatment regimen comprising a folate-containing compound be selected for and optionally administered to the human subject.

Next page shows Table 41A: Folate-responsive biomarkers (i)-(xxi) used in assays, methods, systems and kits described herein, and corresponding folate-responsive conditions (A)-(U). The sequences of human origin shown in Table 41A (including complementary sequences thereof) can provide a basis for designing primers and probes for interrogation of the SNP biomarkers described herein.

Folate-responsive SNP Biomarkers

| Biomarker identifier | SEQ ID NO | Sequence | rs number | Chromosome locus | Gene name |
|---|---|---|---|---|---|
| i | 7 | CTTGAAGGAGAAGGTGTCTGCGGGAG(C/T)CGATTTCATCATCACGCAGCTTTTC | rs1801133 | 1p36.3 | MTHFR |
| ii | 8 | CGAGGCCTTTGCCCTGTGGATTGAGC(A/G)GTGGGGAAAGCTGTATGAGGAGGAG | rs2274976 | 1p36.3 | MTHFR |
| iii | 9 | GGAAGAATATGAAGATATTAGACAGG(A/G)CCATTATGAGTCTCTCAAGGTAAGT | rs1805087 | 1q43 | MTR |
| iv | 10 | CAGGCAAAGGCCATCGCAGAAGAAAT(A/G)TGTGAGCAAGCTGTGGTACATGGAT | rs1801394 | 5p15.31 | MTRR |
| v | 11 | TAAGTTCCATTCCATCTCAGCCCGAA(A/G)TGTTTTCAGAGCCGGAGACCTACACA | rs1006737 | 12p13.33 | CACNA1C (ca ion) |
| vi | 12 | CTGCTGCTGGTATCAGCCTGGAGGAA(A/G)TGAGTGACATCAGTTCTCAGCATTA | rs1883729 | 20q11.2 | DNMT3B |
| vii | 13 | AACCAATCACAACAAGGCAGATAAAG(A/T)AGGATGAGTTGTCAGATTTGATAA | rs7163862 | 15q15.1 | GCHFR (BH4) |
| viii | 14 | GCTTCGGAGCTGGAGCGCATGAATCC(C/T)GGCCCAGGCGGGAAGCTGGGACACG | rs12659 | 21q22.3 | RCF2 |
| ix | 15 | AAGCTGAGAACATCAAGAAGTTCTTA(C/T)AGTAAGTACATCCTCGAAAGTTTAT | rs202676 | 11p11.2 | FOLH1 (GCPII) |
| x | 16 | GGGAGGGCACCCGCAGAGGCCTGCGC(A/G)CTGACACTGCTGAGTGGCTCTGCTC | rs2297291 | 21q22.3 | RCF1 |
| xi | 17 | TGACCCCGAGCTCCGGTCCTGGCGGC(A/G)CCTCGTGTGCTACCTTTGCTTCTAC | rs1051266 | 21q22.3 | RCF1 |
| xii | 18 | CAATAGGAGCGTGTGTTTGAACAGTA(C/T)ACGCCAAACTTCAGTCATTCAAGTA | rs8007267 | 14q22.1-q22.2 | GCH1 (BH4) |
| xiii | 19 | GGCCTAATCAATCCTTCTCATCTTTT(A/G)TACCCACCTTTTGCAGGAAACCTGT | rs7639752 | 3q29 | PCYT1A |
| xiv | 20 | CTGACTCTCCCCGACCCGTCCCACCA(C/T)GGTCTCCACAGCACTCCCGACAGCC | rs6275 | 11q23.2 | DRD2 |
| xv | 21 | GTCCCTGCAGTTTAATTATCCTCAAC(A/G)TTACTGCCATACCCTACATTTTTGG | rs1079596 | 11q23.2 | DRD2 |
| xvi | 22 | CTCACAGTTTGTGGTTGAGACTAAGT(A/G)TGAACAGTGGCACTTTGTGGTCC | rs11240594 | | DRD2 |

-continued

| | | | | | |
|---|---|---|---|---|---|
| xvii | 23 | ACCAAGGAGCAGCGCATCCTGAACCA(C/T)GTGCTGCAGCATGCGGAGCCCGGGA | rs4633 | 22q11.21-q11.23\|22q11.21 | COMT |
| xviii | 24 | CCCAGCGGATGGTGGATTTCGCTGGC(A/G)TGAAGGACAAGGTGTGCATGCCTGA | rs4680 | 22q11.21-q11.23\|22q11.21 | COMT |
| xix | 25 | TAATATGGCCACCCCAACTTTCGTAT(C/G)ATTACTGTTTGTGTGGTATTATCTT | rs250682 | 5p15.3 | SLC6A3 |
| xx | 26 | ATCAGCCCTAGATGCTTGACCAGCTC(C/T)TCGGGCCTCACCTCCTGGTTCTTCC | rs2277820 | 21q22.3 | FTCD |
| xxi | 27 | CTGGGCCAACAAGCTTGAGTGCGATC(C/T)GGTCTGCAATGATGGAGGAATTGCC | rs2236225 | 14q24 | MTHFD1 |

| | Folate-responsive Conditions | | | |
|---|---|---|---|---|
| Biomarker identifier | Condition identifier | Folate-responsive allele | Folate-responsive complementary allele | Pos. No of SNP in the Sequence |
| i | A | T | A | 27 |
| ii | B | A | T | 27 |
| iii | C | G | C | 27 |
| iv | D | G | C | 27 |
| v | E | A | T | 27 |
| vi | F | A | T | 27 |
| vii | G | T | A | 27 |
| viii | H | T | A | 27 |
| ix | I | G | C | 27 |
| x | J | A | T | 27 |
| xi | K | A | T | 27 |
| xii | L | T | A | 27 |
| xiii | M | A | T | 27 |
| xiv | N | T | A | 27 |
| xv | O | T | A | 27 |
| xvi | P | A | T | 27 |
| xvii | Q | C | G | 27 |
| xviii | R | G | C | 27 |
| xix | S | C | G | 27 |
| xx | T | T | A | 27 |
| xxi | U | A | T | 27 |

Among the SNP biomarkers, the inventors discovered that statistically significant treatment effect was observed within all of the assessed genetic modifiers (e.g., race, age, sex, and BMI) for subjects positive for the MTR 2756 AG or GG genotype [associated single-nucleotide polymorphism (SNP) rs1805087] compared to subjects negative for this SNP within the placebo (an antidepressant administered without a folate-comprising compound) or folate-comprising treatment (a folate-comprising compound administered as an adjuvant to the antidepressant) arms of clinical studies (FIGS. 12A-12B). Subjects positive for the COMT CC (rs4633) or GG (rs4680) SNP also show statistically significant treatment effect in at least one genetic moderator category within the placebo (an antidepressant administered without a folate-comprising compound) or folate-comprising treatment (a folate-comprising compound administered as an adjuvant to the antidepressant) arms of clinical studies (FIGS. 12A-12B). Thus, the presence of the MTR (and COMT) SNP biomarkers can allow identification of subjects who are responsive to a folate-comprising treatment, when comparing treated subjects vs. placebo as well as when comparing biomarker positive and biomarker negative subjects within the treatment. Accordingly, another aspect provided herein is a method of treating at least one symptom of depression in a subject comprising administering to a subject, who is diagnosed to have, or have a risk for depression, and is further determined to carry a SNP at position 2756 of SEQ ID NO. 2 or position 27 of SEQ ID NO. 9 (identified by rs1805087) comprising at least one guanine "G" allele or the complement thereof, wherein the SEQ ID NO. 2 and SEQ ID NO. 9 are each independently a portion of a genomic nucleic acid sequence of methionine synthase (MTR), based on the recognition that the presence of the SNP allele(s) is associated with positive-symptom-reducing response to the folate-comprising compound. In some embodiments, the subject can be further determined to carry a SNP at position 677 of SEQ ID NO. 1 or position 27 of SEQ ID NO. 7 (identified by rs1801133) comprising at least one thymine "T" allele or the complement thereof, wherein the SEQ ID NO. 1 and SEQ ID NO. 7 are each independently a portion of a genomic nucleic acid sequence of methylenetetrahydrofolate reductase (MTHFR).

Provided herein is also a method of treating at least one symptom of depression in a subject comprising administering to a subject, who is diagnosed to have, or have a risk for depression, and is further determined to carry a SNP at position 27 of SEQ ID NO. 23 (identified by rs4633) comprising two cytosine "C" alleles or the complement thereof, wherein the SEQ ID NO. 23 is a portion of a genomic nucleic acid sequence of catechol-O-methyltransferase (COMT), based on the recognition that the presence of the SNP allele(s) is associated with positive-symptom-reducing response to the folate-comprising compound.

Provided herein is also a method of treating at least one symptom of depression in a subject comprising administering to a subject, who is diagnosed to have, or have a risk for depression, and is further determined to carry a SNP at position 27 of SEQ ID NO. 24 (identified by rs4680) comprising two guanine "G" alleles or the complement thereof, wherein the SEQ ID NO. 24 is a portion of a genomic nucleic acid sequence of catechol-O-methyltransferase (COMT), based on the recognition that the presence of the SNP allele(s) is associated with positive-symptom-reducing response to the folate-comprising compound.

Provided herein is also a method for selecting a treatment regimen for a subject diagnosed with depression comprising assaying a test sample from the subject for the presence of one of the following SNPs:
(i) a SNP at position 2756 of SEQ ID NO. 2 or position 27 of SEQ ID NO. 9 (identified by rs1805087) comprising at least one guanine "G" allele or the complement thereof, wherein the SEQ ID NO. 2 and SEQ ID NO. 9 are each independently a portion of a genomic nucleic acid sequence of methionine synthase (MTR);
(ii) a SNP at position 27 of SEQ ID NO. 23 (identified by rs4633) comprising two cytosine "C" alleles or the complement thereof, wherein the SEQ ID NO. 23 is a portion of a genomic nucleic acid sequence of catechol-O-methyltransferase (COMT); or
(iii) a SNP at position 27 of SEQ ID NO. 24 (identified by rs4680) comprising two guanine "G" alleles or the complement thereof, wherein the SEQ ID NO. 24 is a portion of a genomic nucleic acid sequence of catechol-O-methyltransferase (COMT), based on the recognition that the presence of the SNP allele(s) is associated with positive-symptom-reducing response to the folate-comprising compound.

In these embodiments, the method can further comprise administering to the subject a folate-comprising compound (optionally in combination with an antidepressant drug), when the subject is determined to carry one of the MTR, COMT (rs4633) and COMT (rs4680) SNP biomarkers.

TABLE 41B

Folate-responsive biomarkers (xxii)-(xxiv) used in assays, methods, systems and kits described herein and corresponding folate-responsive conditions (V)-(X).

| Biomarker identifier | Peripherial biomarker | Condition indentifier | Folate-responsive condition |
|---|---|---|---|
| xxii | SAM, SAH | V | expression ratio of SAM to SAH < a pre-determined reference ratio |
| xxiii | 4-HNE | W | expression level 4-HNE > a first pre-determined reference value |
| xxiv | hsCRP | X | expression of hsCRP > ~2.3 mg/L as measured in a plasma sample |

In some embodiments of this aspect and all other aspects described herein, when the expression ratio of SAM to SAH is smaller than the pre-determined reference ratio, e.g., smaller than a control ratio of SAM/SAH as measured in a biological sample of normal healthy subjects, the subject can be recommended for and/or optionally administered with a treatment regimen comprising a folate-containing compound. In one embodiment, the pre-determined reference ratio of SAM to SAH can be the control ratio of SAM to SAH as measured in a serum sample of normal healthy subjects, wherein the control ratio of SAM to SAH can range from about 4 to about 12. In one embodiment, the control ratio of SAM to SAH as measured in a serum sample of normal healthy subjects can be about 7. In one embodiment, the pre-determined reference ratio of SAM to SAH can be about 3 as measured in plasma sample. In one embodiment, the pre-determined reference ratio of SAM to SAH can be about 2.8, as measured in a plasma sample. In one embodiment, the pre-determined reference ratio of SAM to SAH can be about 2.71, as measured in a plasma sample. In some embodiments, if the expression ratio of SAM to SAH is at least or greater than the pre-determined reference ratio (e.g., at least or greater than 2.71 as measured in a plasma sample), the subject is not recommended for nor administered with a treatment regimen comprising a folate-containing compound. Depending on the test sample source, e.g., a serum sample vs. a urine sample, the pre-determined reference ratio of SAM to SAH for a blood plasma sample can be different from that for, e.g., a urine sample. See, e.g., Stabler S P and Allen R H. 2004 Clinical Chemistry 50: 365-372.

In some embodiments of this aspect and all other aspects described herein, when the expression of 4-HNE in the subject is greater than the first pre-determined reference value, e.g., greater than a control value of 4-HNE as measured in a biological sample of normal healthy subjects, the subject can be recommended for and/or optionally administered with a treatment regimen comprising a folate-containing compound. In one embodiment, the first pre-determined reference value of 4-HNE can be the control value of 4-HNE as measured in a serum sample of the normal healthy subjects, wherein the control value of 4-HNE can be about 0.24 mol per liter of serum, or about 0.04 mg per liter of serum. See, e.g., Gocmen A Y et al. 2008 Clinical Biochemistry 41: 836-840. In one embodiment, the first pre-determined reference value of 4-HNE can be about 3 mg per liter of plasma as measured in a plasma sample. In one embodiment, the first pre-determined reference value of 4-HNE can be about 3.2 mg per liter of plasma as measured in a plasma sample. In one embodiment, the first pre-determined reference value of 4-HNE can be about 3.28 mg per liter of plasma as measured in a plasma sample. In some embodiments, if the expression of 4-HNE is less than the first pre-determined reference value (e.g., less than 3.28 mg per liter of plasma as measured in a plasma sample), the subject is not recommended for nor administered with a treatment regimen comprising a folate-containing compound. Depending on the test sample source, e.g., a blood sample vs. a cerebrospinal fluid sample, the pre-determined reference value for a plasma sample can be different from that for, e.g., a cerebrospinal fluid sample.

In some embodiments, the assay, methods, systems, and/or kits described herein can further comprise determining expression of high-sensitivity c-reactive protein (hsCRP), wherein the hsCRP expression greater than a second pre-determined reference value, e.g., greater than a control value of hsCRP as measured in a biological sample of normal healthy subjects, is indicative of the subject recommended for and optionally administered with a treatment regimen comprising a folate-containing compound. In one embodiment, the second pre-determined reference value of hsCRP can be the control value of hsCRP as measured in a serum sample of normal healthy subjects, wherein the control value of hsCRP can range from about 0.5 mg per liter of serum to about 4.5 mg per liter of serum. See, e.g., Guven S F et al., 2012 Sleep Breath 16: 217-221. In some embodiments, the second pre-determined reference value of hsCRP can be about 2.3 mg per liter of plasma, as measured in a plasma sample. In some embodiments, if the expression of hsCRP is lower than the second pre-determined reference value (e.g., lower than 2.3 mg per liter of plasma, as measured in a plasma sample), then the subject is not recommended for nor administered with a treatment regimen comprising a folate-containing compound. Depending on the test sample source, e.g., a blood sample vs. a cerebrospinal fluid sample, the hsCRP expression a plasma sample can be different from that in, e.g., a cerebrospinal fluid sample.

TABLE 42

Combinations of various folate-responsive biomarkers (i)-(xxv) used in assays, methods, systems and kits described herein. See Tables 41A-41B for additional information of folate-responsive biomarkers (i)-(xxiv).

| | Folate-responsive biomarker identifier | | | | | | | | | | | | | | | | | | | | | | | |
|---|---|---|---|---|---|---|---|---|---|---|---|---|---|---|---|---|---|---|---|---|---|---|---|---|
| | i | ii | iii | iv | v | vi | vii | viii | ix | x | xi | xii | xiii | xiv | xv | xvi | xvii | xviii | xix | xx | xxi | xxii | xxiii | xxiv | xxv (BMI) |
| i |  | x | x | x | x | x | x | x | x | x | x | x | x | x | x | x | x | x | x | x | x | x | x | x | x |
| ii | x |  | x | x | x | x | x | x | x | x | x | x | x | x | x | x | x | x | x | x | x | x | x | x | x |
| iii | x | x |  | x | x | x | x | x | x | x | x | x | x | x | x | x | x | x | x | x | x | x | x | x | x |
| iv | x | x | x |  | x | x | x | x | x | x | x | x | x | x | x | x | x | x | x | x | x | x | x | x | x |
| v | x | x | x | x |  | x | x | x | x | x | x | x | x | x | x | x | x | x | x | x | x | x | x | x | x |
| vi | x | x | x | x | x |  | x | x | x | x | x | x | x | x | x | x | x | x | x | x | x | x | x | x | x |
| vii | x | x | x | x | x | x |  | x | x | x | x | x | x | x | x | x | x | x | x | x | x | x | x | x | x |
| viii | x | x | x | x | x | x | x |  | x | x | x | x | x | x | x | x | x | x | x | x | x | x | x | x | x |
| ix | x | x | x | x | x | x | x | x |  | x | x | x | x | x | x | x | x | x | x | x | x | x | x | x | x |
| x | x | x | x | x | x | x | x | x | x |  | x | x | x | x | x | x | x | x | x | x | x | x | x | x | x |
| xi | x | x | x | x | x | x | x | x | x | x |  | x | x | x | x | x | x | x | x | x | x | x | x | x | x |
| xii | x | x | x | x | x | x | x | x | x | x | x |  | x | x | x | x | x | x | x | x | x | x | x | x | x |
| xiii | x | x | x | x | x | x | x | x | x | x | x | x |  | x | x | x | x | x | x | x | x | x | x | x | x |
| xiv | x | x | x | x | x | x | x | x | x | x | x | x | x |  | x | x | x | x | x | x | x | x | x | x | x |
| xv | x | x | x | x | x | x | x | x | x | x | x | x | x | x |  | x | x | x | x | x | x | x | x | x | x |
| xvi | x | x | x | x | x | x | x | x | x | x | x | x | x | x | x |  | x | x | x | x | x | x | x | x | x |
| xvii | x | x | x | x | x | x | x | x | x | x | x | x | x | x | x | x |  | x | x | x | x | x | x | x | x |
| xviii | x | x | x | x | x | x | x | x | x | x | x | x | x | x | x | x | x |  | x | x | x | x | x | x | x |
| xix | x | x | x | x | x | x | x | x | x | x | x | x | x | x | x | x | x | x |  | x | x | x | x | x | x |
| xx | x | x | x | x | x | x | x | x | x | x | x | x | x | x | x | x | x | x | x |  | x | x | x | x | x |
| xxi | x | x | x | x | x | x | x | x | x | x | x | x | x | x | x | x | x | x | x | x |  | x | x | x | x |
| xxii | x | x | x | x | x | x | x | x | x | x | x | x | x | x | x | x | x | x | x | x | x |  | x | x | x |
| xxiii | x | x | x | x | x | x | x | x | x | x | x | x | x | x | x | x | x | x | x | x | x | x |  | x | x |
| xxiv | x | x | x | x | x | x | x | x | x | x | x | x | x | x | x | x | x | x | x | x | x | x | x |  | x |
| xxv (BMI) | x | x | x | x | x | x | x | x | x | x | x | x | x | x | x | x | x | x | x | x | x | x | x | x |  |

Embodiments of the various aspects described herein relate to determination of appropriate parameters (e.g., genotypes or expression level) of at least two of the biomarkers (i) to (xxiv) in a test sample of a human subject. In some embodiments, a physical biomarker (xxv in Table 42), e.g., obesity indicator, can also be measured, wherein obesity (e.g., defined by a BMI value of at least about 30 kg/m$^2$ or greater; a waist circumference greater than 40 inches (or greater than 120 cm) in men, or greater than 35 inches (or greater than 88 cm) in women; a waist-hip ratio above 0.95 for men or above 0.80 for women; and/or a body fat percentage of at least about 25% in men or at least about 32% in women) indicates a treatment regimen comprising a folate-containing compound be recommended for and/or administered to the human subject. As shown in Table 42, any one of the folate-responsive biomarkers (selected from biomarker (i) to (xxv)) can be detected in combination with at least one other folate-responsive biomarker as indicated by a "x" symbol in the table, including, e.g., at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four other folate responsive biomarkers. By way of example only, considering column 1 of Table 42, a folate responsive biomarker (i) (corresponding to a SNP at position 27 of SEQ ID NO. 7 or at position 677 of SEQ ID NO. 1) can be detected with one or any combinations of other folate-responsive biomarkers (ii)-(xxv). For example, both folate-responsive biomarkers (i) and (iii) can be selected for detection in the assays, methods, systems and kits described herein. In another embodiment, a combination of three folate responsive biomarkers (i), (iii), and (xvii) can be selected for detection in the assays, methods, systems and kits described herein. In another embodiment, a combination of three folate responsive biomarkers (i), (iii), and (xxv) can be selected for detection in the assays, methods, systems and kits described herein.

Methylenetetrahydrofolate Reductase (MTHFR).

Methylenetetrahydrofolate reductase (MTHFR) is an enzyme that in humans is encoded by the MTHFR gene. SEQ ID NO: 1 corresponds to a portion of the genomic nucleic acid sequence of human wild-type or normal MTHFR gene obtained from NCBI database (NCBI Reference Sequence: NM_005957.4), wherein the nucleotide at position 677 and 1298 of SEQ ID NO: 1 are normal (e.g., wild-type) "C" allele and "A" allele, respectively. Methylenetetrahydrofolate reductase catalyzes the conversion of 5,10-methylenetetrahydrofolate to 5-methyltetrahydrofolate, a cosubstrate for homocysteine remethylation to methionine. Genetic variation in this gene has been previously shown to influence susceptibility to occlusive vascular disease, neural tube defects, colon cancer, acute leukemia, Alzheimer's or vascular dementia, and mutations in this gene are associated with methylenetetrahydrofolate reductase deficiency.

The mutation of the MTHFR nucleotide at position 677 of SEQ ID NO: 1 from "C" allele to "T" allele (C677T) results in a change of amino acid residue from alanine to valine at position 222 of the corresponding amino acid sequence (SEQ ID NO: 4). Such amino acid substitution encodes a thermolabile enzyme with reduced activity. People with the thermolabile form of such enzyme generally have increased levels of homocysteine in their blood. Accordingly, in some embodiments, detection of an increase in levels of homocysteine in a blood sample of a subject with patient can be an indicative of a SNP at position 677 (e.g., C677T) of the MTHFR gene (or SEQ ID NO: 1). In some embodiments, detection of valine at position 222 (e.g., A222V) of the corresponding amino acid sequence (SEQ ID NO: 4), e.g., by mass spectrometry, can indicate a SNP at position 677 (e.g., C677T) of the MTHFR gene (or SEQ ID NO: 1).

At nucleotide 1298 of the MTHFR, there are generally two possibilities: "A" or "C". MTHFR 1298A (leading to a Glu at amino acid residue 429) is the most common while 1298C (leading to an Ala substitution at amino acid 429) is less common. In some embodiments, detection of alanine at position 429 (E429A) of the corresponding amino acid sequence (SEQ ID NO: 4) can indicate a SNP at position 1298 of the MTHFR gene (or SEQ ID NO: 1). Without wishing to be bound by theory, previous studies on human recombinant MTHFR have reported that the protein encoded by 1298C cannot be distinguished from 1298A in terms of activity, thermolability, FAD release, or the protective effect of 5-methyl-THF. (See, e.g., Yamada K. et al. (2001). Proc. Natl. Acad. Sci. U.S.A. 98 (26): 14853-8). It is believed that the C mutation (e.g., A1298C) does not appear to affect the MTHFR protein or result in thermolabile MTHFR, or affect homocysteine levels.

Methods for detecting the SNPs of the MTHFR gene, e.g., C677T, A1298C, or G1793A are well known in the art, for examples, including the methods and primers used in U.S. Pat. No. 6,833,243, which is incorporated herein by reference.

Methionine Synthase (MTR).

Methionine synthase also known as MS, MeSe, MetH is an enzyme that in humans is encoded by the MTR gene (5-methyltetrahydrofolate-homocysteine methyltransferase). SEQ ID NO: 2 corresponds to a portion of the genomic nucleic acid sequence of human wild-type or normal MTR gene obtained from NCBI database (NCBI Reference Sequence: NM 000254.2), wherein the nucleotide at position 2756 of SEQ ID NO: 2 is normal (e.g., wild-type) "A" allele. This enzyme is responsible for the regeneration of methionine from homocysteine. Methionine synthase forms part of the S-adenosylmethionine (SAM) biosynthesis and regeneration cycle. A polymorphism in the MTR gene, an A-to-G transition at position 2756 (e.g., A2756G) of SEQ ID NO: 2 causes an amino acid substitution from aspartic acid to glycine at codon 919 (D919G) of the corresponding amino acid sequence (SEQ ID NO: 5). Accordingly, in some embodiments, detection of glycine at position 919 (e.g., D919G) of the corresponding amino acid sequence (SEQ ID NO: 5), e.g., by mass spectrometry, can indicate a SNP at position 2756 (e.g., A2756G) of the MTR gene (or SEQ ID NO: 2).

Methionine Synthase Reductase (MTRR).

Methionine synthase reductase, also known as MSR, is an enzyme that in humans is encoded by the MTRR gene. SEQ ID NO: 3 corresponds to a portion of the genomic nucleic acid sequence of human wild-type or normal MTRR gene obtained from NCBI database (NCBI Reference Sequence: NM_002454.2), wherein the nucleotide at position 66 of SEQ ID NO: 3 is normal (e.g., wild-type) "A" allele. Methionine is an essential amino acid required for protein synthesis and one-carbon metabolism. Its synthesis is catalyzed by the enzyme methionine synthase. Methionine synthase eventually becomes inactive due to the oxidation of its cob(I)alamin cofactor. Methionine synthase reductase regenerates a functional methionine synthase via reductive methylation, and is a member of the ferredoxin-NADP(+) reductase (FNR) family of electron transferases. MTRR polymorphism, an adenine-to-guanine mutation at position 66 (e.g., A66G) of SEQ ID NO: 3 converts an isoleucine to a methionine amino acid (122M) at position 22 of the corresponding amino acid sequence (SEQ ID NO: 6). Accordingly, in some embodiments, detection of methionine at position 22 (e.g., I22M) of the corresponding amino acid sequence (SEQ ID NO: 6), e.g., by mass spectrometry, can indicate a SNP at position 66 (e.g., A66G) of the MTRR gene (or SEQ ID NO: 3).

Catechol-O-Methyltransferase (COMT).

Catechol-O-methyltransferase is an enzyme responsible for the breakdown of dopamine and norepinephrine, e.g., in the prefrontal cortex. Met/Met are more rapid metabolizers than Val/Val subjects in which are associated with cognitive dysfunction and disease pathology. In some embodiments, a hypomethylated state has led to an overexpression of COMT and greater executive dysfunction. COMT polymorphism (identified by rs4680: SEQ ID NO. 24), an adenine-to-guanine mutation at position 27 of SEQ ID NO. 24 converts a valine (Val) to a methionine (Met) amino acid (Val158Met) at the corresponding position of the amino acid sequence. Accordingly, in some embodiments, detection of methionine at position 158 (e.g., V22M) of the corresponding amino acid sequence (SEQ ID NO. 28), e.g., by mass spectrometry, can indicate a SNP at position 27 of SEQ ID NO. 24.

Reduced Folate Carrier 1 &2 (RCF1 and RCF2).

Reduced folate carrier 1 and 2 (at SLC19A1) are receptors that transport 5-MTHF across various membranes including the choroid plexus and blood brain barrier.

Dopamine receptor D2 (DRD2).

Taq1B and H313H are dopamine receptor polymorphisms that effect dopamine transmission, receptor density, and antipsychotic response.

DNA (cytosine-5)-methyltransferase 3 beta (DNMT3B).

DNA (cytosine-5)-methyltransferase 3 beta is s gene encoding a DNA methyltransferase which is believed to function in de novo methylation, rather than maintenance methylation.

Choline-Phosphate Cytidylytransferase A (PCYT1A).

Choline-phosphate Cytidylytransferase A (PCYT1A) is an enzyme that aids in the transformation of phosphatidylcholine to choline.

GTP Cyclohydrolase I (GCH1).

GTP cyclohydrolase I is part of the folate and biopterin biosynthesis pathways. It is responsible for the hydrolysis of guanosine triphosphate (GTP) to form 7,8-dihydroneopterin 3'-triphosphate. GTPCH is encoded by the gene GCH1 and is the rate-limiting enzyme in tetrahydrobiopterin (THB, BH4) biosynthesis. GCH1 is an essential cofactor in monamine synthesis and NO production.

Folate Hydrolase (Prostate-Specific Membrane Antigen) (FOLH1).

FOLH1 is also known as glutamate carboxypeptidase II, which is an enzyme that in humans is encoded by the FOLH1 (folate hydrolase 1) gene. GCPII is a class II membrane glycoprotein. It catalyzes the hydrolysis of N-acetylaspartylglutamate (NAAG) to glutamate and N-acetylaspartate (NAA).

Dopmaine Active Transporter (DAT).

The dopamine transporter (also dopamine active transporter, DAT, SLC6A3) is a membrane-spanning protein that pumps the neurotransmitter dopamine out of the synapse back into cytosol, from which other transporters sequester DA and NE into vesicles for later storage and release.

GTP Cyclohydrolase 1 Feedback Regulatory Protein (GCHFR).

GTP cyclohydrolase 1 feedback regulatory protein is an enzyme that in humans is encoded by the GCHFR gene. GTP cyclohydrolase 1 feedback regulatory protein binds to and mediates tetrahydrobiopterin inhibition of GTP cyclohydrolase 1 which aids in the production of de novo BH4 production.

Calcium Channel, Voltage-Dependent, L Type, Alpha 1C Subunit (CACNA1C).

Gene CACNA1C encodes an alpha-1 subunit of a voltage-dependent calcium channel. Calcium channels mediate the influx of calcium ions into the cell upon membrane polarization.

Formiminotransferase Cyclodeaminase (FTCD).

Formiminotransferase cyclodeaminase is an enzyme that catalyzes the conversion of formiminoglutamate and tetrahydrofolate into formiminotetrahydrofolate and glutamate.

Methylenetetrahydrofolate Dehydrogenase (NADP+Dependent) 1 (MTHFD 1).

Methylenetetrahydrofolate dehydrogenase (NADP+dependent) 1 is a tri-allelic gene that encodes a protein that possesses three distinct enzymatic activities, methylenetetrahydrofolate dehydrogenase, methenyltetrahydrofolate cyclohydrolase and formate-tetrahydrofolate ligase. Each of these activities catalyzes one of three sequential reactions in the interconversion of 1-carbon derivatives of tetrahydrofolate, which are substrates for methionine, thymidylate, and de novo purine syntheses. A common single nucleotide polymorphism (SNP) at nucleotide 1958 of the MTHFD1 gene (or at position 27 of SEQ ID 27) causes a "G" to "A" transition, which results in an arginine to glutamate substitution at amino acid position 653 in the synthetase domain of the enzyme (See, e.g., Hol et al., (1998) "Molecular genetic analysis of the gene encoding the trifunctional enzyme MTHFD (methylenetetrahydrofolate-dehydrogenase, methenyltetrahydrofolate-cyclohydrolase, formyltetrahydrofolate synthetase) in patients with neural tube defects." Clin Genet. 53: 119-25).

S-Adenosyl Methionine (SAM) and S-Adenosyl Homocysteine (SAH).

S-adenosyl methionine, commonly known as SAM, or SAM-e, or AdoMet, is a natural compound found in all living cells. It is one of the most used enzymatic substrates in biochemical reactions, second only to the universal energy storage and transfer molecule, adenosyl triphosphate (ATP).

S-Adenosyl methionine is a common cosubstrate involved in methyl group transfers. It is made from adenosine triphosphate (ATP) and methionine by methionine adenosyltransferase. Transmethylation, transsulfuration, and aminopropylation are the metabolic pathways that use SAM. SAH is formed by the demethylation of S-adenosyl-L-methionine (SAM). Further details about SAM and SAH, including immunoassays for determining SAM, SAH and/or ratios thereof are described in U.S. Pat. App. No.: US 2009/0263879, which is incorporated herein by reference.

4-Hydroxynonenal (4-HNE)

4-Hydroxynonenal, or 4-hydroxy-2-nonenal or 4-HNE or HNE, ($C_9H_{16}O_2$), is an α,β-unsaturated hydroxyalkenal which is produced by lipid peroxidation in cells. 4-HNE is the primary α,β-unsaturated hydroxyalkenal formed in this process. It is found throughout animal tissue, and in higher quantities during oxidative stress due to the increase in the lipid peroxidation chain reaction, due to the increase in stress events. 4-HNE has been believed to play a key role in cell signal transduction, in a variety of pathways from cell cycle events to cellular adhesion. 4-HNE is also considered as possible causal agents of numerous diseases, such as chronic inflammation, neurodegenerative diseases, adult respiratory distress syndrome, atherogenesis, diabetes and different types of cancer.

Protein residues known to react with 4HNE via 1,4-addition are Cys, His, and Lys. Thus, in some embodiments, expression levels of 4-HNE can be determined by measuring expression levels of 4-HNE adducts, e.g., 4-HNE-His. Commercial ELISA kits for measuring 4-HNE adducts, e.g., OxiSelect™ HNE-His Adduct ELISA Kit are available, e.g., from CellBioLabs.

Test Sample and Collection and Preparation Thereof.

Collections of test samples for at least one analysis performed in the assays and/or methods described herein are well known to those skilled in the art. In some embodiments, a test sample subjected to analysis performed in the assays and/or methods described herein are derived from a biological sample of a subject. The term "biological sample" as used herein denotes a sample taken or isolated from a biological organism, e.g., cell lysate, a homogenate of a tissue sample from a subject or a fluid sample from a subject. The term "biological sample" also includes untreated or pre-treated (or pre-processed) biological samples. In some embodiments, the biological sample can be a biological fluid, including, but not limited to, blood (including whole blood, plasma, cord blood and serum), lactation products (e.g., milk), amniotic fluids, sputum, saliva, urine, semen, cerebrospinal fluid, bronchial aspirate, perspiration, mucus, liquefied feces, synovial fluid, lymphatic fluid, tears, tracheal aspirate, and fractions thereof. In other embodiments, the biological sample can include cell lysate and fractions thereof. For example, cells (such as red blood cells, platelets, white blood cells and any cells circulating in the biological fluid described herein) can be harvested and lysed to obtain a cell lysate. In some embodiments, a test sample or a biological sample is a blood sample. In some embodiments, a test sample or a biological sample can comprise a plasma sample. In some embodiments, a test sample or a biological sample can comprise a saliva sample. In some embodiments, a test sample or a biological sample can comprise a buccal sample. In some embodiments, a test sample or a biological sample can comprise a urine sample. In some embodiments, a test sample or a biological sample can comprise a cerebrospinal fluid sample.

A "biological sample" can contain cells from subject, but the term can also refer to non-cellular biological material, such as non-cellular fractions of blood, saliva, or urine, that can be used to measure plasma/serum biomarker expression levels or determine SNPs. In some embodiments, the sample is from a resection, biopsy, or core needle biopsy. In addition, fine needle aspirate samples can be used. Samples can be either paraffin-embedded or frozen tissue.

The sample can be obtained by removing a sample of cells from a subject, but can also be accomplished by using previously isolated cells (e.g. isolated by another person). In addition, the biological sample can be freshly collected or a previously collected sample.

In some embodiments, the test sample or the biological sample can be a frozen biological sample, e.g., a frozen tissue or fluid sample such as urine, blood, serum or plasma. The frozen sample can be thawed before employing methods, assays and systems described herein. After thawing, a frozen sample can be centrifuged before being subjected to methods, assays and systems described herein.

In some embodiments, a test sample or a biological sample can be a nucleic acid product amplified after polymerase chain reaction (PCR). The nucleic acid product can include DNA, RNA and mRNA and can be isolated from a particular biological sample using any of a number of procedures, which are well-known in the art, the particular isolation procedure chosen being appropriate for the particular biological sample. Methods of isolating and analyzing nucleic acid variants as described above are well known to one skilled in the art and can be found, for example in the Molecular Cloning: A Laboratory Manual, 3rd Ed., Sambrook and Russel, Cold Spring Harbor Laboratory Press, 2001.

In some embodiments, the test sample or the biological sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. In addition, or alternatively, chemical and/or biological reagents can be employed to release nucleic acid or protein from the sample.

The skilled artisan is well aware of methods and processes appropriate for pre-processing of test or biological samples, e.g., blood, required for determination of SNPs or expression levels of serum/plasma biomarkers as described herein.

In some embodiments, the test sample or biological sample is a blood sample, e.g., whole blood, plasma, and serum. In some embodiments, the test sample or biological sample is a whole blood sample. In some embodiments, the test sample or biological sample is a serum sample. In some embodiments, the test sample or biological sample is a plasma sample. In some embodiments, the blood sample can be allowed to dry at room temperature from about 1 hour to overnight, or in the refrigerator (low humidity) for up to several months before subjected to analysis, e.g., SNP analysis. See, for example, Ulvik A. and Ueland P. M. (2001) Clinical Chemistry 47: 2050, for methods of SNP genotyping in unprocessed whole blood and serum by real-time PCR.

To collect a blood sample, by way of example only, the patient's blood can be drawn by trained medical personnel directly into anti-coagulants such as citrate, EDTA PGE, and theophylline. The whole blood can be separated into the plasma portion, the cells, and platelets portion by refrigerated centrifugation at 3500 g for 2 minutes. After centrifugation, the supernatant is the plasma and the pellet is RBC. Since platelets have a tendency to adhere to glass, it is preferred that the collection tube be siliconized. Another method of isolating red blood cells (RBCs) is described in Best, C A et al., 2003, J. Lipid Research, 44:612-620.

Alternatively, serum can be collected from the whole blood. By way of example, about 15 mL of whole blood can be drawn for about 6 mL of serum. The blood can be collected in a hard plastic or glass tube; blood will not clot in soft plastic. The whole blood is allowed to stand at room temperature for 30 minutes to 2 hours until a clot has formed. Then, clot can be carefully separated from the sides of the container using a glass rod or wooden applicator stick and the rest of the sample can be left overnight at 4° C. After which, the sample can be centrifuged, and the serum can be transferred into a clean tube. The serum can be clarified by centrifugation at 1000 g for 10 minutes at 4° C. The serum can be stored at −80° C. before analysis. In such embodiments, carotenoids may not be stable for long periods of time. Detailed described of obtaining serum using collection tubes can be found in U.S. Pat. No. 3,837,376 and is incorporated by reference. Blood collection tubes can also be purchased from BD Diagnostic Systems, Greiner Bio-One, and Kendall Company.

The whole blood can be first separated into platelet-rich plasma and cells (white and red blood cells). Platelet rich plasma (PRP) can be isolated from the blood centrifugation of citrated whole blood at 200 g for 20 minutes. The platelet rich plasma is then transferred to a fresh polyethylene tube. This PRP is then centrifuged at 800 g to pellet the platelets and the supernatant (platelet poor plasma [PPP]) can be saved for analysis, e.g., by ELISA, at a later stage. Platelets can be then gently re-suspended in a buffer such as Tyrodes buffer containing 1 U/ml PGE2 and pelleted by centrifugation again. The wash can be repeated twice in this manner before removing the membrane fraction of platelets by centrifugation with Triton X, and lysing the pellet of platelet for platelet-derived PF4 analyses. Platelets can be lysed using 50 mM Tris HCL, 100-120 mM NaCl, 5 mM EDTA, 1% Igepal and Protease Inhibitor Tablet (complete TM mixture, Boehringer Manheim, Indianapolis, Ind.).

In one embodiment, platelets are separated from whole blood and the SNPs or hsCRP transcripts can be determined therefrom. When whole blood is centrifuged as described herein to separate the blood cells from the plasma, a pellet is formed at the end of the centrifugation, with the plasma above it. Centrifugation separates out the blood components (RBC, WBC, and platelets) by their various densities. The RBCs are denser and will be the first to move to the bottom of the collection/centrifugation tube, followed by the smaller white blood cells, and finally the platelets. The plasma fraction is the least dense and is found on top of the pellet. The "buffy coat" which contains the majority of platelets will be sandwiched between the plasma and above the RBCs. Centrifugation of whole blood (with anti-coagulant, PGE and theophylline) can produce an isolated platelet rich "buffy coat" that lies just above the buoy. The buffy coat contains the concentrated platelets and white blood cells.

In another embodiment, platelets can be separated from blood according to methods described in U.S. Pat. No. 4,656,035 using lectin to agglutinate the platelets in whole blood. Alternatively, the methods and apparatus described in U.S. Pat. No. 7,223,346 can be used involving a platelet collection device comprising a centrifugal spin-separator container with a cavity having a longitudinal inner surface in order to collect the "buffy coat" enriched with platelets after centrifugation. As another alternative, the methods and apparatus as described in WO/2001/066172 can be used. Each of these references is incorporated by reference herein.

In another embodiment, platelets can be isolated by the two methods described in A. L. Copley and R. B. Houlihan, Blood, 1947, 2:170-181, which is incorporated by reference herein. Both methods are based on the principle that the platelet layer can be obtained by repeated fractional centrifugation.

In some embodiments, apparatus and related methods are used to obtain the sample, for example, machines described in U.S. Pat. Nos. 4,120,448, 5,879,280 and 7,241,281, which are incorporated herein by reference.

Methods for collecting different types of a test sample are known in the art and can be employed to prepare a test sample for the assays and methods described herein.

SNPs, Polymorphisms and Alleles

The genomes of all organisms undergo spontaneous mutation in the course of their continuing evolution, generating variant forms of progenitor genetic sequences (Gusella, Ann. Rev. Biochem. 55, 831-854 (1986)). The coexistence of multiple forms of a genetic sequence gives rise to genetic polymorphisms, including SNPs.

Approximately 90% of all polymorphisms in the human genome are SNPs. SNPs are single base positions in DNA at which different alleles, or alternative nucleotides, exist in a population. The SNP position (interchangeably referred to herein as SNP, SNP site, SNP allele or SNP locus) is usually preceded by and followed by highly conserved sequences of the allele (e.g., sequences that vary in less than 1/100 or 1/1000 members of the populations). An individual can be homozygous or heterozygous for an allele at each SNP position. A SNP can, in some instances, be referred to as a "cSNP" to denote that the nucleotide sequence containing the SNP is an amino acid coding sequence.

A SNP can arise from a substitution of one nucleotide for another at the polymorphic site. Substitutions can be transitions or transversions. A transition is the replacement of one purine nucleotide by another purine nucleotide, or one pyrimidine by another pyrimidine. A transversion is the replacement of a purine by a pyrimidine, or vice versa. A SNP can also be a single base insertion or deletion variant referred to as an "in/del" (Weber et al., "Human diallelic insertion/deletion polymorphisms", Am J Hum Genet October 2002; 71(4):854-62).

A synonymous codon change, or silent mutation/SNP (the terms "SNP" and "mutation" are used herein interchangeably), is one that does not result in a change of amino acid due to the degeneracy of the genetic code. A substitution that changes a codon coding for one amino acid to a codon coding for a different amino acid (i.e., a non-synonymous codon change) is referred to as a missense mutation. A nonsense mutation results in a type of non-synonymous codon change in which a stop codon is formed, thereby leading to premature termination of a polypeptide chain and a truncated protein. A read-through mutation is another type of non-synonymous codon change that causes the destruction of a stop codon, thereby resulting in an extended polypeptide product. While SNPs can be bi-, tri-, or tetra-allelic, the vast majority of the SNPs are bi-allelic, and are thus often referred to as "bi-allelic markers", or "di-allelic markers".

A major database of human SNPs is maintained at NCBI as dbSNP, and it contains data for unique human SNPs consisting of $1.78 \times 10^8$ submitted SNP (identified by an "ss" number) and $5.2 \times 10^7$ reference SNP (identified by an "rs" number), as of Build History 135: human_9606 based on NCBI human genome build 37.3. The rs numbers are unique, do not change and allow analysis of the particularly identified SNP in any genetic sample. Throughout the specification, the SNPs described herein can also be identified by an "rs" number. For example, the SNP at position 677 of SEQ ID NO: 1 can be identified by rs 1801133; the SNP at position 1298 of SEQ ID NO: 1 can be identified by rs 1801131; the SNP at position 2756 of SEQ ID NO: 2 can be identified by rs 1805087; The SNP at position 66 of SEQ ID NO: 2 can be identified by rs 1801394. With the "rs" numbers known for each SNP, one of skill in the art will be able to determine the position of a specific SNP within a respective chromosome.

While a SNP could conceivably have three or four alleles, nearly all SNPs have only two alleles. Analysis of the SNPs identified herein generally relies on the two alleles that are listed in connection with each SNP. For example, the SNPs at the MTHFR locus described herein are each indicated to have two alleles, "C" or "T" at the position 677 of SEQ ID NO. 1, and "A" or "C" at the position 1298 of SEQ ID NO. 1, wherein SEQ ID NO. 1 is a portion of a genomic nucleic acid sequence of MTHFR. The presence of at least one allele "T" at position 677 of SEQ ID NO. 1 and/or at least one allele "C" at position 1298 of SEQ ID NO. 1 indicates that a subject with depression is recommended for a treatment regimen comprising a folate-containing compound. The SNP at the MTR locus described herein is indicated to have two alleles, "A" or "G". The presence of at least one allele "G" at position 2756 of SEQ ID NO. 2, wherein SEQ ID NO: 2 is a portion of a genomic nucleic acid sequence of methionine synthase (MTR), indicates the subject recommended for a treatment regimen comprising a folate-containing compound. The SNP at the MTRR locus described herein is indicated to have two alleles, "A" or "G". The presence of at least one allele "G" at position 66 of SEQ ID NO. 3, wherein SEQ ID NO. 3 is a portion of a genomic nucleic acid sequence of methionine synthase reductase (MTRR), indicates the subject recommended for a treatment regimen comprising a folate-containing compound.

Those skilled in the art will readily recognize that nucleic acid molecules can be double-stranded molecules and that reference to a particular site on one strand refers, as well, to the corresponding site on a complementary strand. In defining a SNP position, SNP allele, or nucleotide sequence, reference to an adenine "A", a thymine "T" (uridine "U"), a cytosine "C", or a guanine "G" at a particular site on one strand of a nucleic acid molecule also defines the thymine "T" (uridine "U"), adenine "A", guanine "G", or cytosine "C" (respectively) at the corresponding site on a complementary strand of the nucleic acid molecule. Thus, reference can be made to either strand in order to refer to a particular SNP position, SNP allele, or nucleotide sequence. Probes and primers can be designed to hybridize to either strand and SNP genotyping methods disclosed herein can generally target either strand.

Accordingly, the claims are intended to cover analysis of the opposite strand as well. For the opposite-strand analysis, the SNPs at the MTHFR locus is allele "A" at position 677 or allele "G" at position 1298 of the complementary sequence of SEQ ID NO. 1, wherein SEQ ID NO. 1 is a portion of a genomic nucleic acid sequence of methylenetetrahydrofolate reductase (MTHFR); while the SNP at the MTR locus is allele "C" at position 2756 of the complementary sequence of SEQ ID NO. 2, wherein SEQ ID NO. 2 is a portion of a genomic nucleic acid sequence of methionine synthase (MTR); and the SNP at the MTRR locus is allele "C" at position 66 of the complementary sequence of SEQ ID NO. 3, wherein SEQ ID NO. 3 is a portion of a genomic nucleic acid sequence of methionine synthase reductase (MTRR).

Identification method of SNPs can be of either a positive-type (inclusion of an allele) or a negative-type (exclusion of an allele). Positive-type methods determine the identity of a nucleotide contained in a polymorphic site, whereas negative-type methods determine the identity of a nucleotide not present in a polymorphic site. Thus, a wild-type site can be identified either as wild-type or not mutant. For example, at a biallelic polymorphic site where the wild-type allele contains thymine and the mutant allele contains cytosine, a site can be positively determined to be either thymine or cytosine or negatively determined to be not thymine (and thus cytosine) or not cytosine (and thus thymine)

Methods for Detecting the SNPs Disclosed Herein

According to one aspect described herein, a method for determining whether a subject is homozygous for a polymorphism, heterozygous for a polymorphism, or lacking the polymorphism altogether (i.e. homozygous wildtype) is encompassed. As an exemplary embodiment only, a method to detect the C>T variance at position 677 of SEQ ID NO: 1, a method for determining the allele, heterozygous for the C- and T-alleles, or homozygous for the C-allele or the T-allele at the SNP loci are provided. Substantially any method of detecting any allele of the SNPs described herein, such as restriction enzyme digestion, allele-specific probe hybridization, allele-specific primer extension, allele specific amplification, sequencing, 5' nuclease digestion, molecular beacon assay, oligonucleotide ligation assay, size analysis, and single-stranded conformational polymorphism, can be used.

In one embodiment, an allelic discrimination method for identifying the genotypes of SNPs of a human described herein can be used. Such a method may involve the use of distinct oligonucleotide probes, for example one complementary to a sequence having a major allele and another complementary to a sequence having a minor allele. The allelic discrimination method also involves use of at least one, and preferably a pair of amplification primers for amplifying a reference region of the MTHFR, MTR or MTRR locus of a subject. The reference region includes at least a portion of the human MTHFR, MTR or MTRR locus.

For full-length genes and entire protein-coding sequences, a SNP flanking sequence can be, for example, up to about 10 Kb, 9 Kb, 8 Kb, 7 Kb, 6 Kb, 5 Kb, 4 Kb, 3 Kb, 2 Kb, 1 Kb on either side of the SNP. Furthermore, in such instances, the isolated nucleic acid molecule comprises exonic sequences (including protein-coding and/or non-coding exonic sequences), but may also include intronic sequences. Thus, any protein coding sequence may be either contiguous or separated by introns. The important point is that the nucleic acid is isolated from remote and unimportant flanking sequences and is of appropriate length such that it can be subjected to the specific manipulations or uses described herein such as recombinant protein expression, preparation of probes and primers for assaying the SNP position.

The probe is preferably a DNA oligonucleotide having a length in the range from about 20 to about 40 nucleotide residues, preferably from about 20 to about 30 nucleotide residues, and more preferably having a length of about 25 nucleotide residues. In one embodiment, the probe is rendered incapable of extension by a PCR-catalyzing enzyme such as Taq polymerase, for example by having a fluorescent probe attached at one or both ends thereof. Although non-labeled oligonucleotide probes can be used in the kits and methods described herein, the probes are preferably detectably labeled. Exemplary labels include radionuclides, light-absorbing chemical moieties (e.g. dyes), fluorescent moieties, and the like. Preferably, the label is a fluorescent moiety, such as 6-carboxyfluorescein (FAM), 6-carboxy-4,7,2',7'-tetrachlorofluoroscein (TET), rhodamine, JOE (2,7-dimethoxy-4,5-dichloro-6-carboxyfluorescein), HEX (hexachloro-6-carboxyfluorescein), or VIC.

In some embodiments, the probe can comprise both a fluorescent label and a fluorescence-quenching moiety such as 6-carboxy-N,N,N',N'-tetramethylrhodamine (TAMRA), or 4-(4'-dimethlyaminophenylazo)benzoic acid (DABCYL). When the fluorescent label and the fluorescence-quenching moiety are attached to the same oligonucleotide and separated by no more than about 40 nucleotide residues, and preferably by no more than about 30 nucleotide residues, the fluorescent intensity of the fluorescent label is diminished. When one or both of the fluorescent label and the fluorescence-quenching moiety are separated from the oligonucleotide, the intensity of the fluorescent label is no longer diminished. Preferably, the probe for use in the assays, methods, systems and kits described herein can have a fluorescent label attached at or near (i.e. within about 10 nucleotide residues of) one end of the probe and a fluorescence-quenching moiety attached at or near the other end. Degradation of the probe by a PCR-catalyzing enzyme releases at least one of the fluorescent label and the fluorescence-quenching moiety from the probe, thereby discontinuing fluorescence quenching and increasing the detectable intensity of the fluorescent labels. Thus, cleavage of the probe (which, as discussed above, is correlated with complete complementarity of the probe with the target portion) can be detected as an increase in fluorescence of the assay mixture.

If detectably different labels are used, more than one labeled probe can be used. For example, the assay mixture can contain a first probe which is completely complementary to the target portion of the polymorphism of the MTHFR, MTR, or MTRR gene and to which a first label is attached, and a second probe which is completely complementary to the target portion of the wildtype or major allele. In some embodiments, by way of example only, the assay mixture can contain a first probe which is completely complementary to the target portion of the polymorphism of the MTHFR gene and to which a first label is attached, and a second probe which is completely complementary to the target portion of another gene, e.g., MTR or MTRR. When two probes are used, the probes are detectably different from each other, having, for example, detectably different size, absorbance, excitation, or emission spectra, radiative emission properties, or the like. For example, a first probe can be completely complementary to the target portion of the polymorphism and have FAM and TAMRA attached at or near opposite ends thereof. The first probe can be used in the methods, assays, systems and kits described herein together with a second probe which is completely complementary to the target portion of the wildtype allele and has TET and TAMRA attached at or near opposite ends thereof. Fluorescent enhancement of FAM (i.e. effected by cessation of fluorescence quenching upon degradation of the first probe by Taq polymerase) can be detected at one wavelength (e.g. 518 nanometers), and fluorescent enhancement of TET (i.e. effected by cessation of fluorescence quenching upon degradation of the second probe by Taq polymerase) can be detected at a different wavelength (e.g. 582 nanometers).

Any approach that detects mutations or polymorphisms in a gene can be used to detect the presence or absence of SNP biomarkers described herein, including but not limited to single-strand conformational polymorphism (SSCP) analysis (Orita et al. (1989) Proc. Natl. Acad. Sci. USA 86:2766-2770), heteroduplex analysis (Prior et al. (1995) Hum. Mutat. 5:263-268), oligonucleotide ligation (Nickerson et al. (1990) Proc. Natl. Acad. Sci. USA 87:8923-8927) and hybridization assays (Conner et al. (1983) Proc. Natl. Acad. Sci. USA 80:278-282). Traditional Taq polymerase PCR-based strategies, such as PCR-RFLP, allele-specific amplification (ASA) (Ruano and Kidd (1989) Nucleic Acids Res. 17:8392), single-molecule dilution (SMD) (Ruano et al. (1990) Proc. Natl. Acad. Sci. USA 87:6296-6300), and coupled amplification and sequencing (CAS) (Ruano and Kidd (1991) Nucleic Acids Res. 19:6877-6882), are easily performed and highly sensitive methods to determine haplotypes (Michalatos-Beloin et al. (1996) Nucleic Acids Res. 24:4841-4843; Barnes (1994) Proc. Natl. Acad. Sci. USA 91:5695-5699; Ruano and Kidd (1991) Nucleic Acids Res. 19:6877-6882).

Restriction Fragment Length Polymorphism Analysis

In some embodiments, restriction enzymes can be utilized to identify variances or a polymorphic site using "restriction fragment length polymorphism" (RFLP) analysis (Lentes et al., Nucleic Acids Res. 16:2359 (1988); and C. K. McQuitty et al., Hum. Genet. 93:225 (1994)). In RFLP, at least one target polynucleotide is digested with at least one restriction enzyme and the resulting restriction fragments are separated based on mobility in a gel. Typically, smaller fragments migrate faster than larger fragments. Consequently, a target polynucleotide that contains a particular restriction enzyme recognition site will be digested into two or more smaller fragments, which will migrate faster than a larger fragment lacking the restriction enzyme site. Knowledge of the nucleotide sequence of the target polynucleotide, the nature of the polymorphic site, and knowledge of restriction enzyme recognition sequences guide the design of such assays. In another embodiment, restriction site analysis of particular nucleotide sequence to identify a nucleotide at a polymorphic site is determined by the presence or absence of a restriction enzyme site. A large number of restriction enzymes are known in the art and, taken together, they are capable of recognizing at least one allele of many polymorphisms. However, such single nucleotide polymorphisms (SNPs) rarely result in changes in a restriction endonuclease site. Thus, SNPs are rarely detectable by restriction fragment length analysis.

Ligation Based Assays (e.g., Oligonucleotide Ligation Assay)

A number of approaches use DNA ligase, an enzyme that can join two adjacent oligonucleotides hybridized to a DNA template. In Oligonucleotide Ligaton Assay (OLA) the sequence surrounding the mutation site is first amplified and one strand serves as a template for three ligation probes, two of these are ASO (allele-specific oligonucleotides) and a third common probe. Numerous approaches cane be used for the detection of the ligated products, for example the ASOs with differentially labeled with fluorescent of hapten labels and ligated products detected by fluorogenic of colorimetric enzyme-linked immunosorbent assays (To be et al, Nucleic Acid Res, 1996; 24; 3728-32). For electrophorosis-based systems, use of a morbidity modifier taqgs or variation in probe length coupled with fluorescence detection enables the multiplex genotyping of several single nucleotide substitutions in a single tube (Baron et al, 1997; Clinical Chem., 43; 1984-6). When used on arrays, ASOs can be spotted at specific locations or addresses on a chip, PCR amplified DNA can then be added and ligation to labeled oligonucleotides at specific addresses on the array measured (Zhong et al, Proc Natl Acad Sci 2003; 100; 11559-64).

Single-Base Extension

Single base-extension or minisequencing involves annealing an oligonucleotide primer to the single strand of a PCR product and the addition of a single dideoxynucleotide by thermal DNA polymerase. The oligonucleotide is designed to be one base short of the mutation site. The dideoxynucleotide incorporated is complementary to the base at the mutation site. Approaches can use different fluorescent tags or haptens for each of the four different dideoxynucleotides (Pastinen et al, Clin Chem 1996, 42; 1391-7). The dideoxynucleotide differ in molecular weight and this is the basis for single-base extension methods utilizing mass-spectrometry, and genotyping based on the mass of the extended oligonucleotide primer, can be used, for example matrix-assisted laser adsorption/ionization time-of flight mass spectrometry or MALDI-TOF (Li et al, Electrophoresis, 1999, 20; 1258-65), which is quantitative and can be used to calculate the relative allele abundance making the approach suitable for other applications such as gene dosage studies (for example for estimation of allele frequencies on pooled DNA samples).

Minisequencing or Microsequencing by MALDI-TOF can be performed by means known by persons skilled in the art. In a variation of the MALDI-TOF technique, some embodiments can use the Sequenom's Mass Array Technology (www.sequenom.com) (Sauser et al, Nucleic Acid Res, 2000, 28; E13 and Sauser et al, Nucleic Acid Res 2000, 28: E100). and also the GOOD Assay (Sauer S et al, Nucleic Acid Res, 2000; 28, E13 and Sauer et al, Nucleic Acid Res, 2000; 28:E100).

In some embodiments, variations of MALDI-TOF can be performed for analysis of variances in the genes associated with SNPs described herein. For example, MALDI and electrospray ioinization (ESI) (Sauer S. Clin Chem Acta, 2006; 363; 93-105) can also be used in various aspects described herein.

Hybridization Based Genotyping (e.g., Allele-Specific Amplification (ASA))

Allele-specific Amplification is also known as amplification refectory mutation system (ARMS) uses allele specific oligonucleotides (ASO) PCR primers and is an well established and known PCR based method for genotyping (Newton et al, J Med Genet, 1991; 28; 248-51). Typically, one of the two oligonucleotide primers used for the PCR binds to the mutation site, and amplification only takes place if the nucleotide of the mutation is present, with a mismatch being refractory to amplification. The resulting PCR Products can be analyzed by any means known to persons skilled in the art. In a variation of the approach, termed mutagenically separated PCR (MS-PCR) the two ARMS primer of different lengths, one specific for the normal gene and one for the mutation are used, to yield PCR procures of different lengths for the normal and mutant alleles (Rust et al, Nucl Acids Res, 1993; 21; 3623-9). Subsequent gel electrophoresis, for example will show at least one of the two allelic products, with normal, mutant or both (heterozygote) genes. A further variation of this forms the basis of the Masscode System™ (www.bioserve.com) which uses small molecular weight tags covalently attached through a photo-cleavable linker to the ARMS primers, with each ARMS primers labeled with a tag of differing weight (Kokoris et al, 2000, 5; 329-40). A catalogue of numerous tags allows simultaneous amplification/genotyping (multiplexing) of 24 different targets in a single PCR reaction. For any one mutation, genotyping is based on comparison of the relative abundance of the two relevant mass tags by mass spectrometry.

Normal or mutant alleles can be genotyped by measuring the binding of allele-specific oligonucleotides (ASO) hybridization probes. In such embodiments, two ASO probes, one complementary to the normal allele and the other to the mutant allele are hybridized to PCR-amplified DNA spanning the mutation site. In some embodiments, the amplified products can be immobilized on a solid surface and hybridization to radiolabelled oligonucleotides such as known as a 'dot-blot' assay. In alternative embodiments, the binding of the PCR products containing a quantifiable label (e.g., biotin or fluorescent labels) to a solid phase allele-specific oligonucleotide can be measured. Alternatively, for a reverse hybridization assay, or "reverse dot-blot" the binding of PCR products containing a quantifiable label (for example but not limited to biotin or fluorescent labels) to a solid phase allele-specific oligonucleotide can be measured. In some embodiments, the use of microarrays comprising hundreds of ASO immobilized onto a solid support surfaces to form an array of ASO can also be used for large scale genotyping of multiple single polymorphisms simultaneously, for example Affymetrix GENECHIP® Mapping 10K Array, which can easily be performed by persons skilled in the art.

Homogenous Assays

Homogenous assays, also called "closed tube" arrays, genomic DNA and all the reagents required for the amplification and genotyping are added simultaneously. Genotyping can be achieved without any post-amplification processing. In some embodiments, one such homogenous assay is the 5' fluorogenic nuclease assay, also known as the TAQMAN® Assay (Livak et al, Genet Anal, 1999; 14:143-9) and in alternative embodiments Melting curve analyses of FRET probes are used. Such methods are carried out using "real-time" thermocyclers, and utilize two dual-labeled ASO hybridization probes complementary to normal and mutant alleles, where the two probes have different reported labels but a common quencher dye. In such embodiments, the changes in fluorescence characteristics of the probes upon binding to PCR products of target genes during amplification enables "real-time" monitoring of PCR amplification and differences in affinity of the fluorogenic probes for the PCR products of normal and mutant genes enables differentiation of genotypes. The approach uses two dual-labeled ASO hybridization probes complementary to the mutant and normal alleles. The two probes have different fluorescent reported dyes but a common quencher dye. When intact, the probes do not fluoresces due to the proximity of the reporter and quencher dyes. During annealing phase of PCR, two probes compete for hybridization to their target sequences, downstream of the primer sites and are subsequently cleaved by 5' nuclease activity of Thermophilis aquaticus (Taq) polymerase as the primer is extended, resulting in the separation of the reporter dyes from the quencher. Genotyping is determined by measurement of the fluorescent intensity of the two reporter dyes after PCR amplification. Thus, when intact the probes do not fluoresce due to the proximity of the quencher dyes, whereas during the annealing phase of the PCR the probes compete for hybridization of the target sequences and the separation of one of the probes from the quencher which can be detected.

Melting-Curve of FRET Hybridization

Melting-curve analysis of FRET hybridization is another approach that can be used to detect the presence or absence of SNP biomarkers described herein. Briefly, the reaction includes two oligonucleotide probes which when in close proximity forms a fluorescent complex, where one probe often termed the "mutant sensor" probe is designed to specifically hybridize across the mutation site and the other probe (often referred to as the "anchor probe") hybridizes to an adjacent site. Fluorescent light is emitted by the "donor" excites the "acceptor" fluorophore creasing a unique fluorogenic complex, which only forms when the probes bind to adjacent sites on the amplified DNA. The "sensor" probe is complementary to either the normal or the mutant allele. Once PCR is complete, heating of the sample through the melting temperatures of the probe yields a fluorescent temperature curve which differs for the mutant and normal allele.

A variation of the FRET hybridization method is the LCGREEN™ method, which obviates the requirement for fluorescent labeled probes altogether. LCGREEN™ is a sensitive highly fluorogenic double-stranded DNA (dsDNA) binding dye that is used to detect the dissociation of unlabelled probes (Liew et al, Clin Chem, 2004; 50; 1156-64 and Zhou et al, Clin Chem, 2005; 51; 1761 2). The method uses unlabeled allele-specific oligonucleotides probes that are perfectly complementary either to the mutant or normal allele, and the mismatch of the ASO/template double strand DNA complex results in a lower melting temperature and an earlier reduction in fluorescent signal form the dsDNA binding dye with increasing temperature.

The OLA can also be performed by the use of FRET probes (Chen et al, Genome Res, 1998; 8: 549-56). In such an embodiment, the PCR/ligation mix contains PCR primers, a thermostable DNA polymerase without 5' exonuclease activity (to prevent the cleavage of ligation probes during the ligation phase), a thermostable DNA ligase as well as the oligonucleotides for the ligation reaction. The ligation of the ASO each have a different acceptor fluorophore and the third ligation oligonucleotide which binds adjacently to the ASO has a donor fluorophore. The three ligation oligonucleotides are designed to have a lower melting temperature than the annealing temperature for the PCR primers in order to prevent their interference in PCR amplification. Following PCR, the temperature is lowered to allow ligation to proceed. Ligation results in FRET between donor and acceptor dyes, and alleles can be discerned by comparing the fluorescence emission of the two dyes.

Molecular Beacon Assays

Further, variations of the homogenous PCR- and hybridization based techniques to detect polymorphisms can also be used to detect the presence or absence of SNP biomarkers described herein. For example, the use of Molecular Beacons (Tyagi et al, Nat Biotech 1998; 16; 49-53) and SCORPION® Probes (Thelwell et al, Nucleic Acid Res 2000; 28; 3752-61). Molecular Beacons are comprised of oligonucleotides that have fluorescent reporter and dyes at their 5' and 3' ends, with the central portion of the oligonucleotide hybridizing across the target sequence, but the 5' and 3' flanking regions are complementary to each other. When not hybridized to their target sequence, the 5' and 3' flanking regions hybridize to form a stem-loop structure, and there is little fluorescence because of the proximity of the reported and the quencher dyes. However, upon hybridization to their target sequence, the dyes are separated and there is a large increase in the fluorescence. Mismatched probe-target hybrids dissociate at substantially lower temperatures than exactly matched complementary hybrids. There are a number of variations of the "molecular Beacon" approach. In some embodiments, such a variation includes use of SCORPION® Probes which are similar but incorporate a PCR primer sequence as part of the probe (Thelwell et al, Nucleic Acid Res 2000; 28; 3752 61). In another variation, 'duplex' format gives a better fluorescent signal (Solinas et al, Nucleic Acid Res, 2001, 29; E96).

In another embodiment, polymorphisms can be detected by genotyping using a homogenous or real-time analysis on whole blood samples, without the need for DNA extraction or real-time PCR. Such a method is compatible with FRET and TAQMAN® (Cantley et al, Clin Chem, 2005; 51; 2025-30) enabling extremely rapid screening for the particular polymorphism of interest.

Fluorescent Polarization (FP)

In FP, the degree to which the emitted light remains polarized in a particular plane is proportional to the speed at which the molecules rotate and tumble in solution. Under constant pressure, temperature and viscosity, FP is directly related to the molecular weight of a fluorescent species. Therefore, when a small fluorescent molecule is incorporated into a larger molecule, there is an increase in FP. FP can be used in for genotyping of polymorphisms of interest (Chen et al, Genome Res, 1999; 9: 492-8 and Latif et al, Genome Res, 2001; 11; 436-40). FP can be utilized in 5' nuclease assay (as described above), where the oligonucleotide probe is digested to a lower molecule weight species, for example is amenable to analysis by FP, but with the added benefit of not requiring a quencher. For example, Perkin-Elmers AcycloPrime™-FP SNP Detection Kit can be used as a FP minisequencing method. Following PCR amplification, unicoportated primers and nucleotides are degraded enzymatically, the enzymes heat inactivated and a minisequencing reaction using DNA polymerase and fluorescent-labeled dideoxynucleotides performed. FP is then measured, typically in a 96- to 386-well plate format on a FP-plate reader.

Pyrosequencing

In some embodiments, the primer extension reaction and analysis is performed using PYROSEQUENCING™ (Uppsala, Sweden) which essentially is sequencing by synthesis. A sequencing primer, designed directly next to the nucleic acid differing between the disease-causing mutation and the normal allele or the different SNP alleles is first hybridized to a single stranded, PCR amplified DNA template from the individual, and incubated with the enzymes, DNA polymerase, ATP sulfurylase, luciferase and apyrase, and the substrates, adenosine 5' phosphosulfate (APS) and luciferin. One of four deoxynucleotide triphosphates (dNTP), for example, corresponding to the nucleotide present in the mutation or polymorphism, is then added to the reaction. DNA polymerase catalyzes the incorporation of the dNTP into the standard DNA strand. Each incorporation event is accompanied by release of pyrophosphate (PPi) in a quantity equimolar to the amount of incorporated nucleotide. Consequently, ATP sulfurylase converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a PYROGRAM™. Each light signal is proportional to the number of nucleotides incorporated and allows a clear determination of the presence or absence of, for example, the mutation or polymorphism. Thereafter, apyrase, a nucleotide degrading enzyme, continuously degrades unincorporated dNTPs and excess ATP. When degradation is complete, another dNTP is added which corresponds to the dNTP present in for example the selected SNP. Addition of dNTPs is performed one at a time. Deoxyadenosine alfa-thio triphosphate (dATPS) is used as a substitute for the natural deoxyadenosine triphosphate (dATP) since it is efficiently used by the DNA polymerase, but not recognized by the luciferase. For detailed information about reaction conditions for the PYROSEQUENCING, see, e.g. U.S. Pat. No. 6,210,891, which is incorporated herein by reference.

Invader® Assay

Alternatively, an INVADER® assay can be used (Third Wave Technologies, Inc (Madison, Wis.)). This assay is generally based upon a structure-specific nuclease activity of a variety of enzymes, which are used to cleave a target-dependent cleavage structure, thereby indicating the presence of specific nucleic acid sequences or specific variations thereof in a sample (see, e.g. U.S. Pat. No. 6,458,535). For example, an INVADER® operating system (OS), provides a method for detecting and quantifying DNA and RNA. The INVADER® OS is based on a "perfect match" enzyme-substrate reaction. The INVADER® OS uses proprietary CLEAVASE® enzymes (Third Wave Technologies, Inc (Madison, Wis.)), which recognize and cut only the specific structure formed during the INVADER® process which structure differs between the different alleles selected for detection, i.e. the disease-causing allele and the normal allele as well as between the different selected SNPs. Unlike the PCR-based methods, the INVADER® OS relies on linear amplification of the signal generated by the INVADER® process, rather than on exponential amplification of the target.

In the INVADER® process, two short DNA probes hybridize to the target to form a structure recognized by the CLEAVASE® enzyme. The enzyme then cuts one of the probes to release a short DNA "flap." Each released flap binds to a fluorescently-labeled probe and forms another cleavage structure. When the CLEAVASE® enzyme cuts the labeled probe, the probe emits a detectable fluorescence signal.

Mutations or polymorphisms can also be detected using allele-specific hybridization followed by a MALDI-TOF-MS detection of the different hybridization products. In the preferred embodiment, the detection of the enhanced or amplified nucleic acids representing the different alleles is performed using matrix-assisted laser desorption ionization/time-of-flight (MALDI-TOF) mass spectrometric (MS) analysis described in the Examples below. This method differentiates the alleles based on their different mass and can be applied to analyze the products from the various above-described primer-extension methods or the INVADER® process.

Gel Migration-Based Methods (e.g., Single Stranded Conformation Polymorphism)

In other embodiments, alterations in electrophoretic mobility are used to identify the particular allelic variant. For example, single strand conformation polymorphism (SSCP) can be used to detect differences in electrophoretic mobility between mutant and wild type nucleic acids (Orita et al. (1989) Proc Natl. Acad. Sol USA 86:2766; Cotton (1993) Mutat. Res. 285:125-144 and Hayashi (1992) Genet Anal Tech Appl 9:73-79). Single-stranded DNA fragments of sample and control nucleic acids are denatured and allowed to renature. The secondary structure of single-stranded nucleic acids varies according to the sequence, the resulting alteration in electrophoretic mobility enables the detection of even a single base change. Alterations in the mobility of the resultant products are thus indicative of a base change. Suitable controls and knowledge of the "normal" migration patterns of the wild-type alleles can be used to identify polymorphic variants. The DNA fragments can be labeled or detected with labeled probes. The sensitivity of the assay can be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the identity of the allelic variant is obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to insure that it does not completely denature, for, example by adding a GC clamp of approximately 40 bp of high-melting GC rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Other Assays

Other methods for genetic screening can be used to detect the presence or absence of any of the SNP biomarkers described herein, for example, to detect mutations in genomic DNA, cDNA and/or RNA samples. Methods commonly used, or newly developed or methods yet unknown are encompassed for use in detection of the presence or absence of any of the SNP biomarkers described herein. Examples of newly discovered methods include for example, but are not limited to; SNP mapping (Davis et al, Methods Mol Biology, 2006; 351; 75-92); Nanogen Nano Chip, (keen-Kim et al, 2006; Expert Rev Mol Diagnostic, 6; 287-294); Rolling circle amplification (RCA) combined with circularable oligonucleotide probes (c-probes) for the detection of nucleic acids (Zhang et al, 2006: 363; 61-70), luminex XMAP system for detecting multiple SNPs in a single reaction vessel (Dunbar S A, Clin Chim Acta, 2006; 363; 71-82; Dunbar et al, Methods Mol Med, 2005; 114: 147-1471) and enzymatic mutation detection methods (Yeung et al, Biotechniques, 2005; 38; 749-758).

In one embodiment, one method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

In such embodiments, protection from cleavage agents (such as a nuclease, hydroxylamine or osmium tetroxide and with piperidine) can be used to detect mismatched bases in RNA/RNA DNA/DNA, or RNA/DNA heteroduplexes (see, e.g., Myers et al. (1985) Science 230:1242). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene of interest with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249, Cotton et al. (1988) Proc. Natl. Acad. Sci. USA 85:4397; Saleeba et al. (1992) Methods Enzy. 217:286-295. In another embodiment, the control or sample nucleic acid is labeled for detection.

U.S. Pat. No. 4,946,773 describes an RNaseA mismatch cleavage assay that involves annealing single-stranded DNA or RNA test samples to an RNA probe, and subsequent treatment of the nucleic acid duplexes with RNaseA. For the detection of mismatches, the single-stranded products of the RNaseA treatment, electrophoretically separated according to size, are compared to similarly treated control duplexes. Samples containing smaller fragments (cleavage products) not seen in the control duplex are scored as positive. The use of RNaseI for mismatch detection is also described in literature from Promega Biotech. Promega markets a kit containing RNaseI that is reported to cleave three out of four known mismatches.

In one embodiment, a long-range PCR (LR-PCR) is used to detect mutations or polymorphisms. LR-PCR products are genotyped for mutations or polymorphisms using any genotyping methods known to one skilled in the art, and haplotypes inferred using mathematical approaches (e.g., Clark's algorithm (Clark (1990) Mol. Biol. Evol. 7:111-122).

For example, methods including complementary DNA (cDNA) arrays (Shalon et al., Genome Research 6(7):639-45, 1996; Bernard et al., Nucleic Acids Research 24(8): 1435-42, 1996), solid-phase mini-sequencing technique (U.S. Pat. No. 6,013,431, Suomalainen et al. Mol. Biotechnol. June; 15(2):123-31, 2000), ion-pair high-performance liquid chromatography (Doris et al. J. Chromatogr. A can 8; 806(1):47-60, 1998), and 5' nuclease assay or real-time RT-PCR (Holland et al. Proc Natl Acad Sci USA 88: 7276-7280, 1991), or primer extension methods described in the U.S. Pat. No. 6,355,433, can be used.

Another method to detect mutations or polymorphisms is by using fluorescence tagged dNTP/ddNTPs. In addition to use of the fluorescent label in the solid phase mini-sequencing method, a standard nucleic acid sequencing gel can be used to detect the fluorescent label incorporated into the PCR amplification product. A sequencing primer is designed to anneal next to the base differentiating the disease-causing and normal allele or the selected SNP alleles. A primer extension reaction is performed using chain terminating dideoxyribonucleoside triphosphates (ddNTPs) labeled with a fluorescent dye, one label attached to the ddNTP to be added to the standard nucleic acid and another to the ddNTP to be added to the target nucleic acid.

Others have described using the MutS protein or other DNA-repair enzymes for detection of single-base mismatches. Alternative methods for detection of deletion, insertion or substitution mutations that can be used in the practice of various aspects described herein are disclosed in U.S. Pat. Nos. 5,849,483, 5,851,770, 5,866,337, 5,925,525 and 5,928,870, each of which is incorporated herein by reference.

In another embodiment, multiplex PCR procedures using allele-specific primers can be used to simultaneously amplify multiple regions of a target nucleic acid (PCT Application WO89/10414), enabling amplification only if a particular allele is present in a sample. Other embodiments using alternative primer-guided nucleotide incorporation procedures for assaying polymorphic sites in DNA can be used, and have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Nad. Acad. Sci. (U.S.A) 88:1143-1147 (1991); Bajaj et al. (U.S. Pat. No. 5,846,710); Prezant, T. R. et al., Hum Mutat. 1: 159-164 (1992); Ugozzoli, L. et al., GATA 9:107-112 47 (1992); Nyr6n, P. et al., Anal. Biochem. 208:171-175 (1993)).

Other known nucleic acid amplification procedures include transcription-based amplification systems (Malek, L. T. et al., U.S. Pat. No. 5,130,238; Davey, C. et al., European Patent Application 329,822; Schuster et al.) U.S. Pat. No. 5,169,766; Miller, H. I. et al., PCT-Application WO89/06700; Kwoh, D. et al., Proc. Natl. Acad. Sci. (U.S.A) 86:1173 Z1989); Gingeras, T. R. et al., PCT Application WO88/10315)), or isothermal amplification methods (Walker, G. T. et al., Proc. Natl. 4cad Sci. (U.S.A) 89:392-396 (1992)) can also be used.

Another method to determine genetic variation is using "gene chips". The use of microarrays comprising a multiplicity of sequences is becoming increasingly common in the art. Accordingly, a microarray having at least one oligonucleotide probe, as described above, appended thereon, can be used for SNP genotyping to interrogate the presence or absence of at least one SNP described herein and/or additional alleles associated with responsiveness to a folate-containing compound.

Probes can be affixed to surfaces for use as "gene chips." Such gene chips can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes can also be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayyem et al. U.S. Pat. No. 5,952,172 and by Kelley, S. O. et al. (1999) Nucleic Acids Res. 27:4830-4837.

Examples of identifying polymorphisms and applying that information in a way that yields useful information regarding patients can be found, for example, in U.S. Pat. No. 6,472,157; U.S. Patent Application Publications 20020016293, 20030099960, 20040203034; WO 0180896, all of which are hereby incorporated by reference.

In some embodiments, any validated diagnostic test appropriate for SNP determination can be used to determine the presence of at least one or more (e.g., at least two or more, at least there or more) folate-responsive SNP biomarkers in a subject. In some embodiments, a semi-quantitative immunohistochemical assay (IHC) and/or a cytogenetic method, e.g., but not limited to fluorescence in situ hybridization (FISH) can be used to determine the presence of at least one or more (e.g., at least two or more, at least there or more) folate-responsive SNP biomarkers in a subject. For example, in one embodiment, a semi-quantitative immunohistochemical (IHC) assay and/or a cytogenetic method, e.g., but not limited to fluorescence in situ hybridization (FISH) can be used to determine a MTHFR "T" variant and MTR "G" variant from a biological sample, e.g., a buccal swab sample. In one embodiment, a semi-quantitative immunohistochemical (IHC) assay, e.g., as generally described in Dunstan, R W et al. Toxicol Pathol (2011) 39: 988; or a cytogenetic assay such as fluorescence in situ hybridization (FISH) as generally described in Garimberti, E. and Tosi, S. in: Fluorescence in situ hybridization (FISH), Bridger, J. M. & Volpi, E. V., eds., Springer Science and Business Media, (2010), the contents of which are incorporated herein by reference, can be used to determine the presence of at least one or more (e.g., at least two or more, at least there or more) folate-responsive SNP biomarkers in a subject, e.g., to determine a MTHFR "T" variant and MTR "G" variant from a biological sample, e.g., a buccal swab sample.

Determination of Expression Levels of Serum/Plasma/Cerebrospinal Fluid (CSF) Biomarkers (e.g., SAM, SAH, 4-HNE, and/or hsCRP)

At least one of serum/plasma/CSF biomarkers as described herein (e.g., SAM, SAH, 4-HNE, and/or hsCRP) can be measured according to methods known to one skilled in the art. In various embodiments, a blood sample (e.g., including a serum sample and/or a plasma sample) and/or a CSF sample can be collected from a subject and used to measure at least one of serum/plasma/CSF biomarkers as described herein (e.g., SAM, SAH, 4-HNE, and/or hsCRP).

Determining Serum/Plasma/CSF Metabolite Levels (e.g., SAM, SAH, and/or 4-HNE)

Performing measurements of metabolites in a biological sample are known to a skilled artisan. For example, a target metabolite (e.g., SAM, SAH and/or 4-HNE) can be optionally separated (e.g., prior to detection) from a biological sample by gas chromatography (GC), e.g., when interfaced with mass spectrometry (GC-MS), and/or high performance liquid chromatography (HPLC), and/or capillary electrophoresis (CE). CE generally has higher theoretical separation efficiency than HPLC, and is suitable for use with a wider range of metabolite classes than is GC.

Levels of metabolites (e.g., SAM, SAH, and/or 4-HNE) can be detected by any known methods in the art. For example, mass spectrometry (MS) can be used to identify and to quantify metabolites after separation by GC, HPLC (LC-MS), and/or CE. In some embodiments, MS can be used as a stand-alone technology, e.g., the biological sample is infused directly into the mass spectrometer which provides both separation and detection of metabolites (e.g., SAM, SAH, and/or 4-HNE).

In some embodiments, surface-based mass analysis can be used for metabolite analysis. For example, Nanostructure-Initiator MS (NIMS), a desorption/ionization approach that does not require the application of matrix and thereby facilitates small-molecule (i.e., metabolite) identification and analysis. See, e.g., Northen T. R, et al. (October 2007). "Clathrate nanostructures for mass spectrometry". Nature 449 (7165): 1033-6; and Woo H et al. (July 2008). "Nanostructure-initiator mass spectrometry: a protocol for preparing and applying NIMS surfaces for high-sensitivity mass analysis". Nature protocols 3 (8): 1341-9.

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937 (Hillenkamp et al.), and U.S. Pat. No. 5,045,694 (Beavis & Chait). In some embodiments, matrix-assisted laser desorption/ionization (MALDI) can be used for metabolite analysis of a biological sample.

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

In some embodiments, matrix-free desorption/ionization approaches, e.g., but not limited to, secondary ion mass spectrometry (SIMS), and desorption electrospray ionization (DESI), can be applied to the analysis of metabolites (e.g., SAM, SAH and/or 4-EINE) in a biological sample. In some embodiments, ambient ionization methods for mass spectrometry, e.g., laser ablation ESI (LAESI), can be used to analyze metabolite level (e.g., SAM, SAH, and/or 4-EINE) in a biological sample.

In some embodiments, nuclear magnetic resonance (NMR) spectroscopy can be used to measure metabolite level in a biological sample. NMR generally does not rely on separation of the analytes (e.g., target metabolites such as SAM, SAH and/or 4-EINE), and the biological sample can thus be recovered for further analyses. All kinds of small molecule metabolites can be measured simultaneously.

Other methods of detection of metabolites (e.g., SAM, SAH, and/or 4-HNE) in a biological sample can include, but are not limited to, ion-mobility spectrometry, electrochemical detection (coupled to HPLC) and radiolabel (when combined with thin-layer chromatography), mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference. Mass spectrometry methods are well known in the art and have been used to quantify and/or identify molecules (see, e.g., Li et al. (2000) Tibtech 18:151-160; Rowley et al. (2000) Methods 20: 383-397; and Kuster and Mann (1998) Curr. Opin. Structural Biol. 8: 393-400).

For additional information regarding mass spectrometers, see, e.g., Principles of Instrumental Analysis, 3rd edition, Skoog, Saunders College Publishing, Philadelphia, 1985; and Kirk-Othmer Encyclopedia of Chemical Technology, 4$^{th}$ ed. Vol. 15 (John Wiley & Sons, New York 1995), pp. 1071-1094. Software programs such as the Biomarker Wizard program (Ciphergen Biosystems, Inc., Fremont, Calif.) can be used to aid in analyzing mass spectra, e.g., comparing the signal strength of peak values from spectra of a test subject sample and a control sample (e.g., a normal healthy person). The different types of mass spectrometers and MS techniques are well known to those of skill in the art.

In some embodiments, an enzyme-coupled assay can be used to determine metabolite level (e.g., SAM, SAH, and/or 4-HNE) in a biological sample. By way of example only, a stereospecific colorimetric assay of SAM based on an enzyme-coupled reaction, thiopurine methyltransferase-catalyzed thiol methylation (see, e.g., Cannon, L. M, et al, Analytical Biochemistry, 308 (2) 358-363, 2002), can be used to detect SAM level in a biological sample. The assay utilizes stereo-specific characteristics of a recombinant human thiopurine S-transmethyltransferase (TPMT, EC 2.1.1.67) and measures the change of absorbance at 410 nm of 2-nitro-5-thiobenzoic acid (TNB) vs. 2-nitro-5-methylthiobenzoic acid. In some embodiments, an enzyme-coupled assay can be used in combination with mass spectrometry and/or NMR spectroscopy.

Additional metabolite analysis methods, e.g., as described in U.S. Pat. No. 8,344,115, and U.S. Pat. App. Nos. US 2012/0130212, and US 2008/0081375, can be also used for measurement of metabolites (e.g., SAM, SAH, and/or 4-HNE) in a biological sample. The contents of those U.S. Patent applications and patent are incorporated herein by reference.

In some embodiments, the level of 4-HNE in a biological sample can be measured by a HPLC method, for example, as described in Lovell, M A and Markesbery, W R "Analysis of Aldehydic Markers of Lipid Peroxidation in Biological Tissues by HPLC with Fluorescence Detection" *Methods in Pharmacology and Toxicology: Methods in Biological Oxidative Stress*. (Eds.) Hensley K and Floyd R A (2003) p. 17-21, and/or a ELISA method, for example, using a commercially-available ELISA kit designed for detection of HNE protein adducts (e.g., but not limited to ELISA kits from Cell Biolabs, Inc., e.g., Cat. No. STA-338).

In some embodiments, the levels of SAM and/or SAH in a biological sample can be measured by a method comprising liquid chromatograpy and/or mass spectrometry. For example, in one embodiment, the levels of SAM and/or SAH in a biological sample can be measured by an assay that uses stable-isotope-dilution liquid chromatography-mass spectrometry, e.g., as described in Stabler S P and Allen R H "Quantification of serum and urinary S-adenosylmethionine and S-adenosylhomocysteine by stable-isotope-dilution liquid chromatography-mass spectrometry" Clinical Chemistry (2004) 50: 365. In one embodiment, the levels of SAM and/or SAH in a biological sample can be measured by an assay that uses an assay based on coulometric electrochemical detection. For example, a HPLC with coulometric electrochemical detection can be used for simultaneous measurement of SAM and SAH in a biological sample, e.g., as described in Melnyk S. et al. "Measurement of plasma and intracellular S-adenosylmethionine and S-adenosylhomocysteine utilizing coulometric electrochemical detection: alterations with plasma homocysteine and pyridoxal 5'-phosphate concentrations." Clinical Chemistry (2000) 46: 265. The contents of these scientific publications are incorporated herein by reference.

In some embodiments, expression levels of serum/plasma/CSF biomarkers (e.g., hsCRP) can be determined by measuring protein levels. In some embodiments, expression levels of serum/plasma/CSF biomarkers (e.g., hsCRP) can be determined by measuring mRNA levels.

Determining Expression Level by Measuring Protein:

By way of example only, the levels of serum/plasma/CSF biomarkers (e.g., hsCRP) can be measured by contacting a test sample with an antibody-based binding moiety that specifically binds to at least one of the serum/plasma biomarkers described herein, or to a fragment thereof. Formation of the antibody-protein complex is then detected by a variety of methods known in the art.

The term "antibody-based binding moiety" or "antibody" can include immunoglobulin molecules and immunologically active determinants of immunoglobulin molecules, e.g., molecules that contain an antigen binding site which specifically binds (immunoreacts with) to the serum/plasma/CSF proteins (e.g., hsCRP). The term "antibody-based binding moiety" is intended to include whole antibodies, e.g., of any isotype (IgG, IgA, IgM, IgE, etc), and includes fragments thereof which are also specifically reactive with the serum/plasma/CSF proteins (e.g., hsCRP). Antibodies can be fragmented using conventional techniques known in the art. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody-base binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In some embodiments, the antibody-based binding moiety can be detectably labeled.

"Labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. The detection and quantification of the serum/plasma/CSF proteins (e.g., hsCRP) in test samples correlate to the intensity of the signal emitted from the detectably labeled antibody.

In some embodiments, the antibody-based binding moiety can be detectably labeled by linking the antibody to an enzyme. The enzyme, in turn, when exposed to its substrate, will react with the substrate in such a manner as to produce a chemical moiety which can be detected, for example, by spectrophotometric, fluorometric or by visual means. Enzymes which can be used to detectably label the antibodies against the serum/plasma/CSF proteins (e.g., hsCRP) can include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection can also be accomplished using any of a variety of other immunoassays. For example, by radioactively labeling an antibody, it is possible to detect the antibody through the use of radioimmune assays. The radioactive isotope can be detected by such means as the use of a gamma counter or a scintillation counter or by autoradiography. Isotopes which are particularly useful for the purpose of detection are $^{3}$H, $^{131}$I, $^{35}$S, $^{14}$C and $^{125}$I.

It is also possible to label an antibody with a fluorescent compound. When the fluorescently labeled antibody is exposed to light of the proper wavelength, its presence can then be detected due to fluorescence. Examples of the most commonly used fluorescent labeling compounds include, but not limited to, CYE dyes, fluorescein isothiocyanate, rhodamine, phycoerytherin, phycocyanin, allophycocyanin, o-phthaldehyde and fluorescamine.

An antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-antibody is then determined by detecting the presence of luminescence that arises during the course of a chemical reaction. Examples of chemiluminescent labeling compounds can include, but not limited to, luminol, luciferin, isoluminol, theromatic acridinium ester, imidazole, acridinium salt and oxalate ester.

Without limitations, levels of the serum/plasma/CSF proteins (e.g., hsCRP) can be detected by immunoassays, such as enzyme linked immunoabsorbant assay (ELISA), radioimmunoassay (RIA), Immunoradiometric assay (IRMA), Western blotting, immunocytochemistry or immunohistochemistry, each of which are described in more detail below. In some embodiments, immunoassays such as ELISA or RIA can be used for determining expression levels of the serum/plasma/CSF proteins (e.g., hsCRP). Antibody arrays or protein chips can also be employed, see for example U.S. Patent Application Nos: 2003/0013208A1; 2002/0155493A1; 2003/0017515 and U.S. Pat. Nos. 6,329,209; 6,365,418, which are herein incorporated by reference. Commercially available antibodies and/or immunoassays (such as ELISA) for detecting the serum/plasma/CSF proteins (e.g., hsCRP), e.g., from Cell BioLabs, Abcam, Novus Biologicals, and Thermo Scientific Pierce Antibodies, can be used in the assays and/or methods described herein. In one embodiment, a commercially available ELISA kit designed for detection of hsCRP (e.g., from Immuno-Biological Laboratories Inc, Cat. No.: IB59126) can be used to measure level of hsCRP in a biological sample collected from a subject, e.g., but not limited to, a serum sample, a plasma sample and/or a cerebrospinal fluid (CSF) sample.

Immunoassays:

The most common enzyme immunoassay is the "Enzyme-Linked Immunosorbent Assay (ELISA)." ELISA is a technique for detecting and measuring the concentration of an antigen using a labeled (e.g. enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

In a "sandwich ELISA", an antibody (e.g. anti-enzyme) is linked to a solid phase (i.e. a microtiter plate) and exposed to a biological sample containing antigen (e.g. enzyme). The solid phase is then washed to remove unbound antigen. A labeled antibody (e.g. enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", antibody is incubated with a sample containing antigen (i.e. enzyme). The antigen-antibody mixture is then contacted with a solid phase (e.g. a microtiter plate) that is coated with antigen (i.e., enzyme). The more antigen present in the sample, the less free antibody that will be available to bind to the solid phase. A labeled (e.g., enzyme linked) secondary antibody is then added to the solid phase to determine the amount of primary antibody bound to the solid phase.

In an "immunohistochemistry assay" a test sample is tested for specific proteins by exposing the test sample to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or beta-galactosidase), or chemical methods (e.g., DAB/Substrate chromagen). The sample is then analysed microscopically, for example, by light microscopy of a sample stained with a stain that is detected in the visible spectrum, using any of a variety of such staining methods and reagents known to those skilled in the art.

Alternatively, "Radioimmunoassays" can be employed. A radioimmunoassay is a technique for detecting and measuring the concentration of an antigen using a labeled (e.g. radioactively or fluorescently labeled) form of the antigen. Examples of radioactive labels for antigens include $^{3}H$, $^{14}C$, and $^{125}I$. The concentration of antigen enzyme in a test sample or a biological sample can be measured by having the antigen in the biological sample compete with the labeled (e.g. radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by performing a "solid-phase radioimmunoassay" where the antibody is linked (e.g., covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined An "Immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

In some embodiments, Western blotting (Towbin et at., Proc. Nat. Acad. Sci. 76:4350 (1979)) can be used to measure expression levels of the serum/plasma/CSF proteins (e.g., hsCRP), wherein a suitably treated sample is run on an SDS-PAGE gel before being transferred to a solid support, such as a nitrocellulose filter. Detectably labeled anti-enzyme antibodies can then be used to assess enzyme levels, where the intensity of the signal from the detectable label corresponds to the amount of enzyme present. Levels can be quantified, for example by densitometry.

In addition, expression level of at least one of the serum/plasma/CSF biomarkers (e.g., serum/plasma/CSF proteins and/or metabolites) can be determined by mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference. Mass spectrometry methods are well known in the art and have been used to quantify and/or identify molecules (see, e.g., Li et al. (2000) Tibtech 18:151-160; Rowley et al. (2000) Methods 20: 383-397; and Kuster and Mann (1998) Curr. Opin. Structural Biol. 8: 393-400).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937 (Hillenkamp et al.), and U.S. Pat. No. 5,045,694 (Beavis & Chait).

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition, Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094. Software programs such as the Biomarker Wizard program (Ciphergen Biosystems, Inc., Fremont, Calif.) can be used to aid in analyzing mass spectra, e.g., comparing the signal strength of peak values from spectra of a test subject sample and a control sample (e.g., a normal healthy person). The mass spectrometers and their techniques are well known to those of skill in the art.

Determining Expression Level of a Gene or Protein by Measuring mRNA:

Real time PCR is an amplification technique that can be used to determine expression levels of mRNA corresponding to a protein of interest (e.g., hsCRP). (See, e.g., Gibson et al., Genome Research 6:995-1001, 1996; Heid et al., Genome Research 6:986-994, 1996). Real-time PCR evaluates the level of PCR product accumulation during amplification. This technique permits quantitative evaluation of mRNA levels in multiple samples. For mRNA levels, mRNA can be extracted from a biological sample, e.g. a blood sample (such as white blood cells and/or platelets) and cDNA is prepared using standard techniques. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes can be obtained commercially from, for example, Perkin Elmer/Applied Biosystems (Foster City, Calif.). To quantitate the amount of the specific nucleic acid of interest in a sample, a standard curve is generated using a control. Standard curves can be generated using the Ct values determined in the real-time PCR, which are related to the initial concentration of the nucleic acid of interest used in the assay. Standard dilutions ranging from $10^1$-$10^6$ copies of the gene of interest are generally sufficient. In addition, a standard curve is generated for the control sequence. This permits standardization of initial content of the nucleic acid of interest in a test sample to the amount of control for comparison purposes.

Methods of real-time quantitative PCR using TaqMan probes are well known in the art. Detailed protocols for real-time quantitative PCR are provided, for example, for RNA in: Gibson et al., 1996, A novel method for real time quantitative RT-PCR. Genome Res., 10:995-1001; and for DNA in: Heid et al., 1996, Real time quantitative PCR. Genome Res., 10:986-994.

The TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe. This cleavage separates the 5' fluorescent dye and the 3' quenching agent, thereby resulting in an increase in fluorescence as a function of amplification (see, for example, Perkin-Elmer).

In another embodiment, detection of RNA transcripts can be achieved by Northern blotting, wherein a preparation of RNA is run on a denaturing agarose gel, and transferred to a suitable support, such as activated cellulose, nitrocellulose or glass or nylon membranes. Labeled (e.g., radiolabeled) cDNA or RNA is then hybridized to the preparation, washed and analyzed by methods such as autoradiography.

Detection of RNA transcripts can further be accomplished using known amplification methods. For example, mRNA can be reverse-transcribed into cDNA followed by polymerase chain reaction (RT-PCR); or, to use a single enzyme for both steps as described in U.S. Pat. No. 5,322,770, or reverse transcribe mRNA into cDNA followed by symmetric gap lipase chain reaction (RT-AGLCR) as described by R. L. Marshall, et al., PCR Methods and Applications 4: 80-84 (1994). One suitable method for detecting enzyme mRNA transcripts is described in reference Pabic et. al. Hepatology, 37(5): 1056-1066, 2003, which is herein incorporated by reference.

In situ hybridization visualization can also be employed, wherein a radioactively labeled antisense RNA probe is hybridized with target biomarkers in a test sample, washed, cleaved with RNase and exposed to a sensitive emulsion for autoradiography. The samples can be stained with haematoxylin to demonstrate the histological composition of the sample, and dark field imaging with a suitable light filter shows the developed emulsion. Non-radioactive labels such as digoxigenin can also be used.

Alternatively, mRNA expression can be detected on a DNA array, chip or a microarray. Oligonucleotides corresponding to enzyme are immobilized on a chip which is then hybridized with labeled nucleic acids of a test sample obtained from a patient. Positive hybridization signal is obtained with the sample containing biomarker transcripts. Methods of preparing DNA arrays and their use are well known in the art. (See, for example U.S. Pat. Nos. 6,618,6796; 6,379,897; 6,664,377; 6,451,536; 548,257; U.S. 20030157485 and Schena et al. 1995 Science 20:467-470; Gerhold et al. 1999 Trends in Biochem. Sci. 24, 168-173; and Lennon et al. 2000 Drug discovery Today 5: 59-65, which are herein incorporated by reference). Serial Analysis of Gene Expression (SAGE) can also be performed (See for example U.S. Patent Application 20030215858).

Methods for Treating a Human Subject with Depression (e.g., Treating at Least One Symptom of Depression in a Human Subject) and/or Improving the Effectiveness of an Anti-Depressant Drug In accordance with various aspects described herein, if a subject with depression is detected to have the presence of at least one of the conditions (A)-(X) determined in the assay described herein, the subject is recommended for and/or administered with a treatment regimen comprising a folate-containing compound. In such embodiments, the subject can be further administered or prescribed with a treatment regimen comprising an anti-depressant drug and a folate-containing compound. Accordingly, provided herein are also methods for treating a subject with depression. In some embodiments, the method comprises performing any embodiments of the assay for selecting a treatment regimen for a subject with depression described herein. In some embodiments, the method can further comprise prescribing and/or administering a treatment regimen comprising a folate-containing compound to the selected human subject.

In some embodiments, a method for treating a human subject with depression (e.g., treating at least one symptom of depression in a human subject) can comprise administering a composition comprising an effective amount of a folate-containing compound to the human subject, who is diagnosed as having, or having a risk for, depression, and is further determined to carry at least one or more (including at least two, at least three, at least four or more), or any combinations of the conditions (A)-(X) described herein. In some embodiments, the method for treating a human subject with depression (e.g., treating at least one symptom of depression in a human subject) can comprise administering a composition comprising an effective amount of a folate-containing compound to the human subject, who is diagnosed as having, or having a risk for, depression, and is further determined to be obese and carry at least one or more (including at least two, at least three, at least four or more), or any combinations of the conditions (A)-(X) described herein. In some embodiments, the method can further comprise selecting for the human subject a treatment comprising the folate-comprising compound, optionally administered in combination with an anti-depressant drug, based on the recognition that the presence of at least one or any combinations of the folate-responsive conditions described herein is associated with positive-symptom-reducing response to the folate-containing compound. In some embodiments, the method can further comprise administering to the human subject an anti-depressant drug.

In certain embodiments, the method of treating a human subject with depression (e.g., treating at least one symptom of depression in a human subject) can comprise administering a composition comprising an effective amount of a folate-containing compound to the human subject, who is diagnosed as having, or having a risk for, depression, and is further determined to carry at least one of the following SNPs or a combination thereof: (i) a SNP at position 677 of SEQ ID NO. 1 or position 27 of SEQ ID NO. 7 (identified by rs1801133) comprising at least one thymine "T" allele, and (ii) a SNP at position 2756 of SEQ ID NO. 2 or position 27 of SEQ ID NO. 9 (identified by rs1805087) comprising at least one guanine "G" allele. In one embodiment, the human subject can be determined to carry at least a combination of both SNP biomarkers as follows: (i) a SNP at position 677 of SEQ ID NO. 1 or position 27 of SEQ ID NO. 7 (identified by rs1801133) comprising at least one thymine "T" allele, and (ii) a SNP at position 2756 of SEQ ID NO. 2 or position 27 of SEQ ID NO. 9 comprising at least one guanine "G" allele.

In these embodiments, the method can further comprise determining the presence or absence of any of the conditions (A)-(X) described herein.

In some embodiments, the subject administered with a treatment regimen comprising a folate-containing compound can be further determined to be obese (e.g., with a BMI value of at least about 30 kg/m$^2$ or higher; a waist circumference greater than 40 inches (or greater than 120 cm) in men, or greater than 35 inches (or greater than 88 cm) in women; a waist-hip ratio above 0.95 for men or above 0.80 for women; a body fat percentage of at least about 25% in men or at least about 32% in women, or any combinations thereof).

The terms "treatment" and "treating" as used herein, with respect to treatment of a disease, means preventing the progression of the disease, or altering the course of the disorder (for example, but are not limited to, slowing the progression of the disorder), or reversing a symptom of the disorder or reducing one or more symptoms and/or one or more biochemical markers in a subject, preventing one or more symptoms from worsening or progressing, promoting recovery or improving prognosis. For example, in the case of treating depression, therapeutic treatment refers to alleviation of at least one symptom associated with depression. Measurable lessening includes any statistically significant decline in a measurable marker or symptom, such as measuring markers for depression in the blood as described later or assessing the degree of depression, e.g., using the criteria listed in DSM-IV or the efficacy measures as described in the Examples, e.g., HAMD-17, HAMD-28, CGI, Maier or HAMD-7, after treatment. In one embodiment, at least one symptom of depression is alleviated by at least about 10%, at least about 15%, at least about 20%, at least about 30%, at least about 40%, or at least about 50%. In another embodiment, at least one symptom is alleviated by more than 50%, e.g., at least about 60%, or at least about 70%. In one embodiment, at least one symptom is alleviated by at least about 80%, at least about 90% or greater, as compared to a control (e.g., a subject having the same or similar degree of depression as the treated subject is administered without a folate-containing compound, or a subject who has met none of the conditions described herein is administered with treatment regimen comprising a folate-containing compound). In some embodiments, at least one neuropsychological test is improved (e.g., HAMD-17 rating is decreased) by at least about 10%, at least about 15%, at least about 20%, at least about 30%, at least about 40%, or at least about 50%. In another embodiment, at least one neuropsychological test is improved (e.g., HAMD-17 rating is decreased) by more than 50%, e.g., at least about 60%, or at least about 70%. In one embodiment, at least one neuropsychological test is improved (e.g., HAMD-17 rating is decreased) by at least about 80%, at least about 90% or greater, as compared to a control (e.g., a subject having the same or similar degree of depression as the treated subject is administered without a folate-containing compound, or a subject who has met none of the conditions described herein is administered with treatment regimen comprising a folate-containing compound). In some embodiments, at least one symptom of depression can be alleviated by at least about 10%, at least about 15%, at least about 20%, at least about 30%, at least about 40%, or at least about 50% or higher within a period of at least about 10 days, including, e.g., at least about 20 days, at least about 30 days, at least about 40 days, or longer.

In some embodiments, at least one neuropsychological test is improved (e.g., HAMD-17 rating is decreased) by at least about 10%, at least about 15%, at least about 20%, at least about 30%, at least about 40%, or at least about 50% or higher within a period of at least about 10 days, including, e.g., at least about 20 days, at least about 30 days, at least about 40 days, or longer.

In some embodiments of this aspect and all other aspects described herein, a folate-containing compound can be administered in an amount effective to reduce at least one symptom (e.g., but not limited to, low mood, anhedonia, low energy, insomnia, agitation, anxiety and/or weight loss) associated with depression, e.g., major depressive disorders. In some embodiments, the effective amount of a folate-containing compound can provide at least about 0.1 to about 1 mg/kg body weight per day administration to the human subject. In some embodiments, the effective amount of a folate-containing compound can provide at least about 7.5 mg/day to about 50 mg/day administration to the human subject. In one embodiment, the effective amount of a folate-containing compound can provide at least about 15 mg/day of folate administration to the human subject.

The effective amount of the folate-containing compound can be administered to a selected human subject as a single daily dose, or alternatively, in more than one divided doses per day via any suitable administration route, e.g., oral administration.

In some embodiments of this aspect and all other aspects described herein, the treatment regimen can further comprise selecting and optionally administering an antidepressant drug. In some embodiments, the anti-depressant drug can include a selective serotonin reuptake inhibitor, including, but not limited to, fluoxetine, citalopram, paroxetine, escitalopram, sertraline, and any combinations thereof.

The subject with depression being treated with the methods described herein can be a subject currently taking an antidepressant. Accordingly, the methods of treating a human subject with depression described herein can also be used to select a human subject to be treated with the combination of a folate-containing compound and an anti-depressant to improve the effectiveness of an anti-depressant drug currently taken by a subject accordingly. Accordingly, if the human subject currently taking an antidepressant is determined to have at least one (including, e.g., at least two, at least three or more) of the conditions (A)-(X) described herein, the subject can be further administered or prescribed with a folate-containing compound as an adjuvant to the anti-depressant he/she is currently taking.

A further aspect provided herein is a method of determining and/or improving the effectiveness of an anti-depressant drug administered to a human subject, e.g., by determining if the human subject is amenable to folate or a derivative thereof as an adjuvant, e.g., using the assay described herein. In some embodiments of this aspect, the method can further comprise administering or prescribing the subject with a compound containing an effective amount of folate as an adjuvant to the anti-depressant drug, if the subject satisfies at least one of the conditions (A)-(X) provided herein.

In some embodiments, a method of improving the effectiveness of an anti-depressant drug administered to a human subject can comprise administering a composition comprising an effective amount of a folate-containing compound, in combination with an anti-depressant drug, to the human subject, who is diagnosed to have depression, and is further determined to carry at least one or more (including at least two, at least three, at least four or more), or any combinations of the conditions (A)-(X) described herein. In some embodiments, the method of improving the effectiveness of an anti-depressant drug administered to a human subject can comprise administering a composition comprising an effective amount of a folate-containing compound to the human subject, who is diagnosed to have depression, and is further determined to be obese and carry at least one or more (including at least two, at least three, at least four or more), or any combinations of the conditions (A)-(X) described herein. In some embodiments, the method can further comprise selecting for the human subject a treatment comprising the folate-comprising compound, administered in combination with an anti-depressant drug, based on the recognition that the presence of at least one or any combinations of the folate-responsive conditions described herein is associated with increasing the effectiveness of the anti-depressant drug when administered in combination with the folate-containing compound.

In certain embodiments, the method of improving the effectiveness of an anti-depressant drug administered to a human subject can comprise administering a composition comprising an effective amount of a folate-containing compound, in combination with an anti-depressant drug to the human subject, who is diagnosed to have depression, and is further determined to carry at least a combination of the two SNP biomarkers as follows: (i) a SNP at position 677 of SEQ ID NO. 1 or position 27 of SEQ ID NO. 7 (identified by rs1801133) comprising at least one thymine "T" allele, and (ii) a SNP at position 2756 of SEQ ID NO. 2 or position 27 of SEQ ID NO. 9 (identified by rs1805087) comprising at least one guanine "G" allele. In these embodiments, the method can further comprise determining the presence or absence of any of the conditions (A)-(X) described herein.

In other embodiments, if the subject currently taking an antidepressant is determined to have at least one (including, e.g., at least two, at least three or more) of the conditions (A)-(X) described herein, the subject can be administered to a treatment regimen comprising a folate-containing compound without the antidepressant.

In some embodiments, the methods described herein can be used to treat at least one or more core symptoms of depression (e.g., but not limited to low or depressed mood, anhedonia (e.g., loss of interest or pleasure in nearly all activities), low energy levels, guilt, decreased work and interests, psychomotor retardation, agitation, psychic anxiety, somatic anxiety, general somatic symptoms, reduced cognition) in a subject who is determined to have at least one (including, e.g., at least two, at least three or more) of the conditions (A)-(X) described herein.

In some embodiments, the therapeutic effect (e.g., reducing at least one of core symptoms associated with depression) can be synergistic when a human subject, who is determined to carry at least two of the folate-responsive biomarkers (i)-(xxv), is administered with a folate-comprising compound. The term "synergy" or "synergistic" as used herein generally refers to the combined effect of at least two or more agents being greater than the sum of their individual effects. In particular, the term "synergy" or "synergistic" as used herein refers to the combined therapeutic effect associated with a human subject carrying two or more folate-responsive biomarkers that, when the human subject is administered with a treatment comprising a folate-comprising compound, is greater than the sum of the therapeutic effect associated with the individual folate-responsive biomarkers (additive effect). In some embodiments, the synergistic effect can be greater than the additive effect by at least about 10%, at least about 20%, at least about 30%, at least about 40%, at least about 50%, at least about 60%, at least about 70%, at least about 80%, at least about 90%, at least about 95% or more. In some embodiments, the synergistic effect can be greater than the additive effect by at least about 1.5-fold, at least about 2-fold, at least about 3-fold or higher.

In some embodiments, the therapeutic effect can be determined using HAMD-28. Accordingly, in some embodiments, the "synergistic effect" as used herein refers to a total reduction in HAMD-28 score that, when a human subject carrying at least two or more folate-responsive biomarkers is administered with a folate-comprising compound, is greater than the sum of individual reduction in HAMD-28 associated with each respective biomarker. In some embodiments, the synergistic effect on mean change in HAMD-28 can be greater than the additive effect by at least about 10%, at least about 20%, at least about 30%, at least about 40%, at least about 50%, at least about 60%, at least about 70%, at least about 80%, at least about 90%, at least about 95% or more. In some embodiments, the synergistic effect on the mean change in HAMD-28 can be greater than the additive effect by at least about 1.5-fold, at least about 2-fold, at least about 3-fold or higher.

Figure 11:
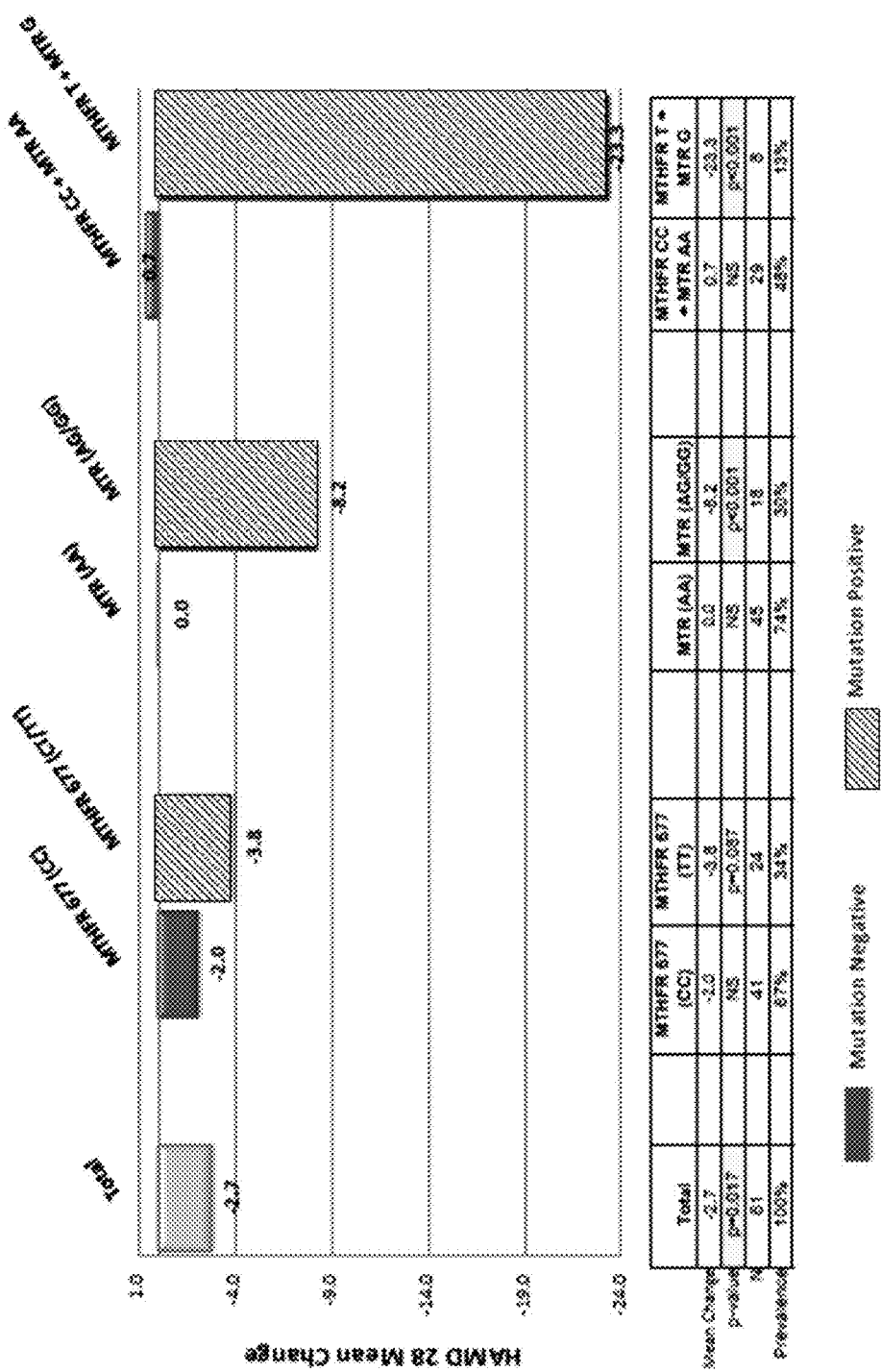
FIG. 11 is a bar graph showing the synergistic effects on HAMD-28 mean change when patients carrying both at least one "T" allele in MTHFR gene and at least one "G" allele in MTR gene were administered with a folate-comprising compound in combination with an antidepressant drug.

By way of example only, FIGS. 8A-8B, and FIG. 11 show that patients who were determined to carry a single folate-responsive biomarker (i) (i.e., at least one "T" variant in the MTHFR) showed a mean change in HAMD-28 of about −3.0 to about −5.0 after administration with a folate-comprising compound (e.g., optionally in combination with an anti-depressant). Table 22 and Table 37 (in the Examples) indicate that patients who were determined to carry a single folate-responsive biomarker (iii) and FIG. 11 (i.e., at least one "G" variant in the MTR gene) showed a mean change in HAMD-28 of about −8.2 after administration with a folate-comprising compound (e.g., optionally in combination with an anti-depressant). When patients carry both of the gene mutations, the patients' mean change in HAMD-28 in response to the treatment comprising a folate-comprising compound (e.g., optionally in combination with an anti-depressant drug) was about −23.3 (see, e.g., Table 11 and Table 37 in the Examples, and FIG. 11), which is not only greater than the effect associated with each biomarker individually, but is also surprisingly greater than the sum of the effects associated with each individual biomarkers (i.e., the additive effect would yield a mean change in HAMD-28 of about −11.2 to about −13.2) by at least about 2-fold.

In contrast, as shown in Tables 37-38 in the Examples, other combinations of gene mutations (e.g., MTR gene and MTRR gene mutations) do not necessarily produce such synergistic effects.

Accordingly, in one aspect, some embodiments provided herein relate to methods of treating a human subject with depression, which comprises administering to the subject a folate-comprising compound (and optionally in combination with an anti-depressant drug), based on the determination that the subject carries at least two folate-responsive markers, the combination of which yields a synergistic effect. In one embodiment, the method of treating a human subject with depression comprises administering to the subject a folate-comprising compound (and optionally in combination with an anti-depressant drug), based on the determination that the subject carries both folate-responsive markers (i) and (iii), i.e., a SNP in MTHFR (identified by rs1801133) comprising at least one thymine "T" allele or the complement thereof, and a SNP in MTR (identified by rsl 805087) comprising at least one guanine "G" allele or the complement thereof.

In another aspect, some embodiments provided herein relates to methods of increasing the effectiveness of an anti-depressant drug administered to a human subject with depression, which comprises administering to the subject a folate-comprising compound in combination with the anti-depressant drug, based on the determination that the subject carries at least two folate-responsive markers, the combination of which yields a synergistic effect. In one embodiment, the method of increasing the effectiveness of an anti-depressant drug comprises administering to the subject a folate-comprising compound in combination with the anti-depressant drug, based on the determination that the subject carries both folate-responsive markers (i) and (iii), i.e., a SNP in MTHFR (identified by rs1801133) comprising at least one thymine "T" allele or the complement thereof, and a SNP in MTR (identified by rs1805087) comprising at least one guanine "G" allele or the complement thereof.

Treatment Regimen Comprising a Folate-Containing Compound

A folate-containing compound included in a treatment regimen can be administered can be administered together via a single dosage form or by separate administration. In certain embodiments, the folate-containing compound can be administered in a single dosage form. For example, the single dosage form can be administered as a single tablet, pill, capsule for oral administration or a solution for parenteral administration. Alternatively, the folate-containing compound can be administered as separate compositions, e.g., as separate tablets or solutions. The length of time between administrations of a sub-dose of a folate-containing compound can be adjusted to achieve the desired therapeutic effect.

In some embodiments, a treatment regimen comprising a folate-containing compound further comprise at least one anti-depressant (e.g., 1, 2, 3 or more antidepressants). A treatment regimen comprising a folate-containing compound and at least one anti-depressant can be administered together via a single dosage form or by separate administration. In certain embodiments, the antidepressant and the folate-containing compound are administered together in a single dosage form. For example, the single dosage form can be administered as a single tablet, pill, capsule for oral administration or a solution for parenteral administration. Alternatively, the antidepressant and the folate-containing compound can be administered as separate compositions, e.g., as separate tablets or solutions. The antidepressant can be administered at the same time as the folate-containing compound, or the antidepressant can be administered intermittently with the folate-containing compound. The length of time between administration of the antidepressant and the folate-containing compound can be adjusted to achieve the desired therapeutic effect. In particular, the folate-containing compound can be administered at any frequency or administration protocol to enhance the efficacy of the antidepressant drug, as compared to efficacy of the antidepressant drug alone (e.g., in the absence of the folate-containing compound).

In some embodiments, the folate-containing compound can be administered only a few minutes (e.g., 1, 2, 5, 10, 30, or 60 min) before or after administration of the antidepressant. Alternatively, the folate-containing compound can be administered several hours (e.g., 2, 4, 6, 10, 12, 24, or 36 hr) before or after administration of the antidepressant. Depending on the half-lives of the antidepressant and the folate-containing compound, in certain embodiments, it can be advantageous to administer more than one dosage of the folate-containing compound between administrations of the antidepressant. For example, the folate-containing compound can be administered at 3 hours and then again at 6 hours following administration of the antidepressant. Alternatively, it can be advantageous to administer more than one dosage of the antidepressant between administrations of the folate-containing compound. Importantly, in some embodiments, the therapeutic effect of each antidepressant and folate-containing compound can overlap for at least a portion of the duration of each therapeutic agent so that the overall therapeutic effect of the combination therapy is attributable in part to the combined of the combination therapy. In some embodiments, the folate-containing compound and the antidepressant can be administered in a pulse administration. In other embodiments, they can be administered as a pulse-chase administration, e.g., where a folate-containing compound is administered for a brief period of time (pulse), followed by administration of the antidepressant for a longer period of time (e.g., chase).

In some embodiments where the antidepressant and the folate-containing compound are administered in separate compositions, the antidepressant and the folate-containing compound can be administrated by the same or different routes. For example, the antidepressant can be administered by intravenous injection while the folate-containing compound can be administered orally, or vice versa. Alternatively, for example, both the antidepressant and folate-containing compound can be administered together by intravenous injection or by oral administration.

In any embodiments of the methods described herein, the adjuvant effect of the folate-containing compound administered in combination with an antidepressant can be additive. The term "additive" as used herein in the context of one agent has an additive effect on a second agent, refers to an increase in effectiveness of a first agent in the presence of a second agent as compared to the use of the first agent alone. Stated in another way, the second agent can function as an agent which enhances the physiological response of an organ or organism to the presence of a first agent. Thus, a second agent will increase the effectiveness of the first agent by increasing an individual's response to the presence of the first agent.

In any embodiments of the methods described herein, the adjuvant effect of the folate-containing compound administered in combination with an antidepressant can be synergistic. The term "synergy" or "synergistic" as used herein refers to the interaction of two or more agents so that their combined effect is greater than each of their individual effects at the same dose alone.

In some embodiments, the treatment regimen can further comprise life-style advice, including, e.g., prescribing an exercise regime, dietary advice, and/or administering another pharmaceutical agent effective in treatment of depression.

Folate or Folate-Containing Compounds

Any art-recognized folate-containing compound can be selected and/or optionally administered to a human subject selected to carry at least one or more conditions (A)-(X) described herein. The term "folate-containing compound" as used herein refers to a compound containing an effective amount of at least one folate for use in the methods described herein. Folate is a form of the water-soluble vitamin B9. The term "folate" as used herein encompasses the naturally-occurring form of folate, folic acid (also known as vitamin B9 or folacin) and metabolites or derivatives thereof such as methylfolate, tetrahydrofolate, and methyltetrahydrofolate. The term "folate" as used herein can also refer to both pteroic acid monoglutamate (folic acid) and reduced forms such as dihydrofolates and tetrahydrofolates, e.g. 5-formyltetrahydrofolic acid, 5-methyltetrahydrofolic acid, 5,10-methylenetetrahydrofolic acid, 5,10-methenyltetrahydrofolic acid, 10-formyltetrahydrofolic acid and tetrahydrofolic acid, polyglutamates thereof, optical isomers thereof (e.g., optically pure natural isomers thereof, and also mixtures of optical isomers such as racemic mixtures), derivatives thereof, pharmaceutically acceptable salts and esters thereof, glucosamine salts thereof, and galactosamine salts thereof.

As used herein, the term "pharmaceutically acceptable salts and esters" refers to pharmacologically acceptable and pharmaceutically acceptable salts and esters. Pharmacologically and pharmaceutically acceptable salts can include, but are not limited to, alkali metal or alkaline earth metal salts, e.g., sodium, potassium, magnesium or calcium salts. Pharmacologically and pharmaceutically acceptable esters can include, but are not limited to, C1-C4 alkyl, C5 cycloalkyl oder C6 cycloalkyl, phenyl, C1-C4 alkylphenyl, benzyl or C1-C4-alkylbenzyl esters. The esters can be monoesters or diesters. Diesters can be homogeneous or heterogeneous. In some embodiments, pharmacologically and pharmaceutically acceptable esters can be homogeneous diesters such as C1-C4 dialkylesters, for example dimethyl- or diethylesters.

In some embodiments, the folate-containing compound can include at least one (including at least two, at least three or more) alkaline metal or alkaline earth metal salt of folate, e.g., but not limited to, a calcium salt of folate.

In some embodiments, the folate-containing compound can include at least one (including at least two, at least three or more) glucosamine salt and/or galactosamine salt of folate (including, e.g., folic acid and reduced folate, e.g., but not limited to, tetrahydrofolate, and derivatives thereof). Examples of glucosamine-folate and/or galactosamine-folate and derivatives thereof, e.g., disclosed in U.S. Pat. No. 7,947,662, can be administered to a human subject in the methods or included in the compositions described herein. In one embodiment, QUATREFOLIC® (Gnosis S.p.A, Milan, IT) or N-[4-[[[(6S)-2-amino-1,4,5,6,7,8-hexahydro-5-methyl-4-oxo-6-pteridinyl]methyl]amino]benzoyl]-L-glutamic acid, glucosamine salt can be administered to a human subject in the methods or included in the compositions described herein.

Folic acid, folate and their metabolites or reduced folates, e.g., methylfolate, are substances that are characterized as vitamins, essential nutrients available in small amounts in leafy vegetables and other foods. Folic acid is itself not biologically active, but it can be biologically converted to tetrahydrofolate and other derivatives after its conversion to dihydrofolic acid in the liver in the presence of appropriate enzymes.

In the form of a series of tetrahydrofolate (THF) compounds, folate derivatives are substrates in a number of single-carbon-transfer reactions and also are involved in the synthesis of dTMP (2'-deoxythymidine-5'-phosphate) from dUMP (2'-deoxyuridine-5'-phosphate).

The pathway leading to the formation of methylfolate such as tetrahydrofolate (THF) begins when folic acid (F), as folate, is reduced to dihydrofolate (DHF), which is then reduced to tetrahydrofolate (THF). The enzyme dihydrofolate reductase catalyses the last step. Accordingly, in some embodiments, for a subject with depression who is deficient in the enzyme dihydrofolate reductase, methyl folate, also known as Me-THF, N5-Methyl-THF, MTHF, 5-MTHF, L-methylfolate, and Levomefolic acid, or a pharmaceutically acceptable salt thereof (e.g., sodium salt, potassium salt, magnesium salt, calcium salt, glucosamine salt, or galactosamine salt), is more desirable for use as a folate-containing compound. For example, methyl folate calcium salt is available by prescription in the United States as DEPLIN® (L-methylfolate calcium salt). Methyl folate calcium salt is also available outside of the United States as METAFOLIN®, BODYFOLIN®, and NUTRIFOLIN®.

Additional examples of folates or folate-containing compounds that can be administered to a subject in the methods or included in the compositions described herein can include, but not limited to, the ones described in the U.S. Pat. No. 4,336,185; U.S. Pat. No. 6,921,754; and U.S. Pat. No. 7,947,662; and U.S. Pat. App. No.: US 2008/0064702, the contents of which are incorporated herein by reference.

Biological Effects of Folate on the Central Nervous System:

The role of folate in central-nervous-system function has been previously discussed, including the essential role of folate in the one-carbon cycle that furnishes SAMe, the principal methyl donor for a broad range of reactions involving the synthesis of neuroactive substances, the formation of membrane phospholipids, and the metabolism of nucleic acids [10]. When administered in parenteral and certain oral forms, SAM has been reported in European studies to have antidepressant efficacy greater than placebo and comparable to that of tricyclic antidepressants [41]. Folate also appears to influence the rate of synthesis of tetrahydrobiopterin [21], a cofactor in the hydroxylation of phenylalanine and tryptophan, rate-limiting steps in the biosynthesis of dopamine, norepinephrine, and serotonin, neurotransmitters postulated to play a role in the pathogenesis of depression. In addition, MTHF has been shown to bind to presynaptic glutamate receptors [42], where it may potentially modulate the release of other neurotransmitters, including the monoamines. Elevated levels of homocysteine, resulting from folate deficiency, can play a role in mediating some of its neuropsychiatric complications by both generating elevated levels of S-adenosyl-homocysteine, which broadly inhibits methylation reactions [43], and also possibly exerting direct excitoxic effects via activity at the N-methyl-aspartate glutamate receptors [44].

Low cerebrospinal fluid levels of the serotonin metabolite 5-hydroxyindole acetic acid and the dopamine metabolite homovanillic acid have been detected, though not always [45], among folate-deficient patients with epilepsy [46], other neuropsychiatric disorders [47], and congenital folate-deficiency states [48]. Whether folate supplementation actually enhances monoamine synthesis or release or furnishes additional SAMe has not yet been established. Human studies examining the impact of supraphysiologic doses of folate on cerebrospinal-fluid metabolites are lacking. Indeed, a previous study in rats yielded the paradoxical finding that folate supplementation and folate deficiency lowered brain serotonin. [47], which can in turn indicate the possibility of a similarly complex pattern in humans.

Folate and Depression:

Neuropsychiatric and depressive symptoms, including apathy, fatigue, insomnia, irritability, and impaired concentration, have been discussed in clinical descriptions of folate-deficiency states associated with malabsorption,[13] anticonvulsant-treated epilepsy, [14, 15] megaloblastic anemia, [16] and dietary folate restriction [1]. Previous studies have reported that as many as one-third of patients among psychiatric cohorts, mainly from the United Kingdom, exhibited low or deficient serum folate values, with generally comparable findings in the few studies that have assessed red blood cell (RBC) folate as a more accurate reflection of tissue folate stores [12, 17, 18]. In the subset of the studies in which depressed patients were compared with psychiatric or non-psychiatric control subjects, depressed patients were reported to have serum folate [2, 19], RBC folate [21], or serum methyltetrahydrofolate (MTHF) [22] levels that were lower than levels in all other groups except for patients with alcoholism who had a similar prevalence of low folate [20]. Furthermore, low serum or RBC folate and serum MTHF were often associated with greater symptom severity among depressed patients [22, 23, 24, 25]. Among studies that failed to demonstrate such relationship between low folate and depression severity, an inverse relationship between folate and the duration of the depressive episode [26] or the length of hospitalization [27] was observed.

Folate Levels and Response to Antidepressant Treatment:

The inventors have previously assessed serum folate and response to the selective serotonin reuptake inhibitor antidepressant, fluoxetine, among 213 adults with major depression [28]. Among those depressed, but otherwise healthy, outpatients, the prevalence of actual folate deficiency (defined as <1.5 ng/mL) was low (2%), whereas borderline low values (1.5-2.5 ng/mL) were more common (17%). Individuals with low or deficient serum folate exhibited a 35% rate of non-response to an adequate course of fluoxetine compared with a 20% rate of non-response among those with serum folate levels in the normal range. A similar result was reported among 22 depressed patients older than 60 years old treated with nortriptyline or sertraline for whom there was an inverse relationship between RBC folate and antidepressant response [29]. Consistent with this finding, in an earlier study of 101 depressed inpatients receiving a variety of treatments, including electroconvulsive therapy, antidepressants, or tryptophan, outcome was significantly poorer for patients with low serum folate [24]. However, for a small number of patients undergoing electroconvulsive therapy, serum MTHF did not appear to correlate with response [22]. Thus, accurate and sensitive predictors of refractoriness to antidepressant treatment have remained elusive [30].

Folate and MTHF Supplementation/Augmentation:

Godfrey et al.[31] administered MTHF (15 mg), an oral form of folate actively transported across the blood-brain barrier, to 24 patients with major depression and low or deficient folate (RBC folate <200 µg/L). In this 6-month, randomized, double-blind trial, those 13 depressed patients who received methylfolate were rated globally as having superior symptom improvement and social adjustment at 3 and 6 months when compared with the 11 patients who were assigned to placebo. However, this report was inconclusive, based on the relatively small sample and need for replication, non-systematic concomitant treatments (e.g., antidepressants, lithium, or no medications), symptom improvement on some but not all measures, and similar, although somewhat less dramatic, response to MTHF among comparably treated patients with schizophrenia, indicating that the positive effects of MTHF may not have been specific to depression. The prior reports extended previous work on folate replacement, reporting improved long-term neuropsychiatric outcome among folate-deficient patients with psychiatric [32] and gastrointestinal [13] disorders and in some, although not all, studies on anticonvulsant-treated patients with epilepsy [14].

The actual clinical relevance of these previous studies, however, is likely to be increasingly limited. Recent work has reported that the prevalence of folate deficiency or borderline low values is lower among contemporary psychiatric cohorts than originally believed [28] and also that Western estimates may not be comparable to other parts of the world including Asia [33]. Moreover, most of the studies on folate and depression are based on data gathered before implementation of folic-acid-fortification programs and the widespread public awareness about the possible health benefits of folate. In the United States, the Food and Drug Administration mandate requiring folic-acid fortification of all enriched grain products by 1998 appears to have exerted a rapid and substantial impact on the prevalence of low and deficient folate in the community, nearly eradicating low serum-folate values (<3 ng/mL) among 350 middle-aged and older adults in the Framingham Offspring Study Cohort [34].

A comparable study is needed on the prevalence of low folate among carefully diagnosed depressed cohorts in this postfortification era, particularly because the extent to which dietary intake contributes to low folate among depressed individuals is not well established [2, 24, 25, 28, 35, 36]. Nevertheless, the prevalence of low folate among depressed sample subjects is believed to be reduced well below the estimates prior to implementation of the folic-acid fortification programs. If so, the more compelling clinical focus for clinicians who treat depression shifts from folate replacement to folate supplementation and to the question of whether supraphysiologic doses of folate, as monotherapy or augmentation of conventional agents, may confer antidepressant benefit among depressed, normofolatemic patients.

Despite tremendous advances in the development of safe and effective antidepressants, as many as 30-40% of depressed patients continue to be symptomatic and functionally impaired despite an adequate course of antidepressant therapy [30]. Thus, the development of novel treatment strategies has considerable public-health significance.

Correlational analyses had reported that, among individuals with major mood disorders, higher folate values predicted better acute [25] and long-term outcome [37]. In the latter study, individuals with unipolar-depression or bipolar-disorder folate levels were boosted with daily low-dose folate supplementation (200 µg) together with pharmacologic prophylaxis of affective symptoms. Further demonstration of the potential antidepressant benefit of folate comes from a double-blind study of 96 non-folate-deficient patients with senile dementia and depressive symptoms in which significant improvement of depression was reported among patients randomized to MTHF (50 mg), similar to that observed on the active antidepressant comparator, trazodone (100 mg/d) [38]. Among 16 elderly non-demented subjects with major depression, an open trial of MTHF (50 mg) also resulted in substantial improvement in depressive symptoms, even among the 14 subjects who had normal baseline serum folate [39].

The inventors have also previously assessed the efficacy of methylfolate as an adjunctive treatment among adults with MDD and inadequate response to an SSRI [40]. Twenty-two adults (59% female; mean age 45.2+/−11.0 years) with DSM-IV MDD, partial or nonresponse to an SSRI after at least 4 weeks of treatment, and a 17-item Hamilton Depression Rating Scale (HAM-D-17) score greater than or equal to 12 were enrolled in this 8-week prospective open trial. Exclusion criteria included current use of anticonvulsants or psychotropics other than an SSRI, or B12 deficiency. Folinic acid was selected as an oral, synthetic, highly bioavailable form of folate that is metabolized to MTHF after absorption and, unlike MTHF, is available for prescription in the United States. Thus, folinic acid was added to SSRIs at 15-30 mg/day. Folate levels rose from 28+/−19 ng/mL to 301+/−203 ng/mL (p<0.001). HAM-D-17 scores among the 16 completers decreased from 19.1+/−3.9 to 12.8+/−7.0 (p<0.01). 31% of completers and 27% of the intent-to-treat (ITT) sample achieved response (with at least 50% reduction in HAM-D-17 scores), and 19% of completers and 18% of the ITT sample achieved remission (HAM-D-17 no greater than 7). In this report, folinic acid appeared to be only modestly effective as an adjunct in SSRI-refractory depressed individuals with normal folate levels, and surprisingly a significant portion of depressed individuals still did not respond to the folinic acid as an adjunct to an antidepressant. Thus, folate augmentation in treatment-resistant depression does not produce an effective response in all individuals [49], and in particular, as many as 29% to 46% of MDD patients show only partial or non-response to an adequate course of an antidepressant [50]. In particular, these reports did not identify in which patients the folate argumentation was effective or those patients where the antidepressant drug efficacy was not enhanced by folate. In fact, none of these reports identify biomarkers or a screen method to identify those subjects in where folate can enhance the efficacy of the antidepressant drug.

The assays and/or methods described herein can be used as a screen to identify and select for particular patients with depression, where a treatment regimen comprising an antidepressant and a folate-containing compound will be beneficial to enhance the therapeutic effect of the antidepressant drug.

In accordance with the assays and/or methods described herein, subjects with depression who have been determined to have the presence of at least one of the conditions described herein (e.g., SNPs and/or plasma/serum biomarkers described herein) can benefit from the therapeutic effect of an antidepressant administered in combination with an effective amount of a folate-containing compound. In some embodiments, the folate-containing compound can comprise L-methylfolate. In some embodiments, the folate-containing compound can comprise 6(S)-5-methyltetrahydrofolate (also known as 6(S)-5-MTHF) or DEPLIN®.

The effective amount of folate for use in the treatment methods described herein can vary, depending upon the types and/or dosage of the antidepressant (if any), types of folate, severity of depression, physical conditions of a subject (e.g., ages, genders, weights). The term "effective amount" as used herein generally refers to an amount of folate or a folate-containing compound that, when administered to a selected subject, can reduce at least one symptom associated with depression as described later, e.g., by at least about 5%, at least about 10%, at least about 20%, at least about 30%, at least about 40%, at least about 50%, at least about 60%, at least about 70%, at least about 80%, at least about 90% or more, as compared to the treatment in the absence of a folate-containing compound.

In some embodiments, the term "effective amount" as used herein refers to an amount of folate or a folate-containing compound, when administered to a selected subject in combination with an antidepressant, can increase the effect (e.g., efficacy or therapeutic effect) of the antidepressant, e.g., by at least about 5%, at least about 10%, at least about 20%, at least about 30%, at least about 40%, at least about 50%, at least about 60%, at least about 70%, at least about 80%, at least about 90% or more, as compared to the treatment with antidepressant alone. Stated another way, the term "effective amount" as used herein refers to an amount of folate or a folate-containing compound, when administered to a selected subject in combination with an antidepressant, can reduce at least one symptom associated with depression as described later, e.g., by at least about 5%, at least about 10%, at least about 20%, at least about 30%, at least about 40%, at least about 50%, at least about 60%, at least about 70%, at least about 80%, at least about 90% or more, as compared to the treatment with antidepressant alone.

In some embodiments, the effective amount of folate in the treatment regimen as described herein can range from about 1 mg/day to about 70 mg/day, from about 1 mg/day to about 50 mg/day, from about 2.5 mg/day to about 40 mg/day, from about 5 mg/day to about 40 mg/day, from about 5 mg/day to about 30 mg/day or from about 7 mg/day to about 15 mg/day. In some embodiments, the effective amount of folate in the treatment regimen as described herein can range from about 7.5 mg/day to about 50 mg/day. In some embodiments, the effective amount of folate in the treatment regimen as described herein can range from about 7.5 mg/day to about 40 mg/day. In some embodiments, the effective amount of folate in a treatment regimen can be about 15 mg/day.

Antidepressants

As used herein, unless otherwise noted, the term "antidepressant" or "anti-depressant" or "antidepressant drug" refers to any pharmaceutical agent which treats depression. In some embodiments, the anti-depressant drug administered to the subject in accordance with the methods described herein can be any conventional pharmaceutical agent which is commonly indicated for treating depression. Examples of antidepressants or antidepressant drugs can include, but are not limited to, mono-amine oxidase inhibitors such as phenelzine, tranylcypromine, and moclobemide; tricyclics such as imipramine, amitriptyline, desipramine, nortriptyline, doxepin, protriptyline, trimipramine, chlomipramine, and amoxapine; tetracyclics such as maprotiline; non-cyclics such as nomifensine; triazolopyridines such as trazodone; serotonin reuptake inhibitors such as fluoxetine, sertraline, paroxetine, citalopram, and fluvoxamine; serotonin receptor antagonists such as nefazadone; serotonin noradrenergic reuptake inhibitors such as venlafaxine, and milnacipran; noradrenergic and specific serotonergic agents such as mirtazapine; noradrenaline reuptake inhibitors such as reboxetine. Additional antidepressants that can be used in the methods described herein can include, but are not limited to, bupropion; natural products such as Kava-Kava, and St. John's Wort; dietary supplements such as s-adenosylmethionine; neuropeptides such as thyrotropin-releasing hormone; compounds targeting neuropeptide receptors such as neurokinin receptor antagonists; and hormones such as triiodothyronine.

In some embodiments, the antidepressant or the antidepressant drug can be a serotonin reuptake inhibitor (SRI) or selective serotonin reuptake inhibitor (SSRI). Examples of SRIs and/or SSRIs include, without limitations, citalopram, escitalopram, fluoxetine, R-fluoxetine, sertraline, paroxetine, fluvoxamine, venlafaxine, duloxetine, dapoxetine, nefazodone, imipramine, imipramine N-oxide, desipramine, pirandamine, dazepinil, nefopam, befuraline, fezolamine, femoxetine, clomipramine, cianoimipramine, litoxetine, cericlamine, seproxetine, WY 27587, WY 27866, imeldine, ifoxetine, tiflucarbine, viqualine, milnacipran, bazinaprine, YM 922, S 33005, F 98214TA, OPC 14523, alaproclate, cyanodothepine, trimipramine, quinupramine, dothiepin, amoxapine, nitroxazepine, McN 5652, McN 5707, Ol 77, Org 6582, Org 6997, Org 6906, amitriptyline, amitriptyline N-oxide, nortriptyline, CL 255. 663, pirlindole, indatraline, LY 113.821, LY 214.281, CGP 6085 A, RU 25.591, napamezole, diclofensine, trazodone, EMD 68.843, BMY 42.569, NS 2389, sercloremine, nitroquipazine, ademethionine, sibutramine and clovoxamine. The SRIs can be used in the form of the base or a pharmaceutically acceptable acid addition salt thereof.

In some embodiments, other therapeutic compounds that can cause an elevation in the extracellular level of 5-HT in the synatic cleft, e.g., tianeptine, can be used as an antidepressant in the methods described herein.

In some embodiments, the antidepressant or the antidepressant drug can be a selective serotonin reuptake inhibitor (SSRI). The term "selective serotonin reuptake inhibitor (SSRI)" as used herein, refers to an inhibitor of the monoamine transporters, which has stronger inhibitory effect at the serotonin transporter than the dopamine and the noradrenaline transporters. Examples of selective serotonin reuptake inhibitors (SSRIs) can include, without limitations, fluoxetine, citalopram, paroxetine, escitalopram, sertraline, and any combinations thereof.

Additional SRIs and/or SSRIs that can be administered to a subject with depression in combination with a folate-containing compound can include, for example, the ones described in the U.S. Pat. App. No.: US 2005/0054688, and US 2008/0138411; and U.S. Pat. Nos. 6,720,003; 6,787,560; 7,893,261; and 7148238.

One skilled in the art would be able to readily determine recommended dosage levels for known and/or marketed antidepressant drugs by consulting appropriate references such as drug package inserts, FDA guidelines, and the Physician's Desk Reference. In some embodiments, the antidepressant drug dose can range from 0.1 mg/day to about 1000 mg/day, from about 0.5 mg/day to about 500 mg/day, from about 1 mg/day to about 400 mg/day, from about 5 mg/day to about 300 mg/day, or from about 10 mg/day to about 200 mg/day. One of skill in the art can readily adjust dosage for each different antidepressant drug, depending on a number of factors such as types and/or potency of antidepressants, severity of depression, physical condition of a subject (e.g., ages, genders, and weights), administration routes, other medications taken by a subject, and any combinations thereof.

Pharmaceutical Compositions for Treatment of Depression

For in vivo administration to subjects who have met at least one (e.g., at least two, at least three or more) of the conditions (A)-(X) determined in the assays described herein, provided herein are pharmaceutical compositions comprising a therapeutically effective amount of a folate-containing compound, and a pharmaceutically acceptable carrier.

In various embodiments, the therapeutically effective amount of a folate-containing compound or folate, optionally administered with an antidepressant or a pharmaceutically salt thereof, is sufficient to increase the degree of improvement in at least one neuropsychological test, e.g., as measured by HAMD-17, HAMD-28 or other efficacy measures as described in the Examples, by at least about 5%, at least about 10%, at least about 20%, at least about 30%, at least about 40%, at least about 50%, at least about 60%, at least about 70%, at least about 80%, or at least about 90%, as compared to the degree of improvement obtained in the absence of the folate-containing compound (e.g., with or without the antidepressant monotherapy). In some embodiments, the therapeutically effective amount of a folate-containing compound or folate, optionally administered with an antidepressant or a pharmaceutically salt thereof, is sufficient to increase the degree of improvement in at least one neuropsychological test, e.g., as measured by HAMD-17, HAMD-28 or other efficacy measures as described in the Examples, by at least about 1-fold, at least about 2-fold, at least about 3-fold, at least about 4-fold, at least about 5-fold or more, as compared to the degree of improvement obtained in the absence of the folate-containing compound (e.g., with or without the antidepressant monotherapy).

In some embodiments, a dose of a folate-containing compound or folate for administration to a human can be in the range of about 0.01 to about 50 mg per kilogram body weight of the recipient per day, in the range of about 0.05 to about 5 mg per kilogram body weight per day, or in the range of about 0.1 to about 1 mg per kilogram body weight per day. In certain embodiments, the desired dose can be presented as one single unit dosage form, e.g., containing about 0.5 mg to about 500 mg, about 5 mg to about 250 mg, about 10 mg to about 100 mg, or about 10 mg to about 50 mg. In some embodiments, one single unit dosage form can provide about 1 mg to about 70 mg folate, about 5 mg to about 60 mg folate, or from about 7 mg to about 50 mg folate. In some embodiments, one single unit dosage form can provide about 7.5 mg to about 50 mg folate. In other embodiments, the desired dose can be presented in two, three, four, five or more sub-doses administered at appropriate intervals throughout the day. These sub-doses can be administered in unit dosage forms, for example, containing about 0.1 mg to about 250 mg, about 1 mg to about 100 mg, about 2 mg to about 20 mg, or about 2 mg to about 10 mg.

In some embodiments, the pharmaceutical composition can further comprise at least one antidepressant. In general, a dose of an antidepressant or a pharmaceutically acceptable salt thereof suitable for administration to a human is in the range of about 0.01 to 50 mg per kilogram body weight of the recipient per day, or in the range of 0.1 to 5 mg per kilogram body weight per day. In certain embodiments, the desired dose can be presented as one single unit dosage form, e.g., containing about 1 mg to about 500 mg, or about 5 mg to about 300 mg. In other embodiments, the desired dose can be presented in two, three, four, five or more sub-doses administered at appropriate intervals throughout the day. These sub-doses can be administered in unit dosage forms, for example, containing about 0.1 mg to about 100 mg or about 1 mg to about 50 mg.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (i) sugars, such as lactose, glucose and sucrose; (ii) starches, such as corn starch and potato starch; (iii) cellulose, and its derivatives, such as sodium carboxymethyl cellulose, methylcellulose, ethyl cellulose, microcrystalline cellulose and cellulose acetate; (iv) powdered tragacanth; (v) malt; (vi) gelatin; (vii) lubricating agents, such as magnesium stearate, sodium lauryl sulfate and talc; (viii) excipients, such as cocoa butter and suppository waxes; (ix) oils, such as peanut oil, cottonseed oil, safflower oil, sesame oil, olive oil, corn oil and soybean oil; (x) glycols, such as propylene glycol; (xi) polyols, such as glycerin, sorbitol, mannitol and polyethylene glycol (PEG); (xii) esters, such as ethyl oleate and ethyl laurate; (xiii) agar; (xiv) buffering agents, such as magnesium hydroxide and aluminum hydroxide; (xv) alginic acid; (xvi) pyrogen-free water; (xvii) isotonic saline; (xviii) Ringer's solution; (xix) ethyl alcohol; (xx) pH buffered solutions; (xxi) polyesters, polycarbonates and/or polyanhydrides; (xxii) bulking agents, such as polypeptides and amino acids (xxiii) serum component, such as serum albumin, HDL and LDL; (xxiv) C2-C12 alchols, such as ethanol; and (xxv) other non-toxic compatible substances employed in pharmaceutical formulations. Wetting agents, coloring agents, release agents, coating agents, sweetening agents, flavoring agents, perfuming agents, preservative and antioxidants can also be present in the formulation.

Pharmaceutically acceptable carriers can vary in a composition described herein, depending on the administration route and formulation. For example, the pharmaceutically acceptable composition described herein can be delivered via injection. These routes for administration (delivery) include, but are not limited to, subcutaneous or parenteral including intravenous, intraarterial, intramuscular, intraperitoneal, intramyocardial, and infusion techniques. In one embodiment, the pharmaceutical acceptable composition is in a form that is suitable for injection. In another embodiment, the pharmaceutical composition is formulated for delivery by a catheter.

When administering a pharmaceutical composition parenterally, it can be generally formulated in a unit dosage injectable form (solution, suspension, emulsion). The pharmaceutical formulations suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g. PBS).

In some embodiments, the pharmaceutical composition can be formulated in an emulsion or a gel.

In some embodiments, the pharmaceutical compositions described herein can be formulated for oral administration or for inhalation. For oral administration, suitable dosage forms can include tablets, troches, cachets, caplets, and capsules, including hard and soft gelatin capsules.

In some embodiments, both an antidepressant and a folate-containing compound can be formulated in a single pharmaceutical composition. For example, both an antidepressant and a folate-containing compound can be formulated in a single tablet for oral administration.

In some embodiments where the antidepressant and folate-containing compound are formulated in a single composition, they can be released from the composition at the same time or at different times. By way of example only, if the folate-containing compound is formulated in an outer layer of a composition (e.g., a tablet or drug-delivery particle) while the antidepressant is formulated in an inner layer of the composition, the folate-containing compound could be released from the composition first with a faster rate, while the antidepressant could be released from the composition later with a slower rate. On the other hand, if the antidepressant and the folate-containing compound are mixed homogenously within the composition, both can be released simultaneously from the composition.

In other embodiments, an antidepressant and a folate-containing compound can be formulated in separate pharmaceutical compositions for the same or different routes of administration during a therapy course. For example, an antidepressant can be formulated for inhalation administration while a folate-containing compound can be formulated for oral administration. In other embodiments, both the antidepressant and folate-containing compound can be formulated for oral administration, e.g., in separate tablets.

The effective amount of folate administered to a selected human subject for treatment of depression as described herein is significantly higher than the typical amount taken as a dietary supplement (between 50-600 mg/day). In some embodiments, the effective amount of folate administered to a selected human subject is at least about 2-fold, at least about 5-fold, at least about 10-fold, at least about 25-fold, at least about 50-fold, at least about 100-fold, at least about 250-fold, at least about 500-fold, at least about 1000-fold or more than the typical amount taken as a dietary supplement. Accordingly, in some embodiments, the folate-containing compound is desirable to be formulated in slow-release or sustained release composition.

Accordingly, in some embodiments, the pharmaceutical compositions comprising a folate-containing compound (with or without an anti-depressant) can be formulated for sustained release or sustained delivery. In some embodiments, the pharmaceutical compositions can be formulated in controlled-release drug-delivery systems, e.g., to provide sustained release of a folate-containing compound (and optionally an anti-depressant). As used herein, the term "sustained release" or "sustained delivery" refers to continual delivery of a therapeutic agent in vivo over a period of time following administration. For example, sustained release can occur over a period of at least about 1 hour, at least about 2 hours, at least about 3 hours, at least about 4 hours, at least about 5 hours, at least about 6 hours, at least about 9 hours, at least about 12 hours, at least about 16 hours, at least about 24 hours following administration. In some embodiments, sustained release can occur over a period of at least about 1 day, at least about 2 days, at least about 3 days, at least about 4 days, at least about 5 days, at least about 6 days, at least about 7 days following administration. In some embodiments, the release of a folate-containing compound from a drug-delivery system can be steady state (zero-order kinetics) with at least about 30% (e.g., including at least about 40%, at least about 50%, at least about 60%, at least about 70%, at least about 80%, at least about 90%, at least about 95% or more) of the folate-containing compound (and optionally an anti-depressant) released between about 3-6 hours post administration, or between about 4-5 hours post administration. In one embodiment, the release of a folate-containing compound (and optionally an anti-depressant) from a drug-delivery system can be steady state (zero-order kinetics) with substantially full release (e.g., ~100%) of the folate-containing compound released between about 3-6 hours post administration, or between about 4-5 hours post administration. In some embodiments, the folate-containing compound can be released from a drug-delivery system at a rate that is slow enough not to overload the intestinal absorption capacity of a patient's duodenum (first ⅓ of the small intestines where ~90% of the absorption occurs for a folate-containing compound, e.g., L-MTHF). In some embodiments, the folate-containing compound and an anti-depressant (if any) can be released from a drug-delivery system concurrently or separately, with the same or a different release rate.

Any drug delivery system (e.g., but not limited to polymer-based) that provides a sustained release of a folate-containing compound (and optionally an anti-depressant) over a pre-determined period of time can be used for administration of a folate-containing compound (and optionally an anti-depressant). In one embodiment, the drug-delivery system can be a caplet design large enough to be blocked by a pyloric valve between the stomach and the duodenum, thus allowing the caplet to slowly and partially dissolve over a desirable period of time, e.g., over a period of about 2-3 hours, during which the folate-containing compound is steadily released from the caplet. As the caplet dissolves to a size that can get through the pyloric valve at which time it completes its steady state release (e.g., an additional period of time, e.g., an additional 2 hours), the caplet can continue to travel into the jejunum (the second third of the small intestines) where absorption is minimal.

In some embodiments, a drug delivery system can use a blend of hydrophilic and hydrophobic polymers to control release of a folate-containing compound (and optionally an anti-depressant) via diffusion through, and erosion of, a polymer matrix.

In some embodiments, a drug delivery system can comprise a folate-containing compound (and optionally an anti-depressant) encapsulated in polymer-based particles. These folate-containing polymer-based particles can be filled into capsules or single-dose sachets for additional control of release.

Controlled-release (e.g., sustained release) drug delivery systems for different administration methods (e.g., oral administration, injection, implantation, inhalation) are known in the art and can be adopted to deliver a folate-containing compound (and optionally an antidepressant) for the treatment methods described herein. See, e.g., International Pat. App. Nos. WO 2012/111961 (oral formulation), WO 2012/131678 (injectable formulation); U.S. Pat. App. Nos. US 2012/0258161 (implantable formulation), US 2001/0038854, US 2001/0033866; and U.S. Pat. No. 8,268,347 (inhalation formulation), the content of which are incorporated herein by reference, for various types of drug-delivery systems to deliver an active agent via various administration routes.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it may be desirable to include isotonic agents, for example, sugars, sodium chloride, and the like.

The compositions can also contain auxiliary substances such as wetting or emulsifying agents, pH buffering agents, gelling or viscosity enhancing additives, preservatives, colors, binders, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. With respect to compositions described herein, however, any vehicle, diluent, or additive used should have to be biocompatible with the antidepressant or a pharmaceutically acceptable salt thereof and/or a folate-containing compound.

The pharmaceutical compositions can be isotonic, i.e., they can have the same osmotic pressure as blood and lacrimal fluid. The desired isotonicity of the compositions of the composition described herein can be accomplished using sodium chloride, or other pharmaceutically acceptable agents such as dextrose, boric acid, sodium tartrate, propylene glycol or other inorganic or organic solutes. In one embodiment, sodium chloride is used in buffers containing sodium ions.

Viscosity of the compositions can be maintained at the selected level using a pharmaceutically acceptable thickening agent. In one embodiment, methylcellulose is used because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

Typically, any additives (in addition to the antidepressant and/or folate-containing compound) can be present in an amount of 0.001 to 50 wt % solution in phosphate buffered saline, and the active ingredient is present in the order of micrograms to milligrams to grams, such as about 0.0001 to about 5 wt %, about 0.0001 to about 1 wt %, about 0.0001 to about 0.05 wt % or about 0.001 to about 20 wt %, about 0.01 to about 10 wt %, and about 0.05 to about 5 wt %. For any therapeutic composition to be administered to a subject with compression, and for any particular method of administration, it is preferred to determine toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan.

Those skilled in the art will recognize that the components of the compositions should be selected to be biocompatible with respect to the active agent, e.g., the antidepressant and/or folate-containing compound. This will present no problem to those skilled in chemical and pharmaceutical principles, or problems can be readily avoided by reference to standard texts or by simple experiments (not involving undue experimentation).

The compositions described herein can be prepared by mixing the ingredients following generally-accepted procedures. For example, the ingredients can be mixed in an appropriate pharmaceutically acceptable carrier and the mixture can be adjusted to the final concentration and viscosity by the addition of water or thickening agent and possibly a buffer to control pH or an additional solute to control tonicity. Generally the pH can vary from about 3 to about 7.5. In some embodiments, the pH of the composition can be about 6.5 to about 7.5. Compositions can be administered in dosages and by techniques well known to those skilled in the medical and veterinary arts taking into consideration such factors as the age, sex, weight, and condition of the particular patient, and the composition form used for administration (e.g., liquid). Dosages for humans or other mammals can be determined without undue experimentation by a skilled artisan.

A still further aspect provided herein relates to uses of a folate-comprising composition in the treatment of depression in a human subject who carries at least one of the conditions (A)-(X) described herein (e.g., but not limited to, either one or both conditions (A) and (C)). Another aspect provided herein relates to a folate-comprising composition in combination with an anti-depressant for use in the treatment of depression in a human subject who carries at least one of the conditions (A)-(X) described herein (e.g., but not limited to, either one or both conditions (A) and (C)). In some embodiments of these aspects described herein, the folate-comprising composition can comprise at least about 5 mg of folate (e.g., about 7.5 mg to about 50 mg of folate). In some embodiments, the folate-comprising composition can be formulated for a pre-determined release profile (e.g., a sustained release). In some embodiments, the human subject is an adult.

Selection of Subjects with Depression

In some embodiments, subjects amenable to assays, methods and compositions described herein can be subjects that have been diagnosed with or suspected of having or developing depression. Accordingly, in some embodiments, subjects that have been diagnosed or suspected of having or developing with depression are selected prior to subjecting them to the assays, methods and/or compositions described herein. In some embodiments, a subject is selected for a treatment regimen comprising a folate-containing compound is being treated for depression. In some embodiments, the subject is specifically administered with a folate-containing compound to enhance (or as an adjuvant) the effect of the antidepressant drug, and not for another reason. For example, a female with depression wishing to become pregnant, or who is pregnant, or is lactating may take prenatal supplements containing folic acid in combination with an antidepressant drug. In such instance, a human subject amenable to the assays, methods and/or compositions described herein is specifically selected for depression before performing the assays and/or methods described herein and/or administering the compositions described herein.

In some embodiments, the subject is specifically administered with a folate-containing compound for treatment of depression, and not for another reason. For example, a human subject diagnosed as having, or have a risk for, depression may take an effective amount of a folate-containing compound (with or without an anti-depressant). In such instance, a human subject amenable to the assays, methods, and/or compositions described herein is specifically selected for depression before performing the assays and/or methods described herein and/or administering the compositions described herein.

The phrase "having a risk for depression" or "suspected of having or developing depression" or "suspected of having or developing major depressive disorder" refers to a subject that presents one or more symptoms indicative of a depression including major depressive disorder (e.g., unexplained insomnia, fatigue, irritability, etc.) or is being screened for depression including major depressive disorder (e.g., during a routine physical), for example, in accordance with the criteria listed in DSM-IV or ICD-10 as discussed below.

As used herein, the term "depression" generally refers to a mental state of depressed mood characterized by feelings of sadness, despair and discouragement. In some embodiments, depression is a clinical symptom, and can include, but not limited to, major depressive disorder (including single episode and recurrent), unipolar depression, treatment-refractory depression, resistant depression, anxious depression and dysthymia (also referred to as dysthymic disorder). Further, the term "depression" can encompass any major depressive disorder, dysthymic disorder, mood disorders due to medical conditions with depressive features, mood disorders due to medical conditions with major depressive-like episodes, substance-induced mood disorders with depressive features and depressive disorder not otherwise specific as defined by their diagnostic criteria, as listed in the American Psychiatric Association's Diagnostic and Statistical Manual of Mental Disorders, 4th Edition (DSM-IV) or any later edition thereof, or the World Health Organization's International Statistical Classification of Diseases and Related Health Problems (ICD-10). In one embodiment, depression is major depressive disorder.

The DSM-IV and ICD-10 provides a common language and standard criteria for the classification of mental disorders, and have been commonly used by a suitably trained general practitioner, or by a psychiatrist or psychologist for diagnosis of depression including major depressive disorders. Symptoms of depression can include, but are not limited to, problems concentrating, remembering, and/or making decisions, changes in eating and/or sleeping habits, a loss of interest in enjoyable activities, difficulty going to work or taking care of daily responsibilities, feelings of guilt and/or hopelessness, slowed thoughts and/or speech, and preoccupation with thoughts of death or suicide. One of skill in the art can determine the score or rating of depression based on DSM-IV or ICD-10.

Other scales or criteria for classification of mental disorders known in the art, e.g., Maier or HAMD-7 scale, or social functioning questionnaire (SFQ), visual analogue scale (VAS), and/or cognitive and physical function questionnaire (CPFQ) can also be used to determine the degree of depression.

During diagnosis for depression, the practitioner can also assess the patient's medical history, discuss the subject's current ways of regulating their mood (healthy or otherwise) such as alcohol and drug use, and/or perform a mental state examination, which is an assessment of the person's current mood and thought content, in particular the presence of themes of hopelessness or pessimism, self-harm or suicide, and an absence of positive thoughts or plans. Additionally, a practitioner can generally perform a medical examination to rule out other non-cognitive causes of depressive symptoms. For example, blood tests measuring TSH and thyroxine can be used to exclude hypothyroidism; basic electrolytes and serum calcium to rule out a metabolic disturbance; and a full blood count including ESR to rule out a systemic infection or chronic disease. Testosterone levels can also be evaluated to diagnose hypogonadism, a cause of depression in men.

Any genetic or biomarker methods known in the art can also be used for diagnosis of depression. For example, U.S. Pat. App. No. US 2010/0273153 describes that the presence of TG7AT haplotype can be indicative of predisposition to major depressive disorder. Additional marker gene for depression such as ATP2A2, SCYA5, STIP1, EEF1A1, GRB10, CASP6, TSSC1, RAB9, NFATC3, TPR, and any others listed in, for example, U.S. Pat. App. No. US 2005/0239110 can also be used for diagnosing depression.

In some embodiments, subjects amenable to assays, methods and compositions described herein are subjects that have been diagnosed with or suspected of having or developing major depressive disorder. A major depressive episode is characterized by the presence of a severely depressed mood that persists for at least two weeks. Episodes can be isolated or recurrent and can be categorized by a skilled practitioner as mild (few symptoms in excess of minimum criteria), moderate, or severe (marked impact on social or occupational functioning).

In some embodiments, subjects amenable to assays, methods and compositions described herein are subjects that have been diagnosed with depression (e.g., major depressive disorder (MDD)) and are resistant to antidepressant monotherapy, i.e., a treatment for depression with a single antidepressant only. The phrase "resistant to antidepressant monotherapy" is used herein in reference to a subject with depression being resistant to at least one antidepressant in one or more classes. This includes subjects with depression that are resistant to at least two, at least three, at least four or more antidepressants in one or more classes. In some embodiments, subjects amenable to assays, methods and compositions described herein are subjects that have been diagnosed with major depressive disorder (MDD) and are resistant to at least one serotonin reuptake inhibitors (SRI), including at least one, at least two, at least three, at least four or more SRIs. In some embodiments, subjects amenable to assays, methods and compositions described herein are subjects that have been diagnosed with major depressive disorder (MDD) and are resistant to at least one selective serotonin reuptake inhibitor (SSRI), including at least two, at least three, at least four or SSRIs.

In some embodiments, subjects who are resistant to antidepressant monotherapy do not show a clinically-relevant reduction (e.g., as evaluated by a physician or a psychologist) in at least one symptom of depression from which they are suffering, after they have been administered with the antidepressant monotherapy for at least about 3 weeks or more, or up to about 3 weeks. Examples of symptoms of depression include, but are not limited to, low or depressed mood, anhedonia, low energy levels, guilt, decreased work and interests, psychomotor retardation, agitation, psychic anxiety, somatic anxiety, general somatic symptoms, reduced cognition or any combinations thereof.

In some embodiments, subjects who are resistant to antidepressant monotherapy do not show a clinically relevant reduction in at least one symptom of depression (e.g., 1, 2, 3, or more symptoms), after they have been administered with the antidepressant monotherapy for at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks or more. In some embodiments, subjects are determined to be treatment resistant if they do not show a clinically relevant reduction in at least one symptom of depression (e.g., 1, 2, 3, or more symptoms), after they have been administered with the antidepressant monotherapy for at least or up to about 3 weeks, at least or up to about 4 weeks, at least or up to about 5 weeks, at least or up to about 6 weeks, at least or up to about 7 weeks, at least or up to about 8, at least or up to about 9 weeks, at least or up to about 10 weeks, at least or up to about 11 weeks, or at least or up to about 12 weeks. The clinically relevant reduction in symptoms of depression can be evaluated by a physician or a psychologist.

In some embodiments, subjects amenable to assays, methods, and compositions described herein are subjects that are diagnosed with treatment-resistant depression (TRD) or treatment-refractory depression. As used interchangeably herein, the term "treatment-resistant depression" or "treatment-refractory depression" refers to a kind of depression that does not respond or is resistant to at least two or more anti-depressant drugs, e.g., at least three or more, or at least four or more anti-depressant drugs. In some embodiments, a subject is diagnosed with a treatment-resistant depression if the subject does not show a clinically relevant reduction in at least one symptom of depression described herein, after he/she has been administered with at least two or more anti-depressant drugs (either individually or in combination) for at least about 3 weeks or more, e.g., at least about 4 weeks, at least about 5 weeks, at least about 6 weeks, at least about 7 weeks, at least about 8 weeks, at least about 9 weeks, at least about 10 weeks, at least about 11 weeks, at least about 12 weeks or more. In some embodiments, a subject is diagnosed with a treatment-resistant depression if the subject does not show a clinically relevant reduction in at least one symptom of depression described herein, after he/she has been administered with at least two or more anti-depressant drugs (either individually or in combination) for up to about 12 weeks, including, e.g., up to about 11 weeks, up to about 10 weeks, up to about 9 weeks, up to about 8 weeks, up to about 7 weeks, up to about 6 weeks, up to about 5 weeks, up to about 4 weeks, or up to about 3 weeks. In some embodiments, a subject is diagnosed with a treatment-resistant depression if the subject does not show a clinically relevant reduction in at least one symptom of depression described herein, after he/she has been administered with at least two or more anti-depressant drugs (either individually or in combination) for at least or up to about 6 weeks, at least or up to about 7 weeks, at least or up to about 8 weeks, at least or up to about 9 weeks, at least or up to about 10 weeks, at least or up to about 11 weeks, or at least or up to about 12 weeks. In some embodiments, the treatment-resistant depression is diagnosed if the subject does not experience clinically relevant improvement in the symptoms of depression after at least or up to about 12 weeks on an antidepressant medication.

In some aspects of all the embodiments described herein, the term "treatment-resistant depression" can also be defined as failing to achieve remission after two treatments or two antidepressants within 4-12 weeks of time.

In some embodiments, subjects amenable to assays, methods, and compositions described herein can be subjects that are diagnosed with treatment-resistant depression (TRD) or treatment-refractory depression and are currently taking non-medicine treatment for TRD, e.g., but not limited to, electroconvulsive therapy, vagus nerve stimulation, transcranial magnetic stimulation, and/or "talk" therapy. These subjects can be recommended for, or administered with, a treatment regimen comprising a folate-comprising compound, alone or in combination with a non-medicine treatment for TRD as described herein. In some embodiments, these subjects can be recommended for, or administered with, a treatment regimen comprising a folate-comprising compound, in combination with at least one antidepressant drug, and optionally non-medicine treatment for TRD. In these embodiments, the antidepressant drug that is recommended for, or administered to, the subjects with TRD, in combination with a folate-comprising compound, can be an antidepressant drug to which the subjects have previously shown resistance, or an antidepressant drug that the subject has never tried.

In some embodiments, the subject selected for the assays, methods and compositions described herein have been in remission from depression and is now diagnosed with a relapse or a predisposition to a relapse. In other embodiments, the subject selected for the assays, methods and compositions described herein have been diagnosed with depression and is currently taking at least an antidepressant.

As used herein, a "subject" can mean a human or an animal. Examples of subjects include primates (e.g., humans, and monkeys). Generally, the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. A patient or a subject includes any subset of the foregoing, e.g., all of the above, or includes one or more groups or species such as humans, primates or rodents. In certain embodiments of the aspects described herein, the subject is a mammal, e.g., a primate, e.g., a human. The terms, "patient", "individual", and "subject" are used interchangeably herein. A subject can be male or female. In some embodiments, the subjects amenable to the assays, methods and/or compositions described herein can be female subjects.

In certain embodiments, the subject is a human subject. Human subjects can come from any ethnicity or race, e.g., including, but not limited to, Caucasian, African American, Asian and Hispanic, African Indian and Alaska Native, Native Hawaiian and other Pacific Islander. In some embodiments, the human subjects amenable to the assays, methods and/or compositions described herein can be Caucasian subjects. As used herein, the term "Caucasian" refers to a member of the white race consisting of individuals of European, north African, or southwest Asian ancestry. In some embodiments, the human subjects amenable to the assays, methods and/or compositions described herein can be African American subjects. In some embodiments, the human subjects amenable to the assays, methods and/or compositions described herein can be Asian subjects. In some embodiments, the human subjects amenable to the assays, methods and/or compositions described herein can be Hispanic subjects.

In some embodiments, the human subjects amenable to the assays, methods and compositions described herein can be of any age. In some embodiments, the human subjects amenable to the assays, methods and/or compositions described can be at an age of at least 18 years old. In other embodiments, human subjects below 18 years can also be subjected to the assays, methods and/or compositions described herein.

Systems and Computer Readable Media for Use in the Assays and/or Methods Described Herein Embodiments of a further aspect also provide for systems (and computer readable media for causing computer systems) to perform an assay for selecting a treatment regimen for a subject with depression based on at least sequence information of the SNP biomarkers (i)-(xxi) described herein and/or expression levels of the peripheral biomarkers (xxii)-(xxiv).

A computer system for obtaining data from at least one test sample obtained from at least one subject is provided. The system comprises: (a) a determination module configured to receive at least one test sample and perform at least one analysis on at least one test sample to determine parameters of at least two biomarkers (i) to (xxiv) described herein; (b) a storage device configured to store output data from the determination module; (c) a computing module, e.g., a non-human machine, comprising specifically-programmed instructions to determine from the output data the presence of at least one condition (A) to (X) described herein; and (d) a display module for displaying a content based in part on the data output from the computing module, wherein the content comprises a signal indicative of the presence of at least one condition (A) to (X) described herein, and optionally the absence of any one of the conditions (A) to (X) described herein, or a signal indicative of the absence of all of the conditions (A) to (X) described herein.

In some embodiments, the determination module can be configured to perform at least one genotyping analysis on at least one test sample to determine the genotypes of at least two loci comprising position 677 of SEQ ID NO. 1 (or position 27 of SEQ ID NO. 7) and position 2756 of SEQ ID NO. 2 (or position 27 of SEQ ID NO. 9). In these embodiments, the computing module can be configured to determine the presence of at least one SNP located at position 677 of SEQ ID NO. 1 (or position 27 of SEQ ID NO. 7) comprising at least one thymine "T" allele, and/or at position 2756 of SEQ ID NO. 2 (or position 27 of SEQ ID NO. 9) comprising at least one guanine "G" allele.

In another embodiment, the determination module can be configured to perform at least one analysis on at least one test sample to determine the presence or absence of at least one of the following conditions:
  i. an expression ratio of s-adenosyl methionine (SAM) to s-adenosyl homocysteine (SAH) smaller than a pre-determined reference ratio;
  ii. expression of 4-hydroxynonenal (4-HNE) greater than a first pre-determined reference value;
  iii. a single nucleotide polymorphism (SNP) at position 677 of SEQ ID NO: 1 comprising at least one thymine "T" allele, wherein the SEQ ID NO: 1 is a portion of a genomic nucleic acid sequence of methylenetetrahydrofolate reductase (MTHFR);
  iv. a SNP at position 2756 of SEQ ID NO: 2 comprising at least one guanine "G" allele, wherein the SEQ ID NO: 2 is a portion of a genomic nucleic acid sequence of methionine synthase (MTR); and
  v. a SNP at position 66 of SEQ ID NO: 3 comprising at least one guanine "G" allele, wherein the SEQ ID NO: 3 is a portion of a genomic nucleic acid sequence of methionine synthase reductase (MTRR).

In these embodiments, the determination module can be further configured to determine the presence or absence of at least one other condition (A)-(X) described herein. For example, in some embodiments, the determination module can be further configured to determine expression of high-sensitivity c-reactive protein (hsCRP). In some embodiments, the determination module can be further configured to determine the presence or absence of a SNP at position 1298 of the SEQ ID NO. 1 comprising at least one cytosine "C" allele.

In some embodiments, the determination module of the computer system can be configured to analyze at least one test sample to determine the presence or absence of at least two of the conditions (i)-(v) described above and expression of hsCRP.

In some embodiments, the determination module of the computer system can further comprise a comparison module adapted to compare the data output from the determination module with reference data stored on the storage device. In some embodiments, the reference data can include, but not limited to, major and/or rare variants of alleles corresponding to the SNPs described herein, a first pre-determined reference value of 4-HNE (e.g., at least 3.2 mg/L or above as measured in a plasma sample), a second pre-determined reference value of hsCRP (e.g., greater than 2.3 mg/L as measured in a plasma sample), a pre-determined reference ratio of SAM/SAH (e.g., less than 2.8 as measured in a plasma sample), and any combinations thereof.

Embodiments of the computer system described herein also comprises a storage device configured to store data output from the determination module; and a display module for displaying a content based in part on the data output from the determination module, wherein the content comprises a signal indicative of the presence of at least one of the conditions (i)-(v) described above, or a signal indicative of the absence of at least one of these conditions. In some embodiments, the content displayed on the display module can further comprise a signal indicative of the subject recommended to receive a treatment regimen comprising a folate-containing compound, or a signal indicative of the subject recommended to receive an alternative treatment regimen.

In some embodiments, the storage device of the computer system can be further configured to store physical information of at least one subject to be tested. Examples of the physical information can include obesity indicator (e.g., BMI) and/or gender of at least one tested subject. In such embodiments, the content displayed on the display module of the computer system can further comprise the obesity indicator (e.g., the BMI value) or a signal indicative of whether the human subject is obese or not (e.g., whether the BMI value is at least 30 kg/m$^2$ or not).

A tangible and non-transitory (e.g., no transitory forms of signal transmission) computer readable medium having computer readable instructions recorded thereon to define software modules for implementing a method on a computer is also provided herein. In one embodiment, the computer readable storage medium comprises: (a) instructions for comparing the data stored on a storage device with reference data to provide a comparison result, wherein the comparison identifies the presence or absence of at least one condition (A)-(X) described herein; and (b) instructions for displaying a content based in part on the data output from the determination module, wherein the content comprises a signal indicative of the presence of at least one of the conditions (A)-(X) described herein, and optionally the absence of any one of these conditions (A)-(X) described herein. In other embodiments, the content can comprise a signal indicative of the absence of all of the conditions (A)-(X) described herein.

In some embodiments, the instructions can be specifically programmed to perform a comparison to identify the presence of at least one SNP located at position 677 of SEQ ID NO. 1 (or position 27 of SEQ ID NO. 7) comprising at least one thymine "T" allele, and/or at position 2756 of SEQ ID NO. 2 (or position 27 of SEQ ID NO. 9) comprising at least one guanine "G" allele.

In other embodiments, the instructions can be specifically programmed to perform a comparison to identify one of the following conditions:
  i. an expression ratio of s-adenosyl methionine (SAM) to s-adenosyl homocysteine (SAH) smaller than a pre-determined reference ratio;
  ii. expression of 4-hydroxynonenal (4 HNE) greater than a pre-determined reference value;
  iii. a single nucleotide polymorphism (SNP) at position 677 of SEQ ID NO: 1 comprising at least one thymine "T" allele, wherein the SEQ ID NO: 1 is a portion of a genomic nucleic acid sequence of methylenetetrahydrofolate reductase (MTHFR);
  iv. a SNP at position 2756 of SEQ ID NO: 2 comprising at least one guanine "G" allele, wherein the SEQ ID NO: 2 is a portion of a genomic nucleic acid sequence of methionine synthase (MTR); and
  v. a SNP at position 66 of SEQ ID NO: 3 comprising at least one guanine "G" allele, wherein the SEQ ID NO: 3 is a portion of a genomic nucleic acid sequence of methionine synthase reductase (MTRR);

In these embodiments, the computer readable medium can further comprise instructions to identify the presence or absence of at least one other condition (A)-(X) described herein. For example, in one embodiment, the computer readable medium can further comprise instructions to identify the presence or absence of a SNP at position 1298 of the SEQ ID NO: 1 comprising at least one cytosine "C" allele. In some embodiments, the computer readable medium can further comprise instructions to compare expression of high-sensitivity c-reactive protein (hsCRP) with the reference data, e.g., pre-determined reference value of hsCRP expression level greater than 2.3 mg/L as measured in a plasma sample.

Embodiments of the display module of the computer readable medium described herein also comprise instructions for displaying a content based in part on the data output from the comparison module, wherein the content comprises a signal indicative of the presence of at least one of the conditions, or a signal indicative of the absence of at least one of the conditions. In some embodiments, the display module can further comprises instructions to display a signal indicative of the subject recommended to receive a treatment regimen comprising a folate-containing compound, or a signal indicative of the subject recommended to receive an alternative treatment regimen.

In some embodiments, the comparison module of the computer readable medium can further comprise instructions to determine if a human subject is obese (e.g., if BMI of at least one subject is at least 30 kg/m² or not). In such embodiments, the display module can further comprise instructions to display the obesity indicator (e.g., the BMI value) or a signal indicative of whether the subject is obese (e.g., whether the BMI value is at least 30 kg/m² or not).

Embodiments of the systems described herein have been described through functional modules, which are defined by computer executable instructions recorded on computer readable media and which cause a computer to perform method steps when executed. The modules have been segregated by function for the sake of clarity. However, it should be understood that the modules need not correspond to discrete blocks of code and the described functions can be carried out by the execution of various code portions stored on various media and executed at various times. Furthermore, it should be appreciated that the modules may perform other functions, thus the modules are not limited to having any particular functions or set of functions.

The computer readable media can be any available tangible media that can be accessed by a computer. Computer readable media includes volatile and nonvolatile, removable and non-removable tangible media implemented in any method or technology for storage of information such as computer readable instructions, data structures, program modules or other data. Computer readable media includes, but is not limited to, RAM (random access memory), ROM (read only memory), EPROM (eraseable programmable read only memory), EEPROM (electrically eraseable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

In some embodiments, the computer readable storage media 700 can include the "cloud" system, in which a user can store data on a remote server, and later access the data or perform further analysis of the data from the remote server.

Computer-readable data embodied on one or more computer-readable media, or computer readable medium 700, may define instructions, for example, as part of one or more programs, that, as a result of being executed by a computer, instruct the computer to perform one or more of the functions described herein (e.g., in relation to system 600, or computer readable medium 700), and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of system 600, or computer readable medium 700 described herein, may be distributed across one or more of such components, and may be in transition there between.

The computer-readable media can be transportable such that the instructions stored thereon can be loaded onto any computer resource to implement the assays and/or methods described herein. In addition, it should be appreciated that the instructions stored on the computer readable media, or computer-readable medium 200, described above, are not limited to instructions embodied as part of an application program running on a host computer. Rather, the instructions may be embodied as any type of computer code (e.g., software or microcode) that can be employed to program a computer to implement the assays and/or methods described herein. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the system described herein can include a determination module, a storage device, and a display module. In some embodiments, the system can further include a comparison module. The functional modules can be executed on one, or multiple, computers, or by using one, or multiple, computer networks. The determination module 602 has computer executable instructions to provide sequence information in computer readable form. As used herein, "sequence information" refers to any nucleotide and/or amino acid sequence, including but not limited to full-length nucleotide and/or amino acid sequences, partial nucleotide and/or amino acid sequences, or mutated sequences. Moreover, information "related to" the sequence information includes detection of the presence or absence of a sequence (e.g., detection of a mutation or deletion), determination of the concentration of a sequence in the sample (e.g., amino acid sequence expression levels, or nucleotide (RNA or DNA) expression levels), and the like. The term "sequence information" is intended to include the presence or absence of post-translational modifications (e.g. phosphorylation, glycosylation, summylation, farnesylation, and the like).

As an example, determination modules 602 for determining sequence information may include known systems for automated sequence analysis including but not limited to Hitachi FMBIO® and Hitachi FMBIO® II Fluorescent Scanners (available from Hitachi Genetic Systems, Alameda, Calif.); Spectrumedix® SCE 9610 Fully Automated 96-Capillary Electrophoresis Genetic Analysis Systems (available from SpectruMedix LLC, State College, Pa.); ABI PRISM® 377 DNA Sequencer, ABED 373 DNA Sequencer, ABI PRISM® 310 Genetic Analyzer, ABI PRISM® 3100 Genetic Analyzer, and ABI PRISM® 3700 DNA Analyzer (available from Applied Biosystems, Foster City, Calif.); Molecular Dynamics FluorImager™ 575, SI Fluorescent Scanners, and Molecular Dynamics FluorImager™ 595 Fluorescent Scanners (available from Amersham Biosciences UK Limited, Little Chalfont, Buckinghamshire, England); GenomyxSC™ DNA Sequencing System (available from Genomyx Corporation (Foster City, Calif.); and Pharmacia ALF™ DNA Sequencer and Pharmacia ALFexpress™ (available from Amersham Biosciences UK Limited, Little Chalfont, Buckinghamshire, England).

Alternative methods for determining sequence information, i.e. determination modules 602, include systems for protein and DNA analysis. For example, mass spectrometry systems including Matrix Assisted Laser Desorption Ionization—Time of Flight (MALDI-TOF) systems and SELDI-TOF-MS ProteinChip array profiling systems; systems for analyzing gene expression data (see, for example, published U.S. Patent Application, Pub. No. U.S. 2003/0194711); systems for array based expression analysis: e.g., HT array systems and cartridge array systems such as GeneChip® AutoLoader, Complete GeneChip® Instrument System, GeneChip® Fluidics Station 450, GeneChip® Hybridization Oven 645, GeneChip® QC Toolbox Software Kit, GeneChip® Scanner 3000 7G plus Targeted Genotyping System, GeneChip® Scanner 3000 7G Whole-Genome Association System, GeneTitan™ Instrument, and GeneChip® Array Station (each available from Affymetrix, Santa Clara, Calif.); automated ELISA systems (e.g., DSX® or DS2® (available from Dynax, Chantilly, Va.) or the Triturus® (available from Grifols USA, Los Angeles, Calif.), The Mago® Plus (available from Diamedix Corporation, Miami, Fla.); Densitometers (e.g. X-Rite-508-Spectro Densitometer® (available from RP Imaging™, Tucson, Ariz.), The HYRYS™ 2 HIT densitometer (available from Sebia Electrophoresis, Norcross, Ga.); automated Fluorescence insitu hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACSVantage SE, (available from Becton Dickinson, Franklin Lakes, N.J.); and radio isotope analyzers (e.g. scintillation counters).

The sequence information of SNPs and/or expression level information of plasma/serum biomarkers determined in the determination module can be read by the storage device 604. As used herein the "storage device" 604 is intended to include any suitable computing or processing apparatus or other device configured or adapted for storing data or information. Examples of electronic apparatus suitable for use with the system described herein can include stand-alone computing apparatus, data telecommunications networks, including local area networks (LAN), wide area networks (WAN), Internet, Intranet, and Extranet, and local and distributed computer processing systems. Storage devices 604 also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device 604 is adapted or configured for having recorded thereon sequence information or expression level information. Such information may be provided in digital form that can be transmitted and read electronically, e.g., via the Internet, on diskette, via USB (universal serial bus) or via any other suitable mode of communication, e.g., the "cloud".

As used herein, "expression level information" refers to any nucleotide and/or amino acid expression level information, including but not limited to full-length nucleotide and/or amino acid sequences, partial nucleotide and/or amino acid sequences, or mutated sequences. Moreover, information "related to" the expression level information includes detection of the presence or absence of a sequence (e.g., presence or absence of an amino acid sequence, nucleotide sequence, or post translational modification), determination of the concentration of a sequence in the sample (e.g., amino acid sequence levels, or nucleotide (RNA or DNA) expression levels, or level of post translational modification), and the like. In some embodiments, the expression level information also includes arithmetic manipulation of expression levels of at least two or more biomarkers (e.g., expression ratio of SAM to SAH).

As used herein, "stored" refers to a process for encoding information on the storage device 604. Those skilled in the art can readily adopt any of the presently known methods for recording information on known media to generate manufactures comprising the sequence information or expression level information.

A variety of software programs and formats can be used to store the sequence information or expression level information on the storage device. Any number of data processor structuring formats (e.g., text file or database) can be employed to obtain or create a medium having recorded thereon the sequence information or expression level information.

By providing sequence information and/or expression level information in computer-readable form, one can use the sequence information and/or expression level information in readable form in the comparison module 606 to compare a specific sequence or expression profile with the reference data within the storage device 604. For example, search programs can be used to identify fragments or regions of the sequences that match a particular sequence (reference data, e.g., sequence information of major or rare alleles corresponding to the SNPs described herein) or direct comparison of the determined expression level can be compared to the reference data expression level (e.g., median expression level information obtained from a population of subjects). The comparison made in computer-readable form provides a computer readable comparison result which can be processed by a variety of means. Content 608 based on the comparison result can be retrieved from the determination module 600 or the comparison module 606 to indicate the presence or absence of at least one SNP and serum/plasma/CSF biomarkers described herein.

In one embodiment the reference data stored in the storage device 604 to be read by the determination module 600 or the comparison module 606 is sequence information data obtained from a control biological sample of the same type as the biological sample to be tested. Alternatively, the reference data are a database, e.g., a part of the entire genome sequence of an organism, or a protein family of sequences, or an expression level profile (RNA, protein or peptide). In one embodiment, the reference data are sequence information and/or expression level profiles that are used to facilitate determining whether a subject with depression should be recommended for a treatment regimen comprising a folate-containing compound.

In one embodiment, the reference data are one or more reference polynucleotide, or polypeptide sequences. In some embodiments, the reference polynucleotide sequences can be derived from nucleotide sequences selected from the group consisting of SEQ ID NO: 1, SEQ ID NO: 2, SEQ ID NO: 3, and a portion there of comprising the nucleotide at the corresponding SNP location, and complements thereof. In some embodiments, the reference polypeptide sequences can be derived from amino acid sequences selected from the group consisting of SEQ ID NO: 4, SEQ ID NO: 5, SEQ ID NO: 6, and a portion thereof comprising an amino acid residue at the corresponding mutation location.

In one embodiment, the reference data are electronically or digitally recorded and annotated from databases including, but not limited to GenBank (NCBI) protein and DNA databases such as genome, ESTs, SNPS, Traces, Celara, Ventor Reads, Watson reads, HGTS, and the like; Swiss Institute of Bioinformatics databases, such as ENZYME, PROSITE, SWISS-2DPAGE, Swiss-Prot and TrEMBL databases; the Melanie software package or the ExPASy WWW server, and the like; the SWISS-MODEL, Swiss-Shop and other network-based computational tools; the Comprehensive Microbial Resource database (available from The Institute of Genomic Research). The resulting information can be stored in a relational data base that may be employed to determine homologies between the reference data or genes or proteins within and among genomes.

The "comparison module" 606 can use a variety of available software programs and formats for the comparison operative to compare sequence information determined in the determination module 602 to reference data. In one embodiment, the comparison module 606 is configured to use pattern recognition techniques to compare sequence information from one or more entries to one or more reference data patterns. The comparison module 606 may be configured using existing commercially-available or freely-available software for comparing patterns, and may be optimized for particular data comparisons that are conducted. The comparison module 606 provides computer readable information related to the sequence information that can include, for example, detection of the presence or absence of a sequence (e.g., detection of a mutation or deletion (protein or DNA), information regarding distinct alleles, detection of post-translational modification, or omission or repetition of sequences); determination of the concentration of a sequence in the sample (e.g., amino acid sequence/protein expression levels, or nucleotide (RNA or DNA) expression levels, or levels of post-translational modification), or determination of an expression profile.

In one embodiment, the comparison module 606 permits the prediction of protein sequences from polynucleotide sequences, permits prediction of open reading frames (ORF), or permits prediction of homologous sequence information in comparison to reference data, i.e., homologous protein domains, homologous DNA or RNA sequences, or homologous exons and/or introns.

In one embodiment, the comparison module 606 uses sequence information alignment programs such as BLAST (Basic Local Alignment Search Tool) or FAST (using the Smith-Waterman algorithm) may be employed individually or in combination. These algorithms determine the alignment between similar regions of sequences and a percent identity between sequences. For example, alignment may be calculated by matching, bases-by-base or amino acid-by amino-acid.

The comparison module 606, or any other module of the system described herein, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular embodiment, users can directly access data (via Hypertext links for example) residing on Internet databases using a HTML interface provided by Web browsers and Web servers. In another embodiment, users can directly access data residing on the "cloud" provided by the cloud computing service providers.

In one embodiment, the comparison module 606 performs comparisons with mass-spectrometry spectra, for example comparisons of peptide fragment sequence information can be carried out using spectra processed in MATLAB with script called "Qcealign" (see for example WO2007/022248, herein incorporated by reference) and "Qpeaks" (Spectrum Square Associates, Ithaca, N.Y.), or Ciphergen Peaks 2.1TM software. The processed spectra can then be aligned using alignment algorithms that align sample data to the control data using minimum entropy algorithm by taking baseline corrected data (see for example WIPO Publication WO2007/022248, herein incorporated by reference). The comparison result can be further processed by calculating ratios. Protein expression profiles can be discerned.

In one embodiment, computational algorithms are used in the comparison module 606 such as expectation-maximization (EM), subtraction and PHASE are used in methods for statistical estimation of haplotypes (see, e.g., Clark, A. G. Mol Biol Evol 7:111-22 (1990); Stephens, M., Smith, N. J. & Donnelly, P. Am J Hum Genet. 68:978-89 (2001); Templeton, A. R., Sing, C. F., Kessling, A. & Humphries, Genetics 120:1145-54 (1988)).

Various algorithms are available which are useful for comparing data and identifying the predictive gene signatures. For example, algorithms such as those identified in Xu et al., Physiol. Genomics 11:11-20 (2002). There are numerous software available for detection of SNPs and polymorphisms that can be used in the comparison module, including, but not limited to: HaploSNPer, a web-based program for detecting SNPs and alleles in user-specified input sequences from both diploid and polyploid species (available on the world-wide web at bioinformatics.nl/tools/haplosnper/; see also Tang et al., BMC Genetics 9:23 (2008)); Polybayes, a tool for SNP discovery in redundant DNA sequences (Marth, G T., et al., Nature Genetics 23(4):452-6 (1999); SSAHA-SNP, a polymorphism detection tool that uses the SSAHA alignment algorithm (available from Wellcome Trust Sanger Institute, Cambridge, United Kingdom, see also Ning Z., et al., Genome Research 11(10):1725-9 (2001)); Polyphred, A SNP discovery package built on phred, phrap, and consed tools (available on the world-wide web, see Nickerson, D A et al., Nucleic Acids Research 25(14):2745-51 (1997)); NovoSNP, a graphical Java-based program (PC/Mac/Linux) to identify SNPs and indels (available on the world-wide web, see Weckx, S. et al., Genome Research 15(3):436-442 (2005)); SNPdetector™, for automated identification of SNPs and mutations in fluorescence-based resequencing reads (available from Affymetrix, Santa Clara, Calif.), see also Zhang et al. PLoS Comput Biol (5):e53 (2005). SNPdetector runs on Unix/Linux platform and is available publicly; Affymetrix (Santa Clara, Calif.) has multiple data analysis software that can be used, for example Genotyping Console™ Software, GeneChip® Sequence Analysis Software (GSEQ), GeneChip® Targeted Genotyping Analysis Software (GTGS) and Expression Console™ Software.

In one embodiment, the comparison module 606 compares gene expression profiles. For example, detection of gene expression profiles can be determined using Affymetrix Microarray Suite software version 5.0 (MAS 5.0) (available from Affymetrix, Santa Clara, Calif.) to analyze the relative abundance of a gene or genes on the basis of the intensity of the signal from probe sets, and the MAS 5.0 data files can be transferred into a database and analyzed with Microsoft Excel and GeneSpring 6.0 software (available from Agilent Technologies, Santa Clara, Calif.). The detection algorithm of MAS 5.0 software can be used to obtain a comprehensive overview of how many transcripts are detected in given samples and allow a comparative analysis of two or more microarray data sets.

In one embodiment, the comparison module 606 compares protein expression profiles. Any available comparison software can be used, including but not limited to, the Ciphergen Express (CE) and Biomarker Patterns Software (BPS) package (available from Ciphergen Biosystems, Inc., Freemont, Calif.). Comparative analysis can be done with protein chip system software (e.g., The Proteinchip Suite (available from Bio-Rad Laboratories, Hercules, Calif.). Algorithms for identifying expression profiles can include the use of optimization algorithms such as the mean variance algorithm (e.g. JMP Genomics algorithm available from JMP Software Cary, N.C.).

In one embodiment, pattern comparison software can be used to determine whether patterns of expression or mutations are indicative of the presence or the absence of the conditions detected in a test sample of a subject.

The comparison module 606 provides computer readable comparison result that can be processed in computer readable form by predefined criteria, or criteria defined by a user, to provide a content based in part on the comparison result that may be stored and output as requested by a user using a display module 610. The display module 610 enables display of a content 608 based in part on the comparison result for the user, wherein the content 608 is a signal indicative of the presence of at least one of the conditions described herein or a signal indicative of the absence of at least one of the conditions described herein. Such signal, can be for example, a display of content 608 indicative of the presence or absence of at least one of the conditions on a computer monitor, a printed page of content 608 indicating the presence or absence of at least one of the conditions from a printer, or a light or sound indicative of the presence or absence of at least one of the conditions.

In various embodiments of the computer system described herein, the comparison module 606 can be integrated into the determination module 602.

The content 608 based on the comparison result can also include an expression profile of one or more plasma/serum biomarkers described herein. In one embodiment, the content 608 based on the comparison includes a sequence of a particular gene or protein and a determination of the presence of one or more mutations, or specific post-translational modification. In one embodiment, the content 608 based on the comparison result is merely a signal indicative of the presence or absence of at least one of the conditions described herein. In some embodiments, the content 608 can be a signal indicative of an obesity indicator (e.g., a BMI value) or a signal indicative of whether the subject is obese (e.g., whether the BMI value is at least 30 $kg/m^2$ or not). In some embodiments, the content 608 can be a signal indicative of the subject recommended to receive a treatment regimen comprising a folate-containing compound, or a signal indicative of the subject recommended to receive an alternative treatment regimen.

In one embodiment, the content 608 based on the comparison result is displayed a on a computer monitor. In one embodiment, the content 608 based on the comparison result is displayed through printable media. The display module 610 can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content 608 based on the comparison result. It should be understood that other modules of the system described herein can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces. The requests so formulated with the user's Web browser are transmitted to a Web application which formats them to produce a query that can be employed to extract the pertinent information related to the sequence information, e.g., display of an indication of the presence or absence of mutation or deletion (DNA or protein); display of expression levels of an amino acid sequence (protein); display of nucleotide (RNA or DNA) expression levels; display of expression, SNP, or mutation profiles, or haplotypes, or display of information based thereon. In one embodiment, the sequence information of the reference sample data is also displayed.

In any embodiments, the comparison module can be executed by a computer implemented software as discussed earlier. In such embodiments, a result from the comparison module can be displayed on an electronic display. The result can be displayed by graphs, numbers, characters or words. In additional embodiments, the results from the comparison module can be transmitted from one location to at least one other location. For example, the comparison results can be transmitted via any electronic media, e.g., internet, fax, phone, a "cloud" system, and any combinations thereof. Using the "cloud" system, users can store and access personal files and data or perform further analysis on a remote server rather than physically carrying around a storage medium such as a DVD or thumb drive.

The system 600, and computer readable medium 700, is merely illustrative embodiments for performing assays for selecting a treatment regimen for a subject with depression, based on expression level information or sequence information, and is not intended to limit the scope of the inventions described herein. Variations of system 600, and computer readable medium 700, are possible and are intended to fall within the scope of the inventions described herein.

The modules of the machine, or used in the computer readable medium, may assume numerous configurations. For example, function may be provided on a single machine or distributed over multiple machines.

Kits

Based on the identification of SNPs and/or peripheral markers associated with a response to the use of a folate-containing compound, one aspect described herein also provides for the design and preparation of detection reagents needed to identify the SNPs and/or peripheral markers disclosed herein in a test sample of a subject. For example, the detection reagents can be designed and prepared to identify SNPs in MTHFR locus and MTR locus and optionally MTRR locus involved in assays and methods described herein, and/or measure expression levels of SAM, SAH and 4-HNE in a test sample. Examples of detection reagents that can be used to identify the disclosed SNPs in a test sample can include a primer and a probe, wherein the probe can selectively hybridize the SNP-containing nucleic acid molecules, as compared to a nucleic acid molecule which does not contain the SNP at the same nucleotide position. Examples of detection regents that can be used to measure expression levels of peripheral proteins (e.g., SAM, SAH and/or 4-HNE) in a test sample can include antibodies against such proteins, or a primer and a probe, wherein the probe specifically hybridizes to a nucleic acid molecule corresponding to such proteins.

Accordingly, provided herein include kits for selecting a treatment regimen for a subject with depression. In some embodiments, the kits can be used for monitoring the efficacy response of a subject treated with a combination therapy comprising a folate-containing compound, for example as shown in Example 5. The kits can include at least one reagent specific for detecting for the presence or absence of SNP markers (i)-(xxi) described herein (e.g., MTHFR C677T, MTR A2756G, and/or MTRR A66G) and/or antibodies specific for detecting peripheral biomarkers (xxii)-(xxiv) (e.g., SAM, SAH, and 4-HNE), and instructions for determining that the subject is recommended for a treatment regimen comprising a folate-containing compound if the presence of at least one of the conditions described herein is detected in a test sample (e.g., a blood sample, a saliva sample, a buccal sample, a urine sample or a cerebrospinal fluid sample) of the subject, for example, the procedures as shown in Example 5. The kit can optionally include a nucleic acid for detection of the gene of interest.

In one embodiment, a kit can comprise an oligonucleotide array affixed with a plurality of oligonucleotide probes that interrogate no more than 30 SNPs (including no more than 25 SNPs, no more than 20 SNPs, no more than 15 SNPs, no more than 10 SNPs, no more than 5 SNPs or less), wherein the SNPs comprise at least two or any combinations of the conditions (A)-(U) described herein (e.g., but not limited to, a combination of conditions (A) and (C)); and an optional container containing a detectable label (e.g., comprising a fluorescent molecule) to be conjugated to a nucleotide molecule derived from a test sample of a human subject; and at least one reagent. Examples of a reagent that can be included in the kit can include, without limitations, a restriction enzyme, a universal adaptor to be conjugated to a nucleotide molecule, a primer complementary to the universal adaptor, a wash agent, and any combinations thereof.

In some embodiments, the plurality of oligonucleotide probes affixed to an oligonucleotide array can interrogate about 2-30 SNPs, e.g., about 3-25 SNPs, about 3-20 SNPs, about 3-10 SNPs, or about 3-5 SNPs, wherein the SNPs comprise at least two or any combinations of the conditions (A)-(U) described herein (e.g., but not limited to, a combination of conditions (A) and (C)).

In an alternative embodiment, a kit can comprise a plurality of oligonucleotide primers that bind to at least one allele of no more than 30 SNPs (including no more than 25 SNPs, no more than 20 SNPs, no more than 15 SNPs, no more than 10 SNPs, no more than 5 SNPs or less), wherein each subset of oligonucleotide primers that bind to a specific allele of a SNP is labeled with a distinct reporter, and wherein said SNPs comprise at least two or any combinations of the SNP conditions (A)-(U) described herein (e.g., but not limited to a combination of conditions (A) and (C)); and at least one reagent, e.g., but not limited to, free nucleotide bases, a polymerase, or both.

In some embodiments, the plurality of oligonucleotide primers can bind to at least one allele of about 2-30 SNPs, e.g., about 3-25 SNPs, about 3-20 SNPs, about 3-10 SNPs, or about 3-5 SNPs, wherein the SNPs comprise at least two or any combinations of the conditions (A)-(U) described herein (e.g., but not limited to, a combination of conditions (A) and (C)).

Additional reagents included in the kit can vary with the selection of a genotyping assay, e.g., but not limited to, allele-specific probe hybridization, allele-specific primer extension, allele-specific amplification, sequencing, 5' nuclease digestion, molecular beacon assay, DNA chip analysis, oligonucleotide ligation assay, size analysis, single-stranded conformation polymorphism, polymerase chain reaction (PCR), real-time quantitative PCR, and any combinations thereof.

In some embodiments, the kit can further comprise at least one reagent to determine expression of at least one biomarker described herein (e.g., SAM, SAH, 4-HNE and hsCRP). For example, in one embodiment, the kit can further comprise a solid substrate support affixed with at least one protein-based binding moiety (e.g., an antibody) that specifically binds to one or more of the biomarkers described herein. Exemplary solid substrate support can include, but not limited to, a microtiter plate for ELISA, a dipstick, a magnetic bead, or any combinations thereof. Different solid substrate supports can be selected based on various types of expression assays, e.g., but not limited to, western blot, enzyme linked absorbance assay, mass spectrometry, immunoassay, flow cytometry, immunohistochemical analysis, and any combinations thereof.

In another embodiment, the kit can further comprise at least one primer designed to probe one or more biomarkers described herein.

Embodiments of the various aspects described herein can also be described by any one of the following numbered paragraphs.

1. An assay for selecting a treatment regimen for a human subject with depression, comprising:
    (a) subjecting a test sample from a human subject, who is diagnosed as having depression or having a risk for depression, to at least one genotyping assay adapted to determine the genotypes of at least two loci, wherein said at least two loci are:
       i. position 677 of SEQ ID NO. 1 or position 27 of SEQ ID NO. 7 (identified by rs1801133), wherein the SEQ ID NO. 1 and SEQ ID NO. 7 are each independently a portion of a genomic nucleic acid sequence of methylenetetrahydrofolate reductase (MTHFR);

ii. position 2756 of SEQ ID NO. 2 or position 27 of SEQ ID NO. 9 (identified by rs1805087), wherein the SEQ ID NO. 2 and SEQ ID NO. 9 are each independently a portion of a genomic nucleic acid sequence of methionine synthase (MTR); and (b) detecting from the genotypes of said at least two loci the presence of a single nucleotide polymorphism (SNP) selected from the following:
   i. a SNP677 at position 677 of SEQ ID NO. 1 or position 27 of SEQ ID NO. 7 comprising at least one thymine "T" allele;
   ii. a SNP2756 at position 2756 of SEQ ID NO. 2 or position 27 of SEQ ID NO. 9 comprising at least one guanine "G" allele; and
   iii. a combination of at least one SNP677 T allele and at least one SNP2756 G allele; and if at least one of T allele at position SNP677 or at least one G allele at position SNP2756 or both at least one T allele at position SNP677 and at least one G allele at position SNP2756 is detected, then selecting, and optionally administering, a treatment regimen comprising an effective amount of a folate-containing compound.

2. The assay of paragraph 1, wherein if neither SNP677 T allele nor SNP2756 G allele is detected then selecting a treatment regimen without a folate-containing compound.

3. An assay for selecting a treatment regimen for a human subject having depression, comprising:
subjecting a test sample of the human subject, who is diagnosed as having depression or having a risk for depression, to at least one assay to detect the presence or absence of at least one of the following conditions:
   i. an expression ratio of s-adenosyl methionine (SAM) to s-adenosyl homocysteine (SAH) smaller than a pre-determined reference ratio;
   ii. expression of 4-hydroxynonenal (4-HNE) greater than a first pre-determined reference value;
   iii. a single nucleotide polymorphism (SNP) at position 677 of SEQ ID NO. 1 or position 27 of SEQ ID NO. 7 (identified by rs1801133) comprising at least one thymine "T" allele, wherein the SEQ ID NO. 1 and SEQ ID NO. 7 are each independently a portion of a genomic nucleic acid sequence of methylenetetrahydrofolate reductase (MTHFR);
   iv. a SNP at position 2756 of SEQ ID NO. 2 or position 27 of SEQ ID NO. 9 comprising at least one guanine "G" allele, wherein the SEQ ID NO. 2 and SEQ ID NO. 9 are each independently a portion of a genomic nucleic acid sequence of methionine synthase (MTR); and
   v. a SNP at position 66 of SEQ ID NO. 3 or position 27 of SEQ ID NO. 10 comprising at least one guanine "G" allele, wherein the SEQ ID NO. 3 and SEQ ID NO. 10 are each independently a portion of a genomic nucleic acid sequence of methionine synthase reductase (MTRR);

and if at least one of said conditions is detected to be present then recommending that a treatment regimen comprising a folate-containing compound be selected; and if none of these conditions is determined to be present then recommending a treatment regimen without a folate-containing compound.

4. The assay of any one of the preceding paragraphs, further comprising determining a parameter of at least one biomarker from the following:
   i. genotype of a SNP locus at position 1793 of SEQ ID NO. 1 or position 27 of SEQ ID NO. 8 (identified by rs2274976), wherein SEQ ID NO. 1 and SEQ ID NO. 8 are each independently a portion of a genomic nucleic acid sequence of methylenetetrahydrofolate reductase (MTHFR);
   ii. genotype of a SNP locus at position 66 of SEQ ID NO. 3 or position 27 of SEQ ID NO. (identified by rs1801394), wherein the SEQ ID NO. 3 and SEQ ID NO. 10 are each independently a portion of a genomic nucleic acid sequence of methionine synthase reductase (MTRR);
   iii. genotype of a SNP locus at rs1006737 (position 27 of SEQ ID NO. 11), wherein the SEQ ID NO. 11 is a portion of a genomic nucleic acid sequence of calcium channel, voltage-dependent, L type, alpha 1C subunit (CACNA1C);
   iv. genotype of a SNP locus at rs1883729 (position 27 of SEQ ID NO. 12), wherein the SEQ ID NO. 12 is a portion of a genomic nucleic acid sequence of DNA (cytosine-5)-methyltransferase 3 beta (DNMT3B);
   v. genotype of a SNP locus at rs7163862 (position 27 of SEQ ID NO. 13), wherein the SEQ ID NO. 13 is a portion of a genomic nucleic acid sequence of GTP cyclohydrolase 1 feedback regulatory protein (GCHFR);
   vi. genotype of a SNP locus at rs12659 (position 27 of SEQ ID NO. 14), wherein the SEQ ID NO. 14 is a portion of a genomic nucleic acid sequence of reduced folate carrier protein (RCF2);
   vii. genotype of a SNP locus at rs202676 (position 27 of SEQ ID NO. 15), wherein the SEQ ID NO. 15 is a portion of a genomic nucleic acid sequence of folate hydrolase (prostate-specific membrane antigen) 1 (FOLH1);
   viii. genotype of a SNP locus at rs2297291 (position 27 of SEQ ID NO. 16), wherein the SEQ ID NO. 16 is a portion of a genomic nucleic acid sequence of reduced folate carrier protein (RCF1);
   ix. genotype of a SNP locus at rs1051266 (position 27 of SEQ ID NO. 17), wherein the SEQ ID NO. 17 is a portion of a genomic nucleic acid sequence of reduced folate carrier protein (RCF1);
   x. genotype of a SNP locus at rs8007267 (position 27 of SEQ ID NO. 18), wherein the SEQ ID NO. 18 is a portion of a genomic nucleic acid sequence of GTP cyclohydrolase 1 (GCH1);
   xi. genotype of a SNP locus at rs7639752 (position 27 of SEQ ID NO. 19), wherein the SEQ ID NO. 19 is a portion of a genomic nucleic acid sequence of choline-phosphate cytidylyltransferase A (PCYT1A);
   xii. genotype of a SNP locus at rs6275 (position 27 of SEQ ID NO. 20), wherein the SEQ ID NO. 20 is a portion of a genomic nucleic acid sequence of dopamine receptor D2 (DRD2);
   xiii. genotype of a SNP locus at rs1079596 (position 27 of SEQ ID NO. 21), wherein the SEQ ID NO. 21 is a portion of a genomic nucleic acid sequence of dopamine receptor D2 (DRD2);
   xiv. genotype of a SNP locus at rs11240594 (position 27 of SEQ ID NO. 22), wherein the SEQ ID NO. 22 is a portion of a genomic nucleic acid sequence of dopamine receptor D2 (DRD2);

xv. genotype of a SNP locus at rs4633 (position 27 of SEQ ID NO. 23), wherein the SEQ ID NO. 23 is a portion of a genomic nucleic acid sequence of catechol-β-methyltransferase (COMT);

xvi. genotype of a SNP locus at rs4680 (position 27 of SEQ ID NO. 24), wherein the SEQ ID NO. 24 is a portion of a genomic nucleic acid sequence of catechol-β-methyltransferase (COMT);

xvii. genotype of a SNP locus at rs250682 (position 27 of SEQ ID NO. 25, wherein the SEQ ID NO. 25 is a portion of a genomic nucleic acid sequence of solute carrier family 6 (neurotransmitted transported, dopamine), member 3 (SLC6A3);

xviii. genotype of a SNP locus at rs2277820 (position 27 of SEQ ID NO. 26), wherein the SEQ ID NO. 26 is a portion of a genomic nucleic acid sequence of formiminotransferase cyclodeaminase (FTCD);

xix. genotype of a SNP locus at rs2236225 (position 27 of SEQ ID NO. 27), wherein the SEQ ID NO. 27 is a portion of a genomic nucleic acid sequence of methylenetetrahydrofolate dehydrogenase (NADP+ dependent) 1 (MTHFD1);

xx. an obesity indicator (e.g., a BMI value);

xxi. expressions of SAM and SAH;

xxii. expression of 4-HNE;

xxiii. expression of hsCRP; and any combinations thereof

5. The assay of paragraph 4, further comprising determining, from the determined parameter of said at least one biomarker, the presence of at least one condition from the following:

i. a SNP at position 1793 of SEQ ID NO. 1 or position 27 of SEQ ID NO. 8 comprising at least one adenine "A" allele;

ii. a SNP at position 66 of SEQ ID NO. 3 or position 27 of SEQ ID NO. 10 comprising at least one guanine "G" allele;

iii. a SNP at rs1006737 (position 27 of SEQ ID NO. 11) comprising at least one adenine "A" allele;

iv. a SNP at rs1883729 (position 27 of SEQ ID NO. 12) comprising at least one adenine "A" allele;

v. a SNP at rs7163862 (position 27 of SEQ ID NO. 13) comprising at least one thymine "T" allele;

vi. a SNP at rs12659 (position 27 of SEQ ID NO. 14) comprising at least one thymine "T" allele;

vii. a SNP at rs202676 (position 27 of SEQ ID NO. 15) comprising at least one guanine "G" allele;

viii. a SNP at rs2297291 (position 27 of SEQ ID NO. 16) comprising at least one adenine "A" allele;

ix. a SNP at rs1051266 (position 27 of SEQ ID NO. 17) comprising at least one adenine "A" allele;

x. a SNP at rs8007267 (position 27 of SEQ ID NO. 18) comprising at least one thymine "T" allele;

xi. a SNP at rs7639752 (position 27 of SEQ ID NO. 19) comprising at least one adenine "A" allele;

xii. a SNP at rs6275 (position 27 of SEQ ID NO. 20) comprising at least one thymine "T" allele;

xiii. a SNP at rs1079596 (position 27 of SEQ ID NO. 21) comprising at least one thymine "T" allele;

xiv. a SNP at rs11240594 (position 27 of SEQ ID NO. 22) comprising at least one adenine "A" allele;

xv. a SNP at rs4633 (position 27 of SEQ ID NO. 23) comprising at least one cytosine "C" allele;

xvi. a SNP at rs4680 (position 27 of SEQ ID NO. 24) comprising at least one guanine "G" allele;

xvii. a SNP at rs250682 (position 27 of SEQ ID NO. 25) comprising at least one cytosine "C" allele;

xviii. a SNP at rs2277820 (position 27 of SEQ ID NO. 26) comprising at least one thymine "T" allele; and xix. a SNP at rs2236225 (position 27 of SEQ ID NO. 27) comprising at least one adenine "A" allele;

xx. obesity (e.g., defined by a BMI value of 30 kg/m$^2$ or greater);

xxi. an expression ratio of SAM to SAH smaller than a pre-determined reference ratio;

xxii. an expression of 4-HNE greater than a first pre-determined reference value;

xxiii. an expression of hsCRP greater than a second pre-determined reference value (e.g., greater than about 2.3 mg per liter as measured in a plasma sample); and any combinations thereof; and if at least one of the condition is detected, then selecting, and optionally administering, a treatment regimen comprising an effective amount of a folate-containing compound.

6. An assay for selecting a treatment regimen for a human subject having depression, comprising:

(a) subjecting a test sample of the human subject, who is diagnosed as having depression or having a risk for depression, to at least one analysis to determine parameters of at least two biomarkers from:

i. genotype of a SNP locus at position 677 of SEQ ID NO. 1 or position 27 of SEQ ID NO. 7 (identified by rs1801133), wherein the SEQ ID NO. 1 and SEQ ID NO. 7 are each independently a portion of a genomic nucleic acid sequence of methylenetetrahydrofolate reductase (MTHFR);

ii. genotype of a SNP locus at rs2274976 (position 1793 of SEQ ID NO. 1 or position 27 of SEQ ID NO. 8), wherein the SEQ ID NO. 1 and SEQ ID NO. 8 are each independently a portion of a genomic nucleic acid sequence of methylenetetrahydrofolate reductase (MTHFR);

iii. genotype of a SNP locus at position 2756 of SEQ ID NO. 2 or position 27 of SEQ ID NO. 9 (identified by rs1805087), wherein the SEQ ID NO. 2 and SEQ ID NO. 9 are each independently a portion of a genomic nucleic acid sequence of methionine synthase (MTR);

iv. genotype of a SNP locus at position 66 of SEQ ID NO. 3 or position 27 of SEQ ID NO. 10 (identified by rs1801394), wherein the SEQ ID NO. 3 and SEQ ID NO. 10 are each independently a portion of a genomic nucleic acid sequence of methionine synthase reductase (MTRR);

v. genotype of a SNP locus at rs1006737 (position 27 of SEQ ID NO. 11, wherein the SEQ ID NO. 11 is a portion of a genomic nucleic acid sequence of calcium channel, voltage-dependent, L type, alpha 1C subunit (CACNA1C));

vi. genotype of a SNP locus at rs1883729 (position 27 of SEQ ID NO. 12, wherein the SEQ ID NO. 12 is a portion of a genomic nucleic acid sequence of DNA (cytosine-5)-methyltransferase 3 beta (DNMT3B));

vii. genotype of a SNP locus at rs7163862 (position 27 of SEQ ID NO. 13, wherein the SEQ ID NO. 13 is a portion of a genomic nucleic acid sequence of GTP cyclohydrolase 1 feedback regulatory protein (GCHFR));

viii. genotype of a SNP locus at rs12659 (position 27 of SEQ ID NO. 14, wherein the SEQ ID NO. 14 is a portion of a genomic nucleic acid sequence of reduced folate carrier protein (RCF2));

ix. genotype of a SNP locus at rs202676 (position 27 of SEQ ID NO. 15, wherein the SEQ ID NO. 15 is a portion of a genomic nucleic acid sequence of folate hydrolase (prostate-specific membrane antigen) 1 (FOLH1));

x. genotype of a SNP locus at rs2297291 (position 27 of SEQ ID NO. 16, wherein the SEQ ID NO. 16 is a portion of a genomic nucleic acid sequence of reduced folate carrier protein (RCF1));

xi. genotype of a SNP locus at rs1051266 (position 27 of SEQ ID NO. 17, wherein the SEQ ID NO. 17 is a portion of a genomic nucleic acid sequence of reduced folate carrier protein (RCF1));

xii. genotype of a SNP locus at rs8007267 (position 27 of SEQ ID NO. 18, wherein the SEQ ID NO. 18 is a portion of a genomic nucleic acid sequence of GTP cyclohydrolase 1 (GCH1));

xiii. genotype of a SNP locus at rs7639752 (position 27 of SEQ ID NO. 19, wherein the SEQ ID NO. 19 is a portion of a genomic nucleic acid sequence of choline-phosphate cytidylyltransferase A (PCYT1A));

xiv. genotype of a SNP locus at rs6275 (position 27 of SEQ ID NO. 20, wherein the SEQ ID NO. 20 is a portion of a genomic nucleic acid sequence of dopamine receptor D2 (DRD2));

xv. genotype of a SNP locus at rs1079596 (position 27 of SEQ ID NO. 21), wherein the SEQ ID NO. 21 is a portion of a genomic nucleic acid sequence of dopamine receptor D2 (DRD2);

xvi. genotype of a SNP locus at rs11240594 (position 27 of SEQ ID NO. 22), wherein the SEQ ID NO. 22 is a portion of a genomic nucleic acid sequence of dopamine receptor D2 (DRD2);

xvii. genotype of a SNP locus at rs4633 (position 27 of SEQ ID NO. 23, wherein the SEQ ID NO. 23 is a portion of a genomic nucleic acid sequence of catechol-O-methyltransferase (COMT));

xviii. genotype of a SNP locus at rs4680 (position 27 of SEQ ID NO. 24), wherein the SEQ ID NO. 24 is a portion of a genomic nucleic acid sequence of catechol-O-methyltransferase (COMT);

xix. genotype of a SNP locus at rs250682 (position 27 of SEQ ID NO. 25, wherein the SEQ ID NO. 25 is a portion of a genomic nucleic acid sequence of solute carrier family 6 (neurotransmitted transported, dopamine), member 3 (SLC6A3));

xx. genotype of a SNP locus at rs2277820 (position 27 of SEQ ID NO. 26, wherein the SEQ ID NO. 26 is a portion of a genomic nucleic acid sequence of formiminotransferase cyclodeaminase (FTCD)); and xxi. genotype of a SNP locus at rs2236225 (position 27 of SEQ ID NO. 27, wherein the SEQ ID NO. 27 is a portion of a genomic nucleic acid sequence of methylenetetrahydrofolate dehydrogenase (NADP+ dependent) 1 (MTHFD1));

xxii. an obesity indicator (e.g., a BMI value);

xxiii. level of expression of SAM and SAH;

xxiv. level of expression of 4-HNE;

xxv. level of expression of hsCRP; and any combinations thereof;

(b) detecting, optionally with a non-human machine, from the parameters of said at least two biomarkers, the presence of at least one condition selected from the following:

i. a SNP at position 677 of SEQ ID NO. 1 or position 27 of SEQ ID NO. 7 comprising at least one thymine "T" allele;

ii. a SNP at rs2274976 (position 1793 of SEQ ID NO. 1 or position 27 of SEQ ID NO. 8) comprising at least one adenine "A" allele;

iii. a SNP at position 2756 of SEQ ID NO. 2 or position 27 of SEQ ID NO. 9 comprising at least one guanine "G" allele;

iv. a SNP at position 66 of SEQ ID NO. 3 or position 27 of SEQ ID NO. 10 comprising at least one guanine "G" allele;

v. a SNP at rs1006737 (position 27 of SEQ ID NO. 11) comprising at least one adenine "A" allele;

vi. a SNP at rs1883729 (position 27 of SEQ ID NO. 12) comprising at least one adenine "A" allele;

vii. a SNP at rs7163862 (position 27 of SEQ ID NO. 13) comprising at least one thymine "T" allele;

viii. a SNP at rs12659 (position 27 of SEQ ID NO. 14) comprising at least one thymine "T" allele;

ix. a SNP at rs202676 (position 27 of SEQ ID NO. 15) comprising at least one guanine "G" allele;

x. a SNP at rs2297291 (position 27 of SEQ ID NO. 16) comprising at least one adenine "A" allele;

xi. a SNP at rs1051266 (position 27 of SEQ ID NO. 17) comprising at least one adenine "A" allele;

xii. a SNP at rs8007267 (position 27 of SEQ ID NO. 18) comprising at least one thymine "T" allele;

xiii. a SNP at rs7639752 (position 27 of SEQ ID NO. 19) comprising at least one adenine "A" allele;

xiv. a SNP at rs6275 (position 27 of SEQ ID NO. 20) comprising at least one thymine "T" allele;

xv. a SNP at rs1079596 (position 27 of SEQ ID NO. 21) comprising at least one thymine "T" allele;

xvi. a SNP at rs11240594 (position 27 of SEQ ID NO. 22) comprising at least one adenine "A" allele;

xvii. a SNP at rs4633 (position 27 of SEQ ID NO. 23) comprising at least one cytosine "C" allele;

xviii. a SNP at rs4680 (position 27 of SEQ ID NO. 24) comprising at least one guanine "G" allele;

xix. a SNP at rs250682 (position 27 of SEQ ID NO. 25) comprising at least one cytosine "C" allele;

xx. a SNP at rs2277820 (position 27 of SEQ ID NO. 26) comprising at least one thymine "T" allele;

xxi. a SNP at rs2236225 (position 1958 of SEQ ID NO. 27) comprising at least one adenine "A" allele;

xxii. obesity (e.g., defined by a BMI value of at least 30 kg/m$^2$ or greater);

xxiii. an expression level ratio of SAM to SAH smaller than a pre-determined reference ratio;

xxiv. an expression level of 4-HNE greater than a first pre-determined reference value;

xxv. an expression of hsCRP greater than a second pre-determined reference value (e.g., about 2.3 mg per liter of plasma as measured in a plasma sample); and any combinations thereof, and if at least one of said conditions is detected, then selecting and optionally administering a treatment regimen comprising an effective amount of a folate-containing compound.

7. The assay of any of the preceding paragraphs, wherein the pre-determined reference ratio is a control ratio of SAM/SAH as measured in a biological sample of normal healthy subjects.
8. The assay of any of the preceding paragraphs, wherein the pre-determined reference ratio is about 3.0 or about 2.8 if measured in a plasma sample.
9. The assay of any of the preceding paragraphs, wherein the first predetermined reference value is a control value of 4-HNE as measured in a biological sample of normal healthy subjects.
10. The assay of any of the preceding paragraphs, wherein the first predetermined reference value is about 3.0 mg per liter of plasma or about 3.2 mg per liter of plasma as measured in a plasma sample.
11. The assay of any of the preceding paragraphs, wherein the test sample is analyzed to determine at least two of the conditions.
12. The assay of any of the preceding paragraphs, wherein the test sample is analyzed to determine at least three of the conditions.
13. The assay of any of the preceding paragraphs, wherein the test sample comprises a blood sample.
14. The assay of any of the preceding paragraphs, wherein the test sample comprises a urine sample.
15. The assay of any of the preceding paragraphs, wherein the test sample comprises a buccal sample.
16. The assay of any of the preceding paragraphs, wherein the test sample comprises a saliva sample.
17. The assay of any of the preceding paragraphs, wherein the genotyping comprises the step of amplifying the test sample with a set of primers flanking any one of the SNPs.
18. The assay of paragraph 17, wherein at least two sets of primers amplifying at least two of the SNPs are used in a multiplex amplification assay.
19. The assay of any of the preceding paragraphs, wherein the test sample comprises a protein sample, and the test sample comprising a protein sample is subjected to at least one analysis selected from the group consisting of western blot, enzyme linked absorbance assay, mass spectrometry, immunoassay, flow cytometry, immunohistochemical analysis, and any combinations thereof
20. The assay of any of the preceding paragraphs, wherein the treatment regimen further comprises selecting and optionally administering an antidepressant drug.
21. The assay of paragraph 20, wherein the anti-depressant drug comprises a selective serotonin reuptake inhibitor.
22. The assay of any of the preceding paragraphs, wherein the depression is major depressive disorder.
23. A method for treating a human subject with depression, comprising administering a composition comprising an effective amount of a folate-containing compound to a human subject, who is diagnosed to have depression or have a risk for depression, and is further determined to carry at least one of the following single nucleotide polymorphisms (SNPs) or a combination thereof:
    i. a SNP at position 677 of SEQ ID NO. 1 or position 27 of SEQ ID NO. 7 (identified by rs1801133) comprising at least one thymine "T" allele, wherein the SEQ ID NO. 1 and SEQ ID NO. 7 are each independently a portion of a genomic nucleic acid sequence of methylenetetrahydrofolate reductase (MTHFR); and
    ii. a SNP at position 2756 of SEQ ID NO. 2 or position 27 of SEQ ID NO. 9 comprising at least one guanine "G" allele, wherein the SEQ ID NO. 2 and SEQ ID NO. 9 are each independently a portion of a genomic nucleic acid sequence of methionine synthase (MTR).
24. A method for treating a human subject with depression, comprising
    a. determining the genotypes of at least two loci in a biological sample of a subject, who is diagnosed as having depression or having a risk for depression, wherein said at least two loci are:
        i. SNP677, wherein the SNP677 is position 677 of SEQ ID NO. 1 or position 27 of SEQ ID NO. 7 (identified by rs1801133), wherein the SEQ ID NO. 1 and SEQ ID NO. 7 are each independently a portion of a genomic nucleic acid sequence of methylenetetrahydrofolate reductase (MTHFR); and
        ii. SNP2756, wherein the SNP2756 is position 2756 of SEQ ID NO. 2 or position 27 of SEQ ID NO. 9 (identified by rs1805087), wherein the SEQ ID NO. 2 and SEQ ID NO. 9 are each independently a portion of a genomic nucleic acid sequence of methionine synthase (MTR); and
    b. administering a treatment regimen comprising a composition comprising an effective amount of a folate-containing compound to the subject if at least one of the following conditions is detected:
        i. at least one thymine "T" allele at SNP677;
        ii. at least one guanine "G" allele at SNP2756; or
        iii. at least one thymine "T" allele at SNP677 and at least one guanine "G" allele at SNP2756.
25. A method of improving the effectiveness of an anti-depressant drug administered to a human subject, comprising administering a composition comprising an effective amount of a folate-containing compound, in combination with the anti-depressant drug, to the human subject if the human subject is determined to carry any one of the following single nucleotide polymorphisms (SNPs) or a combination thereof:
    i. a SNP at position 677 of SEQ ID NO. 1 or position 27 of SEQ ID NO. 7 (identified by rs1801133) comprising at least one thymine "T" allele, wherein the SEQ ID NO. 1 and SEQ ID NO. 7 are each independently a portion of a genomic nucleic acid sequence of methylenetetrahydrofolate reductase (MTHFR); and
    ii. a SNP at position 2756 of SEQ ID NO. 2 or position 27 of SEQ ID NO. 9 comprising at least one guanine "G" allele, wherein the SEQ ID NO. 2 and SEQ ID NO. 9 are each independently a portion of a genomic nucleic acid sequence of methionine synthase (MTR).
26. The method of any of the preceding paragraphs, wherein the subject is further determined to carry at least one of the following conditions or any combinations thereof:
    i. a SNP at rs2274976 (position 1793 of SEQ ID NO. 1 or position 27 of SEQ ID NO. 8) comprising at least one adenine "A" allele;
    ii. a SNP at position 66 of SEQ ID NO. 3 or position 27 of SEQ ID NO. 10 comprising at least one guanine "G" allele, wherein the SEQ ID NO. 3 and SEQ ID NO. 10 are each independently a portion of a genomic nucleic acid sequence of methionine synthase reductase (MTRR);

iii. a SNP at rs1006737 (position 27 of SEQ ID NO. 11) comprising at least one adenine "A" allele, wherein the SEQ ID NO. 11 is a portion of a genomic nucleic acid sequence of calcium channel, voltage-dependent, L type, alpha 1C subunit (CACNA1C);
iv. a SNP at rs1883729 (position 27 of SEQ ID NO. 12) comprising at least one adenine "A" allele, wherein the SEQ ID NO. 12 is a portion of a genomic nucleic acid sequence of DNA (cytosine-5)-methyltransferase 3 beta (DNMT3B);
v. a SNP at rs7163862 (position 27 of SEQ ID NO. 13) comprising at least one thymine "T" allele, wherein the SEQ ID NO. 13 is a portion of a genomic nucleic acid sequence of GTP cyclohydrolase 1 feedback regulatory protein (GCHFR);
vi. a SNP at rs12659 (position 27 of SEQ ID NO. 14) comprising at least one thymine "T" allele, wherein the SEQ ID NO. 14 is a portion of a genomic nucleic acid sequence of reduced folate carrier protein (RCF2);
vii. a SNP at rs202676 (position 27 of SEQ ID NO. 15) comprising at least one guanine "G" allele, wherein the SEQ ID NO. 15 is a portion of a genomic nucleic acid sequence of folate hydrolase (prostate-specific membrane antigen) 1 (FOLH1);
viii. a SNP at rs2297291 (position 27 of SEQ ID NO. 16) comprising at least one adenine "A" allele, wherein the SEQ ID NO. 16 is a portion of a genomic nucleic acid sequence of reduced folate carrier protein (RCF1);
ix. a SNP at rs1051266 (position 27 of SEQ ID NO. 17) comprising at least one adenine "A" allele, wherein the SEQ ID NO. 17 is a portion of a genomic nucleic acid sequence of reduced folate carrier protein (RCF1);
x. a SNP at rs8007267 (position 27 of SEQ ID NO. 18) comprising at least one thymine "T" allele, wherein the SEQ ID NO. 18 is a portion of a genomic nucleic acid sequence of GTP cyclohydrolase 1 (GCH1);
xi. a SNP at rs7639752 (position 27 of SEQ ID NO. 19) comprising at least one adenine "A" allele, wherein the SEQ ID NO. 19 is a portion of a genomic nucleic acid sequence of choline-phosphate cytidylyltransferase A (PCYT1A);
xii. a SNP at rs6275 (position 27 of SEQ ID NO. 20) comprising at least one thymine "T" allele), wherein the SEQ ID NO. 20 is a portion of a genomic nucleic acid sequence of dopamine receptor D2 (DRD2);
xiii. a SNP at rs1079596 (position 27 of SEQ ID NO. 21) comprising at least one thymine "T" allele), wherein the SEQ ID NO. 21 is a portion of a genomic nucleic acid sequence of dopamine receptor D2 (DRD2);
xiv. a SNP at rs11240594 (position 27 of SEQ ID NO. 22) comprising at least one adenine "A" allele), wherein the SEQ ID NO. 22 is a portion of a genomic nucleic acid sequence of dopamine receptor D2 (DRD2);
xv. a SNP at rs4633 (position 27 of SEQ ID NO. 23) comprising at least one cytosine "C" allele, wherein the SEQ ID NO. 23 is a portion of a genomic nucleic acid sequence of catechol-O-methyltransferase (COMT);
xvi. a SNP at rs4680 (position 27 of SEQ ID NO. 24) comprising at least one guanine "G" allele, wherein the SEQ ID NO. 24 is a portion of a genomic nucleic acid sequence of catechol-O-methyltransferase (COMT);
xvii. a SNP at rs250682 (position 27 of SEQ ID NO. 25) comprising at least one cytosine "C" allele, wherein the SEQ ID NO. 25 is a portion of a genomic nucleic acid sequence of solute carrier family 6 (neurotransmitted transported, dopamine), member 3 (SLC6A3);
xviii. a SNP at rs2277820 (position 27 of SEQ ID NO. 26) comprising at least one thymine "T" allele, wherein the SEQ ID NO. 26 is a portion of a genomic nucleic acid sequence of formiminotransferase cyclodeaminase (FTCD); and
xix. a SNP at rs2236225 (position 27 of SEQ ID NO. 27) comprising at least one adenine "A" allele, wherein the SEQ ID NO. 27 is a portion of a genomic nucleic acid sequence of methylenetetrahydrofolate dehydrogenase (NADP+ dependent) 1 (MTHFD1);
xx. obesity (e.g., defined by a BMI value of at least 30 kg/m$^2$ or greater);
xxi. an expression ratio of SAM to SAH smaller than a pre-determined ratio;
xxii. an expression of 4-HNE greater than a first pre-determined reference value; and
xxiii. an expression of hsCRP greater than a second pre-determined reference value (e.g., greater than about 2.3 mg per liter of plasma as measured in a plasma sample).

27. A method for treating a human subject with depression, comprising administering a composition comprising an effective amount of a folate-containing compound to the human subject having been diagnosed with depression or with a risk for depression, and is further determined to carry at least one of the following conditions or any combinations thereof:
i. a SNP at position 677 of SEQ ID NO. 1 or position 27 of SEQ ID NO. 7 (identified by rs1801133) comprising at least one thymine "T" allele, wherein the SEQ ID NO. 1 and SEQ ID NO. 7 are each independently a portion of a genomic nucleic acid sequence of methylenetetrahydrofolate reductase (MTHFR);
ii. a SNP at rs2274976 (position 1793 of SEQ ID NO. 1 or position 27 of SEQ ID NO. 8) comprising at least one adenine "A" allele, wherein the SEQ ID NO. 1 and SEQ ID NO. 8 are each independently a portion of a genomic nucleic acid sequence of methylenetetrahydrofolate reductase (MTHFR);
iii. a SNP at position 2756 of SEQ ID NO. 2 or position 27 of SEQ ID NO. 9 comprising at least one guanine "G" allele, wherein the SEQ ID NO. 2 and SEQ ID NO. 9 are each independently a portion of a genomic nucleic acid sequence of methionine synthase (MTR);
iv. a SNP at position 66 of SEQ ID NO. 3 or position 27 of SEQ ID NO. 10 comprising at least one guanine "G" allele, wherein the SEQ ID NO. 3 and SEQ ID NO. 10 are each independently a portion of a genomic nucleic acid sequence of methionine synthase reductase (MTRR);
v. a SNP at rs1006737 (position 27 of SEQ ID NO. 11) comprising at least one adenine "A" allele, wherein the SEQ ID NO. 11 is a portion of a genomic nucleic acid sequence of calcium channel, voltage-dependent, L type, alpha 1C subunit (CACNA1C);

vi. a SNP at rs1883729 (position 27 of SEQ ID NO. 12) comprising at least one adenine "A" allele, wherein the SEQ ID NO. 12 is a portion of a genomic nucleic acid sequence of DNA (cytosine-5)-methyltransferase 3 beta (DNMT3B);

vii. a SNP at rs7163862 (position 27 of SEQ ID NO. 13) comprising at least one thymine "T" allele, wherein the SEQ ID NO. 13 is a portion of a genomic nucleic acid sequence of GTP cyclohydrolase 1 feedback regulatory protein (GCHFR);

viii. a SNP at rs12659 (position 27 of SEQ ID NO. 14) comprising at least one thymine "T" allele, wherein the SEQ ID NO. 14 is a portion of a genomic nucleic acid sequence of reduced folate carrier protein (RCF2);

ix. a SNP at rs202676 (position 27 of SEQ ID NO. 15) comprising at least one guanine "G" allele, wherein the SEQ ID NO. 15 is a portion of a genomic nucleic acid sequence of folate hydrolase (prostate-specific membrane antigen) 1 (FOLH1);

x. a SNP at rs2297291 (position 27 of SEQ ID NO. 16) comprising at least one adenine "A" allele, wherein the SEQ ID NO. 16 is a portion of a genomic nucleic acid sequence of reduced folate carrier protein (RCF1);

xi. a SNP at rs1051266 (position 27 of SEQ ID NO. 17) comprising at least one adenine "A" allele, wherein the SEQ ID NO. 17 is a portion of a genomic nucleic acid sequence of reduced folate carrier protein (RCF1);

xii. a SNP at rs8007267 (position 27 of SEQ ID NO. 18) comprising at least one thymine "T" allele, wherein the SEQ ID NO. 18 is a portion of a genomic nucleic acid sequence of GTP cyclohydrolase 1 (GCH1);

xiii. a SNP at rs7639752 (position 27 of SEQ ID NO. 19) comprising at least one adenine "A" allele, wherein the SEQ ID NO. 19 is a portion of a genomic nucleic acid sequence of choline-phosphate cytidylyltransferase A (PCYT1A);

xiv. a SNP at rs6275 (position 27 of SEQ ID NO. 20) comprising at least one thymine "T" allele), wherein the SEQ ID NO. 20 is a portion of a genomic nucleic acid sequence of dopamine receptor D2 (DRD2);

xv. a SNP at rs1079596 (position 27 of SEQ ID NO. 21) comprising at least one thymine "T" allele), wherein the SEQ ID NO. 21 is a portion of a genomic nucleic acid sequence of dopamine receptor D2 (DRD2);

xvi. a SNP at rs11240594 (position 27 of SEQ ID NO. 22) comprising at least one adenine "A" allele), wherein the SEQ ID NO. 22 is a portion of a genomic nucleic acid sequence of dopamine receptor D2 (DRD2);

xvii. a SNP at rs4633 (position 27 of SEQ ID NO. 23) comprising at least one cytosine "C" allele, wherein the SEQ ID NO. 23 is a portion of a genomic nucleic acid sequence of catechol-O-methyltransferase (COMT);

xviii. a SNP at rs4680 (position 27 of SEQ ID NO. 24) comprising at least one guanine "G" allele, wherein the SEQ ID NO. 24 is a portion of a genomic nucleic acid sequence of catechol-O-methyltransferase (COMT);

xix. a SNP at rs250682 (position 27 of SEQ ID NO. 25) comprising at least one cytosine "C" allele, wherein the SEQ ID NO. 25 is a portion of a genomic nucleic acid sequence of solute carrier family 6 (neurotransmitted transported, dopamine), member 3 (SLC6A3);

xx. a SNP at rs2277820 (position 27 of SEQ ID NO. 26) comprising at least one thymine "T" allele, wherein the SEQ ID NO. 26 is a portion of a genomic nucleic acid sequence of formiminotransferase cyclodeaminase (FTCD); and xxi. a SNP at rs2236225 (position 27 of SEQ ID NO. 27) comprising at least one adenine "A" allele, wherein the SEQ ID NO. 27 is a portion of a genomic nucleic acid sequence of methylenetetrahydrofolate dehydrogenase (NADP+ dependent) 1 (MTHFD1);

xxii. obesity (e.g., defined by a BMI value of at least 30 $kg/m^2$ or greater);

xxiii. an expression ratio of SAM to SAH smaller than a pre-determined ratio;

xxiv. an expression of 4-HNE greater than a first pre-determined reference value; and xxv. an expression of hsCRP greater than a second pre-determined reference value (e.g., greater than about 2.3 mg per liter of plasma as measured in a plasma sample).

28. A method of treating depression in a human subject comprising detecting at least one of the following conditions in a biological sample from the human subject and if any one of them is present then administering to the human subject a treatment regimen comprising an effective amount of a folate-containing compound, wherein said at least one of the conditions is selected from the following:

i. a SNP at position 677 of SEQ ID NO. 1 or position 27 of SEQ ID NO. 7 (identified by rs1801133) comprising at least one thymine "T" allele;

ii. a SNP at rs2274976 (position 1793 of SEQ ID NO. 1 or position 27 of SEQ ID NO. 8) comprising at least one adenine "A" allele;

iii. a SNP at position 2756 of SEQ ID NO. 2 or position 27 of SEQ ID NO. 9 comprising at least one guanine "G" allele;

iv. a SNP at position 66 of SEQ ID NO. 3 or position 27 of SEQ ID NO. 10 comprising at least one guanine "G" allele;

v. a SNP at rs1006737 (position 27 of SEQ ID NO. 11) comprising at least one adenine "A" allele;

vi. a SNP at rs1883729 (position 27 of SEQ ID NO. 12) comprising at least one adenine "A" allele;

vii. a SNP at rs7163862 (position 27 of SEQ ID NO. 13) comprising at least one thymine "T" allele;

viii. a SNP at rs12659 (position 27 of SEQ ID NO. 14) comprising at least one thymine "T" allele;

ix. a SNP at rs202676 (position 27 of SEQ ID NO. 15) comprising at least one guanine "G" allele;

x. a SNP at rs2297291 (position 27 of SEQ ID NO. 16) comprising at least one adenine "A" allele;

xi. a SNP at rs1051266 (position 27 of SEQ ID NO. 17) comprising at least one adenine "A" allele;

xii. a SNP at rs8007267 (position 27 of SEQ ID NO. 18) comprising at least one thymine "T" allele;

xiii. a SNP at rs7639752 (position 27 of SEQ ID NO. 19) comprising at least one adenine "A" allele;

xiv. a SNP at rs6275 (position 27 of SEQ ID NO. 20) comprising at least one thymine "T" allele;

xv. a SNP at rs1079596 (position 27 of SEQ ID NO. 21) comprising at least one thymine "T" allele;

xvi. a SNP at rs11240594 (position 27 of SEQ ID NO. 22) comprising at least one adenine "A" allele;

xvii. a SNP at rs4633 (position 27 of SEQ ID NO. 23) comprising at least one cytosine "C" allele;
xviii. a SNP at rs4680 (position 27 of SEQ ID NO. 24) comprising at least one guanine "G" allele;
xix. a SNP at rs250682 (position 27 of SEQ ID NO. 25) comprising at least one cytosine "C" allele;
xx. a SNP at rs2277820 (position 27 of SEQ ID NO. 26) comprising at least one thymine "T" allele;
xxi. a SNP at rs2236225 (position 1958 of SEQ ID NO. 27) comprising at least one adenine "A" allele;
xxii. obesity (e.g., defined by a BMI value of at least 30 kg/m² or greater);
xxiii. an expression level ratio of SAM to SAH smaller than a pre-determined reference ratio;
xxiv. an expression level of 4-HNE greater than a first pre-determined reference value;
xxv. an expression of hsCRP greater than a second pre-determined reference value (e.g., greater than about 2.3 mg per liter of plasma as measured in a plasma sample); and any combinations thereof 29. The method of any of the preceding paragraphs, wherein the subject is further determined to carry at least two of the conditions or more.
30. The method of any of the preceding paragraphs, wherein the effective amount of the folate-containing compound ranges from about 0.1 to about 1 mg/kg body weight per day.
31. The method of any of the preceding paragraphs, wherein the effective amount of the folate-containing compound is about 7.5 mg/day to about 50 mg/day.
32. The method of any of the preceding paragraphs, wherein the effective amount of the folate-containing compound is about 15 mg/day.
33. The method of any of the preceding paragraphs, wherein the effective amount of the folate-containing compound is administered as a single daily dose.
34. The method of any of the preceding paragraphs, wherein the effective amount of the folate-containing compound is administered in more than one divided doses per day.
35. The method of any of the preceding paragraphs, wherein the administration is oral.
36. The method of any of the preceding paragraphs, wherein the composition is formulated to release at least a portion of the folate-containing compound over a period of at least about 3-6 hours, upon the administration of the composition, wherein the release is optionally a steady-state release.
37. The method of any of the preceding paragraphs, further comprising selecting and optionally administering an anti-depressant drug in combination with the folate-containing compound.
38. The method of paragraph 37, wherein the anti-depressant drug comprises a selective serotonin reuptake inhibitor.
39. The method of paragraph 38, wherein the selective serotonin reuptake inhibitor is selected from the group consisting of fluoxetine, citalopram, paroxetine, escitalopram, sertraline, and any combinations thereof
40. The method of any of the preceding paragraphs, wherein the subject who is diagnosed as having depression is resistant to at least one antidepressant monotherapy.
41. The method of any of the preceding paragraphs, wherein the depression is major depressive disorder.
42. The method of any of the preceding paragraphs, wherein the test sample comprises a buccal sample.
43. The method of any of the preceding paragraphs, wherein the test sample comprises a saliva sample.
44. The method of any of the preceding paragraphs, wherein the test sample comprises a blood sample.
45. The method of any of the preceding paragraphs, wherein the test sample comprises a urine sample.
46. A computer system for obtaining data from at least one test sample obtained from at least one subject, the system comprising:
    (a) at least one determination module configured to receive said at least one test sample and perform at least one analysis on said at least one test sample to determine the presence or absence of at least one of the following conditions or any combinations thereof:
        i. an expression ratio of s-adenosyl methionine (SAM) to s-adenosyl homocysteine (SAH) smaller than a pre-determined reference ratio;
        ii. expression of 4-hydroxynonenal (4-HNE) greater than a first pre-determined reference value;
        iii. a single nucleotide polymorphism (SNP) at position 677 of SEQ ID NO. 1 or position 27 of SEQ ID NO. 7 (identified by rs1801133) comprising at least one thymine "T" allele, wherein the SEQ ID NO. 1 and SEQ ID NO. 7 are each independently a portion of a genomic nucleic acid sequence of methylenetetrahydrofolate reductase (MTHFR);
        iv. a SNP at position 2756 of SEQ ID NO. 2 or position 27 of SEQ ID NO. 9 comprising at least one guanine "G" allele, wherein the SEQ ID NO. 2 and SEQ ID NO. 9 are each independently a portion of a genomic nucleic acid sequence of methionine synthase (MTR); and
        v. a SNP at position 66 of SEQ ID NO. 3 or position 27 of SEQ ID NO. 10 comprising at least one guanine "G" allele, wherein the SEQ ID NO. 3 and SEQ ID NO. 10 are each independently a portion of a genomic nucleic acid sequence of methionine synthase reductase (MTRR);
    (b) at least one storage device configured to store data output from said determination module; and
    (d) at least one display module for displaying a content based in part on the data output from said determination module, wherein the content comprises a signal indicative of the presence of at least one of these conditions, and optionally the absence of any one of these conditions, or a signal indicative of the absence of all of these conditions.
47. The computer system of paragraph 46, wherein said determination module is configured to analyze said at least one test sample to determine the presence or absence of at least two of the conditions.
48. The computer system of paragraph 46 or 47, wherein said determination module further comprises a comparison module adapted to compare said data output from said determination module with reference data stored on said storage device.
49. A computer system for obtaining data from at least one test sample obtained from at least one subject, the system comprising:
    (a) a determination module configured to receive said at least one test sample and perform at least one genotyping analysis on said at least one test sample to determine the genotypes of at least two loci, wherein said at least two loci comprise:
        (i) position 677 of SEQ ID NO. 1 or position 27 of SEQ ID NO. 7 (identified by rs1801133), wherein the SEQ ID NO. 1 and SEQ ID NO. 7 are each independently a portion of a genomic nucleic acid sequence of methylenetetrahydrofolate reductase (MTHFR);

(ii) position 2756 of SEQ ID NO. 2 or position 27 of SEQ ID NO. 9 (identified by rs1805087), wherein the SEQ ID NO. 2 and SEQ ID NO. 9 are each independently a portion of a genomic nucleic acid sequence of methionine synthase (MTR); and (iii) optionally, position 66 of SEQ ID NO. 3 or position 27 of SEQ ID NO. 10 (identified by rs1801394), wherein the SEQ ID NO. 3 and SEQ ID NO. 10 are each independently a portion of a genomic nucleic acid sequence of methionine synthase reductase (MTRR);

(b) a storage device configured to store output data from said determination module;

(c) a computing module comprising specifically-programmed instructions to determine from the output data the presence of at least one single nucleotide polymorphism (SNP) from the following:
  i. a SNP at position 677 of SEQ ID NO. 1 or position 27 of SEQ ID NO. 7 comprising at least one thymine "T" allele;
  ii. a SNP at position 2756 of SEQ ID NO. 2 or position 27 of SEQ ID NO. 9 comprising at least one guanine "G" allele; and
  iii. optionally a SNP at the position 66 of SEQ ID NO. 3 or position 27 of SEQ ID NO. 10 comprising at least one guanine "G" allele.

(d) a display module for displaying a content based in part on the data output from said computing module, wherein the content comprises a signal indicative of the presence of at least one of these SNPs, and optionally the absence of any one of these SNPs, or a signal indicative of the absence of all of these SNPs.

50. The computer system of any one of the preceding paragraphs, wherein said determination module is further determine a parameter of at least one of the following biomarkers or any combinations thereof:
  i. genotype of a SNP locus at rs2274976 (position 1793 of SEQ ID NO. 1 or position 27 of SEQ ID NO. 8), wherein the SEQ ID NO. 1 and SEQ ID NO. 8 are each independently a portion of a genomic nucleic acid sequence of methylenetetrahydrofolate reductase (MTHFR);
  ii. genotype of a SNP locus at rs1006737 (position 27 of SEQ ID NO. 11, wherein the SEQ ID NO. 11 is a portion of a genomic nucleic acid sequence of calcium channel, voltage-dependent, L type, alpha 1C subunit (CACNA1C));
  iii. genotype of a SNP locus at rs1883729 (position 27 of SEQ ID NO. 12, wherein the SEQ ID NO. 12 is a portion of a genomic nucleic acid sequence of DNA (cytosine-5)-methyltransferase 3 beta (DNMT3B));
  iv. genotype of a SNP locus at rs7163862 (position 27 of SEQ ID NO. 13, wherein the SEQ ID NO. 13 is a portion of a genomic nucleic acid sequence of GTP cyclohydrolase 1 feedback regulatory protein (GCHFR));
  v. genotype of a SNP locus at rs12659 (position 27 of SEQ ID NO. 14, wherein the SEQ ID NO. 14 is a portion of a genomic nucleic acid sequence of reduced folate carrier protein (RCF2));
  vi. genotype of a SNP locus at rs202676 (position 27 of SEQ ID NO. 20, wherein the SEQ ID NO. 15 is a portion of a genomic nucleic acid sequence of folate hydrolase (prostate-specific membrane antigen) 1 (FOLH1));
  vii. genotype of a SNP locus at rs2297291 (position 27 of SEQ ID NO. 16, wherein the SEQ ID NO. 16 is a portion of a genomic nucleic acid sequence of reduced folate carrier protein (RCF1));
  viii. genotype of a SNP locus at rs1051266 (position 27 of SEQ ID NO. 17, wherein the SEQ ID NO. 17 is a portion of a genomic nucleic acid sequence of reduced folate carrier protein (RCF1));
  ix. genotype of a SNP locus at rs8007267 (position 27 of SEQ ID NO. 18, wherein the SEQ ID NO. 18 is a portion of a genomic nucleic acid sequence of GTP cyclohydrolase 1 (GCH1));
  x. genotype of a SNP locus at rs7639752 (position 27 of SEQ ID NO. 19, wherein the SEQ ID NO. 19 is a portion of a genomic nucleic acid sequence of choline-phosphate cytidylyltransferase A (PCYT1A));
  xi. genotype of a SNP locus at rs6275 (position 27 of SEQ ID NO. 20, wherein the SEQ ID NO. 20 is a portion of a genomic nucleic acid sequence of dopamine receptor D2 (DRD2));
  xii. genotype of a SNP locus at rs1079596 (position 27 of SEQ ID NO. 21), wherein the SEQ ID NO. 21 is a portion of a genomic nucleic acid sequence of dopamine receptor D2 (DRD2);
  xiii. genotype of a SNP locus at rs11240594 (position 27 of SEQ ID NO. 22), wherein the SEQ ID NO. 22 is a portion of a genomic nucleic acid sequence of dopamine receptor D2 (DRD2);
  xiv. genotype of a SNP locus at rs4633 (position 27 of SEQ ID NO. 23, wherein the SEQ ID NO. 23 is a portion of a genomic nucleic acid sequence of catechol-β-methyltransferase (COMT));
  xv. genotype of a SNP locus at rs4680 (position 27 of SEQ ID NO. 24), wherein the SEQ ID NO. 24 is a portion of a genomic nucleic acid sequence of catechol-β-methyltransferase (COMT);
  xvi. genotype of a SNP locus at rs250682 (position 27 of SEQ ID NO. 25, wherein the SEQ ID NO. 25 is a portion of a genomic nucleic acid sequence of solute carrier family 6 (neurotransmitted transported, dopamine), member 3 (SLC6A3));
  xvii. genotype of a SNP locus at rs2277820 (position 27 of SEQ ID NO. 26, wherein the SEQ ID NO. 26 is a portion of a genomic nucleic acid sequence of formiminotransferase cyclodeaminase (FTCD)); and
  xviii. genotype of a SNP locus at rs2236225 (position 27 of SEQ ID NO. 27, wherein the SEQ ID NO. 27 is a portion of a genomic nucleic acid sequence of methylenetetrahydrofolate dehydrogenase (NADP+ dependent) 1 (MTHFD1));
  xix. an obesity indicator (e.g., a BMI value);
  xx. level of expression of SAM and SAH;
  xxi. level of expression of 4-HNE;
  xxii. level of expression of hsCRP.

51. The computer system of paragraph 50, wherein said computing module is further adapted to determine the presence of at least one of the following conditions or any combinations thereof:
  i. a SNP at rs2274976 (position 1793 of SEQ ID NO. 1 or position 27 of SEQ ID NO. 8) comprising at least one adenine "A" allele;

ii. a SNP at rs1006737 (position 27 of SEQ ID NO. 11) comprising at least one adenine "A" allele;
iii. a SNP at rs1883729 (position 27 of SEQ ID NO. 12) comprising at least one adenine "A" allele;
iv. a SNP at rs7163862 (position 27 of SEQ ID NO. 13) comprising at least one thymine "T" allele;
v. a SNP at rs12659 (position 27 of SEQ ID NO. 14) comprising at least one thymine "T" allele;
vi. a SNP at rs202676 (position 27 of SEQ ID NO. 15) comprising at least one guanine "G" allele;
vii. a SNP at rs2297291 (position 27 of SEQ ID NO. 16) comprising at least one adenine "A" allele;
viii. a SNP at rs1051266 (position 27 of SEQ ID NO. 17) comprising at least one adenine "A" allele;
ix. a SNP at rs8007267 (position 27 of SEQ ID NO. 18) comprising at least one thymine "T" allele;
x. a SNP at rs7639752 (position 27 of SEQ ID NO. 19) comprising at least one adenine "A" allele;
xi. a SNP at rs6275 (position 27 of SEQ ID NO. 20) comprising at least one thymine "T" allele;
xii. a SNP at rs1079596 (position 27 of SEQ ID NO. 21) comprising at least one thymine "T" allele;
xiii. a SNP at rs11240594 (position 27 of SEQ ID NO. 22) comprising at least one adenine "A" allele;
xiv. a SNP at rs4633 (position 27 of SEQ ID NO. 23) comprising at least one cytosine "C" allele;
xv. a SNP at rs4680 (position 27 of SEQ ID NO. 24) comprising at least one guanine "G" allele;
xvi. a SNP at rs250682 (position 27 of SEQ ID NO. 25) comprising at least one cytosine "C" allele;
xvii. a SNP at rs2277820 (position 27 of SEQ ID NO. 26) comprising at least one thymine "T" allele;
xviii. a SNP at rs2236225 (position 27 of SEQ ID NO. 27) comprising at least one adenine "A" allele;
xix. obesity (e.g., defined by a BMI value of at least 30 kg/m² or greater);
xx. an expression level ratio of SAM to SAH smaller than a pre-determined reference ratio;
xxi. an expression level of 4-HNE greater than a first pre-determined reference value;
xxii. an expression of hsCRP greater than a second pre-determined reference value (e.g., greater than about 2.3 mg per liter of plasma as measured in a plasma sample).

52. A computer system for obtaining data from at least one test sample obtained from at least one subject, the system comprising:
(a) a determination module configured to receive said at least one test sample and perform at least one analysis on said at least one test sample to determine parameters of at least two biomarkers, wherein the parameters of said at least two biomarkers are selected from the following:
   i. genotype of a single nucleotide polymorphism (SNP) locus at position 677 of SEQ ID NO. 1 or position 27 of SEQ ID NO. 7 (identified by rs1801133), wherein the SEQ ID NO. 1 and SEQ ID NO. 7 are each independently a portion of a genomic nucleic acid sequence of methylenetetrahydrofolate reductase (MTHFR);
   ii. genotype of a SNP locus at rs2274976 (position 1793 of SEQ ID NO. 1 or position 27 of SEQ ID NO. 8), wherein the SEQ ID NO. 1 and SEQ ID NO. 8 are each independently a portion of a genomic nucleic acid sequence of methylenetetrahydrofolate reductase (MTHFR);
   iii. genotype of a SNP locus at position 2756 of SEQ ID NO. 2 or position 27 of SEQ ID NO. 9 (identified by rs1805087), wherein the SEQ ID NO. 2 and SEQ ID NO. 9 are each independently a portion of a genomic nucleic acid sequence of methionine synthase (MTR);
   iv. genotype of a SNP locus at position 66 of SEQ ID NO. 3 or position 27 of SEQ ID NO. 10 (identified by rs1801394), wherein the SEQ ID NO. 3 and SEQ ID NO. 10 are each independently a portion of a genomic nucleic acid sequence of methionine synthase reductase (MTRR);
   v. genotype of a SNP locus at rs1006737 (position 27 of SEQ ID NO. 11), wherein the SEQ ID NO. 11 is a portion of a genomic nucleic acid sequence of calcium channel, voltage-dependent, L type, alpha 1C subunit (CACNA1C);
   vi. genotype of a SNP locus at rs1883729 (position 27 of SEQ ID NO. 12), wherein the SEQ ID NO. 12 is a portion of a genomic nucleic acid sequence of DNA (cytosine-5)-methyltransferase 3 beta (DNMT3B);
   vii. genotype of a SNP locus at rs7163862 (position 27 of SEQ ID NO. 13), wherein the SEQ ID NO. 13 is a portion of a genomic nucleic acid sequence of GTP cyclohydrolase 1 feedback regulatory protein (GCHFR);
   viii. genotype of a SNP locus at rs12659 (position 27 of SEQ ID NO. 14), wherein the SEQ ID NO. 14 is a portion of a genomic nucleic acid sequence of reduced folate carrier protein (RCF2);
   ix. genotype of a SNP locus at rs202676 (position 27 of SEQ ID NO. 15), wherein the SEQ ID NO. 15 is a portion of a genomic nucleic acid sequence of folate hydrolase (prostate-specific membrane antigen) 1 (FOLH1);
   x. genotype of a SNP locus at rs2297291 (position 27 of SEQ ID NO. 16), wherein the SEQ ID NO. 16 is a portion of a genomic nucleic acid sequence of reduced folate carrier protein (RCF1);
   xi. genotype of a SNP locus at rs1051266 (position 27 of SEQ ID NO. 17), wherein the SEQ ID NO. 17 is a portion of a genomic nucleic acid sequence of reduced folate carrier protein (RCF1);
   xii. genotype of a SNP locus at rs8007267 (position 27 of SEQ ID NO. 18), wherein the SEQ ID NO. 18 is a portion of a genomic nucleic acid sequence of GTP cyclohydrolase 1 (GCH1);
   xiii. genotype of a SNP locus at rs7639752 (position 27 of SEQ ID NO. 19), wherein the SEQ ID NO. 19 is a portion of a genomic nucleic acid sequence of choline-phosphate cytidylyltransferase A (PCYT1A);
   xiv. genotype of a SNP locus at rs6275 (position 27 of SEQ ID NO. 20), wherein the SEQ ID NO. 20 is a portion of a genomic nucleic acid sequence of dopamine receptor D2 (DRD2);
   xv. genotype of a SNP locus at rs1079596 (position 27 of SEQ ID NO. 21), wherein the SEQ ID NO. 21 is a portion of a genomic nucleic acid sequence of dopamine receptor D2 (DRD2);
   xvi. genotype of a SNP locus at rs11240594 (position 27 of SEQ ID NO. 22), wherein the SEQ ID NO. 22 is a portion of a genomic nucleic acid sequence of dopamine receptor D2 (DRD2);
   xvii. genotype of a SNP locus at rs4633 (position 27 of SEQ ID NO. 23), wherein the SEQ ID NO. 23 is a portion of a genomic nucleic acid sequence of catechol-β-methyltransferase (COMT);
xviii. genotype of a SNP locus at rs4680 (position 27 of SEQ ID NO. 24), wherein the SEQ ID NO. 24 is a portion of a genomic nucleic acid sequence of catechol-β-methyltransferase (COMT);
xix. genotype of a SNP locus at rs250682 (position 27 of SEQ ID NO. 25), wherein the SEQ ID NO. 25 is a portion of a genomic nucleic acid sequence of solute carrier family 6 (neurotransmitted transported, dopamine), member 3 (SLC6A3);
xx. genotype of a SNP locus at rs2277820 (position 27 of SEQ ID NO. 26), wherein the SEQ ID NO. 26 is a portion of a genomic nucleic acid sequence of formiminotransferase cyclodeaminase (FTCD);
xxi. genotype of a SNP locus at rs2236225 (position 27 of SEQ ID NO. 27), wherein the SEQ ID NO. 27 is a portion of a genomic nucleic acid sequence of methylenetetrahydrofolate dehydrogenase (NADP+ dependent) 1 (MTHFD1);
xxii. expressions of SAM and SAH;
xxiii. expression of 4-HNE;
xxiv. expression of hsCRP; and any combinations thereof (b) a storage device configured to store output data from said determination module;

(c) a computing module comprising specifically-programmed instructions to determine from the output data the presence of at least one condition from the following:
  i. a SNP at position 677 of SEQ ID NO. 1 or position 27 of SEQ ID NO. 7 comprising at least one thymine "T" allele;
  ii. a SNP at rs2274976 (position 1793 of SEQ ID NO. 1 or position 27 of SEQ ID NO. 8) comprising at least one adenine "A" allele;
  iii. a SNP at position 2756 of SEQ ID NO. 2 or position 27 of SEQ ID NO. 9 comprising at least one guanine "G" allele;
  iv. a SNP at position 66 of SEQ ID NO. 3 or position 27 of SEQ ID NO. 10 comprising at least one guanine "G" allele;
  v. a SNP at rs1006737 (position 27 of SEQ ID NO. 11) comprising at least one adenine "A" allele;
  vi. a SNP at rs1883729 (position 27 of SEQ ID NO. 12) comprising at least one adenine "A" allele;
  vii. a SNP at rs7163862 (position 27 of SEQ ID NO. 13) comprising at least one thymine "T" allele;
  viii. a SNP at rs12659 (position 27 of SEQ ID NO. 14) comprising at least one thymine "T" allele;
  ix. a SNP at rs202676 (position 27 of SEQ ID NO. 15) comprising at least one guanine "G" allele;
  x. a SNP at rs2297291 (position 27 of SEQ ID NO. 16) comprising at least one adenine "A" allele;
  xi. a SNP at rs1051266 (position 27 of SEQ ID NO. 17) comprising at least one adenine "A" allele;
  xii. a SNP at rs8007267 (position 27 of SEQ ID NO. 18) comprising at least one thymine "T" allele;
  xiii. a SNP at rs7639752 (position 27 of SEQ ID NO. 19) comprising at least one adenine "A" allele;
  xiv. a SNP at rs6275 (position 27 of SEQ ID NO. 20) comprising at least one thymine "T" allele;
  xv. a SNP at rs1079596 (position 27 of SEQ ID NO. 21) comprising at least one thymine "T" allele;
  xvi. a SNP at rs11240594 (position 27 of SEQ ID NO. 22) comprising at least one adenine "A" allele;
  xvii. a SNP at rs4633 (position 27 of SEQ ID NO. 23) comprising at least one cytosine "C" allele;
  xviii. a SNP at rs4680 (position 27 of SEQ ID NO. 24) comprising at least one guanine "G" allele;
  xix. a SNP at rs250682 (position 27 of SEQ ID NO. 25) comprising at least one cytosine "C" allele;
  xx. a SNP at rs2277820 (position 27 of SEQ ID NO. 26) comprising at least one thymine "T" allele; and
  xxi. a SNP at rs2236225 (position 27 of SEQ ID NO. 27) comprising at least one adenine "A" allele;
  xxii. an expression ratio of SAM to SAH smaller than a pre-determined reference ratio;
  xxiii. an expression of 4-HNE greater than a first pre-determined reference value;
  xxiv. an expression of hsCRP greater than a second pre-determined reference value (e.g., greater than about 2.3 mg per liter of plasma as measured in a plasma sample); and any combinations thereof (d) a display module for displaying a content based in part on the data output from said computing module, wherein the content comprises a signal indicative of the presence of at least one of the conditions, and optionally the absence of any one of the conditions, or a signal indicative of the absence of all of the conditions.

53. The computer system of any of the preceding paragraphs, wherein the pre-determined reference ratio of SAM/SAH is a control ratio of SAM/SAH as measured in a biological sample of normal healthy subjects.

54. The computer system of any of the preceding paragraphs, wherein the pre-determined reference ratio is about 3.0 or about 2.8 as measured in a plasma sample.

55. The computer system of any of the preceding paragraphs, wherein the first predetermined reference value is a control value of 4-HNE as measured in a biological sample of normal healthy subjects.

56. The computer system of any of the preceding paragraphs, wherein the first predetermined reference value is about 3.0 mg per liter or about 3.2 mg per liter as measured in a plasma sample.

57. The computer system of any of the preceding paragraphs, wherein the determination module is configured to determine parameters of at least three biomarkers or more.

58. The computer system of any of the preceding paragraphs, wherein the computing module is configured to determine the presence of at least two conditions or more.

59. The computer system of any of the preceding paragraphs, wherein said computing module further comprises a comparison module adapted to compare said output data from said determination module with reference data stored on said storage device.

60. The computer system of any of the preceding paragraphs, wherein the storage device is further configured to store physical information of said at least one subject.

61. The computer system of paragraph 60, wherein the physical information comprises an obesity indicator (e.g., BMI) of said at least one subject.

62. The computer system of any of the preceding paragraphs, wherein the content displayed on said display module further comprises the obesity indicator (e.g., the BMI value) or a signal indicative of whether the subject is obese (e.g., whether the BMI value is at least 30 kg/m$^2$ or not).

63. The computer system of any of the preceding paragraphs, wherein the content displayed on said display module further comprises a signal indicative of the subject recommended to receive a treatment regimen comprising a folate-containing compound, or a signal indicative of the subject recommended to receive an alternative treatment regimen without a folate-containing compound.

64. The computer system of any of the preceding paragraphs, wherein the depression is major depressive disorder.

65. A computer readable medium having computer readable instructions recorded thereon to define software modules for implementing a method on a computer, said computer readable storage medium comprising:
    (a) instructions for comparing the data stored on a storage device with reference data to provide a comparison result, wherein the comparison identifies the presence or absence of at least one of the following conditions or any combinations thereof:
        i. an expression ratio of s-adenosyl methionine (SAM) to s-adenosyl homocysteine (SAH) smaller than a pre-determined reference ratio;
        ii. expression of 4-hydroxynonenal (4-HNE) greater than a first pre-determined reference value;
        iii. a single nucleotide polymorphism (SNP) at position 677 of SEQ ID NO. 1 or position 27 of SEQ ID NO. 7 (identified by rs1801133) comprising at least one thymine "T" allele, wherein the SEQ ID NO. 1 and SEQ ID NO. 7 are each independently a portion of a genomic nucleic acid sequence of methylenetetrahydrofolate reductase (MTHFR);
        iv. a SNP at position 2756 of SEQ ID NO. 2 or position 27 of SEQ ID NO. 9 comprising at least one guanine "G" allele, wherein the SEQ ID NO. 2 and SEQ ID NO. 9 are each independently a portion of a genomic nucleic acid sequence of methionine synthase (MTR); and
        v. a SNP at position 66 of SEQ ID NO. 3 or position 27 of SEQ ID NO. 10 comprising at least one guanine "G" allele, wherein the SEQ ID NO. 3 and SEQ ID NO. 10 are each independently a portion of a genomic nucleic acid sequence of methionine synthase reductase (MTRR);
    (b) instructions for displaying a content based in part on the data output from said determination module, wherein the content comprises a signal indicative of the presence of at least one of the conditions, and optionally the absence of any one of the conditions, or a signal indicative of the absence of all of the conditions.

66. A computer readable medium having computer readable instructions recorded thereon to define software modules for implementing a method on a computer, said computer readable storage medium comprising:
    (a) instructions for comparing the data stored on a storage device with reference data to provide a comparison result, wherein the comparison identifies the presence or absence of at least one of the following conditions:
        i. a single nucleotide polymorphism (SNP) at position 677 of SEQ ID NO. 1 or position 27 of SEQ ID NO. 7 (identified by rs1801133) comprising at least one thymine "T" allele, wherein the SEQ ID NO. 1 and SEQ ID NO. 7 are each independently a portion of a genomic nucleic acid sequence of methylenetetrahydrofolate reductase (MTHFR);
        ii. a SNP at position 2756 of SEQ ID NO. 2 or position 27 of SEQ ID NO. 9 comprising at least one guanine "G" allele, wherein the SEQ ID NO. 2 and SEQ ID NO. 9 are each independently a portion of a genomic nucleic acid sequence of methionine synthase (MTR); and
    (b) instructions for displaying a content based in part on the data output from said determination module, wherein the content comprises a signal indicative of the presence of at least one of the conditions, and optionally the absence of any one of the conditions, or a signal indicative of the absence of all of the conditions.

67. The computer readable medium of any of the preceding paragraphs, further comprising instructions to identify the presence or absence of at least one of the following conditions or any combinations thereof:
    i. a SNP at rs2274976 (position 1793 of SEQ ID NO. 1 or position 27 of SEQ ID NO. 8) comprising at least one adenine "A" allele, wherein the SEQ ID NO. 1 and SEQ ID NO. 8 are each independently a portion of a genomic nucleic acid sequence of methylenetetrahydrofolate reductase (MTHFR);
    ii. a SNP at position 66 of SEQ ID NO. 3 or position 27 of SEQ ID NO. 10 comprising at least one guanine "G" allele, wherein the SEQ ID NO. 3 and SEQ ID NO. 10 are each independently a portion of a genomic nucleic acid sequence of methionine synthase reductase (MTRR);
    iii. a SNP at rs1006737 (position 27 of SEQ ID NO. 11) comprising at least one adenine "A" allele, wherein the SEQ ID NO. 11 is a portion of a genomic nucleic acid sequence of calcium channel, voltage-dependent, L type, alpha 1C subunit (CACNA1C);
    iv. a SNP at rs1883729 (position 27 of SEQ ID NO. 12) comprising at least one adenine "A" allele, wherein the SEQ ID NO. 12 is a portion of a genomic nucleic acid sequence of DNA (cytosine-5)-methyltransferase 3 beta (DNMT3B);
    v. a SNP at rs7163862 (position 27 of SEQ ID NO. 13) comprising at least one thymine "T" allele, wherein the SEQ ID NO. 13 is a portion of a genomic nucleic acid sequence of GTP cyclohydrolase 1 feedback regulatory protein (GCHFR);
    vi. a SNP at rs12659 (position 27 of SEQ ID NO. 14) comprising at least one thymine "T" allele, wherein the SEQ ID NO. 14 is a portion of a genomic nucleic acid sequence of reduced folate carrier protein (RCF2);
    vii. a SNP at rs202676 (position 27 of SEQ ID NO. 15) comprising at least one guanine "G" allele, wherein the SEQ ID NO. 15 is a portion of a genomic nucleic acid sequence of folate hydrolase (prostate-specific membrane antigen) 1 (FOLH1);
    viii. a SNP at rs2297291 (position 27 of SEQ ID NO. 16) comprising at least one adenine "A" allele, wherein the SEQ ID NO. 16 is a portion of a genomic nucleic acid sequence of reduced folate carrier protein (RCF1);
    ix. a SNP at rs1051266 (position 27 of SEQ ID NO. 17) comprising at least one adenine "A" allele, wherein the SEQ ID NO. 17 is a portion of a genomic nucleic acid sequence of reduced folate carrier protein (RCF1);
    x. a SNP at rs8007267 (position 27 of SEQ ID NO. 18) comprising at least one thymine "T" allele, wherein the SEQ ID NO. 18 is a portion of a genomic nucleic acid sequence of GTP cyclohydrolase 1 (GCH1);

xi. a SNP at rs7639752 (position 27 of SEQ ID NO. 19) comprising at least one adenine "A" allele, wherein the SEQ ID NO. 19 is a portion of a genomic nucleic acid sequence of choline-phosphate cytidylyltransferase A (PCYT1A);

xii. a SNP at rs6275 (position 27 of SEQ ID NO. 20) comprising at least one thymine "T" allele, wherein the SEQ ID NO. 20 is a portion of a genomic nucleic acid sequence of dopamine receptor D2 (DRD2);

xiii. a SNP at rs1079596 (position 27 of SEQ ID NO. 21) comprising at least one thymine "T" allele, wherein the SEQ ID NO. 21 is a portion of a genomic nucleic acid sequence of dopamine receptor D2 (DRD2);

xiv. a SNP at rs11240594 (position 27 of SEQ ID NO. 22) comprising at least one adenine "A" allele, wherein the SEQ ID NO. 22 is a portion of a genomic nucleic acid sequence of dopamine receptor D2 (DRD2);

xv. a SNP at rs4633 (position 27 of SEQ ID NO. 23) comprising at least one cytosine "C" allele, wherein the SEQ ID NO. 23 is a portion of a genomic nucleic acid sequence of catechol-O-methyltransferase (COMT);

xvi. a SNP at rs4680 (position 27 of SEQ ID NO. 24) comprising at least one guanine "G" allele, wherein the SEQ ID NO. 24 is a portion of a genomic nucleic acid sequence of catechol-O-methyltransferase (COMT);

xvii. a SNP at rs250682 (position 27 of SEQ ID NO. 25) comprising at least one cytosine "C" allele, wherein the SEQ ID NO. 25 is a portion of a genomic nucleic acid sequence of solute carrier family 6 (neurotransmitted transported, dopamine), member 3 (SLC6A3);

xviii. a SNP at rs2277820 (position 27 of SEQ ID NO. 26) comprising at least one thymine "T" allele, wherein the SEQ ID NO. 26 is a portion of a genomic nucleic acid sequence of formiminotransferase cyclodeaminase (FTCD); and xix. a SNP at rs2236225 (position 27 of SEQ ID NO. 27) comprising at least one adenine "A" allele, wherein the SEQ ID NO. 27 is a portion of a genomic nucleic acid sequence of methylenetetrahydrofolate dehydrogenase (NADP+ dependent) 1 (MTHFD1);

xx. obesity (e.g., defined by a BMI value of at least 30 kg/m² or greater);

xxi. an expression ratio of SAM to SAH smaller than a pre-determined ratio;

xxii. an expression of 4-HNE greater than a first pre-determined reference value; and xxiii. an expression of hsCRP greater than a second pre-determined reference value (e.g., about 2.3 mg per liter of plasma as measured in a plasma sample).

68. A computer readable medium having computer readable instructions recorded thereon to define software modules for implementing a method on a computer, said computer readable storage medium comprising:

(a) instructions for comparing the data stored on a storage device with reference data to provide a comparison result, wherein the comparison identifies the presence or absence of at least one of the following conditions:

i. a SNP at position 677 of SEQ ID NO. 1 or position 27 of SEQ ID NO. 7 (identified by rs1801133) comprising at least one thymine "T" allele, wherein the SEQ ID NO. 1 and SEQ ID NO. 7 are each independently a portion of a genomic nucleic acid sequence of methylenetetrahydrofolate reductase (MTHFR);

ii. a SNP at rs2274976 (position 1793 of SEQ ID NO. 1 or position 27 of SEQ ID NO. 8) comprising at least one adenine "A" allele, wherein the SEQ ID NO. 1 and SEQ ID NO. 8 are each independently a portion of a genomic nucleic acid sequence of methylenetetrahydrofolate reductase (MTHFR);

iii. a SNP at position 2756 of SEQ ID NO. 2 or position 27 of SEQ ID NO. 9 comprising at least one guanine "G" allele, wherein the SEQ ID NO. 2 and SEQ ID NO. 9 are each independently a portion of a genomic nucleic acid sequence of methionine synthase (MTR);

iv. a SNP at position 66 of SEQ ID NO. 3 or position 27 of SEQ ID NO. 10 comprising at least one guanine "G" allele, wherein the SEQ ID NO. 3 and SEQ ID NO. 10 are each independently a portion of a genomic nucleic acid sequence of methionine synthase reductase (MTRR);

v. a SNP at rs1006737 (position 27 of SEQ ID NO. 11) comprising at least one adenine "A" allele, wherein the SEQ ID NO. 11 is a portion of a genomic nucleic acid sequence of calcium channel, voltage-dependent, L type, alpha 1C subunit (CACNA1C);

vi. a SNP at rs1883729 (position 27 of SEQ ID NO. 12) comprising at least one adenine "A" allele, wherein the SEQ ID NO. 12 is a portion of a genomic nucleic acid sequence of DNA (cytosine-5)-methyltransferase 3 beta (DNMT3B);

vii. a SNP at rs7163862 (position 27 of SEQ ID NO. 13) comprising at least one thymine "T" allele, wherein the SEQ ID NO. 13 is a portion of a genomic nucleic acid sequence of GTP cyclohydrolase 1 feedback regulatory protein (GCHFR);

viii. a SNP at rs12659 (position 27 of SEQ ID NO. 14) comprising at least one thymine "T" allele, wherein the SEQ ID NO. 14 is a portion of a genomic nucleic acid sequence of reduced folate carrier protein (RCF2);

ix. a SNP at rs202676 (position 27 of SEQ ID NO. 15) comprising at least one guanine "G" allele, wherein the SEQ ID NO. 15 is a portion of a genomic nucleic acid sequence of folate hydrolase (prostate-specific membrane antigen) 1 (FOLH1);

x. a SNP at rs2297291 (position 27 of SEQ ID NO. 16) comprising at least one adenine "A" allele, wherein the SEQ ID NO. 16 is a portion of a genomic nucleic acid sequence of reduced folate carrier protein (RCF1);

xi. a SNP at rs1051266 (position 27 of SEQ ID NO. 17) comprising at least one adenine "A" allele, wherein the SEQ ID NO. 17 is a portion of a genomic nucleic acid sequence of reduced folate carrier protein (RCF1);

xii. a SNP at rs8007267 (position 27 of SEQ ID NO. 18) comprising at least one thymine "T" allele, wherein the SEQ ID NO. 18 is a portion of a genomic nucleic acid sequence of GTP cyclohydrolase 1 (GCH1);

xiii. a SNP at rs7639752 (position 27 of SEQ ID NO. 19) comprising at least one adenine "A" allele, wherein the SEQ ID NO. 19 is a portion of a genomic nucleic acid sequence of choline-phosphate cytidylyltransferase A (PCYT1A);

xiv. a SNP at rs6275 (position 27 of SEQ ID NO. 20) comprising at least one thymine "T" allele, wherein the SEQ ID NO. 20 is a portion of a genomic nucleic acid sequence of dopamine receptor D2 (DRD2);

xv. a SNP at rs1079596 (position 27 of SEQ ID NO. 21) comprising at least one thymine "T" allele, wherein the SEQ ID NO. 21 is a portion of a genomic nucleic acid sequence of dopamine receptor D2 (DRD2);

xvi. a SNP at rs11240594 (position 27 of SEQ ID NO. 22) comprising at least one adenine "A" allele, wherein the SEQ ID NO. 22 is a portion of a genomic nucleic acid sequence of dopamine receptor D2 (DRD2);

xvii. a SNP at rs4633 (position 27 of SEQ ID NO. 23) comprising at least one cytosine "C" allele, wherein the SEQ ID NO. 23 is a portion of a genomic nucleic acid sequence of catechol-O-methyltransferase (COMT);

xviii. a SNP at rs4680 (position 27 of SEQ ID NO. 24) comprising at least one guanine "G" allele, wherein the SEQ ID NO. 24 is a portion of a genomic nucleic acid sequence of catechol-O-methyltransferase (COMT);

xix. a SNP at rs250682 (position 27 of SEQ ID NO. 25) comprising at least one cytosine "C" allele, wherein the SEQ ID NO. 25 is a portion of a genomic nucleic acid sequence of solute carrier family 6 (neurotransmitted transported, dopamine), member 3 (SLC6A3);

xx. a SNP at rs2277820 (position 27 of SEQ ID NO. 26) comprising at least one thymine "T" allele, wherein the SEQ ID NO. 26 is a portion of a genomic nucleic acid sequence of formiminotransferase cyclodeaminase (FTCD); and xxi. a SNP at rs2236225 (position 27 of SEQ ID NO. 27) comprising at least one adenine "A" allele, wherein the SEQ ID NO. 27 is a portion of a genomic nucleic acid sequence of methylenetetrahydrofolate dehydrogenase (NADP+ dependent) 1 (MTHFD1);

xxii. obesity (e.g., defined by a BMI value of at least 30 kg/m$^2$ or greater);

xxiii. an expression ratio of SAM to SAH smaller than a pre-determined ratio;

xxiv. an expression of 4-HNE greater than a first pre-determined reference value;

xxv. an expression of hsCRP greater than a second pre-determined reference value (e.g., about 2.3 mg per liter of plasma as measured in a plasma sample); and any combinations thereof; and (b) instructions for displaying a content based in part on the data output from said determination module, wherein the content comprises a signal indicative of the presence of at least one of the conditions, and optionally the absence of any one of the conditions, or a signal indicative of the absence of all of the conditions.

69. The computer readable medium of paragraph 68, further comprising instructions to display a signal indicative of the subject recommended to receive a treatment regimen comprising a folate-containing compound, or a signal indicative of the subject recommended to receive an alternative treatment regimen without a folate-containing compound.

70. The computer readable medium of any of the preceding paragraphs, wherein the depression is major depressive disorder.

71. A kit comprising:

an oligonucleotide array affixed with a plurality of oligonucleotide probes that interrogate no more than 30 single nucleotide polymorphisms (SNPs), wherein said SNPs comprise at least two of the following SNPs or any combinations thereof:

i. a SNP at position 677 of SEQ ID NO. 1 or position 27 of SEQ ID NO. 7 (identified by rs1801133) comprising at least one thymine "T" allele, wherein the SEQ ID NO. 1 and SEQ ID NO. 7 are each independently a portion of a genomic nucleic acid sequence of methylenetetrahydrofolate reductase (MTHFR);

ii. a SNP at rs2274976 (position 1793 of SEQ ID NO. 1 or position 27 of SEQ ID NO. 8) comprising at least one adenine "A" allele, wherein the SEQ ID NO. 1 and SEQ ID NO. 8 are each independently a portion of a genomic nucleic acid sequence of methylenetetrahydrofolate reductase (MTHFR);

iii. a SNP at position 2756 of SEQ ID NO. 2 or position 27 of SEQ ID NO. 9 comprising at least one guanine "G" allele, wherein the SEQ ID NO. 2 and SEQ ID NO. 9 are each independently a portion of a genomic nucleic acid sequence of methionine synthase (MTR);

iv. a SNP at position 66 of SEQ ID NO. 3 or position 27 of SEQ ID NO. 10 comprising at least one guanine "G" allele, wherein the SEQ ID NO. 3 and SEQ ID NO. 10 are each independently a portion of a genomic nucleic acid sequence of methionine synthase reductase (MTRR);

v. a SNP at rs1006737 (position 27 of SEQ ID NO. 11) comprising at least one adenine "A" allele, wherein the SEQ ID NO. 11 is a portion of a genomic nucleic acid sequence of calcium channel, voltage-dependent, L type, alpha 1C subunit (CACNA1C);

vi. a SNP at rs1883729 (position 27 of SEQ ID NO. 12) comprising at least one adenine "A" allele, wherein the SEQ ID NO. 12 is a portion of a genomic nucleic acid sequence of DNA (cytosine-5)-methyltransferase 3 beta (DNMT3B);

vii. a SNP at rs7163862 (position 27 of SEQ ID NO. 13) comprising at least one thymine "T" allele, wherein the SEQ ID NO. 13 is a portion of a genomic nucleic acid sequence of GTP cyclohydrolase 1 feedback regulatory protein (GCHFR);

viii. a SNP at rs12659 (position 27 of SEQ ID NO. 14) comprising at least one thymine "T" allele, wherein the SEQ ID NO. 14 is a portion of a genomic nucleic acid sequence of reduced folate carrier protein (RCF2);

ix. a SNP at rs202676 (position 27 of SEQ ID NO. 15) comprising at least one guanine "G" allele, wherein the SEQ ID NO. 15 is a portion of a genomic nucleic acid sequence of folate hydrolase (prostate-specific membrane antigen) 1 (FOLH1);

x. a SNP at rs2297291 (position 27 of SEQ ID NO. 16) comprising at least one adenine "A" allele, wherein the SEQ ID NO. 16 is a portion of a genomic nucleic acid sequence of reduced folate carrier protein (RCF1);

xi. a SNP at rs1051266 (position 27 of SEQ ID NO. 17) comprising at least one adenine "A" allele, wherein the SEQ ID NO. 17 is a portion of a genomic nucleic acid sequence of reduced folate carrier protein (RCF1);

xii. a SNP at rs8007267 (position 27 of SEQ ID NO. 18) comprising at least one thymine "T" allele, wherein the SEQ ID NO. 18 is a portion of a genomic nucleic acid sequence of GTP cyclohydrolase 1 (GCH1);

xiii. a SNP at rs7639752 (position 27 of SEQ ID NO. 19) comprising at least one adenine "A" allele, wherein the SEQ ID NO. 19 is a portion of a genomic nucleic acid sequence of choline-phosphate cytidylyltransferase A (PCYT1A);

xiv. a SNP at rs6275 (position 27 of SEQ ID NO. 20) comprising at least one thymine "T" allele, wherein the SEQ ID NO. 20 is a portion of a genomic nucleic acid sequence of dopamine receptor D2 (DRD2);

xv. a SNP at rs1079596 (position 27 of SEQ ID NO. 21) comprising at least one thymine "T" allele, wherein the SEQ ID NO. 21 is a portion of a genomic nucleic acid sequence of dopamine receptor D2 (DRD2);

xvi. a SNP at rs11240594 (position 27 of SEQ ID NO. 22) comprising at least one adenine "A" allele, wherein the SEQ ID NO. 22 is a portion of a genomic nucleic acid sequence of dopamine receptor D2 (DRD2);

xvii. a SNP at rs4633 (position 27 of SEQ ID NO. 23) comprising at least one cytosine "C" allele, wherein the SEQ ID NO. 23 is a portion of a genomic nucleic acid sequence of catechol-O-methyltransferase (COMT);

xviii. a SNP at rs4680 (position 27 of SEQ ID NO. 24) comprising at least one guanine "G" allele, wherein the SEQ ID NO. 24 is a portion of a genomic nucleic acid sequence of catechol-O-methyltransferase (COMT);

xix. a SNP at rs250682 (position 27 of SEQ ID NO. 25) comprising at least one cytosine "C" allele, wherein the SEQ ID NO. 25 is a portion of a genomic nucleic acid sequence of solute carrier family 6 (neurotransmitted transported, dopamine), member 3 (SLC6A3);

xx. a SNP at rs2277820 (position 27 of SEQ ID NO. 26) comprising at least one thymine "T" allele, wherein the SEQ ID NO. 26 is a portion of a genomic nucleic acid sequence of formiminotransferase cyclodeaminase (FTCD); and xxi. a SNP at rs2236225 (position 27 of SEQ ID NO. 27) comprising at least one adenine "A" allele, wherein the SEQ ID NO. 27 is a portion of a genomic nucleic acid sequence of methylenetetrahydrofolate dehydrogenase (NADP+ dependent) 1 (MTHFD1); and an optional container containing a detectable label to be conjugated to a nucleotide molecule derived from a test sample of a subject; and at least one reagent.

72. A kit comprising:
an oligonucleotide array affixed with a plurality of oligonucleotide probes that interrogate no more than 5 single nucleotide polymorphisms (SNPs), said SNPs comprising:
(i) a SNP at position 677 of SEQ ID NO. 1 or position 27 of SEQ ID NO. 7 (identified by rs1801133), wherein the SEQ ID NO. 1 and SEQ ID NO. 7 are each independently a portion of a genomic nucleic acid sequence of methylenetetrahydrofolate reductase (MTHFR);
(ii) a SNP at position 2756 of SEQ ID NO. 2 or position 27 of SEQ ID NO. 9 (identified by rs1805087), wherein the SEQ ID NO. 2 and SEQ ID NO. 9 are each independently a portion of a genomic nucleic acid sequence of methionine synthase (MTR);
an optional container containing a detectable label to be conjugated to a nucleotide molecule derived from a test sample of a subject; and
at least one reagent.

73. The kit of paragraph 71 or 72, wherein the at least one reagent is selected from the group consisting of a restriction enzyme, a universal adaptor to be conjugated to a nucleotide molecule, a primer complementary to the universal adaptor, a wash agent, and any combinations thereof 74. The kit of any of paragraphs 71-73, wherein the detectable label comprises a fluorescent molecule.

75. A kit comprising:
a plurality of oligonucleotide primers that bind to at least one allele of no more than 30 single nucleotide polymorphisms (SNPs), wherein each subset of oligonucleotide primers that bind to a specific allele of a SNP is labeled with a distinct reporter, and wherein said SNPs comprise at least two of the following SNPs or any combinations thereof:
i. a single nucleotide polymorphism (SNP) at position 677 of SEQ ID NO. 1 or position 27 of SEQ ID NO. 7 (identified by rs1801133) comprising at least one thymine "T" allele, wherein the SEQ ID NO. 1 and SEQ ID NO. 7 are each independently a portion of a genomic nucleic acid sequence of methylenetetrahydrofolate reductase (MTHFR);
ii. a SNP at rs2274976 (position 1793 of SEQ ID NO. 1 or position 27 of SEQ ID NO. 8) comprising at least one adenine "A" allele, wherein the SEQ ID NO. 1 and SEQ ID NO. 8 are each independently a portion of a genomic nucleic acid sequence of methylenetetrahydrofolate reductase (MTHFR);
iii. a SNP at position 2756 of SEQ ID NO. 2 or position 27 of SEQ ID NO. 9 comprising at least one guanine "G" allele, wherein the SEQ ID NO. 2 and SEQ ID NO. 9 are each independently a portion of a genomic nucleic acid sequence of methionine synthase (MTR);
iv. a SNP at position 66 of SEQ ID NO. 3 or position 27 of SEQ ID NO. 10 comprising at least one guanine "G" allele, wherein the SEQ ID NO. 3 and SEQ ID NO. 10 are each independently a portion of a genomic nucleic acid sequence of methionine synthase reductase (MTRR);
v. a SNP at rs1006737 (position 27 of SEQ ID NO. 11) comprising at least one adenine "A" allele, wherein the SEQ ID NO. 11 is a portion of a genomic nucleic acid sequence of calcium channel, voltage-dependent, L type, alpha 1C subunit (CACNA1C);

vi. a SNP at rs1883729 (position 27 of SEQ ID NO. 12) comprising at least one adenine "A" allele, wherein the SEQ ID NO. 12 is a portion of a genomic nucleic acid sequence of DNA (cytosine-5)-methyltransferase 3 beta (DNMT3B);

vii. a SNP at rs7163862 (position 27 of SEQ ID NO. 13) comprising at least one thymine "T" allele, wherein the SEQ ID NO. 13 is a portion of a genomic nucleic acid sequence of GTP cyclohydrolase 1 feedback regulatory protein (GCHFR);

viii. a SNP at rs12659 (position 27 of SEQ ID NO. 14) comprising at least one thymine "T" allele, wherein the SEQ ID NO. 14 is a portion of a genomic nucleic acid sequence of reduced folate carrier protein (RCF2);

ix. a SNP at rs202676 (position 27 of SEQ ID NO. 15) comprising at least one guanine "G" allele, wherein the SEQ ID NO. 15 is a portion of a genomic nucleic acid sequence of folate hydrolase (prostate-specific membrane antigen) 1 (FOLH1);

x. a SNP at rs2297291 (position 27 of SEQ ID NO. 16) comprising at least one adenine "A" allele, wherein the SEQ ID NO. 16 is a portion of a genomic nucleic acid sequence of reduced folate carrier protein (RCF1);

xi. a SNP at rs1051266 (position 27 of SEQ ID NO. 17) comprising at least one adenine "A" allele, wherein the SEQ ID NO. 17 is a portion of a genomic nucleic acid sequence of reduced folate carrier protein (RCF1);

xii. a SNP at rs8007267 (position 27 of SEQ ID NO. 18) comprising at least one thymine "T" allele, wherein the SEQ ID NO. 18 is a portion of a genomic nucleic acid sequence of GTP cyclohydrolase 1 (GCH1);

xiii. a SNP at rs7639752 (position 27 of SEQ ID NO. 19) comprising at least one adenine "A" allele, wherein the SEQ ID NO. 19 is a portion of a genomic nucleic acid sequence of choline-phosphate cytidylyltransferase A (PCYT1A);

xiv. a SNP at rs6275 (position 27 of SEQ ID NO. 20) comprising at least one thymine "T" allele, wherein the SEQ ID NO. 20 is a portion of a genomic nucleic acid sequence of dopamine receptor D2 (DRD2);

xv. a SNP at rs1079596 (position 27 of SEQ ID NO. 21) comprising at least one thymine "T" allele, wherein the SEQ ID NO. 21 is a portion of a genomic nucleic acid sequence of dopamine receptor D2 (DRD2);

xvi. a SNP at rs11240594 (position 27 of SEQ ID NO. 22) comprising at least one adenine "A" allele, wherein the SEQ ID NO. 22 is a portion of a genomic nucleic acid sequence of dopamine receptor D2 (DRD2);

xvii. a SNP at rs4633 (position 27 of SEQ ID NO. 23) comprising at least one cytosine "C" allele, wherein the SEQ ID NO. 23 is a portion of a genomic nucleic acid sequence of catechol-O-methyltransferase (COMT);

xviii. a SNP at rs4680 (position 27 of SEQ ID NO. 24) comprising at least one guanine "G" allele, wherein the SEQ ID NO. 24 is a portion of a genomic nucleic acid sequence of catechol-O-methyltransferase (COMT);

xix. a SNP at rs250682 (position 27 of SEQ ID NO. 25) comprising at least one cytosine "C" allele, wherein the SEQ ID NO. 25 is a portion of a genomic nucleic acid sequence of solute carrier family 6 (neurotransmitted transported, dopamine), member 3 (SLC6A3);

xx. a SNP at rs2277820 (position 27 of SEQ ID NO. 26) comprising at least one thymine "T" allele, wherein the SEQ ID NO. 26 is a portion of a genomic nucleic acid sequence of formiminotransferase cyclodeaminase (FTCD); and xxi. a SNP at rs2236225 (position 27 of SEQ ID NO. 27) comprising at least one adenine "A" allele, wherein the SEQ ID NO. 27 is a portion of a genomic nucleic acid sequence of methylenetetrahydrofolate dehydrogenase (NADP+ dependent) 1 (MTHFD1); and at least one reagent.

76. A kit comprising:
   a plurality of oligonucleotide primers that bind to at least one allele of no more than 5 single nucleotide polymorphisms (SNPs), wherein each subset of oligonucleotide primers that bind to a specific allele of a SNP is labeled with a distinct reporter, and wherein said SNPs comprise the following SNPs:
   (i) a SNP at position 677 of SEQ ID NO. 1 or position 27 of SEQ ID NO. 7 (identified by rs1801133) comprising at least one thymine "T" allele, wherein the SEQ ID NO. 1 and SEQ ID NO. 7 are each independently a portion of a genomic nucleic acid sequence of methylenetetrahydrofolate reductase (MTHFR);
   (ii) a SNP at position 2756 of SEQ ID NO. 2 or position 27 of SEQ ID NO. 9 comprising at least one guanine "G" allele, wherein the SEQ ID NO. 2 and SEQ ID NO. 9 are each independently a portion of a genomic nucleic acid sequence of methionine synthase (MTR); and
   at least one reagent.

77. The kit of any of paragraphs 75-76, wherein said at least one reagent comprises free nucleotide bases, a polymerase, or both.

78. A kit for selecting a treatment regimen for a subject with depression, comprising
   at least one reagent for determining in a test sample of a human subject diagnosed as having depression or having a risk for depression, the presence or absence of the following SNPs:
   i. a single nucleotide polymorphism (SNP) at position 677 of SEQ ID NO. 1 or position 27 of SEQ ID NO. 7 (identified by rs1801133) comprising at least one thymine "T" allele, wherein the SEQ ID NO. 1 and SEQ ID NO. 7 are each independently a portion of a genomic nucleic acid sequence of methylenetetrahydrofolate reductase (MTHFR); and
   ii. a SNP at position 2756 of SEQ ID NO. 2 or position 27 of SEQ ID NO. 9 comprising at least one guanine "G" allele, wherein the SEQ ID NO. 2 and SEQ ID NO. 9 are each independently a portion of a genomic nucleic acid sequence of methionine synthase (MTR); and
   instructions for use in the assay of any of paragraphs 1-69, in the method of any of paragraphs 70-129, or in the system of any of paragraphs 130-171, or any combinations thereof 79. The kit of paragraph 78, wherein said SNPs further comprises one or any combination of the following:
   i. a SNP at rs2274976 (position 1793 of SEQ ID NO. 1 or position 27 of SEQ ID NO. 8) comprising at least one adenine "A" allele, wherein the SEQ ID NO. 1 and SEQ ID NO. 9 are each independently a portion of a genomic nucleic acid sequence of methylenetetrahydrofolate reductase (MTHFR);
   ii. a SNP at position 66 of SEQ ID NO. 3 or position 27 of SEQ ID NO. 10 comprising at least one guanine "G" allele, wherein the SEQ ID NO. 3 and SEQ ID NO. 10 are each independently a portion of a genomic nucleic acid sequence of methionine synthase reductase (MTRR);
   iii. a SNP at rs1006737 (position 27 of SEQ ID NO. 11) comprising at least one adenine "A" allele, wherein the SEQ ID NO. 11 is a portion of a genomic nucleic acid sequence of calcium channel, voltage-dependent, L type, alpha 1C subunit (CACNA1C);
   iv. a SNP at rs1883729 (position 27 of SEQ ID NO. 12) comprising at least one adenine "A" allele, wherein the SEQ ID NO. 12 is a portion of a genomic nucleic acid sequence of DNA (cytosine-5)-methyltransferase 3 beta (DNMT3B);
   v. a SNP at rs7163862 (position 27 of SEQ ID NO. 13) comprising at least one thymine "T" allele, wherein the SEQ ID NO. 13 is a portion of a genomic nucleic acid sequence of GTP cyclohydrolase 1 feedback regulatory protein (GCHFR);
   vi. a SNP at rs12659 (position 27 of SEQ ID NO. 14) comprising at least one thymine "T" allele, wherein the SEQ ID NO. 14 is a portion of a genomic nucleic acid sequence of reduced folate carrier protein (RCF2);
   vii. a SNP at rs202676 (position 27 of SEQ ID NO. 15) comprising at least one guanine "G" allele, wherein the SEQ ID NO. 15 is a portion of a genomic nucleic acid sequence of folate hydrolase (prostate-specific membrane antigen) 1 (FOLH1);
   viii. a SNP at rs2297291 (position 27 of SEQ ID NO. 16) comprising at least one adenine "A" allele, wherein the SEQ ID NO. 16 is a portion of a genomic nucleic acid sequence of reduced folate carrier protein (RCF1);
   ix. a SNP at rs1051266 (position 27 of SEQ ID NO. 17) comprising at least one adenine "A" allele, wherein the SEQ ID NO. 17 is a portion of a genomic nucleic acid sequence of reduced folate carrier protein (RCF1);
   x. a SNP at rs8007267 (position 27 of SEQ ID NO. 18) comprising at least one thymine "T" allele, wherein the SEQ ID NO. 18 is a portion of a genomic nucleic acid sequence of GTP cyclohydrolase 1 (GCH1);
   xi. a SNP at rs7639752 (position 27 of SEQ ID NO. 19) comprising at least one adenine "A" allele, wherein the SEQ ID NO. 19 is a portion of a genomic nucleic acid sequence of choline-phosphate cytidylyltransferase A (PCYT1A);
   xii. a SNP at rs6275 (position 27 of SEQ ID NO. 20) comprising at least one thymine "T" allele, wherein the SEQ ID NO. 20 is a portion of a genomic nucleic acid sequence of dopamine receptor D2 (DRD2);
   xiii. a SNP at rs1079596 (position 27 of SEQ ID NO. 21) comprising at least one thymine "T" allele, wherein the SEQ ID NO. 21 is a portion of a genomic nucleic acid sequence of dopamine receptor D2 (DRD2);
   xiv. a SNP at rs11240594 (position 27 of SEQ ID NO. 22) comprising at least one adenine "A" allele, wherein the SEQ ID NO. 22 is a portion of a genomic nucleic acid sequence of dopamine receptor D2 (DRD2);
   xv. a SNP at rs4633 (position 27 of SEQ ID NO. 23) comprising at least one cytosine "C" allele, wherein the SEQ ID NO. 23 is a portion of a genomic nucleic acid sequence of catechol-O-methyltransferase (COMT);
   xvi. a SNP at rs4680 (position 27 of SEQ ID NO. 24) comprising at least one guanine "G" allele, wherein the SEQ ID NO. 24 is a portion of a genomic nucleic acid sequence of catechol-O-methyltransferase (COMT);
   xvii. a SNP at rs250682 (position 27 of SEQ ID NO. 25) comprising at least one cytosine "C" allele, wherein the SEQ ID NO. 25 is a portion of a genomic nucleic acid sequence of solute carrier family 6 (neurotransmitted transported, dopamine), member 3 (SLC6A3);
   xviii. a SNP at rs2277820 (position 27 of SEQ ID NO. 26) comprising at least one thymine "T" allele, wherein the SEQ ID NO. 26 is a portion of a genomic nucleic acid sequence of formiminotransferase cyclodeaminase (FTCD); and
   xix. a SNP at rs2236225 (position 27 of SEQ ID NO. 27) comprising at least one adenine "A" allele, wherein the SEQ ID NO. 27 is a portion of a genomic nucleic acid sequence of methylenetetrahydrofolate dehydrogenase (NADP+ dependent) 1 (MTHFD1).

80. The kit of any of the preceding paragraphs, further comprising a solid substrate support affixed with at least one protein-based binding moiety that specifically binds to a biomarker selected from the group consisting of SAM, SAH, 4-HNE and hsCRP.

81. The kit of paragraph 80, wherein the protein-based binding moiety comprises an antibody.

82. The kit of paragraph 80 or 81, wherein the solid substrate support is a microtiter plate for ELISA.

83. The kit of paragraph 80 or 81, wherein the solid substrate support is a dipstick.

84. The kit of paragraph 80 or 81, wherein the solid substrate support comprises a magnetic bead.

85. The kit of any of the preceding paragraphs, further comprising at least one primer designed to probe a biomarker selected from the group consisting of SAM, SAH, 4-HNE, and hsCRP.

86. The kit of any of the preceding paragraphs, wherein the depression is major depressive disorder.

87. A method for selecting a treatment regimen for a human subject with depression, comprising:
   a. obtaining a test sample from the human subject diagnosed as having depression;
   b. subjecting the test sample to at least one analysis to determine parameters of at least two biomarkers, wherein the parameters of said at least two biomarkers are selected from the following:
      i. genotype of a SNP locus at position 677 of SEQ ID NO. 1 or position 27 of SEQ ID NO. 7 (identified by rs1801133), wherein the SEQ ID NO. 1 and SEQ ID NO. 7 are each independently a portion of a genomic nucleic acid sequence of methylenetetrahydrofolate reductase (MTHFR);

ii. genotype of a SNP locus at rs2274976 (position 1793 of SEQ ID NO. 1 or position 27 of SEQ ID NO. 8), wherein the SEQ ID NO. 1 and SEQ ID NO. 8 are each independently a portion of a genomic nucleic acid sequence of methylenetetrahydrofolate reductase (MTHFR);

iii. genotype of a SNP locus at position 2756 of SEQ ID NO. 2 or position 27 of SEQ ID NO. 9 (identified by rs1805087), wherein the SEQ ID NO. 2 and SEQ ID NO. 9 are each independently a portion of a genomic nucleic acid sequence of methionine synthase (MTR);

iv. genotype of a SNP locus at position 66 of SEQ ID NO. 3 or position 27 of SEQ ID NO. 10 (identified by rs1801394), wherein the SEQ ID NO. 3 and SEQ ID NO. 10 are each independently a portion of a genomic nucleic acid sequence of methionine synthase reductase (MTRR);

v. genotype of a SNP locus at rs1006737 (position 27 of SEQ ID NO. 11), wherein the SEQ ID NO. 11 is a portion of a genomic nucleic acid sequence of calcium channel, voltage-dependent, L type, alpha 1C subunit (CACNA1C);

vi. genotype of a SNP locus at rs1883729 (position 27 of SEQ ID NO. 12), wherein the SEQ ID NO. 12 is a portion of a genomic nucleic acid sequence of DNA (cytosine-5)-methyltransferase 3 beta (DNMT3B);

vii. genotype of a SNP locus at rs7163862 (position 27 of SEQ ID NO. 13), wherein the SEQ ID NO. 13 is a portion of a genomic nucleic acid sequence of GTP cyclohydrolase 1 feedback regulatory protein (GCHFR);

viii. genotype of a SNP locus at rs12659 (position 27 of SEQ ID NO. 14), wherein the SEQ ID NO. 14 is a portion of a genomic nucleic acid sequence of reduced folate carrier protein (RCF2);

ix. genotype of a SNP locus at rs202676 (position 27 of SEQ ID NO. 15), wherein the SEQ ID NO. 15 is a portion of a genomic nucleic acid sequence of folate hydrolase (prostate-specific membrane antigen) 1 (FOLH1);

x. genotype of a SNP locus at rs2297291 (position 27 of SEQ ID NO. 16), wherein the SEQ ID NO. 16 is a portion of a genomic nucleic acid sequence of reduced folate carrier protein (RCF1);

xi. genotype of a SNP locus at rs1051266 (position 27 of SEQ ID NO. 17, wherein the SEQ ID NO. 17 is a portion of a genomic nucleic acid sequence of reduced folate carrier protein (RCF1));

xii. genotype of a SNP locus at rs8007267 (position 27 of SEQ ID NO. 18), wherein the SEQ ID NO. 18 is a portion of a genomic nucleic acid sequence of GTP cyclohydrolase 1 (GCH1);

xiii. genotype of a SNP locus at rs7639752 (position 27 of SEQ ID NO. 19), wherein the SEQ ID NO. 19 is a portion of a genomic nucleic acid sequence of choline-phosphate cytidylyltransferase A (PCYT1A);

xiv. genotype of a SNP locus at rs6275 (position 27 of SEQ ID NO. 20), wherein the SEQ ID NO. 20 is a portion of a genomic nucleic acid sequence of dopamine receptor D2 (DRD2);

xv. genotype of a SNP locus at rs1079596 (position 27 of SEQ ID NO. 21), wherein the SEQ ID NO. 21 is a portion of a genomic nucleic acid sequence of dopamine receptor D2 (DRD2);

xvi. genotype of a SNP locus at rs11240594 (position 27 of SEQ ID NO. 22), wherein the SEQ ID NO. 22 is a portion of a genomic nucleic acid sequence of dopamine receptor D2 (DRD2);

xvii. genotype of a SNP locus at rs4633 (position 27 of SEQ ID NO. 23), wherein the SEQ ID NO. 23 is a portion of a genomic nucleic acid sequence of catechol-β-methyltransferase (COMT);

xviii. genotype of a SNP locus at rs4680 (position 27 of SEQ ID NO. 24), wherein the SEQ ID NO. 24 is a portion of a genomic nucleic acid sequence of catechol-β-methyltransferase (COMT);

xix. genotype of a SNP locus at rs250682 (position 27 of SEQ ID NO. 250, wherein the SEQ ID NO. 25 is a portion of a genomic nucleic acid sequence of solute carrier family 6 (neurotransmitted transported, dopamine), member 3 (SLC6A3);

xx. genotype of a SNP locus at rs2277820 (position 27 of SEQ ID NO. 26), wherein the SEQ ID NO. 26 is a portion of a genomic nucleic acid sequence of formiminotransferase cyclodeaminase (FTCD);

xxi. genotype of a SNP locus at rs2236225 (position 27 of SEQ ID NO. 27), wherein the SEQ ID NO. 27 is a portion of a genomic nucleic acid sequence of methylenetetrahydrofolate dehydrogenase (NADP+ dependent) 1 (MTHFD1);

xxii. expressions of SAM and SAH;

xxiii. expression of 4-HNE;

xxiv. expression of hsCRP; and any combinations thereof; and c. determining, from the parameters of said at least two biomarkers, the presence of at least one condition selected from the following:

i. a SNP at position 677 of SEQ ID NO. 1 or position 27 of SEQ ID NO. 7 comprising at least one thymine "T" allele;

ii. a SNP at rs2274976 (position 1793 of SEQ ID NO. 1 or position 27 of SEQ ID NO. 8) comprising at least one adenine "A" allele;

iii. a SNP at position 2756 of SEQ ID NO. 2 or position 27 of SEQ ID NO. 9 comprising at least one guanine "G" allele;

iv. a SNP at position 66 of SEQ ID NO. 3 or position 27 of SEQ ID NO. 10 comprising at least one guanine "G" allele;

v. a SNP at rs1006737 (position 27 of SEQ ID NO. 11) comprising at least one adenine "A" allele;

vi. a SNP at rs1883729 (position 27 of SEQ ID NO. 12) comprising at least one adenine "A" allele;

vii. a SNP at rs7163862 (position 27 of SEQ ID NO. 13) comprising at least one thymine "T" allele;

viii. a SNP at rs12659 (position 27 of SEQ ID NO. 14) comprising at least one thymine "T" allele;

ix. a SNP at rs202676 (position 27 of SEQ ID NO. 15) comprising at least one guanine "G" allele;

x. a SNP at rs2297291 (position 27 of SEQ ID NO. 16) comprising at least one adenine "A" allele;

xi. a SNP at rs1051266 (position 27 of SEQ ID NO. 17) comprising at least one adenine "A" allele;

xii. a SNP at rs8007267 (position 27 of SEQ ID NO. 18) comprising at least one thymine "T" allele;

xiii. a SNP at rs7639752 (position 27 of SEQ ID NO. 19) comprising at least one adenine "A" allele;

xiv. a SNP at rs6275 (position 27 of SEQ ID NO. 20) comprising at least one thymine "T" allele;

xv. a SNP at rs1079596 (position 27 of SEQ ID NO. 21) comprising at least one thymine "T" allele;

xvi. a SNP at rs11240594 (position 27 of SEQ ID NO. 22) comprising at least one adenine "A" allele;
xvii. a SNP at rs4633 (position 27 of SEQ ID NO. 23) comprising at least one cytosine "C" allele;
xviii. a SNP at rs4680 (position 27 of SEQ ID NO. 24) comprising at least one guanine "G" allele;
xix. a SNP at rs250682 (position 27 of SEQ ID NO. 25) comprising at least one cytosine "C" allele;
xx. a SNP at rs2277820 (position 27 of SEQ ID NO. 26) comprising at least one thymine "T" allele; and
xxi. a SNP at rs2236225 (position 27 of SEQ ID NO. 27) comprising at least one adenine "A" allele;
xxii. an expression ratio of SAM to SAH smaller than a pre-determined reference ratio;
xxiii. an expression of 4-HNE greater than a first pre-determined reference value;
xxiv. an expression of hsCRP greater than a second pre-determined reference value (e.g., greater than about 2.3 mg per liter of plasma as measured in a plasma sample); and any combinations thereof;
d. providing a result output setting forth whether at least one of said condition is detected from the test sample and if at least one condition is detected, then selecting and optionally administering a treatment regimen comprising an effective amount of a folate-containing compound to the human subject.

88. A method for selecting a treatment regimen for a subject with depression, comprising:
a. obtaining a test sample from the human subject diagnosed as having depression;
b. subjecting the test sample to at least one analysis to determine parameters of at least two biomarkers, wherein the parameters of said at least two biomarkers comprise the following:
i. genotype of a SNP locus at position 677 of SEQ ID NO. 1 or position 27 of SEQ ID NO. 7 (identified by rs1801133), wherein the SEQ ID NO. 1 and SEQ ID NO. 7 are each independently a portion of a genomic nucleic acid sequence of methylenetetrahydrofolate reductase (MTHFR);
ii. genotype of a SNP locus at position 2756 of SEQ ID NO. 2 or position 27 of SEQ ID NO. 9 (identified by rs1805087), wherein the SEQ ID NO. 2 and SEQ ID NO. 9 are each independently a portion of a genomic nucleic acid sequence of methionine synthase (MTR);
c. determining, from the determined parameters of said at least two biomarkers, the presence of at least one condition of the following or a combination thereof:
i. a SNP at position 677 of SEQ ID NO. 1 comprising at least one thymine "T" allele;
ii. a SNP at position 2756 of SEQ ID NO. 2 comprising at least one guanine "G" allele;
d. providing a result output setting forth whether at least one of said condition is detected from the test sample and if at least one condition or both is detected, then selecting and optionally administering a treatment regimen comprising an effective amount of a folate-containing compound to the human subject.

89. The method of paragraph 88, wherein the test sample is further subjected to determine a parameter of at least one of the following biomarkers or any combinations thereof:
i. genotype of a SNP locus at rs2274976 (position 1793 of SEQ ID NO. 1 or position 27 of SEQ ID NO. 8), wherein the SEQ ID NO. 1 and SEQ ID NO. 8 are each independently a portion of a genomic nucleic acid sequence of methylenetetrahydrofolate reductase (MTHFR);
ii. genotype of a SNP locus at position 66 of SEQ ID NO. 3 or position 27 of SEQ ID NO. (identified by rs1801394), wherein the SEQ ID NO. 3 and SEQ ID NO. 10 are each independently a portion of a genomic nucleic acid sequence of methionine synthase reductase (MTRR);
iii. genotype of a SNP locus at rs1006737 (position 27 of SEQ ID NO. 11), wherein the SEQ ID NO. 11 is a portion of a genomic nucleic acid sequence of calcium channel, voltage-dependent, L type, alpha 1C subunit (CACNA1C);
iv. genotype of a SNP locus at rs1883729 (position 27 of SEQ ID NO. 12), wherein the SEQ ID NO. 12 is a portion of a genomic nucleic acid sequence of DNA (cytosine-5)-methyltransferase 3 beta (DNMT3B);
v. genotype of a SNP locus at rs7163862 (position 27 of SEQ ID NO. 13), wherein the SEQ ID NO. 13 is a portion of a genomic nucleic acid sequence of GTP cyclohydrolase 1 feedback regulatory protein (GCHFR);
vi. genotype of a SNP locus at rs12659 (position 27 of SEQ ID NO. 14), wherein the SEQ ID NO. 14 is a portion of a genomic nucleic acid sequence of reduced folate carrier protein (RCF2);
vii. genotype of a SNP locus at rs202676 (position 27 of SEQ ID NO. 15), wherein the SEQ ID NO. 15 is a portion of a genomic nucleic acid sequence of folate hydrolase (prostate-specific membrane antigen) 1 (FOLH1);
viii. genotype of a SNP locus at rs2297291 (position 27 of SEQ ID NO. 16), wherein the SEQ ID NO. 16 is a portion of a genomic nucleic acid sequence of reduced folate carrier protein (RCF1);
ix. genotype of a SNP locus at rs1051266 (position 27 of SEQ ID NO. 17, wherein the SEQ ID NO. 17 is a portion of a genomic nucleic acid sequence of reduced folate carrier protein (RCF1));
x. genotype of a SNP locus at rs8007267 (position 27 of SEQ ID NO. 18), wherein the SEQ ID NO. 18 is a portion of a genomic nucleic acid sequence of GTP cyclohydrolase 1 (GCH1);
xi. genotype of a SNP locus at rs7639752 (position 27 of SEQ ID NO. 19), wherein the SEQ ID NO. 19 is a portion of a genomic nucleic acid sequence of choline-phosphate cytidylyltransferase A (PCYT1A);
xii. genotype of a SNP locus at rs6275 (position 27 of SEQ ID NO. 20), wherein the SEQ ID NO. 20 is a portion of a genomic nucleic acid sequence of dopamine receptor D2 (DRD2);
xiii. genotype of a SNP locus at rs1079596 (position 27 of SEQ ID NO. 21), wherein the SEQ ID NO. 21 is a portion of a genomic nucleic acid sequence of dopamine receptor D2 (DRD2);
xiv. genotype of a SNP locus at rs11240594 (position 27 of SEQ ID NO. 22), wherein the SEQ ID NO. 22 is a portion of a genomic nucleic acid sequence of dopamine receptor D2 (DRD2);
xv. genotype of a SNP locus at rs4633 (position 27 of SEQ ID NO. 23), wherein the SEQ ID NO. 23 is a portion of a genomic nucleic acid sequence of catechol-β-methyltransferase (COMT);
xvi. genotype of a SNP locus at rs4680 (position 27 of SEQ ID NO. 24), wherein the SEQ ID NO. 24 is a portion of a genomic nucleic acid sequence of catechol-β-methyltransferase (COMT);
xvii. genotype of a SNP locus at rs250682 (position 27 of SEQ ID NO. 25), wherein the SEQ ID NO. 25 is a portion of a genomic nucleic acid sequence of solute carrier family 6 (neurotransmitted transported, dopamine), member 3 (SLC6A3);
xviii. genotype of a SNP locus at rs2277820 (position 27 of SEQ ID NO. 26), wherein the SEQ ID NO. 26 is a portion of a genomic nucleic acid sequence of formiminotransferase cyclodeaminase (FTCD);
xix. genotype of a SNP locus at rs2236225 (position 27 of SEQ ID NO. 27), wherein the SEQ ID NO. 27 is a portion of a genomic nucleic acid sequence of methylenetetrahydrofolate dehydrogenase (NADP+ dependent) 1 (MTHFD1);
xx. expressions of SAM and SAH;
xxi. expression of 4-HNE; and
xxii. expression of hsCRP.

90. The method of paragraph 89, further comprising determining the presence of at least one of the following conditions or any combinations thereof:
    i. a SNP at rs2274976 (position 1793 of SEQ ID NO. 1 or position 27 of SEQ ID NO. 8) comprising at least one adenine "A" allele;
    ii. a SNP at position 66 of SEQ ID NO. 3 or position 27 of SEQ ID NO. 10 comprising at least one guanine "G" allele;
    iii. a SNP at rs1006737 (position 27 of SEQ ID NO. 11) comprising at least one adenine "A" allele;
    iv. a SNP at rs1883729 (position 27 of SEQ ID NO. 12) comprising at least one adenine "A" allele;
    v. a SNP at rs7163862 (position 27 of SEQ ID NO. 13) comprising at least one thymine "T" allele;
    vi. a SNP at rs12659 (position 27 of SEQ ID NO. 14) comprising at least one thymine "T" allele;
    vii. a SNP at rs202676 (position 27 of SEQ ID NO. 15) comprising at least one guanine "G" allele;
    viii. a SNP at rs2297291 (position 27 of SEQ ID NO. 16) comprising at least one adenine "A" allele;
    ix. a SNP at rs1051266 (position 27 of SEQ ID NO. 17) comprising at least one adenine "A" allele;
    x. a SNP at rs8007267 (position 27 of SEQ ID NO. 18) comprising at least one thymine "T" allele;
    xi. a SNP at rs7639752 (position 27 of SEQ ID NO. 19) comprising at least one adenine "A" allele;
    xii. a SNP at rs6275 (position 27 of SEQ ID NO. 20) comprising at least one thymine "T" allele;
    xiii. a SNP at rs1079596 (position 27 of SEQ ID NO. 21) comprising at least one thymine "T" allele;
    xiv. a SNP at rs11240594 (position 27 of SEQ ID NO. 22) comprising at least one adenine "A" allele;
    xv. a SNP at rs4633 (position 27 of SEQ ID NO. 23) comprising at least one cytosine "C" allele;
    xvi. a SNP at rs4680 (position 27 of SEQ ID NO. 24) comprising at least one guanine "G" allele;
    xvii. a SNP at rs250682 (position 27 of SEQ ID NO. 25) comprising at least one cytosine "C" allele;
    xviii. a SNP at rs2277820 (position 27 of SEQ ID NO. 26) comprising at least one thymine "T" allele; and
    xix. a SNP at rs2236225 (position 27 of SEQ ID NO. 27) comprising at least one adenine "A" allele;
    xx. an expression ratio of SAM to SAH smaller than a pre-determined reference ratio;
    xxi. an expression of 4-HNE greater than a first pre-determined reference value; and
    xxii. an expression of hsCRP greater than a second pre-determined reference value (e.g., greater than about 2.3 mg per liter of plasma as measured in a plasma sample).

91. The method of any of the preceding paragraphs, wherein the predetermined reference value is about 3.0 mg per liter as measured in a plasma sample.
92. The method of any of the preceding paragraphs, wherein the predetermined reference value is about 3.2 mg per liter as measured in a plasma sample.
93. The method of any of the preceding paragraphs, wherein the step (b) further comprises optionally packing and shipping the test sample to a test facility.
94. The method of paragraph 93, wherein the test facility is a third-party CLIA-certified service provider.
95. The method of any of the preceding paragraphs, wherein the step (d) is performed by a non-human machine.
96. The method of any of the preceding paragraphs, further comprising determining an obesity indicator (e.g., measuring a BMI value) of the subject.
97. The method of any of the preceding paragraphs, wherein at least three of the foregoing biomarker parameters are determined
98. The method of any of the preceding paragraphs, wherein the depression is major depressive disorder.
99. A folate-comprising composition for use in the treatment of depression in a human subject who carries at least one of the following single nucleotide polymorphisms or a combination thereof:
    a. at least one thymine "T" allele at SNP677, wherein the SNP677 is at position 677 of SEQ ID NO. 1 or position 27 of SEQ ID NO. 7 (identified by rs1801133), wherein the SEQ ID NO. 1 and SEQ ID NO. 7 are each independently a portion of a genomic nucleic acid sequence of methylenetetrahydrofolate reductase (MTHFR); and
    b. at least one guanine "G" allele at SNP2756, wherein the SNP2756 is at position 2756 of SEQ ID NO. 2 or position 27 of SEQ ID NO. 9 (identified by rs1805087), wherein the SEQ ID NO. 2 and SEQ ID NO. 9 are each independently a portion of a genomic nucleic acid sequence of methionine synthase (MTR).
100. A folate-comprising composition for use in the treatment of depression in a human subject who carries at least one of the following conditions or any combination thereof:
    a. at least one thymine "T" allele at SNP locus at position 677 of SEQ ID NO. 1 or position 27 of SEQ ID NO. 7 (identified by rs1801133), wherein the SEQ ID NO. 1 and SEQ ID NO. 7 are each independently a portion of a genomic nucleic acid sequence of methylenetetrahydrofolate reductase (MTHFR);
    b. at least one adenine "A" allele at SNP locus at rs2274976 (position 1793 of SEQ ID NO. 1 or position 27 of SEQ ID NO. 8), wherein the SEQ ID NO. 1 and SEQ ID NO. 8 are each independently a portion of a genomic nucleic acid sequence of methylenetetrahydrofolate reductase (MTHFR);
    c. at least one guanine "G" allele at SNP locus at position 2756 of SEQ ID NO. 2 or position 27 of SEQ ID NO. 9 (identified by rs1805087), wherein the SEQ ID NO. 2 and SEQ ID NO. 9 are each independently a portion of a genomic nucleic acid sequence of methionine synthase (MTR);
d. at least one guanine "G" allele at SNP locus at position 66 of SEQ ID NO. 3 or position 27 of SEQ ID NO. 10 (identified by rs1801394), wherein the SEQ ID NO. 3 and SEQ ID NO. 10 are each independently a portion of a genomic nucleic acid sequence of methionine synthase reductase (MTRR);
e. at least one adenine "A" allele at SNP locus at rs1006737 (position 27 of SEQ ID NO. 11, wherein the SEQ ID NO. 11 is a portion of a genomic nucleic acid sequence of calcium channel, voltage-dependent, L type, alpha 1C subunit (CACNA1C));
f. at least one adenine "A" allele at SNP locus at rs1883729 (position 27 of SEQ ID NO. 12, wherein the SEQ ID NO. 12 is a portion of a genomic nucleic acid sequence of DNA (cytosine-5)-methyltransferase 3 beta (DNMT3B));
g. at least one thymine "T" allele at SNP locus at rs7163862 (position 27 of SEQ ID NO. 13, wherein the SEQ ID NO. 13 is a portion of a genomic nucleic acid sequence of GTP cyclohydrolase 1 feedback regulatory protein (GCHFR));
h. at least one thymine "T" allele at SNP locus at rs12659 (position 27 of SEQ ID NO. 14, wherein the SEQ ID NO. 14 is a portion of a genomic nucleic acid sequence of reduced folate carrier protein (RCF2));
i. at least one guanine "G" allele at SNP locus at rs202676 (position 27 of SEQ ID NO. 15, wherein the SEQ ID NO. 15 is a portion of a genomic nucleic acid sequence of folate hydrolase (prostate-specific membrane antigen) 1 (FOLH1));
j. at least one adenine "A" allele at SNP locus at rs2297291 (position 27 of SEQ ID NO. 16, wherein the SEQ ID NO. 16 is a portion of a genomic nucleic acid sequence of reduced folate carrier protein (RCF1));
k. at least one adenine "A" allele at SNP locus at rs1051266 (position 27 of SEQ ID NO. 17), wherein the SEQ ID NO. 17 is a portion of a genomic nucleic acid sequence of reduced folate carrier protein (RCF1);
l. at least one thymine "T" allele at SNP locus at rs8007267 (position 27 of SEQ ID NO. 18, wherein the SEQ ID NO. 18 is a portion of a genomic nucleic acid sequence of GTP cyclohydrolase 1 (GCH1));
m. at least one adenine "A" allele at SNP locus at rs7639752 (position 27 of SEQ ID NO. 19, wherein the SEQ ID NO. 19 is a portion of a genomic nucleic acid sequence of choline-phosphate cytidylyltransferase A (PCYT1A));
n. at least one thymine "T" allele at SNP locus at rs6275 (position 27 of SEQ ID NO. 20, wherein the SEQ ID NO. 20 is a portion of a genomic nucleic acid sequence of dopamine receptor D2 (DRD2));
o. at least one thymine "T" allele at SNP locus at rs1079596 (position 27 of SEQ ID NO. 21), wherein the SEQ ID NO. 21 is a portion of a genomic nucleic acid sequence of dopamine receptor D2 (DRD2);
p. at least one adenine "A" allele at SNP locus at rs11240594 (position 27 of SEQ ID NO. 22), wherein the SEQ ID NO. 22 is a portion of a genomic nucleic acid sequence of dopamine receptor D2 (DRD2);
q. at least one cytosine "C" allele at SNP locus at rs4633 (position 27 of SEQ ID NO. 23, wherein the SEQ ID NO. 23 is a portion of a genomic nucleic acid sequence of catechol-O-methyltransferase (COMT));
r. at least one guanine "G" allele at SNP locus at rs4680 (position 27 of SEQ ID NO. 24), wherein the SEQ ID NO. 24 is a portion of a genomic nucleic acid sequence of catechol-O-methyltransferase (COMT);
s. at least one cytosine "C" allele at SNP locus at rs250682 (position 27 of SEQ ID NO. 25, wherein the SEQ ID NO. 25 is a portion of a genomic nucleic acid sequence of solute carrier family 6 (neurotransmitted transported, dopamine), member 3 (SLC6A3));
t. at least one thymine "T" allele at SNP locus at rs2277820 (position 27 of SEQ ID NO. 26, wherein the SEQ ID NO. 26 is a portion of a genomic nucleic acid sequence of formiminotransferase cyclodeaminase (FTCD)); and
u. at least one adenine "A" allele at SNP locus at rs2236225 (position 27 of SEQ ID NO. 27, wherein the SEQ ID NO. 27 is a portion of a genomic nucleic acid sequence of methylenetetrahydrofolate dehydrogenase (NADP+ dependent) 1 (MTHFD1));
v. obesity (e.g., defined by BMI value of at least 30 kg/m2 or greater);
w. an expression level ratio of SAM to SAH smaller than a pre-determined reference ratio;
x. an expression level of 4-HNE greater than a first pre-determined reference value; and
y. an expression of hsCRP greater than a second pre-determine reference value (e.g., greater than about 2.3 mg per liter of plasma as measured in a plasma sample).

101. A folate-comprising composition in combination with an anti-depressant for use in the treatment of depression in a human subject who carries at least one of the following single nucleotide polymorphisms or a combination thereof:
a. a SNP677 at position 677 of SEQ ID NO. 1 or position 27 of SEQ ID NO. 7 (identified by rs1801133) comprising at least one thymine "T" allele; and
b. a SNP2756 at position 2756 of SEQ ID NO. 2 or position 27 of SEQ ID NO. 9 comprising at least one guanine "G" allele.

102. A folate-comprising composition in combination with an anti-depressant for use in the treatment of depression in a human subject who carries at least one of the following conditions or any combination thereof:
a. at least one thymine "T" allele at SNP locus at position 677 of SEQ ID NO. 1 or position 27 of SEQ ID NO. 7 (identified by rs1801133), wherein the SEQ ID NO. 1 and SEQ ID NO. 7 are each independently a portion of a genomic nucleic acid sequence of methylenetetrahydrofolate reductase (MTHFR);
b. at least one adenine "A" allele at SNP locus at rs2274976 (position 1793 of SEQ ID NO. 1 or position 27 of SEQ ID NO. 8), wherein the SEQ ID NO. 1 and SEQ ID NO. 8 are each independently a portion of a genomic nucleic acid sequence of methylenetetrahydrofolate reductase (MTHFR);
c. at least one guanine "G" allele at SNP locus at position 2756 of SEQ ID NO. 2 or position 27 of SEQ ID NO. 9 (identified by rs1805087), wherein the SEQ ID NO. 2 and SEQ ID NO. 9 are each independently a portion of a genomic nucleic acid sequence of methionine synthase (MTR);

d. at least one guanine "G" allele at SNP locus at position 66 of SEQ ID NO. 3 or position 27 of SEQ ID NO. 10 (identified by rs1801394), wherein the SEQ ID NO. 3 and SEQ ID NO. 10 are each independently a portion of a genomic nucleic acid sequence of methionine synthase reductase (MTRR);

e. at least one adenine "A" allele at SNP locus at rs1006737 (position 27 of SEQ ID NO. 11, wherein the SEQ ID NO. 11 is a portion of a genomic nucleic acid sequence of calcium channel, voltage-dependent, L type, alpha 1C subunit (CACNA1C));

f. at least one adenine "A" allele at SNP locus at rs1883729 (position 27 of SEQ ID NO. 12, wherein the SEQ ID NO. 12 is a portion of a genomic nucleic acid sequence of DNA (cytosine-5)-methyltransferase 3 beta (DNMT3B));

g. at least one thymine "T" allele at SNP locus at rs7163862 (position 27 of SEQ ID NO. 13, wherein the SEQ ID NO. 13 is a portion of a genomic nucleic acid sequence of GTP cyclohydrolase 1 feedback regulatory protein (GCHFR));

h. at least one thymine "T" allele at SNP locus at rs12659 (position 27 of SEQ ID NO. 14, wherein the SEQ ID NO. 14 is a portion of a genomic nucleic acid sequence of reduced folate carrier protein (RCF2));

i. at least one guanine "G" allele at SNP locus at rs202676 (position 27 of SEQ ID NO. 15, wherein the SEQ ID NO. 15 is a portion of a genomic nucleic acid sequence of folate hydrolase (prostate-specific membrane antigen) 1 (FOLH1));

j. at least one adenine "A" allele at SNP locus at rs2297291 (position 27 of SEQ ID NO. 16, wherein the SEQ ID NO. 16 is a portion of a genomic nucleic acid sequence of reduced folate carrier protein (RCF1));

k. at least one adenine "A" allele at SNP locus at rs1051266 (position 27 of SEQ ID NO. 17), wherein the SEQ ID NO. 17 is a portion of a genomic nucleic acid sequence of reduced folate carrier protein (RCF1);

l. at least one thymine "T" allele at SNP locus at rs8007267 (position 27 of SEQ ID NO. 18, wherein the SEQ ID NO. 18 is a portion of a genomic nucleic acid sequence of GTP cyclohydrolase 1 (GCH1));

m. at least one adenine "A" allele at SNP locus at rs7639752 (position 27 of SEQ ID NO. 19, wherein the SEQ ID NO. 19 is a portion of a genomic nucleic acid sequence of choline-phosphate cytidylyltransferase A (PCYT1A));

n. at least one thymine "T" allele at SNP locus at rs6275 (position 27 of SEQ ID NO. 20, wherein the SEQ ID NO. 20 is a portion of a genomic nucleic acid sequence of dopamine receptor D2 (DRD2));

o. at least one thymine "T" allele at SNP locus at rs1079596 (position 27 of SEQ ID NO. 21), wherein the SEQ ID NO. 21 is a portion of a genomic nucleic acid sequence of dopamine receptor D2 (DRD2);

p. at least one adenine "A" allele at SNP locus at rs11240594 (position 27 of SEQ ID NO. 22), wherein the SEQ ID NO. 22 is a portion of a genomic nucleic acid sequence of dopamine receptor D2 (DRD2);

q. at least one cytosine "C" allele at SNP locus at rs4633 (position 27 of SEQ ID NO. 23, wherein the SEQ ID NO. 23 is a portion of a genomic nucleic acid sequence of catechol-O-methyltransferase (COMT));

r. at least one guanine "G" allele at SNP locus at rs4680 (position 27 of SEQ ID NO. 24), wherein the SEQ ID NO. 24 is a portion of a genomic nucleic acid sequence of catechol-O-methyltransferase (COMT);

s. at least one cytosine "C" allele at SNP locus at rs250682 (position 27 of SEQ ID NO. 25, wherein the SEQ ID NO. 25 is a portion of a genomic nucleic acid sequence of solute carrier family 6 (neurotransmitted transported, dopamine), member 3 (SLC6A3));

t. at least one thymine "T" allele at SNP locus at rs2277820 (position 27 of SEQ ID NO. 26, wherein the SEQ ID NO. 26 is a portion of a genomic nucleic acid sequence of formiminotransferase cyclodeaminase (FTCD)); and u. at least one adenine "A" allele at SNP locus at rs2236225 (position 27 of SEQ ID NO. 27, wherein the SEQ ID NO. 27 is a portion of a genomic nucleic acid sequence of methylenetetrahydrofolate dehydrogenase (NADP+ dependent) 1 (MTHFD1));

v. obesity (e.g., defined by BMI value of at least 30 $kg/m^2$ or greater);

w. an expression level ratio of SAM to SAH smaller than a pre-determined reference ratio;

x. an expression level of 4-HNE greater than a first pre-determined reference value; and y. an expression of hsCRP greater than a second pre-determined reference value (e.g., greater than about 2.3 mg per liter of plasma as measured in a plasma sample).

103. The composition of any one of the preceding paragraphs, wherein the folate-comprising composition comprises at least about 5 mg of folate.

104. The composition of any one of the preceding paragraphs, wherein the folate-comprising composition comprises about 7.5-50 mg of folate.

105. The composition of any one of the preceding paragraphs, wherein the folate-comprising composition further comprises a pre-determined release profile.

106. The composition of paragraph 105, wherein the pre-determined release profile comprises a sustained release profile.

107. The composition of paragraph 106, wherein the sustained release is a steady-state release.

108. The composition of paragraph 105, wherein the pre-determined release profile comprises a pulsatile release profile.

109. The composition of paragraph 105, wherein the pre-determined release profile comprises a chrono-controlled release profile.

110. The composition of any of paragraphs 105-109, wherein the folate-comprising composition is formulated to release at least 30% of the folate-containing compound over a period of at least about 3-6 hours, upon the administration of the composition.

111. The composition of any of the preceding paragraphs, wherein the depression is a major depressive disorder.

112. A method for treating at least one symptom of depression in a human subject, comprising administering a composition comprising an effective amount of a folate-comprising compound to a human subject, who is diagnosed to have depression or have a risk for depression, and is further determined to carry a combination of at least two of the following biomarkers:
i. a SNP at position 677 of SEQ ID NO. 1 or position 27 of SEQ ID NO. 7 (identified by rs1801133) comprising at least one thymine "T" allele or the complement thereof, wherein the SEQ ID NO. 1 and SEQ ID NO. 7 are each independently a portion of a genomic nucleic acid sequence of methylenetetrahydrofolate reductase (MTHFR);
ii. a SNP at position 2756 of SEQ ID NO. 2 or position 27 of SEQ ID NO. 9 (identified by rs1805087) comprising at least one guanine "G" allele or the complement thereof, wherein the SEQ ID NO. 2 and SEQ ID NO. 9 are each independently a portion of a genomic nucleic acid sequence of methionine synthase (MTR),
iii. a SNP at position 1793 of SEQ ID NO. 1 or position 27 of SEQ ID NO. 8 (identified by rs2274976) comprising at least one adenine "A" allele or the complement thereof, wherein the SEQ ID NO. 1 and SEQ ID NO. 8 are each independently a portion of a genomic nucleic acid sequence of methylenetetrahydrofolate reductase (MTHFR);
iv. a SNP at position 66 of SEQ ID NO. 3 or position 27 of SEQ ID NO. 10 (identified by rs1801394) comprising at least one guanine "G" allele or the complement thereof, wherein the SEQ ID NO. 3 and SEQ ID NO. 10 are each independently a portion of a genomic nucleic acid sequence of methionine synthase reductase (MTRR);
v. a SNP at position 27 of SEQ ID NO. 11 (identified by rs1006737) comprising at least one adenine "A" allele or the complement thereof, wherein the SEQ ID NO. 11 is a portion of a genomic nucleic acid sequence of calcium channel, voltage-dependent, L type, alpha 1C subunit (CACNA1C);
vi. a SNP at position 27 of SEQ ID NO. 12 (identified by rs1883729) comprising at least one adenine "A" allele or the complement thereof, wherein the SEQ ID NO. 12 is a portion of a genomic nucleic acid sequence of DNA (cytosine-5)-methyltransferase 3 beta (DNMT3B);
vii. a SNP at position 27 of SEQ ID NO. 13 (identified by rs7163862) comprising at least one thymine "T" allele or the complement thereof, wherein the SEQ ID NO. 13 is a portion of a genomic nucleic acid sequence of GTP cyclohydrolase 1 feedback regulatory protein (GCHFR);
viii. a SNP at position 27 of SEQ ID NO. 14 (identified by rs12659) comprising two thymine "T" allele or the complement thereof, wherein the SEQ ID NO. 14 is a portion of a genomic nucleic acid sequence of reduced folate carrier protein (RCF2);
ix. a SNP at position 27 of SEQ ID NO. 15 (identified by rs202676) comprising at least one guanine "G" allele or the complement thereof, wherein the SEQ ID NO. 15 is a portion of a genomic nucleic acid sequence of folate hydrolase (prostate-specific membrane antigen) 1 (FOLH1);
x. a SNP at position 27 of SEQ ID NO. 16 (identified by rs2297291) comprising two adenine "A" alleles or the complement thereof, wherein the SEQ ID NO. 16 is a portion of a genomic nucleic acid sequence of reduced folate carrier protein (RCF1);
xi. a SNP at position 27 of SEQ ID NO. 17 (identified by rs1051266) comprising two adenine "A" alleles or the complement thereof, wherein the SEQ ID NO. 17 is a portion of a genomic nucleic acid sequence of reduced folate carrier protein (RCF1);
xii. a SNP at position 27 of SEQ ID NO. 18 (identified by rs8007267) comprising at least one thymine "T" allele or the complement thereof, wherein the SEQ ID NO. 18 is a portion of a genomic nucleic acid sequence of GTP cyclohydrolase 1 (GCH1);
xiii. a SNP at position 27 of SEQ ID NO. 19 (identified by rs7639752) comprising at least one adenine "A" allele or the complement thereof, wherein the SEQ ID NO. 19 is a portion of a genomic nucleic acid sequence of choline-phosphate cytidylyltransferase A (PCYT1A);
xiv. a SNP at position 27 of SEQ ID NO. 20 (identified by rs6275) comprising two thymine "T" alleles or the complement thereof, wherein the SEQ ID NO. 20 is a portion of a genomic nucleic acid sequence of dopamine receptor D2 (DRD2);
xv. a SNP at position 27 of SEQ ID NO. 21 (identified by rs1079596) comprising at least one thymine "T" allele or the complement thereof, wherein the SEQ ID NO. 21 is a portion of a genomic nucleic acid sequence of dopamine receptor D2 (DRD2);
xvi. a SNP at position 27 of SEQ ID NO. 22 (identified by rs11240594) comprising at least one adenine "A" allele or the complement thereof, wherein the SEQ ID NO. 22 is a portion of a genomic nucleic acid sequence of dopamine receptor D2 (DRD2);
xvii. a SNP at position 27 of SEQ ID NO. 23 (identified by rs4633) comprising two cytosine "C" alleles or the complement thereof, wherein the SEQ ID NO. 23 is a portion of a genomic nucleic acid sequence of catechol-O-methyltransferase (COMT);
xviii. a SNP at position 27 of SEQ ID NO. 24 (identified by rs4680) comprising two guanine "G" alleles or the complement thereof, wherein the SEQ ID NO. 24 is a portion of a genomic nucleic acid sequence of catechol-O-methyltransferase (COMT);
xix. a SNP at position 27 of SEQ ID NO. 25 (identified by rs250682) comprising at least one cytosine "C" allele or the complement thereof, wherein the SEQ ID NO. 25 is a portion of a genomic nucleic acid sequence of solute carrier family 6 (neurotransmitter transported, dopamine), member 3 (SLC6A3);
xx. a SNP at position 27 of SEQ ID NO. 26 (identified by rs2277820) comprising at least one thymine "T" allele or the complement thereof, wherein the SEQ ID NO. 26 is a portion of a genomic nucleic acid sequence of formiminotransferase cyclodeaminase (FTCD);
xxi. a SNP at position 27 of SEQ ID NO. 27 (identified by rs2236225) comprising at least one adenine "A" allele or the complement thereof, wherein the SEQ ID NO. 27 is a portion of a genomic nucleic acid sequence of methylenetetrahydrofolate dehydrogenase (NADP+ dependent) 1 (MTHFD1);
xxii. obesity;
xxiii. an expression ratio of SAM to SAH smaller than a pre-determined reference ratio;
xxiv. an expression of 4-HNE greater than a first pre-determined reference value; and
xxv. an expression of hsCRP greater than a second pre-determined reference value, based on the recognition that the combination of said at least two of the biomarkers is associated with positive-symptom-reducing response to the folate-comprising compound.

113. The method of paragraph 112, wherein the combination of said at least two biomarkers comprises the following:
   i. a SNP at position 677 of SEQ ID NO. 1 or position 27 of SEQ ID NO. 7 (identified by rs1801133) comprising at least one thymine "T" allele or the complement thereof, wherein the SEQ ID NO. 1 and SEQ ID NO. 7 are each independently a portion of a genomic nucleic acid sequence of methylenetetrahydrofolate reductase (MTHFR); and
   ii. a SNP at position 2756 of SEQ ID NO. 2 or position 27 of SEQ ID NO. 9 (identified by rs1805087) comprising at least one guanine "G" allele or the complement thereof, wherein the SEQ ID NO. 2 and SEQ ID NO. 9 are each independently a portion of a genomic nucleic acid sequence of methionine synthase (MTR).
114. The method of paragraph 112 or 113, wherein the combination of said at least two biomarkers further comprises at least one of the biomarkers (iii)-(xxv).
115. The method of any of paragraphs 112-114, wherein the obesity is characterized by at least one of the following obesity indicators:
   a. a BMI value greater than 30 kg/m$^2$;
   b. a waist circumference greater than 40 inches (or greater than 120 cm) in men, or greater than 35 inches (or greater than 88 cm) in women;
   c. a waist-hip ratio above 0.95 for men or above 0.80 for women; and
   d. a body fat percentage of at least about 25% in men or at least about 32% in women.
116. The method of any of paragraphs 112-115, further comprising assaying a biological sample obtained from the subject for determination of the presence of said at least two biomarkers.
117. The method of paragraph 116, wherein the biological sample comprises a sample selected from a blood sample, a urine sample, a buccal sample, a saliva sample or a cerebrospinal fluid sample.
118. The method of paragraph 116 or 117, wherein the assaying comprises amplifying the biological sample with at least one set of primers flanking any one of the SNPs.
119. The method of paragraph 118, wherein at least two sets of primers amplifying at least two of the SNPs are used in a multiplex amplification assay.
120. The method of any of paragraphs 116-119, wherein the assaying comprises separating and/or detecting the presence of SAM, SAH, 4-HNE, hsCRP or any combinations thereof in the biological sample with gas chromatography, mass spectrometry, high performance liquid chromatography, nuclear magnetic resonance (NMR) spectroscopy, an enzyme-coupled-assay, or any combinations thereof
121. The method of any of paragraphs 112-120, wherein the pre-determined reference ratio of SAM/SAH is a control ratio of SAM/SAH as measured in a biological sample of normal healthy subjects.
122. The method of paragraph 121, wherein the control ratio of SAM/SAM as measured in a serum sample of the normal healthy subjects ranges from about 4 to about 12.
123. The method of any of paragraphs 112-120, wherein the pre-determined reference ratio of SAM/SAM is about 3.0 as measured in a plasma sample.
124. The method of any of paragraphs 112-123, wherein the first pre-determined reference value of 4-HNE is a control value of 4-HNE as measured in a biological sample of normal healthy subjects.
125. The method of paragraph 124, wherein the control value of 4-HNE as measured in a serum sample of the normal healthy subjects is about 0.24 µmol per liter of serum (or about 0.04 mg per liter of serum).
126. The method of any of paragraphs 112-123, wherein the first pre-determined reference value of 4-HNE is about 3 mg per liter of plasma as measured in a plasma sample.
127. The method of any of paragraphs 112-126, wherein the second pre-determined reference value of hsCRP is a control value of hsCRP as measured in a biological sample of normal healthy subjects.
128. The method of paragraph 127, wherein the control value of hsCRP as measured in a serum sample of the normal healthy subjects ranges from about 0.5 mg per liter of serum to about 4.5 mg per liter of serum.
129. The method of any of paragraphs 112-126, wherein the second pre-determined reference value of hsCRP is about 2.3 mg per liter of plasma as measured in a plasma sample.
130. The method of any of paragraphs 112-129, further comprising determining a body measurement of the subject.
131. The method of paragraph 130, wherein the body measurement comprises weight, height, waist circumference, hip circumference, body fat percentage, or any combinations thereof
132. The method of any of paragraphs 112-131, wherein the effective amount of the folate-comprising compound is about 7.5 mg/day to about 50 mg/day.
133. The method of any of paragraphs 112-132, wherein the effective amount of the folate-comprising compound is administered as a single daily dose.
134. The method of any of paragraphs 112-132, wherein the effective amount of the folate-comprising compound is administered in more than one divided doses per day.
135. The method of any of paragraphs 112-134, wherein the administration is oral.
136. The method of any of paragraphs 112-135, wherein the composition is formulated to release at least a portion of the folate-comprising compound over a period of at least about 3-6 hours, upon the administration of the composition.
137. The method of paragraph 136, wherein the release is a steady-state release.
138. The method of any of paragraphs 112-137, further comprising administering to the subject an anti-depressant drug.
139. The method of paragraph 138, wherein the administration of the anti-depressant drug in combination with the folate-comprising compound increases the effectiveness of the anti-depressant drug.
140. The method of paragraph 138 or 139, wherein the anti-depressant drug comprises a selective serotonin reuptake inhibitor.
141. The method of paragraph 140, wherein the selective serotonin reuptake inhibitor is selected from the group consisting of fluoxetine, citalopram, paroxetine, escitalopram, sertraline, and any combinations thereof
142. The method of any of paragraphs 112-141, further comprising selecting for the subject a treatment comprising the folate-comprising compound, optionally administered in combination with the anti-depressant drug.

143. The method of any of paragraphs 112-142, wherein the depression is major depressive disorder.
144. The method of any of paragraphs 112-143, wherein the subject who is diagnosed as having depression is resistant to at least one antidepressant monotherapy.
145. The method of any of paragraphs 112-144, wherein the subject is an adult subject.
146. The method of any of paragraphs 112-145, wherein the at least one symptom of depression is selected from low or depressed mood, anhedonia, low energy levels, guilt, decreased work and interests, psychomotor retardation, agitation, psychic anxiety, somatic anxiety, general somatic symptoms, reduced cognition or any combinations thereof
147. A method of improving the effectiveness of an anti-depressant drug administered to a human subject, comprising administering a composition comprising an effective amount of a folate-comprising compound, in combination with the anti-depressant drug, to the human subject who is diagnosed to have depression and is further determined to carry a combination of at least two of the following biomarkers:
    i. a SNP at position 677 of SEQ ID NO. 1 or position 27 of SEQ ID NO. 7 (identified by rs1801133) comprising at least one thymine "T" allele or the complement thereof, wherein the SEQ ID NO. 1 and SEQ ID NO. 7 are each independently a portion of a genomic nucleic acid sequence of methylenetetrahydrofolate reductase (MTHFR);
    ii. a SNP at position 2756 of SEQ ID NO. 2 or position 27 of SEQ ID NO. 9 (identified by rs1805087) comprising at least one guanine "G" allele or the complement thereof, wherein the SEQ ID NO. 2 and SEQ ID NO. 9 are each independently a portion of a genomic nucleic acid sequence of methionine synthase (MTR),
    iii. a SNP at position 1793 of SEQ ID NO. 1 or position 27 of SEQ ID NO. 8 (identified by rs2274976) comprising at least one adenine "A" allele or the complement thereof, wherein the SEQ ID NO. 1 and SEQ ID NO. 8 are each independently a portion of a genomic nucleic acid sequence of methylenetetrahydrofolate reductase (MTHFR);
    iv. a SNP at position 66 of SEQ ID NO. 3 or position 27 of SEQ ID NO. 10 (identified by rs1801394) comprising at least one guanine "G" allele or the complement thereof, wherein the SEQ ID NO. 3 and SEQ ID NO. 10 are each independently a portion of a genomic nucleic acid sequence of methionine synthase reductase (MTRR);
    v. a SNP at position 27 of SEQ ID NO. 11 (identified by rs1006737) comprising at least one adenine "A" allele or the complement thereof, wherein the SEQ ID NO. 11 is a portion of a genomic nucleic acid sequence of calcium channel, voltage-dependent, L type, alpha 1C subunit (CACNA1C);
    vi. a SNP at position 27 of SEQ ID NO. 12 (identified by rs1883729) comprising at least one adenine "A" allele or the complement thereof, wherein the SEQ ID NO. 12 is a portion of a genomic nucleic acid sequence of DNA (cytosine-5)-methyltransferase 3 beta (DNMT3B);
    vii. a SNP at position 27 of SEQ ID NO. 13 (identified by rs7163862) comprising at least one thymine "T" allele or the complement thereof, wherein the SEQ ID NO. 13 is a portion of a genomic nucleic acid sequence of GTP cyclohydrolase 1 feedback regulatory protein (GCHFR);
    viii. a SNP at position 27 of SEQ ID NO. 14 (identified by rs12659) comprising two thymine "T" allele or the complement thereof, wherein the SEQ ID NO. 14 is a portion of a genomic nucleic acid sequence of reduced folate carrier protein (RCF2);
    ix. a SNP at position 27 of SEQ ID NO. 15 (identified by rs202676) comprising at least one guanine "G" allele or the complement thereof, wherein the SEQ ID NO. 15 is a portion of a genomic nucleic acid sequence of folate hydrolase (prostate-specific membrane antigen) 1 (FOLH1);
    x. a SNP at position 27 of SEQ ID NO. 16 (identified by rs2297291) comprising two adenine "A" alleles or the complement thereof, wherein the SEQ ID NO. 16 is a portion of a genomic nucleic acid sequence of reduced folate carrier protein (RCF1);
    xi. a SNP at position 27 of SEQ ID NO. 17 (identified by rs1051266) comprising two adenine "A" alleles or the complement thereof, wherein the SEQ ID NO. 17 is a portion of a genomic nucleic acid sequence of reduced folate carrier protein (RCF1);
    xii. a SNP at position 27 of SEQ ID NO. 18 (identified by rs8007267) comprising at least one thymine "T" allele or the complement thereof, wherein the SEQ ID NO. 18 is a portion of a genomic nucleic acid sequence of GTP cyclohydrolase 1 (GCH1);
    xiii. a SNP at position 27 of SEQ ID NO. 19 (identified by rs7639752) comprising at least one adenine "A" allele or the complement thereof, wherein the SEQ ID NO. 19 is a portion of a genomic nucleic acid sequence of choline-phosphate cytidylyltransferase A (PCYT1A);
    xiv. a SNP at position 27 of SEQ ID NO. 20 (identified by rs6275) comprising two thymine "T" alleles or the complement thereof, wherein the SEQ ID NO. 20 is a portion of a genomic nucleic acid sequence of dopamine receptor D2 (DRD2);
    xv. a SNP at position 27 of SEQ ID NO. 21 (identified by rs1079596) comprising at least one thymine "T" allele or the complement thereof, wherein the SEQ ID NO. 21 is a portion of a genomic nucleic acid sequence of dopamine receptor D2 (DRD2);
    xvi. a SNP at position 27 of SEQ ID NO. 22 (identified by rs11240594) comprising at least one adenine "A" allele or the complement thereof, wherein the SEQ ID NO. 22 is a portion of a genomic nucleic acid sequence of dopamine receptor D2 (DRD2);
    xvii. a SNP at position 27 of SEQ ID NO. 23 (identified by rs4633) comprising two cytosine "C" alleles or the complement thereof, wherein the SEQ ID NO. 23 is a portion of a genomic nucleic acid sequence of catechol-O-methyltransferase (COMT);
    xviii. a SNP at position 27 of SEQ ID NO. 24 (identified by rs4680) comprising two guanine "G" alleles or the complement thereof, wherein the SEQ ID NO. 24 is a portion of a genomic nucleic acid sequence of catechol-O-methyltransferase (COMT);
    xix. a SNP at position 27 of SEQ ID NO. 25 (identified by rs250682) comprising at least one cytosine "C" allele or the complement thereof, wherein the SEQ ID NO. 25 is a portion of a genomic nucleic acid sequence of solute carrier family 6 (neurotransmitted transported, dopamine), member 3 (SLC6A3);

xx. a SNP at position 27 of SEQ ID NO. 26 (identified by rs2277820) comprising at least one thymine "T" allele or the complement thereof, wherein the SEQ ID NO. 26 is a portion of a genomic nucleic acid sequence of formiminotransferase cyclodeaminase (FTCD);

xxi. a SNP at position 27 of SEQ ID NO. 27 (identified by rs2236225) comprising at least one adenine "A" allele or the complement thereof, wherein the SEQ ID NO. 27 is a portion of a genomic nucleic acid sequence of methylenetetrahydrofolate dehydrogenase (NADP+ dependent) 1 (MTHFD1);

xxii. obesity;

xxiii. an expression ratio of SAM to SAH smaller than a pre-determined reference ratio;

xxiv. an expression of 4-HNE greater than a first pre-determined reference value; and xxv. an expression of hsCRP greater than a second pre-determined reference value, based on the recognition that the combination of said at least two of the biomarkers is associated with increasing the effectiveness of the anti-depressant drug when administered in combination with the folate-comprising compound.

148. The method of paragraph 147, wherein the combination of said at least two biomarkers comprises the following:

i. a SNP at position 677 of SEQ ID NO. 1 or position 27 of SEQ ID NO. 7 (identified by rs1801133) comprising at least one thymine "T" allele or the complement thereof, wherein the SEQ ID NO. 1 and SEQ ID NO. 7 are each independently a portion of a genomic nucleic acid sequence of methylenetetrahydrofolate reductase (MTHFR); and ii. a SNP at position 2756 of SEQ ID NO. 2 or position 27 of SEQ ID NO. 9 (identified by rs1805087) comprising at least one guanine "G" allele or the complement thereof, wherein the SEQ ID NO. 2 and SEQ ID NO. 9 are each independently a portion of a genomic nucleic acid sequence of methionine synthase (MTR).

149. The method of paragraph 147 or 148, wherein the combination of said at least two biomarkers further comprises at least one of the biomarkers (iii)-(xxv).

150. The method of any of paragraphs 147-149, wherein the obesity is characterized by at least one of the following obesity indicators:

a. a BMI value greater than 30 kg/m$^2$;

b. a waist circumference greater than 40 inches (or greater than 120 cm) in men, or greater than 35 inches (or greater than 88 cm) in women;

c. a waist-hip ratio above 0.95 for men or above 0.80 for women; and d. a body fat percentage of at least about 25% in men or at least about 32% in women.

151. The method of any of paragraphs 147-150, further comprising assaying a biological sample obtained from the subject for determination of the presence of said at least two biomarkers.

152. The method of paragraph 151, wherein the biological sample comprises a sample selected from a blood sample, a urine sample, a buccal sample, a saliva sample or a cerebrospinal fluid sample.

153. The method of paragraph 151 or 152, wherein the assaying comprises amplifying the biological sample with at least one set of primers flanking any one of the SNPs.

154. The method of paragraph 153, wherein at least two sets of primers amplifying at least two of the SNPs are used in a multiplex amplification assay.

155. The method of any of paragraphs 151-154, wherein the assaying comprises separating and/or detecting the presence of SAM, SAH, 4-HNE, hsCRP or any combinations thereof in the biological sample with gas chromatography, mass spectrometry, high performance liquid chromatography, nuclear magnetic resonance (NMR) spectroscopy, an enzyme-coupled-assay, or any combinations thereof 156. The method of any of paragraphs 147-155, wherein the pre-determined reference ratio of SAM/SAH is a control ratio of SAM/SAH as measured in a biological sample of normal healthy subjects.

157. The method of paragraph 156, wherein the control ratio of SAM/SAH as measured in a serum sample of the normal healthy subjects ranges from about 4 to about 12.

158. The method of any of paragraphs 147-155, wherein the pre-determined reference ratio of SAM/SAH is about 3.0 as measured in a plasma sample.

159. The method of any of paragraphs 147-58, wherein the first pre-determined reference value of 4-HNE is a control value of 4-HNE as measured in a biological sample of normal healthy subjects.

160. The method of paragraph 159, wherein the control value of 4-HNE as measured in a serum sample of the normal healthy subjects is about 0.24 μmol per liter of serum (or about 0.04 mg per liter of serum).

161. The method of any of paragraphs 147-158, wherein the first pre-determined reference value of 4-HNE is about 3 mg per liter of plasma as measured in a plasma sample.

162. The method of any of paragraphs 147-161, wherein the second pre-determined reference value of hsCRP is a control value of hsCRP as measured in a biological sample of normal healthy subjects.

163. The method of paragraph 162, wherein the control value of hsCRP as measured in a serum sample of the normal healthy subjects ranges from about 0.5 mg per liter of serum to about 4.5 mg per liter of serum.

164. The method of any of paragraphs 147-162, wherein the second pre-determined reference value of hsCRP is about 2.3 mg per liter of plasma as measured in a plasma sample.

165. The method of any of paragraphs 147-164, further comprising determining a body measurement of the subject.

166. The method of paragraph 165, wherein the body measurement comprises weight, height, waist circumference, hip circumference, body fat percentage, or any combinations thereof 167. The method of any of paragraphs 147-166, wherein the effective amount of the folate-comprising compound is about 7.5 mg/day to about 50 mg/day.

168. The method of any of paragraphs 147-167, wherein the effective amount of the folate-comprising compound is administered as a single daily dose.

169. The method of any of paragraphs 147-167, wherein the effective amount of the folate-comprising compound is administered in more than one divided doses per day.

170. The method of any of paragraphs 147-169, wherein the administration is oral.

171. The method of any of paragraphs 147-170, wherein the composition is formulated to release at least a portion of the folate-comprising compound over a period of at least about 3-6 hours, upon the administration of the composition.
172. The method of paragraph 171, wherein the release is a steady-state release.
173. The method of any of paragraphs 147-172, wherein the anti-depressant drug comprises a selective serotonin reuptake inhibitor.
174. The method of paragraph 173, wherein the selective serotonin reuptake inhibitor is selected from the group consisting of fluoxetine, citalopram, paroxetine, escitalopram, sertraline, and any combinations thereof
175. The method of any of paragraphs 147-174, further comprising selecting for the subject a treatment comprising the folate-comprising compound administered in combination with the anti-depressant drug.
176. The method of any of paragraphs 147-175, wherein the depression is major depressive disorder.
177. The method of any of paragraphs 147-176, wherein the subject who is diagnosed as having depression is resistant to at least one antidepressant monotherapy.
178. The method of any of paragraphs 147-177, wherein the subject is an adult subject.
179. The method of any of paragraphs 147-178, wherein the method of improving the effectiveness of an anti-depressant drug administered to a human subject results in improvement of at least one symptom of depression selected from low or depressed mood, anhedonia, low energy levels, guilt, decreased work and interests, psychomotor retardation, agitation, psychic anxiety, somatic anxiety, general somatic symptoms, reduced cognition or any combinations thereof
180. A method of treating at least one symptom of depression in a subject comprising administering a composition comprising an effective amount of a folate-comprising compound to a subject, who is diagnosed to have, or have a risk for depression, and is further determined to carry a SNP at position 2756 of SEQ ID NO. 2 or position 27 of SEQ ID NO. 9 (identified by rs1805087) comprising at least one guanine "G" allele or the complement thereof, wherein the SEQ ID NO. 2 and SEQ ID NO. 9 are each independently a portion of a genomic nucleic acid sequence of methionine synthase (MTR), based on the recognition that the presence of the SNP allele(s) is associated with positive-symptom-reducing response to the folate-comprising compound.
181. The method of paragraph 180, wherein the subject is further determined to carry a SNP at position 677 of SEQ ID NO. 1 or position 27 of SEQ ID NO. 7 (identified by rs1801133) comprising at least one thymine "T" allele or the complement thereof, wherein the SEQ ID NO. 1 and SEQ ID NO. 7 are each independently a portion of a genomic nucleic acid sequence of methylenetetrahydrofolate reductase (MTHFR).
182. A method of treating at least one symptom of depression in a subject comprising administering a composition comprising an effective amount of a folate-comprising compound to a subject, who is diagnosed to have, or have a risk for depression, and is further determined to carry a SNP at position 27 of SEQ ID NO. 23 (identified by rs4633) comprising two cytosine "C" alleles or the complement thereof, wherein the SEQ ID NO. 23 is a portion of a genomic nucleic acid sequence of catechol-O-methyltransferase (COMT), based on the recognition that the presence of the SNP allele(s) is associated with positive-symptom-reducing response to the folate-comprising compound.
183. A method of treating at least one symptom of depression in a subject comprising administering a composition comprising an effective amount of a folate-comprising compound to a subject, who is diagnosed to have, or have a risk for depression, and is further determined to carry a SNP at position 27 of SEQ ID NO. 24 (identified by rs4680) comprising two guanine "G" alleles or the complement thereof, wherein the SEQ ID NO. 24 is a portion of a genomic nucleic acid sequence of catechol-O-methyltransferase (COMT), based on the recognition that the presence of the SNP allele(s) is associated with positive-symptom-reducing response to the folate-comprising compound.
184. A method of improving the effectiveness of an anti-depressant drug administered to a human subject, comprising administering a composition comprising an effective amount of a folate-comprising compound, in combination with the anti-depressant drug, to the human subject who is diagnosed to have depression or have a risk for depression, and is further determined to carry a SNP at position 2756 of SEQ ID NO. 2 or position 27 of SEQ ID NO. 9 (identified by rs1805087) comprising at least one guanine "G" allele or the complement thereof, wherein the SEQ ID NO. 2 and SEQ ID NO. 9 are each independently a portion of a genomic nucleic acid sequence of methionine synthase (MTR), based on the recognition that the presence of the SNP is associated with increasing the effectiveness of the anti-depressant drug when administered in combination with the folate-comprising compound.
185. The method of paragraph 184, wherein the subject is further determined to carry a SNP at position 677 of SEQ ID NO. 1 or position 27 of SEQ ID NO. 7 (identified by rs1801133) comprising at least one thymine "T" allele or the complement thereof, wherein the SEQ ID NO. 1 and SEQ ID NO. 7 are each independently a portion of a genomic nucleic acid sequence of methylenetetrahydrofolate reductase (MTHFR).
186. A method of improving the effectiveness of an anti-depressant drug administered to a human subject, comprising administering a composition comprising an effective amount of a folate-comprising compound, in combination with the anti-depressant drug, to the human subject who is diagnosed to have depression or have a risk for depression, and is further determined to carry a SNP at position 27 of SEQ ID NO. 23 (identified by rs4633) comprising two cytosine "C" alleles or the complement thereof, wherein the SEQ ID NO. 23 is a portion of a genomic nucleic acid sequence of catechol-β-methyltransferase (COMT), based on the recognition that the presence of the SNP is associated with increasing the effectiveness of the anti-depressant drug when administered in combination with the folate-comprising compound.
187. A method of improving the effectiveness of an anti-depressant drug administered to a human subject, comprising administering a composition comprising an effective amount of a folate-comprising compound, in combination with the anti-depressant drug, to the human subject who is diagnosed to have depression or have a risk for depression, and is further determined to carry a SNP at position 27 of SEQ ID NO. 24 (identified by rs4680) comprising two guanine "G" alleles or the complement thereof, wherein the SEQ ID NO. 24 is a portion of a genomic nucleic acid sequence of catechol-β-methyltransferase (COMT), based on the recognition that the presence of the SNP is associated with increasing the effectiveness of the anti-depressant drug when administered in combination with the folate-comprising compound.

188. A method for selecting a treatment regimen for a subject diagnosed with depression comprising:
assaying a test sample from the subject for the presence of one of the following SNPs:
(a) a SNP at position 2756 of SEQ ID NO. 2 or position 27 of SEQ ID NO. 9 (identified by rs1805087) comprising at least one guanine "G" allele or the complement thereof, wherein the SEQ ID NO. 2 and SEQ ID NO. 9 are each independently a portion of a genomic nucleic acid sequence of methionine synthase (MTR);
(b) a SNP at position 27 of SEQ ID NO. 23 (identified by rs4633) comprising two cytosine "C" alleles or the complement thereof, wherein the SEQ ID NO. 23 is a portion of a genomic nucleic acid sequence of catechol-O-methyltransferase (COMT); or
(c) a SNP at position 27 of SEQ ID NO. 24 (identified by rs4680) comprising two guanine "G" alleles or the complement thereof, wherein the SEQ ID NO. 24 is a portion of a genomic nucleic acid sequence of catechol-O-methyltransferase (COMT); and
optionally administering to the subject a folate-comprising compound (optionally in combination with an antidepressant drug), when the subject is determined to carry one of the MTR, COMT (rs4633) and COMT (rs4680) SNP biomarkers.

Some Selected Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one aspect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The term "adjuvant" as used herein generally refers to any agent or entity which increases the effect of another agent or entity. In certain embodiments, the term "adjuvant" is used herein in reference to a folate-containing compound as an adjuvant to increase or enhance the effect (e.g., efficacy and/or therapeutic effect) of an antidepressant drug.

As used herein, the term "polyglutamates" refers to folates that have at least two or more glutamate groups.

The term "normal healthy subject" refers to a subject who has no symptoms of any diseases or disorders, or who is not identified with any diseases or disorders, or who is not on any medication treatment, or a subject who is identified as healthy by physicians based on medical examinations.

The term "derivative" as used herein refers to a chemical substance related structurally to another, i.e., an "original" substance, which can be referred to as a "parent" compound. A "derivative" can be made from the structurally-related parent compound in one or more steps. In some embodiments, the general physical and chemical properties of a derivative can be similar to or different from the parent compound.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane polarized light in different directions). Enantiomers generally have identical physical properties, such as melting points and boiling points, and also have identical spectroscopic properties. Enantiomers can differ from each other with respect to their interaction with plane polarized light and with respect to biological activity.

The designations "R" and "S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses. The designations or prefixes "(+) and (−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture" refers to a mixture of the two enantiomers of one compound, in any ratio. An ideal racemic mixture is one wherein there is a 50:50 mixture of both enantiomers of a compound such that the optical rotation of the (+) enantiomer cancels out the optical rotation of the (−) enantiomer.

The term "nucleic acid" is well known in the art. A "nucleic acid" as used herein will generally refer to a molecule (i.e., strand) of DNA, RNA or a derivative or analog thereof, comprising a nucleobase. A nucleobase includes, for example, a naturally occurring purine or pyrimidine base found in DNA (e.g. an adenine "A," a guanine "G" a thymine "T" or a cytosine "C") or RNA (e.g. an A, a G. an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

The term "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length.

The term "oligonucleotide," as used herein refers to primers and probes described herein, and is defined as a nucleic acid molecule comprised of at least two or more ribo- or deoxyribonucleotides. The exact size of the oligonucleotide will depend on various factors and on the particular application and use of the oligonucleotide. The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and the method used. For example, for diagnostic applications, depending on the complexity of the target sequence, an oligonucleotide probe typically contains 15-25 or more nucleotides, although it may contain fewer nucleotides. The probes as disclosed herein are selected to be substantially complementary to different strands of a particular target nucleic acid sequence. This means that the probes must be sufficiently complementary so as to be able to "specifically hybridize" or anneal with their respective target strands. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarily with the sequence of the target nucleic acid to anneal therewith specifically.

In the context of some embodiments of various aspects described herein, the term "probe" refers to a molecule which can detectably distinguish between target molecules differing in structure (e.g. nucleic acid or protein sequence). Detection can be accomplished in a variety of different ways depending on the type of probe used and the type of target molecule. Thus, for example, detection may be based on discrimination on detection of specific binding. Examples of such specific binding include antibody binding and nucleic acid, antibody binding to protein, nucleic acid binding to nucleic acid, or aptamer binding to protein or nucleic acid. Thus, for example, probes can include enzyme substrates, antibodies and antibody fragments, and preferably nucleic acid hybridization probes.

The term "specifically hybridize" refers to the association between two single-stranded nucleic acid molecules of sufficient complementary sequence to permit such hybridization under pre-determined conditions generally used in the art (sometimes the sequences are referred to as "substantially complementary"). In particular, the term specifically hybridize also refers to hybridization of an oligonucleotide with a substantially complementary sequence as compared to non-complementary sequence.

The term "specifically" as used herein with reference to a probe which is used to specifically detect a sequence difference, refers to a probe that identifies a particular sequence difference based on exclusive hybridization to the sequence difference under stringent hybridization conditions and/or on exclusive amplification or replication of the sequence difference.

In its broadest sense, the term "substantially" as used herein in respect to "substantially complementary", or when used herein with respect to a nucleotide sequence in relation to a reference or target nucleotide sequence, means a nucleotide sequence having a percentage of identity between the substantially complementary nucleotide sequence and the exact complementary sequence of the reference or target nucleotide sequence of at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of at least 10 nucleotides, or at least 11, 12, 13, 14, 15, 16, 17, 18, 19, 20, 21, 22 or up to 50 nucleotides of the entire length of the nucleic acid sequence to the reference sequence (if not specified otherwise below). Sequence comparisons can be carried out using default GAP analysis with the University of Wisconsin GCG, SEQWEB application of GAP, based on the algorithm of Needleman and Wunsch (Needleman and Wunsch (1970) J MoI. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions.

In its broadest sense, the term "substantially identical", when used herein with respect to a nucleotide sequence, means a nucleotide sequence corresponding to a reference or target nucleotide sequence, wherein the percentage of identity between the substantially identical nucleotide sequence and the reference or target nucleotide sequence is at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of 10-22 nucleotides, such as at least 10, 11, 12, 13, 14, 15, 16, 17, 18, 19, 20, 21, 22 or up to 50 nucleotides of a nucleic acid sequence to the reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J MoI. Biol. 48: 443-453; as defined above).

A nucleotide sequence "substantially identical" to a reference nucleotide sequence hybridizes to the exact complementary sequence of the reference nucleotide sequence (i.e. its corresponding strand in a double-stranded molecule) under low stringency conditions, preferably medium stringency conditions, most preferably high stringency conditions (as defined above). Homologues of a specific nucleotide sequence include nucleotide sequences that encode an amino acid sequence that is at least 24% identical, at least 35% identical, at least 50% identical, at least 65% identical to the reference amino acid sequence, as measured using the parameters described above, wherein the amino acid sequence encoded by the homolog has the same biological activity as the protein encoded by the specific nucleotide. The term "substantially non-identical" refers to a nucleotide sequence that does not hybridize to the nucleic acid sequence under stringent conditions. The term "substantially identical", when used herein with respect to a polypeptide, means a protein corresponding to a reference polypeptide, wherein the polypeptide has substantially the same structure and function as the reference protein, e.g. where only changes in amino acids sequence not affecting the polypeptide function occur. When used for a polypeptide or an amino acid sequence, the percentage of identity between the substantially similar and the reference polypeptide or amino acid sequence is at least 24%, at least 30%, at least 45%, at least 60%, at least 75%, at least 90%, at least 95%, at least 99%, using default GAP analysis parameters as described above. Homologues are amino acid sequences that are at least 24% identical, more preferably at least 35% identical, yet more preferably at least 50% identical, yet more preferably at least 65% identical to the reference polypeptide or amino acid sequence, as measured using the parameters described above, wherein the amino acid sequence encoded by the homolog has the same biological activity as the reference polypeptide.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "complementary" or "complement" as used herein refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is anti-parallel to the first region if the residue is thymine or uracil. Similarly, it is known that a cytosine residue of a first nucleic acid strand is capable of base pairing with a residue of a second nucleic acid strand which is anti-parallel to the first strand if the residue is guanine. A first region of a nucleic acid is complementary to a second region of the same or a different nucleic acid if, when the two regions are arranged in an anti-parallel fashion, at least one nucleotide residue of the first region is capable of base pairing with a residue of the second region. Preferably, the first region comprises a first portion and the second region comprises a second portion, whereby, when the first and second portions are arranged in an anti-parallel fashion, such that at least about 50%, and preferably at least about 75%, at least about 90%, or at least about 95% or at least 100% of the nucleotide residues of the first portion are capable of base pairing with nucleotide residues in the second portion. More preferably, all nucleotide residues of the first portion are capable of base pairing with nucleotide residues in the second portion.

The terms "variant", "variance", "mutation" or "polymorphism" are used interchangeably herein, and refer to a difference in nucleic acid sequence among members if a population of individuals. Polymorphisms can sometimes be referred to as "single nucleotide polymorphism" or "SNP" when they vary at a single nucleotide. In some embodiments, polymorphisms can be synonymous or nonsynonymous. Synonymous polymorphisms when present in the coding region or non-coding region typically do not result in an amino acid change, but can result in altered mRNA stability or altered alternative splice sites. Nonsynonymous polymorphism, when present in the coding region, can result in the alteration of one or more codons resulting in an amino acid replacement in the amino acid chain. Such mutations and polymorphisms may be either heterozygous or homozygous within an individual. Homozygous individuals have identical alleles at one or more corresponding loci on homologous chromosomes, while heterozygous individuals have two different alleles at one or more corresponding loci on homologous chromosomes. A polymorphism is thus said to be "allelic," in that, due to the existence of the polymorphism, some members of a species carry a gene with one sequence (e.g., the normal or wild-type "allele"), whereas other members may have an altered sequence (e.g., the variant or, mutant "allele").

The term "genotype" refers to the specific allelic composition of an entire cell or a certain gene, whereas the term "phenotype" refers to the detectable outward manifestations of a specific genotype.

The term "allele", as used herein, refers to one member of a pair of different forms of a gene. As used herein alleles refer to coding and to non-coding sequences. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions and insertions of nucleotides. An allele of a gene can also be a form of a gene containing a mutation.

As used herein, the term "administer" refers to the placement of a composition into a subject by a method or route which results in at least partial localization of the composition at a desired site such that desired effect is produced. Routes of administration suitable for the methods described herein can include both local and systemic administration. Generally, local administration results in a higher amount of an antidepressant (e.g., SSRI) and/or a folate-containing compound being delivered to a specific location (e.g., serotonin receptors in the central and/or peripheral nervous systems) as compared to the entire body of the subject, whereas, systemic administration results in delivery of an antidepressant (e.g., SSRI) and/or a folate-containing compound to essentially the entire body of the subject. In some embodiments, the compositions described herein are administered to subjects with depression orally. In other embodiments, the compositions described herein can be administered to subjects with depression by injection.

EXAMPLES

The examples presented herein, in part, relate to the use of a folate-containing compound, e.g., 6(S)-5-MTHF, alone or as an adjunct to an antidepressant drug for treating a patient with depression, e.g., major depressive disorder (MDD). The examples presented herein also relate to methods to identify genetic polymorphisms, peripheral biomarkers and clinical features involved in selecting patients with depression for receiving a folate-containing compound, e.g., as an adjunctive treatment to an antidepressant drug, e.g., a selective serotonin reuptake inhibitor (SSRI). Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the paragraphs to the invention, but are rather intended to be exemplary of certain embodiments. Any variations in the exemplified methods which occur to the skilled artisan are intended to fall within the scope of the present invention.

Example 1

A Double-Blind, Placebo Controlled Study of a Folate-Containing Compound Among SSRI-Resistant Outpatients with Major Depressive Disorder (MDD)

Exemplary Study Design

Using the sequential parallel design [51] (see, for example, FIGS. 1A-1B, and 2), the 60-day, double-blind treatment, either administration with a folate-containing compound (e.g., a 6(S)-5-MTHF) or a placebo as an adjunct to an SSRI, can be divided into two phases of 30 days each, with assessments performed every 10 days. During the first phase of the double-blind treatment, eligible patients can be randomized to 30 days of treatment with either 6(S)-5-MTHF (15 mg/day) (n=19) or placebo (n=56), with a 2:3:3 ratio for random assignment to the treatment sequences drug/drug (referring to 6(S)-5-MTHF), placebo/placebo, and placebo/drug. By way of example only, if there is a 10% drop-out rate during the first phase, 50 patients on placebo would complete the first 30-day phase, 17 patients on 15 mg/day 6(S)-5-MTHF would complete the first phase. Patients randomly assigned to the drug/drug sequence stay on the same 6(S)-5-MTHF dose (15 mg/day) during the second phase, regardless of whether patients have responded during the first phase or have not. For those randomly assigned to the placebo/placebo sequence, both responders and non-responders to placebo during the first phase (n=25) remain on placebo during the second phase. On the other hand, for those randomly assigned to the placebo/drug sequence, both responders and non-responders to placebo during the first phase (n=25) go on to receive 15 mg/day 6(S)-5-MTHF during the second phase. In some embodiments, some of the placebo-treated patients (e.g., about 27% of the placebo-treated patients) can respond during the first phase, and that a portion of the remaining placebo non-responders (e.g., about 9% of the placebo non-responders) during the first phase can go on to respond during the second phase, while a larger portion of 6(S)-5-MTHF-treated patients (e.g., about 48% of the 6(S)-5-MTHF-treated patients) can respond during the first phase, and that a portion of the placebo non-responders (e.g., about 35% of placebo non-responders) during the first phase can go on to respond to 15 mg/day 6(S)-5-MTHF during the second phase. Data from the previous double-blind, placebo-controlled study (Trial 1) can be pooled into the instant study (Trial 2) to provide a more accurate estimate of the placebo effect size, with a weighted average from the two Phases 1 (one from Trial 1 and one from Trial 2) and two Phases 2 (one from Trial 1 and one from Trial 2). With 148 patients randomized to placebo during phase 1 or to stay on placebo during phase 2 following non-response to placebo in Trial 1; and with patients randomized to placebo during phase 1 (n=56) or to stay on placebo during phase 2 following non-response to placebo in Trial 2 (n=18) in Trial 2, and a weighted average response rate of approximately 19% across Trials 1 and 2 (total n=222); and patients randomized to 15 mg/day 6(S)-5-MTHF during phase 1 (n=19) or to 15 mg/day 6(S)-5-MTHF during phase 2 following non-response to placebo (n=18) and a weighted average response rate of approximately 41.5% (total n=37) in Trial 2, the statistical power to show a drug-placebo difference in response rates is greater than 0.8.

Subject Selection

Inclusion Criteria:

(1) Age 18-65; (2) Written informed consent; (3) Meet DSM-IV criteria (by Structured Clinical Interview for DSM-IV-SCID-I/P) for MDD, current patients; (4) Quick Inventory of Depressive Symptomatology—Self-Rated (QIDS-SR) [52] score of at least 12 at both screen and baseline visits; (5) Patients treated with an SSRI at adequate doses, e.g., as shown in Table 1 (defined as 20 mg/day or more of fluoxetine, citalopram, or paroxetine, 10 mg/day or more of escitalopram, and 50 mg/day or more of sertraline) during the current episode for at least 8 weeks; and (6) During the baseline visit, patients must be on a stable dose of SSRI for the past 4 weeks.

In some embodiments, 40% of patients selected for Trial 2 study were on starting doses. In some embodiments, 90% of patients selected for Trial 2 study had not been maximized in therapeutic dose range.

TABLE 1

Mean doses of SSRIs at baseline — Trial 2

| | Dose (number of patients) | | | Mean Dose |
|---|---|---|---|---|
| Fluoxetine | 20 mg (6) | 40 mg (10) | 60 mg (2) | 35.5 mg |
| Citalopram | 20 mg (3) | 40 mg (8) | 60 mg (2) | 38.5 mg |
| Paroxetine | 20 mg (2) | 30 mg (1) | 40 mg (1) | 27.5 mg |
| Escitalopram | 10 mg (4) | 20 mg (7) | 30 mg (1) | 17.5 mg |
| Sertraline | 50 mg (4) | 100 mg (9) | 200 mg (1) | 92.9 mg |

Exclusion Criteria:

(1) Pregnant women or women of child bearing potential who are not using a medically accepted means of contraception (to include oral contraceptive or implant, condom, diaphragm, spermicide, intrauterine device, tubal ligation, or partner with vasectomy); (2) Patients who no longer meet DSM-IV criteria for MDD during the baseline visit; (3) Patients who demonstrate a greater than 25% decrease in depressive symptoms as reflected by the QIDS-SR total score—screen to baseline; (4) Patients with serious suicide or homicide risk, as assessed by evaluating clinician; (5) Patients with unstable medical illness including cardiovascular, hepatic, renal, respiratory, endocrine, neurological, or hematological disease; (6) Patients with the following DSM-IV diagnoses: substance use disorders active within the last six months, any bipolar disorder (current or past), any psychotic disorder (current or past); (7) Patients with a history of a seizure disorder or clinical evidence of untreated hypothyroidism; (8) Patients requiring excluded medications (see Table 2 for details); (9) Patients with psychotic features in the current episode or a history of psychotic features, as assessed by SCID; (10) Patients with prior course of MTHF augmentation, or intolerance to MTHF at any dose; (11) Patients with any investigational psychotropic drug within the last 3 months; (12) Patients who have failed more than 2 adequate antidepressant trials during the current Major Depressive Episode. Some examples of adequate dosage of an antidepressant trial include either greater than 150 mg of imipramine (or its tricyclic equivalent), greater than 60 mg of phenelzine (or its monoamine oxidase inhibitor equivalent), greater than 20 mg of fluoxetine (or its SSRI-equivalent), greater than 150 mg of bupropion, greater than 300 mg of trazodone (or nefazodone), or greater than 150 mg of venlafaxine. A trial of adequate duration was defined as one during which the patient was on any given antidepressant at an adequate dose for a minimum of 6 weeks; and (13) Patients with a history of antidepressant-induced hypomania.

Human Subjects Involvement and Characteristics:

A total of 75 individuals age 18-65 with MDD are involved. Subjects must be medically stable as defined in the protocol described herein. Patients excluded from the study include patients at acute risk for suicide, active substance abuse or dependence, with mild depression, inadequately treated with SSRIs or who have failed more than 2 trials, who have received MTHF for depression in the past, and those with psychosis or bipolar illness. Patients below the age of 18 or over the age of 65 are also excluded.

Drugs Allowed or Excluded as Concomitant Medications During the Study

Drugs that may be given to the patient include any prescription or OTC medication such as aspirin, acetaminophen and cold preparations not specifically excluded by the protocol. Patients requiring concomitant drug therapy with excluded drugs are discontinued from the study. Table 2 shows a list of drugs allowed (Y) and not allowed (N) as concomitant medications. Some of the drug classes in Table 2 have a numeric value within parentheses, referring to additional notes shown below.

TABLE 2

Concomitant drug therapy

| Drug Class | Episodic Use | Chronic Use |
|---|---|---|
| Analgesics (non-narcotic) | Y | Y |
| Anorexiants | N | N |
| Anxiolytic benzodiazepines (1) | Y | Y |
| Anti-anginal agents | Y | Y |
| Antiarrhythmics | Y | Y |
| Anti-asthma agents | Y | Y |
| Anticoagulants | N | Y |
| Antidepressants (2) | N | Y |
| Antihypertensives (3) | Y | Y |
| Anti-inflammatory agents (NSAIDS) | Y | Y |
| Anti-nauseants | Y | Y |
| Cough/Cold Preparations | Y | Y |
| Diuretics | Y | Y |
| Hormones (4) | N | Y |
| H2 Blockers | Y | Y |
| Insulin | N | Y |
| Non-benzodiazepine sedatives (1) | Y | Y |
| Oral Hypoglycemic Agents | N | Y |
| Psychotropic agents (other) (2) | N | Y |
| Steroids | N | Y |
| Vitamins/Dietary Supplements (5) | N | Y |

(1) Benzodiazepine anxiolytics and non-benzodiazepine sedative-hypnotics noted above are allowed only if subjects are on a stable regimen for at least 2 weeks prior to baseline at doses no greater than the following or their equivalent: clonazepam 1.0 qd and zolpidem 10 mg qhs.
(2) Patients must have been treated prior to study entry with adequate doses of SSRIs (e.g. minimum doses: fluoxetine/paroxetine/citalopram 20 mg/day, escitalopram 10 mg/day, sertraline 50 mg/day) for at least 8 weeks with only non-response. They must be on an SSRI at the time of study enrollment and they must have been at the current dose for at least 4 weeks at the baseline visit. Patients must also agree to continue to take their SSRI medication at the same dose while being treated with 6(S)-5-MTHF. If patients are on other psychotropic drugs as well, they must have been at the current dose of the psychotropic drug for at least 4 weeks, and they must also agree to continue to take their medication at the same dose while being treated with 6(S)-5-MTHF.
(3) Propranolol, metoprolol, acebutolol, reserpine, clonidine and aldomet are excluded.
(4) Adequate thyroid replacement which has been stable for 6 months or more is acceptable as is estrogen replacement for post-menopausal women or the use of oral contraceptives, the initiation of which does not coincide with the onset or exacerbation of depression.
(5) Standard multivitamins with or without minerals are allowed (with no more than 400 mcg folate and 6 mcg B12) if initiated at least 12 weeks prior to Baseline. Dietary supplements with putative CNS activity are excluded including SAMe, St. John's Wort, DHEA, Inositol, Ginko biloba and Omega-3-fatty acids including DHA and Flax Seed Oil.

Subject Enrollment

Seventy-five subjects enter double-blind treatment over 12 months (Trial 2, total enrollment Trials 1 and 2 is 225). This trial is conducted according to the FDA guidelines. Written informed consent is obtained from all patients before protocol-specified procedures are carried out. The subjects are drawn primarily from an outpatient sample of patients with MDD, diagnosed by the use of the Structured Clinical Interview for DSM-IV Axis I Disorders—Patient Edition (SCID-I/P). At study entry, subjects must meet SCID criteria for a depressive episode, and have a QIDS-SR score of at least 12 at both the screen and baseline visits. In addition, their current major depressive episode (MDE) must be considered resistant to SSRIs: during the current MDE, all patients must have received at least one prior trial of an SSRI at an adequate dose and duration, as defined by the MGH Antidepressant Treatment Response Questionnaire (MGH-ATR) [53]. The MGH-ATR defines an adequate trial of SSRIs as 10 mg or more of escitalopram, 20 mg or more of fluoxetine, citalopram, or paroxetine, 50 mg or more of sertraline for a minimum of 6 weeks. In addition, during the baseline visit, patients must be on a stable dose of SSRI for the past 4 weeks or more.

Study Procedures

Once patients agree to participate in the study by signing the informed consent document, a full medical and psychiatric history is taken and a physical examination is performed. Screen rating scales are performed. Screened and eligible patients are asked to return two weeks later for a baseline visit when they are randomized to double-blind treatment with placebo or 6(S)-5-MTHF 15 mg/day with the study design outlined above. The double-blind treatment lasts 60 days, during which patients are seen every 10 days (Visits 1 to 6 of Phase 1—See Table 4 below). Subjects are assigned randomization numbers in consecutive order. The randomization list is provided by a computer-generated random-number list and is maintained by the research pharmacist. In addition, the presence of any side effect or adverse event is carefully documented with the SAFTEE-SI [54]. Reasons for premature discontinuation, including intolerable side effects, are recorded.

All concomitant medications taken during the study is recorded in the case report form, along with dosage information and start and stop dates. Patients requiring excluded drugs (see Table 2 for details) are discontinued from the study. Medication management and clinical ratings are performed by the study clinicians.

For patients randomly assigned to the drug/drug sequence, the dose of 6(S)-5-MTHF is 15 mg/day during both phases of the study. For patients randomly assigned to the placebo/drug sequence, the dose of 6(S)-5-MTHF is 15 mg/day during the second phase of the study as well. All patients are asked to take one tablet of blinded study medication in the morning, in addition to their stable dose of ongoing SSRI treatment. Each study medication tablet is either 15 mg of 6(S)-5-MTHF or matching placebo. Therefore, for patients randomly assigned to the placebo/placebo sequence, the tablets of study medication are placebo during both phases of the study. For patients randomly assigned to the drug/drug sequence, the tablets are 15 mg of 6(S)-5-MTHF during both phases of the study. For patients randomly assigned to the placebo/drug sequence, the tablets are placebo during the first phase of the study, while the tablets are 15 mg of 6(S)-5-MTHF during the second phase of the study.

Subjects unable to tolerate the study medications are withdrawn from the study. Patients need to comply with the dosage regimen and to take all medications as instructed. All patients are instructed to return any excess medication at each visit. A pill count is done to corroborate the study drug record. Protocol violation is defined as less than 80% compliance by pill count.

Specimen Collection Procedure

Blood samples should be taken from subjects after overnight fasting. The following specimens as shown in Table 3 are included for metabolic testing.

TABLE 3

Specimens and metabolic tests

| Specimen | Metabolic Test | Minimum volume Required |
|---|---|---|
| Plasma | homocysteine, hs-CRP, SAMe, ADMA, MDA, 4-HNE, MMA | 2.5 ml |
| Serum | Folate, vitamin B12 and B6 | 1 ml |
| Whole blood hemolysate | Red cell folate | 1 ml |
| Whole blood | MTHFR and MS genotyping | 2 ml |

Specimen Collection Instructions

Plasma:

About 5 ml of blood is withdrawn into a sodium heparin vacutainer tube. Specimens should be centrifuged within one hour of collection at ~2000 g for ~10 minutes. About 2 ml of plasma are aliquoted into 2 plastic storage vials (~1 ml in each). The vials are labeled and frozen at −80° C.

Serum:

About 5 ml of blood is withdrawn into a vacutainer tube (plain red top), which contains no additive. The blood-containing tube is left to stand at room temperature for 20 about minutes and allowed to clot. The sample is then centrifuge at ~2000 g for ~10 minutes. Approximately 2 ml of plasma is aliquoted into 2 plastic storage vials (~1 ml in each). The vials are labeled and frozen at −20° C. or −80° C.

Whole Blood Hemolysate:

100 μL of fully suspended heparinized blood is accurately pipetted into a test tube with a pre-made solution, followed by vortexing and freezing at −20° C. or −80° C.

Whole Blood:

About 5 mls of blood is withdrawn into a EDTA vacutainer tube (lavender top). About 4 ml of whole blood is aliquoted into 2 plastic storage vials (~2 ml each). The vials are labeled and frozen at −20° C. or −80° C.

Efficacy Measures

Any neuropsychological tests can be used to measure efficacy response of a patient treated with a placebo or 6(S)-5-MTHF in conjunction with an SSRI. The primary efficacy measure can include the change in 17-item Hamilton Rating Scale for Depression (HAM-D-17) [55] score. In this study, a response is, for example, defined as a 50% or greater reduction in HAM-D-17 score from baseline. A remission is, for example, defined as a HAM-D-17 score less than 8 at endpoint. Secondary measures of efficacy can include change in CGI-severity, with "clinical response defined" as CGI-S of 1 or 2 at endpoint. Patients with a CGI-I score greater than 5 at any post baseline visit or a 50 percent or greater worsening of depressive symptoms from baseline to that visit are discontinued from the study. Subjects are also discontinued from the study with any emergence of suicidality, homicidality, mania, or psychosis. Additional exemplary instruments that can be administered according to the study schedule include the following:

(1) Structured Clinical Interview for DSM-IV: The SCID-I/P, administered by the clinician, proceeds by modules to diagnose the different Axis I disorders. Questions are asked exactly as written, and each is based on the individual criteria from DSM-IV. Answers are generally rated on a scale of 1-3 (1=doubtful, 2=probable, 3=definite), and, based on the number of positive answers, a diagnosis is determined by a clinician. While the entire SCID-I/P is administered at screen, the mood module is administered at each follow up visit.

(2) The MGH Antidepressant Treatment History Questionnaire (MGH-ATR) [53]: The MGH-ATR provides specific criteria for the adequate dose and adequate length of a trial for it to be considered a failure, thus allowing clinicians to systematically collect data aimed at assessing the degree of treatment-resistance of the current major depressive episode.

(3) The 28-item Hamilton Depression Scale (HAM-D-28) [55]: This version allows scoring of the HAM-D-17, 21-, 25-, and 28-item scales. This instrument is completed by the clinician by using a structured interview and defined anchor points, and aims to quantify the degree of depression over the past 7 days. The HAM-D is the most widely studied instrument for depression, and its reliability and validity are high.

(4) Clinical Global Impressions—Severity and Improvement (CGI-S, CGI-I): These two instruments are scored 1-7 by the clinician based on assessment of the patient's clinical status. They measure, based on history and scores on other instruments: a) Depressive severity (CGI-S) and b) Clinical Improvement (CGI-I). Patient rated versions of both scales are also utilized (the PGI-S/I).

(5) QIDS-SR [52]: This is a brief (16-item) self-report inventory of core depressive symptoms such as sleep, depressed mood, appetite, concentration, suicidal ideation, interest, energy, psychomotor retardation or agitation.

(6) The Massachusetts General Hospital Cognitive and Physical Functioning Questionnaire: This is a brief (7-item) self-report inventory to assess rates of significant cognitive symptoms, sleepiness, and fatigue.

(7) The Massachusetts General Hospital Sexual Functioning Questionnaire [56]: This is a self-rating scale that measures common symptoms of sexual dysfunction, such as reduced libido and orgasm difficulties.

(8) The Visual Analog Scale [57]: This is a brief (8-item) self-report scale to measure painful symptoms of depression during treatment with the study medication (6(S)-5-MTHF) or placebo.

Safety Measurements

Once the patient has agreed to participate in the study by signing the informed consent document, vital signs (weight, and standing and supine pulse and blood pressure) are recorded at each visit and a physical exam is performed at screen and visit 6 (Day 60, or Phase I endpoint). Consumptive habits (e.g., smoking, alcohol, and caffeinated beverages) are recorded at baseline, Day 30, Day 60, Day 150, Day 240, Day 330, and Day 420 (or endpoint)(See Tables 4 & 5 below). A urine pregnancy test (for women of childbearing potential) is also administered at the screen visit and visit 3 (day 30). Pregnant women may not enroll in this study.

Additionally, baseline blood samples are collected for the assessment of genetic polymorphism for (i) T677C allele for the methylenetetrahydrofolate reductase (MTHFR), (ii) A1298C allele for the MTHFR gene, (iii) A66G allele for the methionine synthase reductase gene, and (iv) A2746G allele for the methionine synthase gene.

Further, baseline, Day 30, Day 60, and Day 420 (or endpoint) blood samples are collected for the measurement of plasma folate, RBC folate, plasma homocysteine, vitamin B12, MMA (methylmalonic acid), SAMe, asymmetrical dimethylarginine (ADMA), malondialdehyde (MDA), 4-hydroxynonenal (4-HNE), F2-Isoprostanes, and high-sensitivity C-Reactive Protein (hs-CRP).

Adverse Side Effects or Events

Documentation of the presence of any side effect or adverse event is completed at every visit using the SAFTEE-SI. Subjects can contact a clinician at any time between visits concerning adverse events or worsening of symptoms. Suicidal ideation is assessed at each visit. Subjects who are felt by the study clinician to be at high risk for suicide are discontinued from the study and referred for hospitalization and further treatment if clinically indicated (See Tables 4 & 5 below).

TABLE 4

Schedule of Clinician/Subject Ratings & Plasma Tests - Double Blind Phase

| Measurement | Screen Day −14 | Baseline Day 0 | Visit 1 Day 10 | Visit 2 Day 20 | Visit 3 Day 30 Endpoint Phase 1 | Visit 4 Day 40 | Visit 5 Day 50 | Visit 6 Day 60 Endpoint Phase 2 |
|---|---|---|---|---|---|---|---|---|
| SCID | x | | | | | | | |
| SCID Mood Module | | x | x | x | x | x | x | x |
| MGH ATR | x | | | | | | | |
| HAM-D-28 | x | x | x | x | x | x | x | x |
| CGI | x | x | x | x | x | x | x | x |
| QIDS-SR | x | x | x | x | x | x | x | x |
| MGH-CPFQ | x | x | x | x | x | x | x | x |
| MGH-SFQ | x | x | x | x | x | x | x | x |
| SAFTEE-SI | x | x | x | x | x | x | x | x |
| Physical Exam | x | | | | | | | x |
| Vital Signs | x | x | x | x | x | x | x | x |
| Pregnancy Test | x | | | | x | | | |
| Consumptive Habits | | x | | | x | | | x |
| Plasma Folate | | x | | | x | | | x |
| RBC Folate | | x | | | x | | | x |
| Plasma Homocysteine | | x | | | x | | | x |
| B12 | | x | | | x | | | x |
| ADMA | | x | | | x | | | x |
| MDA | | x | | | x | | | x |
| 4-HNE | | x | | | x | | | x |
| SAMe | | x | | | x | | | x |
| hs-CRP | | x | | | x | | | x |
| F24-Iosoprostanes | | x | | | x | | | x |
| T677C | | x | | | | | | |
| A1298C | | x | | | | | | |
| A66G | | x | | | | | | |
| A2746G | | x | | | | | | |

TABLE 5

Schedule of Clinician/Subject Ratings & Plasma Tests — Follow Up Phase

| Measurement | Visit 7 Day 150 | Visit 8 Day 240 | Visit 9 Day 330 | Visit 10 Day 420 Endpoint |
|---|---|---|---|---|
| SCID Mood Module | x | x | x | x |
| HAM-D-28 | x | x | x | x |
| CGI | x | x | x | x |
| QIDS-SR | x | x | x | x |
| MGH-CPFQ | x | x | x | x |
| MGH-SFQ | x | x | x | x |
| SAFTEE-SI | x | x | x | x |
| Vital Signs | x | x | x | x |
| Consumptive Habits | x | x | x | x |
| RBC Folate | | | | x |
| Plasma Folate | | | | x |
| Plasma Homocysteine | | | | x |
| B12 | | | | x |
| ADMA | | | | x |
| MDA | | | | x |
| 4-HNE | | | | x |
| SAMe | | | | x |
| hs-CRP | | | | x |
| F2-Isoprostanes | | | | x |

Termination

Acceptable reasons for early discontinuation include the following: 1) request of patient, 2) decision of physician, 3) serious adverse event, 4) protocol violation, 5) worsening of depression or clinical deterioration requiring hospitalization.

Exemplary Data Management

Clinical data at each visit are recorded using a standardized clinician assessment form and a set of patient rating scales. Edited and corrected data are added to a database that is ready to be used as input to statistical software (e.g., STATA) for data development and analysis. All data are stored in locked file cabinets. No identifiers other than study ID's are included in the data. Study staff and subjects may have the option to enter clinical data into the database directly, using DatStat Illume™, a platform for electronic data capture that streamlines data collection and management, and ensures data integrity, resulting in improved data quality. Subjects and/or research staff enter survey responses into electronic assessment forms, and the responses are then transmitted securely via encrypted connection and stored in a secured database.

Exemplary Statistical Analyses

General Considerations:

Data are entered and error-checked at each clinical site involved in the study. Study staff and subjects may have the option to enter self-evaluations into the system directly using DatStat Illume™. The process of data entry is supervised by the DCRP staff. Once the data set is entered and checked, analyses are conducted. Both a completer analysis of all patients finishing the trial and an intent-to-treat analysis examining all patients enrolled into the trial are used to define the severity of depression at endpoint. Examination of both study completers and all patients randomized can provide the broadest assessment of the effects of treatment in trials of such kind. The data from Trial 2 can be pooled with those from Trial 1 with the sequential parallel comparison design, to provide an estimate of the placebo response based on a larger sample size. According to the sequential parallel comparison design analytical plan, the effect of the active treatment is assessed using a z-score. Under the null hypothesis of no drug-placebo difference, the z score has a mean of 0. Let p1, q1 be the response rates to the first administration of drug and placebo respectively and let p2, q2 be the responses rates to the second treatment. To analyze these data, a statistic based on h=w(p1−q1)+(1−w)(p2−q2) is used. The weight (w) and the randomization fraction (a) are chosen to maximize the power of the test, based on the alternative hypothesis. The randomization fraction (a) can be involved in calculation of p1, q1, p2, and/or q2. For example, multiplying the total sample size by the randomization fraction (a) to obtain the denominator of the response rates, e.g., p1. The standard error for h requires a special formula because some of the same patients who are included in the estimation of p2, q2 are included in the estimation of p1, q1. The computation is facilitated by considering a table of outcomes, where in this case p1, p2, q1, q2 are the theoretical probabilities rather than the observed relative frequencies. A more detailed description of the analyses is described in the Fava et al reference on the sequential parallel comparison design [51].

Analysis of Study Attrition:

A detailed analysis of the number and timing of study dropouts is calculated. Potential differences between treatment groups in dropouts are examined with a Fisher's Exact test; if even weak trends (p<0.05) indicative of differential dropout are detected, a more detailed survival analysis is completed to illustrate the timing and magnitude of these differences. These dropout analyses can be used to better understand the outcomes depicted by the following analyses.

Analyses of the Magnitude of Responses:

The magnitude of response between the two treatment groups can be measured by a decrease in baseline HAM-D-17 scores. One-way analysis of covariance (adjusting for baseline HAM-D-17 scores) can be used to assess differences in HAM-D-17 scores at endpoint, pooling data from Trials 1 and 2 and from both phases by using the sequential parallel design.

Analyses of Percentage of Responders and Remitters:

An exemplary statistical test for analysis of differences in proportion of responders in the treatment conditions is a Fisher's Exact test, pooling data from Trials 1 and 2 and from both phases by using the sequential parallel design. Logistic regression analysis can also be carried out, with response or non-response and remission or non-remissions as the dependent variables, with the baseline HAM-D score, gender, and age, as the independent variables. Exploratory covariate analysis can be carried out to investigate any differences in remission rates seen with gender, age, and other variables.

Analyses of the Number of Adverse Events:

One-way analysis of variance can be used to assess differences in total number of SAFTEE-SI AEs between baseline and endpoint.

Analyses of Predictors of a Greater 6(S)-5-MTHF/Placebo Difference in Response Rates:

Folate levels are classified as either low (<=2.5 ng/ml) or normal; and homocysteine levels as either normal or elevated (>=13.2 mmol/liter). The presence or absence of at least one T677C allele for the MTHFR gene are entered as a dichotomous variable (present or absent). A 2×2 Analysis of Variance (ANOVA) can be used to test whether the presence of a low serum-folate level predicts a greater drug/placebo difference in response. Using folate as an example predicator, the presence or absence of a low serum-folate level along with treatment assignment can be entered in a 2×2, factorial ANOVA, using depression improvement scores (baseline minus endpoint HAM-D-17 scores) as the dependant variable. The effect of the predictor can be indicated by the interaction term, reflecting the potential differential effect of 6(S)-5-MTHF on individuals with low vs. normal folate. Similar analyses (i.e. separate 2×2 ANOVA's) can be performed substituting the presence of low folate levels for the presence of other predictors as described herein. Similarly, the effect of other predictors can be indicated by the interaction term representing the potential modulating influence of those variables.

Example 2

Evaluation of the Efficacy of 6(S)-5-MTHF as an Augmentation Strategy in MDD Patients (Trial 1)

Using the study design and sequential parallel design as described in Example 1, a 60-day, multi-center, double-blind, placebo-controlled study (Trial 1) on the efficacy of oral 6(S)-5-MTHF augmentation of selective serotonin reuptake inhibitors (SSRIs) has been completed in 148 patients with major depressive disorder (MDD) resistant to treatment with SSRIs. The study involved the enrollment of a total of 148 patients with MDD over the course of 12 months across 10 medical centers or hospitals in the United States. Outpatients suffering from MDD were treated with either 7.5 mg/day of 6(S)-5-MTHF or with placebo as an adjuvant to SSRIs for 60 days using the sequential parallel comparison design [51]. In accordance with the sequential parallel design [51], the 60-day, double-blind treatment was divided into two phases of 30 days each, with assessments performed every 10 days. As shown in FIG. 1A, during the first phase of double-blind treatment, 148 eligible patients were randomized to 30 days of treatment with either 7.5 mg/day of 6(S)-5-MTHF ("drug") or placebo, with a 2:3:3 ratio for random assignment to the treatment sequences drug/drug, placebo/placebo, and placebo/drug. Patients randomly assigned to the drug/drug sequence had their 6(S)-5-MTHF dose increased from 7.5 mg/day to 15 mg/day during the second phase, regardless of whether patients had responded during the first phase (n=12) or had not (n=20). For those randomly assigned to the placebo/placebo sequence, both responders and non-responders to placebo during the first phase remained on placebo during the second phase. On the other hand, for those randomly assigned to the placebo/drug sequence, both responders and non-responders to placebo during the first phase went on to receive 7.5 mg/day of 6(S)-5-MTHF during the second phase.

The findings from Trial 1, as shown in Tables 6-7, indicate that the 7.5 mg/day 6(S)-5-MTHF is not effective to act as an adjunct to the SSRIs. While 6(S)-5-MTHF does not appear to cause any adverse side effect when administered with an SSRI, there was no significant difference in efficacy outcome (as measured by various parameters such as HDRS-17, QIDS-SR and CGI-S) between MDD patients treated with an SSRI in combination with either 7.5 mg/day 6(S)-5-MTHF or placebo.

TABLE 6

Efficacy results of MDD patients having 7.5 mg/day 6(S)-5-MTHF or placebo as an adjunct to an SSRI

| Scale | Outcome | Adjunct L-methyl-folate Phase 1 | Adjunct Placebo Phase 1 | Adjunct L-methyl-folate Phase 2* | Adjunct Placebo Phase 2* | Pooled Adjunct L-methyl-folate† | Pooled Adjunct Placebo† | p-value‡ |
|---|---|---|---|---|---|---|---|---|
| N | | 36 | 112 | 35 | 33 | | | |
| Completers (N) | | 91.6% (33) | 87.5% (98) | 85.7% (30) | 90.9% (30) | | | |
| HDRS-17 | Mean baseline score (SD) | 18.8 (4.2) | 19.9 (4.8) | 16.2 (3.4) | 16.8 (4.7) | 17.5 | 18.4 | |
| HDRS-17 | % Response (N) | 19.4% (7) | 28.5% (32) | 17.1% (6) | 9.0% (3) | 18.3% | 18.8% | 0.92 |
| HDRS-17 | % Remission (N) | 11.1% (4) | 17.8% (20) | 14.2% (5) | 6.0% (2) | 12.7% | 11.9% | 0.15 |
| HDRS-17 | Mean score reduction (SD) | −4.3 (5.0) | −6.3% (6.6) | −3.1 (4.2) | −2.1 (4.9) | −3.70 | −4.2 | 0.87 |
| QIDS-SR | Mean baseline score (SD) | 20.7 (4.7) | 21.0 (5.0) | 15.5 (5.9) | 17.0 (5.5) | 18.1 | 19.0 | |
| QIDS-SR | % Response (N) | 25.0% (9) | 28.5% (28) | 8.5% (3) | 9.0% (3) | 16.8% | 18.8% | 0.70 |
| QIDS-SR | % Remission (N) | 0.0% (0) | 8.9% (10) | 8.5% (3) | 3.0% (1) | 4.3% | 6.0% | 0.58 |
| QIDS-SR | Mean score reduction (SD) | −4.6 (5.1) | −6.9 (6.2) | −1.9 (4.1) | −2.5 (4.1) | −3.25 | −4.73 | 0.07 |
| CGI-S | Mean baseline score (SD) | 4.1 (0.5) | 4.2 (0.6) | 3.8 (0.7) | 3.9 (0.7) | 4.0 | 4.1 | |
| CGI-S | Mean score reduction (SD) | −0.5 (0.9) | −0.7 (1.0) | −0.5 (0.7) | −0.4 (0.8) | −0.53 | −0.59 | 0.96 |

*According to the SPCD model, only Phase 1 completers/non-responders (according to the HDRS-17) are analyzed in Phase 2.
†Pooled results from Phase 1 and 2.
‡SPCD anlayses using Fava et al method for dichotomous measures (2003) and Tamura and Huang (2007) method for continuous measures.

TABLE 7

Adverse side- effects of an SSRI administered with or without 6(S)-5-MTHF

| Side Effect Category | Placebo (n = 112)* Frequency (%) | L-methylfolate 7.5 mg (n = 94)* Frequency (%) | NNH | L-methylfolate 15 mg (n = 30)* Frequency (%) | NNH | Two-tailed p-value |
|---|---|---|---|---|---|---|
| Gastrointestinal | 23 (20.1%) | 9 (9.6%) | <placebo | 3 (10.0%) | <placebo | 0.06 |
| Sleep | 12 (10.7%) | 3 (3.2%) | <placebo | 2 (6.7%) | <placebo | 0.11 |
| Psychological | 12 (10.7%) | 2 (2.1%) | <placebo | 2 (6.7%) | <placebo | 0.05 |
| Somatic | 22 (19.6%) | 9 (9.6%) | <placebo | 3 (10.0%) | <placebo | 0.09 |
| Infectious | 13 (11.6%) | 6 (6.4%) | <placebo | 2 (6.7%) | <placebo | 0.38 |
| Cardiovascular | 4 (3.6%) | 0 (0%) | <placebo | 2 (6.7%) | <placebo | 0.08 |
| Sexual | 0 (0%) | 0 (0%) | =placebo | 0 (0%) | =placebo | 0.99 |
| Miscellaneous | 3 (2.7%) | 1 (1.1%) | <placebo | 2 (6.7%) | <placebo | 0.24 |

*n is based on total number of subjects that received placebo or L-methylfolate 7.5 mg or 15 mg at some point during the trial.

However, an increase in dose of 6(S)-5-MTHF from 7.5 mg/day to 15 mg/day in the patients assigned to the drug/drug sequence during the second phase demonstrated an significant increase in the response and remission rate, e.g., an increase by at least 2-fold, as compared to the group taking placebo with the SSRIs (24% vs 9%, p=0.1: Such result is not included in Table 6). Accordingly, a higher dose of oral 6(S)-5-MTHF augmentation, 15 mg/day, was determined to be used in Trial 2.

Example 3

Evaluation of the Efficacy of 6(S)-5-MTHF as an Augmentation Strategy in MDD Patients (Trial 2)

Figure 1B:
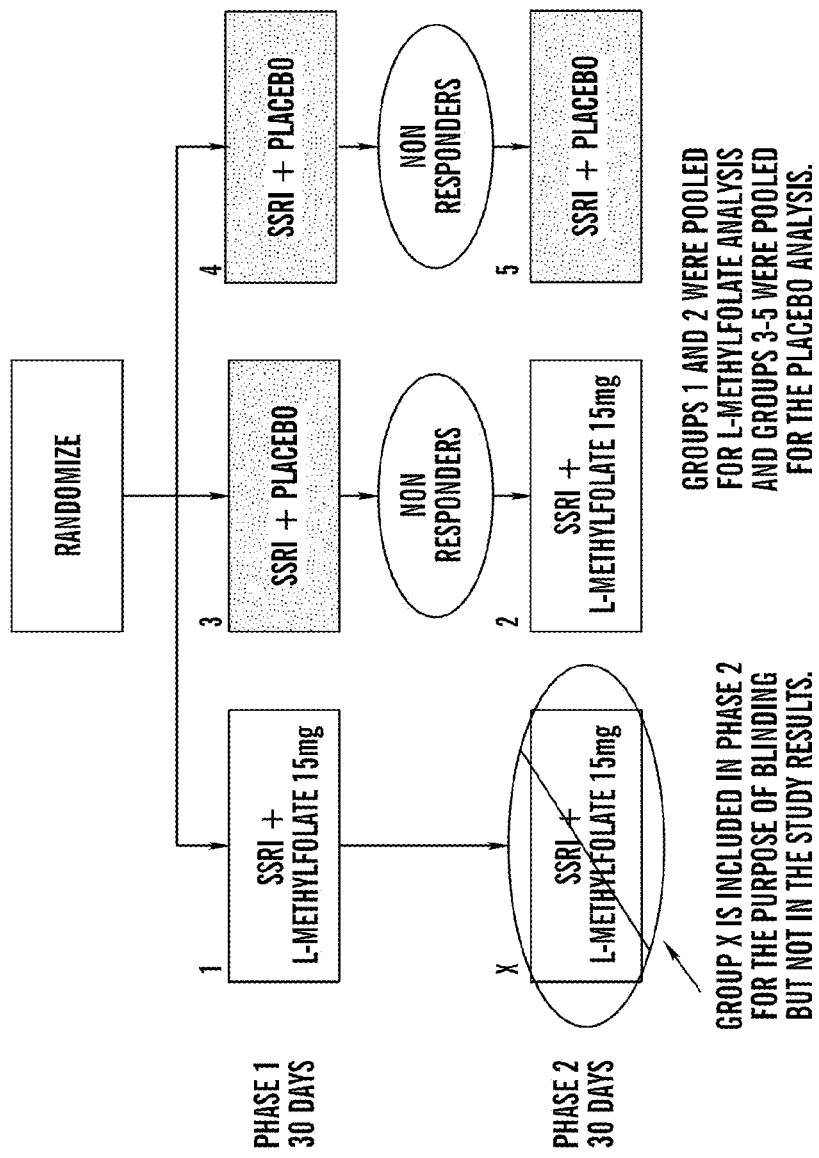

Using the study design and sequential parallel design as described in Example 1, this Example 3 shows a 60-day, multi-center, double-blind, placebo-controlled pilot study (Trial 2) on the efficacy of a higher dose (15 mg qd) oral 6(S)-5-MTHF augmentation of selective serotonin reuptake inhibitors (SSRIs) in 75 patients with major depressive disorder (MDD) resistant to treatment with SSRIs. The design of Trial 2 (as shown in FIG. 1B) was identical to that of Trial 1, with the exception of the dosing of 6(S)-5-MTHF, which was 15 mg/day throughout the trial for those patients assigned to the placebo-drug group and to the drug-drug group.

Figure 2:
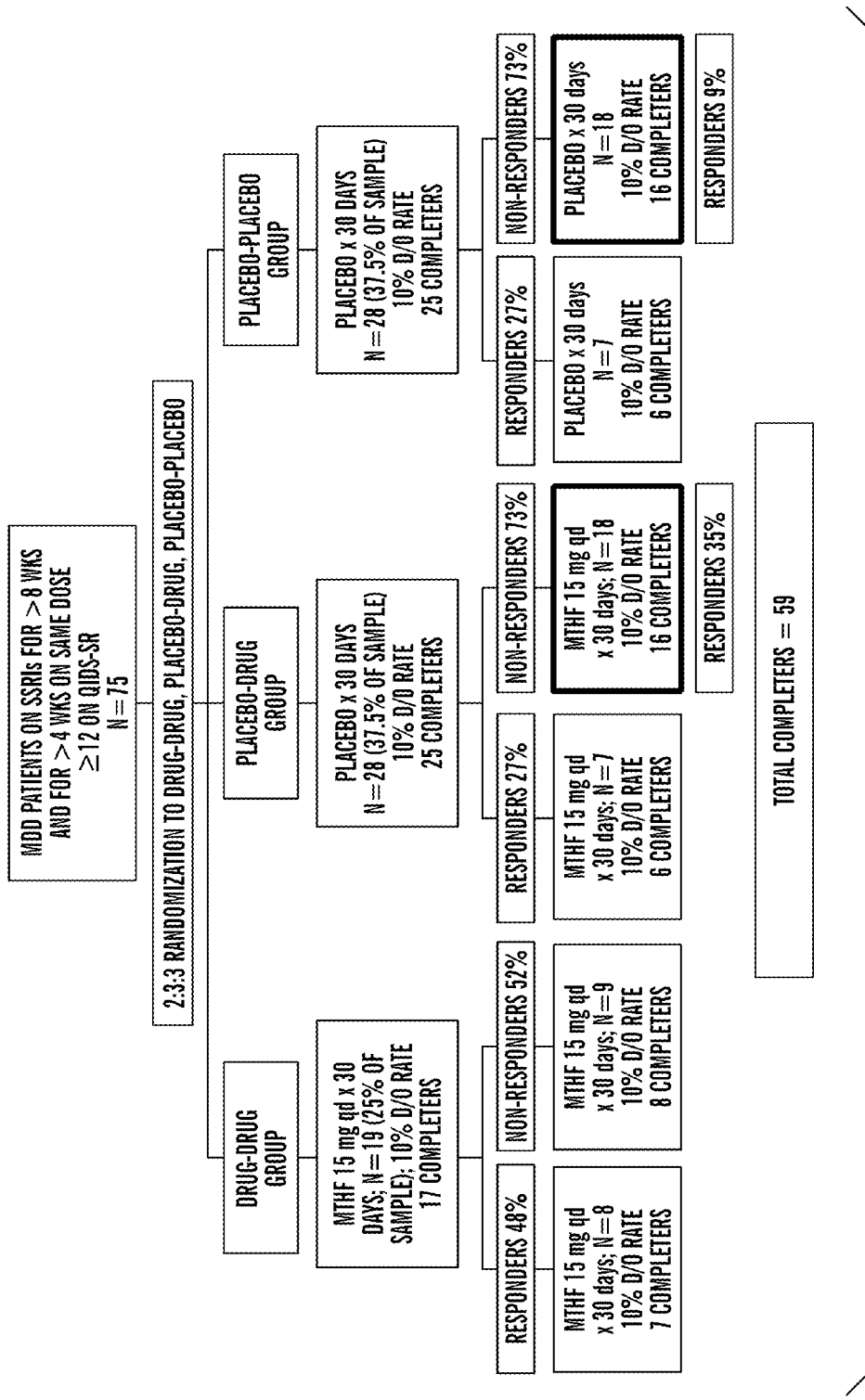
FIG. 2 shows a schematic diagram of an exemplary double-blind, placebo-controlled study of 6(S)-5-MTHF among SSRI-resistant outpatients with major depressive disorder (MDD) using sequential parallel comparison. As an example, 10% dropout rate is assumed. The percent response and non-response rates provided in this figure are only meant to indicate the relative efficacy effect, but do not mean to be construed as or limited by the absolute values of the indicated percentages.

The critical clinical purpose of this study was to determine whether the use of a higher dose of oral 6(S)-5-MTHF as an adjunct to SSRIs would be more effective than placebo as an adjunct to SSRIs in reducing depressive symptoms in outpatients with MDD with partial or no response to SSRI treatment. An additional aim of the study was to demonstrate the safety and tolerability of 6(S)-5-MTHF 15 mg/day augmentation. The study involves the enrollment of a total of 75 patients with MDD over the course of 12 months across 6 different medical centers or hospitals across the United States. Outpatients suffering from MDD were treated with either 6(S)-5-MTHF 15 mg/day or with placebo for 60 days using the sequential parallel comparison design [51]. FIG. 2 shows the actual number of completers in each group by the end of the study.

Figure 3A:
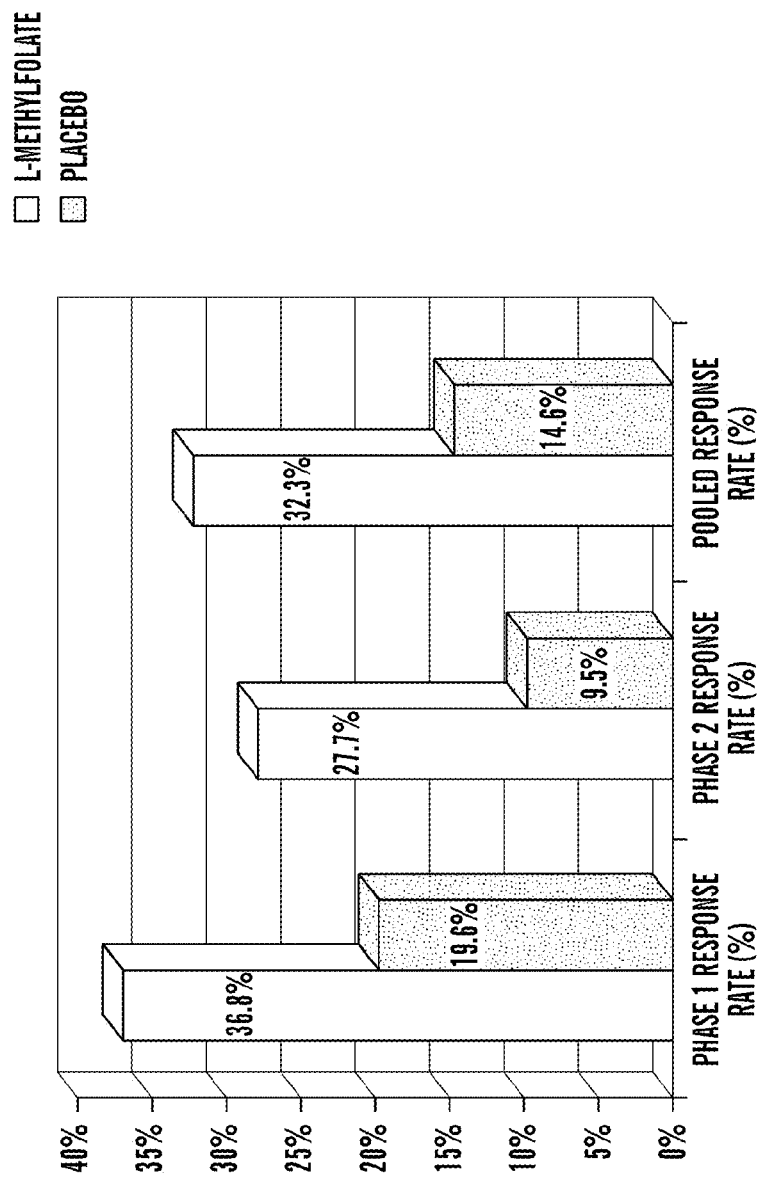
FIGS. 3A-3E show effects of treating MDD patients with a folate-containing compound, e.g., as an adjunct to an SSRI in Trial 2.

FIG. 3A shows that there is a statistically significant difference in the percentage of responders (50% or greater reduction in HAM-D-17 at endpoint) in the two treatment conditions (i.e., SSRI+15 mg/day of 6(S)-5-MTHF vs. SSRI+placebo) after 30 days. Using the sequential parallel comparison design [51], it was determined that the response rate is higher for the 6(S)-5-MTHF group than the placebo group, with the response rate on placebo estimated from Trials 1 and 2.

Figure 3B:
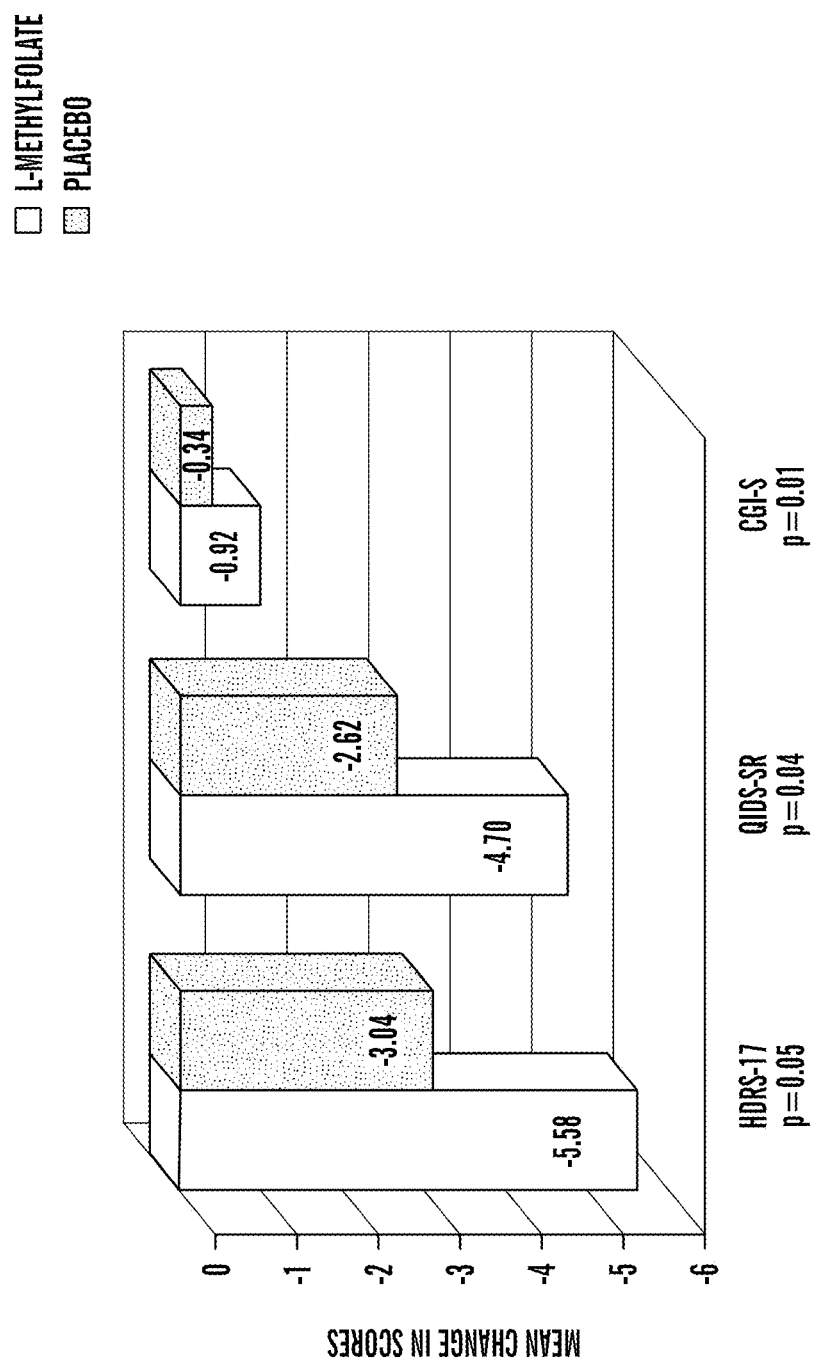

FIG. 3B shows that there is a statistically significant difference between the two treatment conditions (i.e., SSRI+ 15 mg/day of 6(S)-5-MTHF vs. SSRI+placebo) after 30 days in the degree of improvement, as measured by the change in the 17-item Hamilton Depression Rating Scale (HAM-D-17) score from baseline to endpoint, QID-SR, or Clinical Global Impressions-Severity (CGI-S), using the sequential parallel comparison design [51]. Using the sequential parallel comparison design [51], it was determined that there is a greater degree of reduction in the scores of HAM-D-17, QIDS-SR and CGI-S, respectively, in the 6(S)-5-MTHF group than in the placebo group, with the change on placebo estimated from Trials 1 and 2.

Figure 3C:
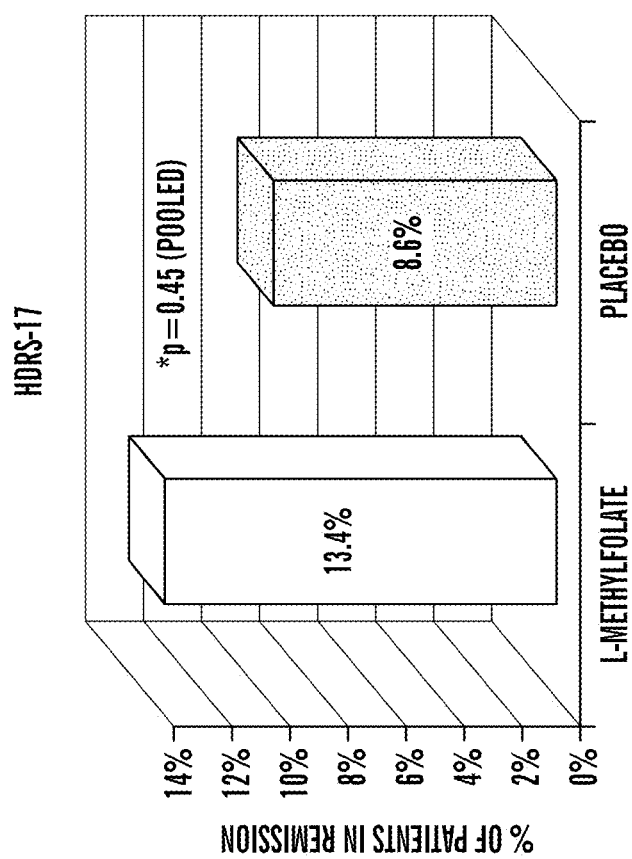
Figure 3D:
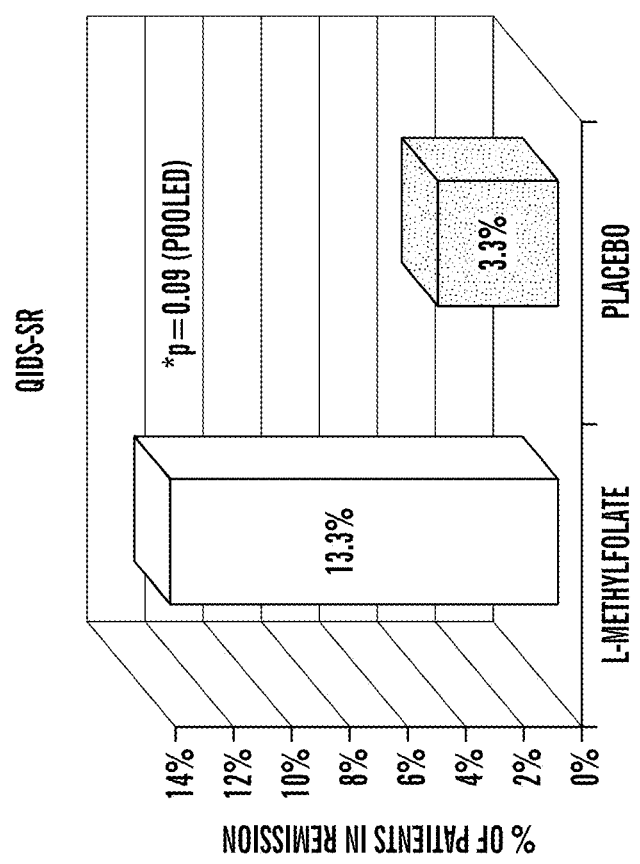

FIGS. 3C-3D show that there is no significant difference in the percentage of remitters (HAM-D-17 score <8 at end point or QIDS-SR score 5 at end point) in the two treatment conditions (i.e., SSRI+15 mg/day of 6(S)-5-MTHF vs. SSRI+placebo) after 30 days.

The results of FIGS. 3A-3D are summarized in Table 8 below.

TABLE 8

Efficacy results of MDD patients having 15 mg/day 6(S)-5-MTHF or placebo as an adjunct to an SSRI

| Outcome | | Adjunct L-methyl-folate Phase 1 | Adjunct Placebo Phase 1 | Adjunct L-methyl-folate Phase 2 | Adjunct Placebo Phase 2 | Pooled Adjunct L-methyl-folate | Pooled Adjunct Placebo | p-value |
|---|---|---|---|---|---|---|---|---|
| N | | 19 | 56 | 18 | 21 | | | |
| Completers (N) | | 89.4% (17) | 89.2% (50) | 83.3% (15) | 90.4% (19) | | | |
| HDRS-17 | Mean baseline score (SD) | 21.2 (4.1) | 21.2 (3.2) | 19.5 (3.8) | 17.6 (4.5) | 20.4 | 19.4 | |
| HDRS-17 | % Response (N) | 36.8% (7) | 19.6% (11) | 27.7% (5) | 9.5% (2) | 32.3% | 14.6% | 0.04 |
| HDRS-17 | % Remission (N) | 15.7% (3) | 12.5% (7) | 11.1% (2) | 4.7% (1) | 13.4% | 8.6% | 0.45 |
| HDRS-17 | Mean score reduction (SD) | −7.5 (5.5) | −4.4 (5.8) | −3.8 (6.2) | −1.7 (4.7) | −5.58 | −3.04 | 0.05 |
| QIDS-SR | Mean baseline score (SD) | 15.7 (5.8) | 17.2 (5.5) | 17.3 (4.8) | 17.1 (5.6) | 16.5 | 17.2 | |
| QIDS-SR | % Response (N) | 36.8% (7) | 21.4% (12) | 11.1% (2) | 4.7% (1) | 23.9% | 13.1% | 0.15 |
| QIDS-SR | % Remission (N) | 21.0% (4) | 1.7% (1) | 5.5% (1) | 4.7% (1) | 13.3% | 3.3% | 0.09 |
| QIDS-SR | Mean score reduction (SD) | −8.1 (5.3) | −5.7 (5.6) | −1.3 (4.9) | −0.5 (4.9) | −4.7 | −2.62 | 0.04 |
| CGI-S | Mean baseline score (SD) | 4.6 (0.6) | 4.4 (0.6) | 4.0 (0.6) | 3.9 (0.8) | 4.4 | 4.2 | |
| CGI-S | Mean score reduction (SD) | −1.3 (0.9) | −0.6 (1.0) | −0.5 (1.0) | −0.1 (0.6) | −0.92 | −0.34 | 0.01 |

*According to the SPCD model, only phase 1 completers/non-responders (according to the HDRS-17) are analyzed in Phase 2.
Pooled results from Phases 1 and 2.
SPCD anlayses using Fava et al method for dichotomous measures (2003) and Tamura and Huang (2007) method for continuous measures.

Table 9 shows that there are no significant differences in the number of adverse events, as measured by the SAFTEE-SI between the two treatment groups (i.e., SSRI+15 mg/day of 6(S)-5-MTHF vs. SSRI+placebo).

TABLE 9

Adverse side-effects of an SSRI administered with 15 mg/day of 6(S)-5-MTHF or placebo

| Side Effect Category | Placebo (n = 54)* Frequency (%) | L-methylfolate 15 mg (n = 42)* Frequency (%) | NNH | Two-tailed p-value |
|---|---|---|---|---|
| Gastrointestinal | 8 (14.8%) | 7 (16.7%) | 53 | 0.98 |
| Sleep | 3 (5.5%) | 1 (2.4%) | <placebo | 0.80 |
| Psychological | 9 (16.7%) | 4 (9.5%) | <placebo | 0.47 |
| Somatic | 16 (29.6%) | 6 (14.3%) | <placebo | 0.13 |

TABLE 9-continued

Adverse side-effects of an SSRI administered
with 15 mg/day of 6(S)-5-MTHF or placebo

| Side Effect Category | Placebo (n = 54)* Frequency (%) | L-methylfolate 15 mg (n = 42)* Frequency (%) | NNH | Two-tailed p-value |
|---|---|---|---|---|
| Infectious | 7 (13.0%) | 5 (11.9%) | <placebo | 0.66 |
| Cardiovascular | 0 (0%) | 0 (0%) | =placebo | 0.99 |
| Sexual | 0 (0%) | 1 (2.4%) | 98 | 0.90 |
| Miscellaneous | 5 (9.3%) | 1 (2.4%) | <placebo | 0.34 |

*it is based on total number of subjects that recieved placebo or L-methylfolate 7.5 mg or 15 mg at some point during the trial.

Figure 3E:
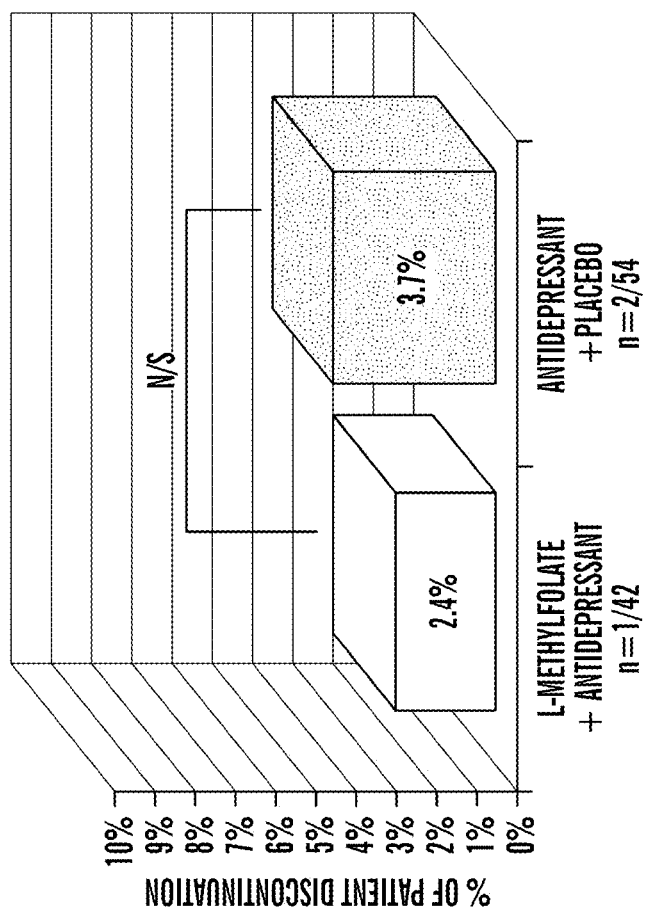

As shown in FIG. 3E, there is no difference in discontinuation from the study due to overall adverse side-effects or exclusion events. The patient administered with 6(S)-5-MTHF as an adjunct to his/her SSRI was removed from the trial due to mood elevation. The medical history of the patient indicated bipolar disorder which was not detected at the baseline visit.

Follow-Up Study

At the end of the double-blind study, both responders and non-responders who have completed the double-blind phase have the option of receiving free, open-label adjunctive treatment with 15 mg/day of 6(S)-5-MTHF for 12 months. Subjects who agree to receive open-label treatment with 6(S)-5-MTHF for 12 months are assessed every three (3) months until the end of the follow-up phase. During each visit, patients are administered the HAM-D-28, the CGI, the QIDS-SR, the SAFTEE-SI, the MGH-CPFQ, and the MGH-SFQ (See, e.g., Table 10 below). The dose of their concomitant SSRI can be adjusted during the 12 months of follow-up, as can the dose of 6(S)-5-MTHF (e.g., up to 15 mg twice a day). Subjects are also allowed to change their antidepressant during the course of the follow-up, if deemed appropriate. For patients who refuse the 12 months of free follow-up care, a referral to a psychiatrist is offered.

Table 10 shows that remitters at the end of double-blind phase who received adjunctive treatment with 15 mg/day of 6(S)-5-MTHF did not have a relapse during a 12-month maintenance phase.

TABLE 10

Follow-up results on remitters during the 12-month maintenance phase

| | Remitters at end of double-blind phase (HAM-D-17 < 8) entering maintenance phase | Relapsers (HAM-D-17 > 15) during 12-month maintenance phase, administered with 15 mg/day 6(S)-5-MTHF as an adjuvant |
|---|---|---|
| Trial 1 | 2 | 0 (1 subject had not relapsed at 9-month visit but did not return for 12-month visit) |
| Trial 2 | 9 | 0 |

Example 4

Identification of Biomarkers for Selecting Patients with Depression for a Treatment Comprising a Folate-Containing Compound in Combination with an SSRI A double-blind, placebo-controlled study of 6(S)-5-MTHF among SSRI resistant outpatients with major depressive disorder (MDD) is performed, as described in Examples 1-3, to identify genetic polymorphisms, peripheral biomarkers and/or clinical features that are associated with a greater efficacy response when a patient is administered with a folate-containing compound (e.g., 6(S)-5-MTHF) in addition to an antidepressant drug, e.g., an SSRI.

Figure 4A:
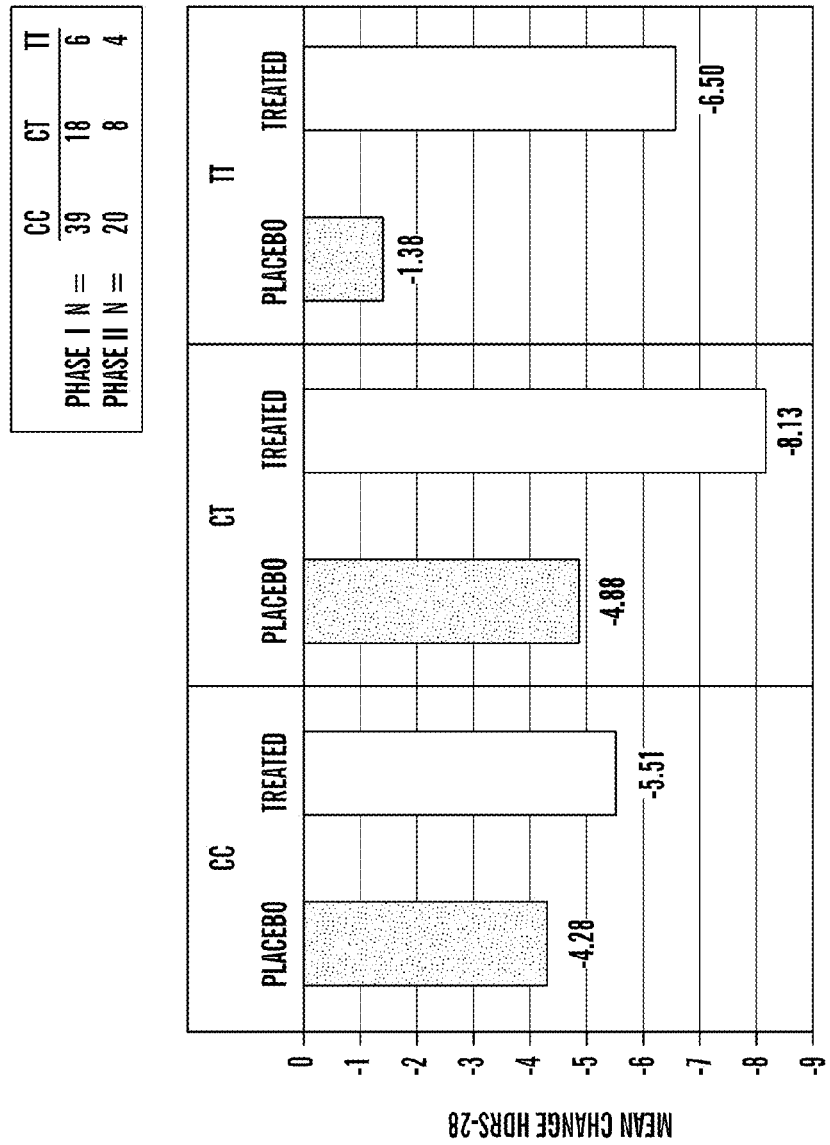
FIGS. 4A-4B show effects of a single genetic polymorphism (SNP) in the MTHFR gene (MTHFR C677T) on the efficacy of the treatment comprising a folate-containing compound (e.g., 6(S)-5-MTHF) and optionally an SSRI in a patient with depression.
Figure 4B:
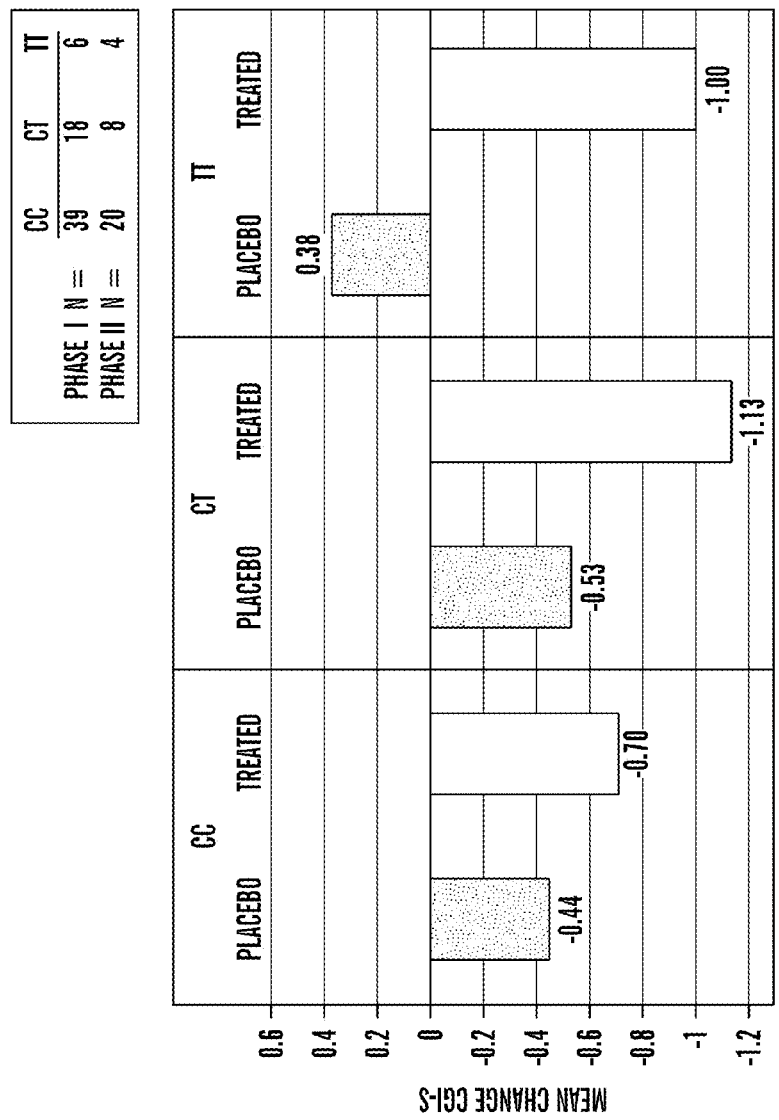

FIGS. 4A-4B show the effect of the single genetic polymorphism (SNP) at the MTHFR gene (MTHFR C677T) on the efficacy of the treatment comprising a folate-containing compound (e.g., 6(S)-5-MTHF) and an SSRI in a patient with depression, as measured by HDRS-28 (28-item Hamilton Depression Rating Scale) and CGI-S (Clinical Global Impression-Severity), respectively. The findings of FIGS. 4A-4B indicate that patients having at least one T allele (e.g., CT or TT) at the position 677 of the SEQ ID NO: 1, corresponding to a portion of the genomic sequence of the MTHFR gene, demonstrate a greater degree of improvement in the HDRS-28 or CGI-S test when they are treated with a folate-containing compound in combination with an SSRI, as compared to patients with no T allele detected at the position 677 of the SEQ ID NO: 1.

Figure 5A:
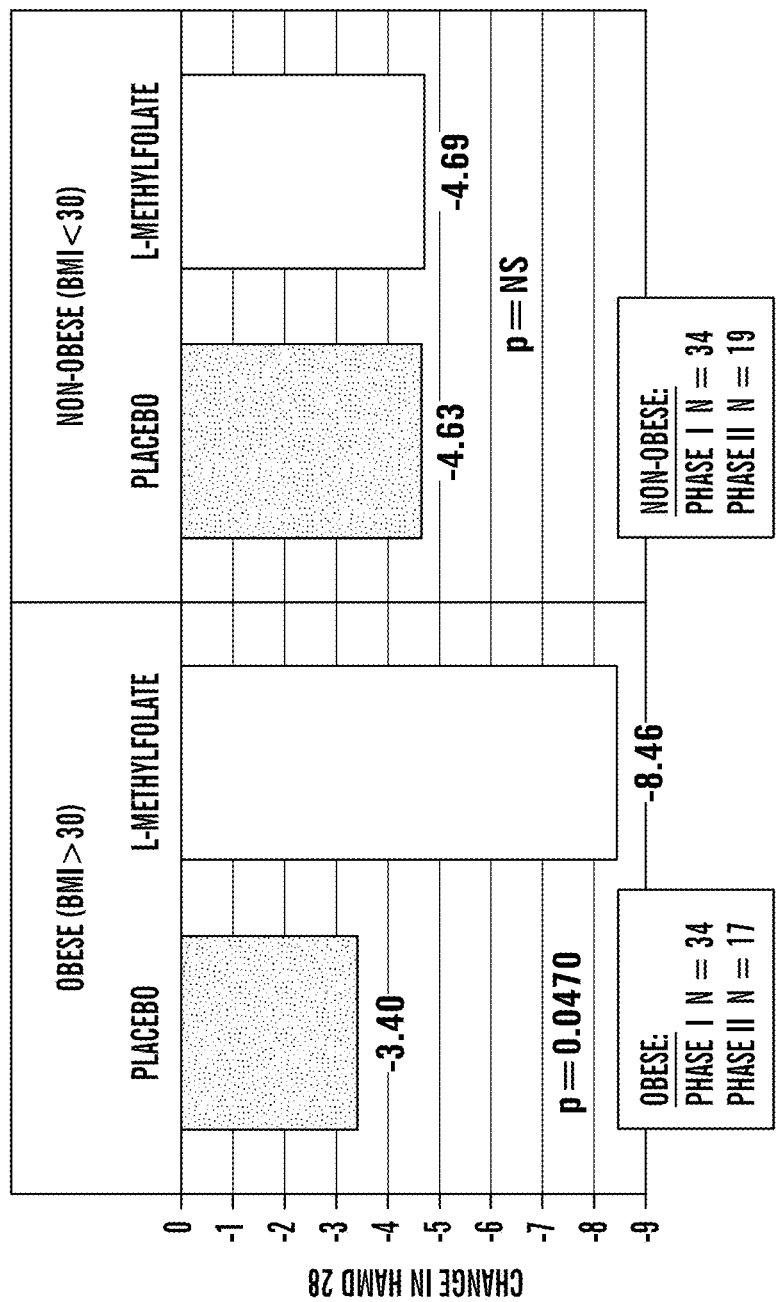
FIGS. 5A-5B show effects of obesity (i.e., BMI is at least 30 kg/m² or above) on the efficacy of the treatment comprising a folate-containing compound (e.g., 6(S)-5-MTHF) and optionally an SSRI in a patient with depression.
Figure 5B:
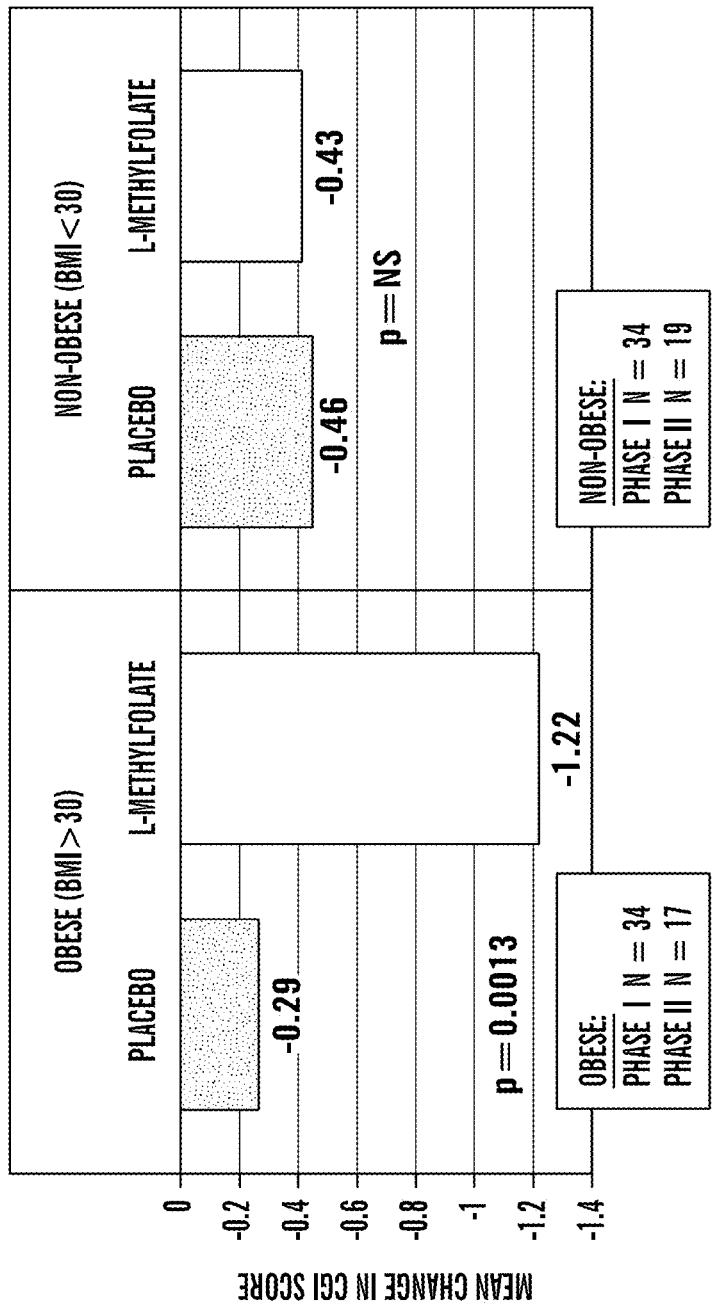
Figure 6:
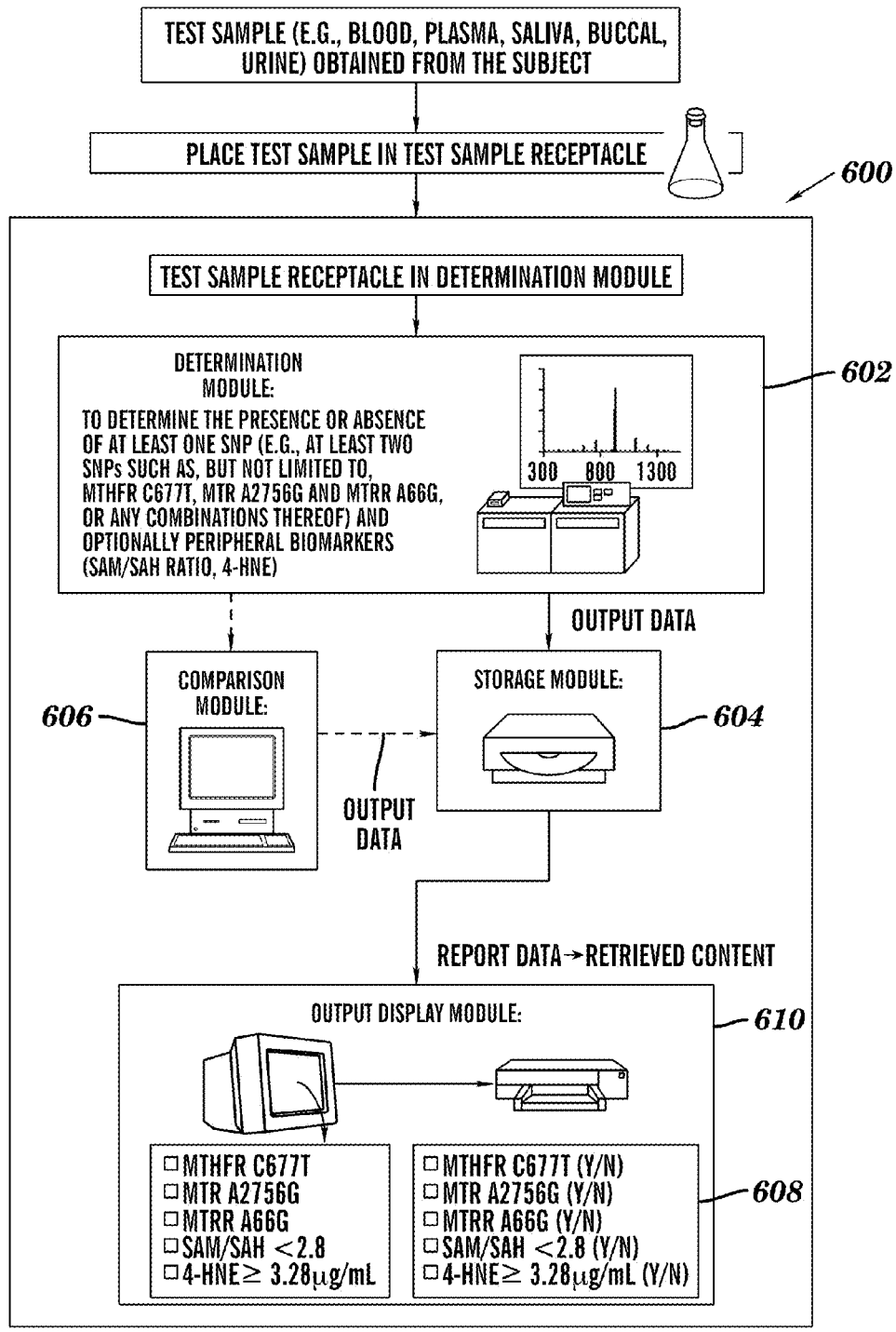
FIG. 6 is a block diagram showing an exemplary system for use in the methods described here, e.g., for selecting a treatment regimen for a subject with depression.
Figure 7:
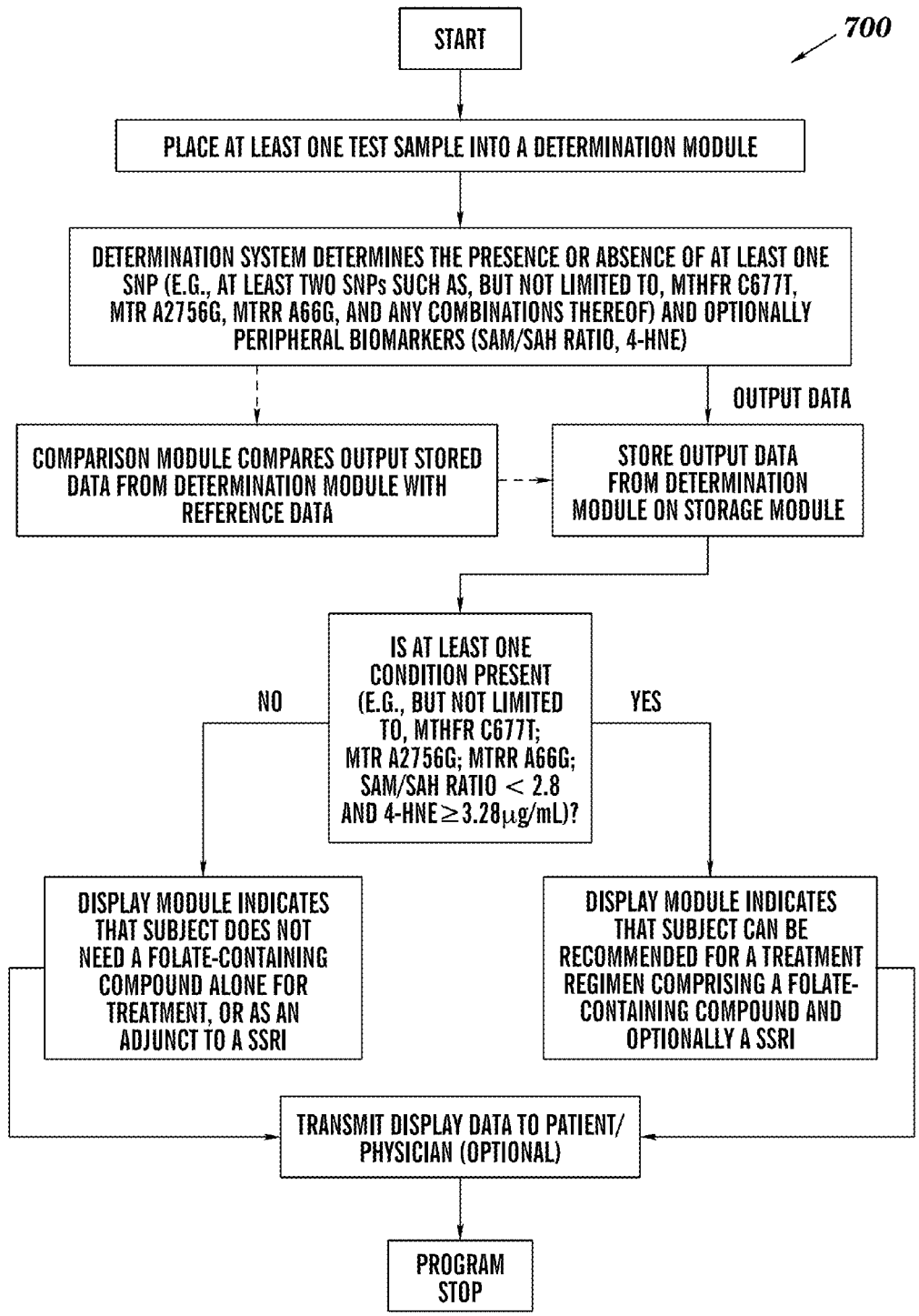
FIG. 7 is an exemplary set of instructions on a computer readable storage medium for use with the systems described herein.

FIGS. 5A-5B show the effect of obesity (i.e., BMI is at least 30 kg/m² or above) on the efficacy of the treatment comprising a folate-containing compound (e.g., 6(S)-5-MTHF) and an SSRI in a patient with depression, as measured by HAMD-28 (28-item Hamilton Depression Rating Scale) and CGI-S (Clinical Global Impression-Severity), respectively. The findings of FIGS. 5A-5B indicate that obese patients (i.e., with a BMI at least 30 kg/m² or above) demonstrate a greater degree of improvement in the HAMD-28 or CGI-S test when they are treated with a folate-containing compound in combination with an SSRI, as compared to non-obese patients.

Some exemplary predictors for greater efficacy response rates in patients receiving 6(S)-5-MTHF in combination with their respective SSRIs in combination with SSRIs, can include low plasma and/or RBC folate levels, low plasma B12 and SAM levels, low ratios of SAM/SAH levels, an elevated plasma homocysteine level, presence of folate receptor autoantibodies (FRAs), asymmetrical dimethylarginine (ADMA), malondialdehyde (MDA), 4-hydroxynonenal (4-HNE), high-sensitivity C-Reactive Protein (hs-CRP), F2-Isoprostanes (8-OH-Dg), brain derived neutropic factor (BDNF) levels, and the following genetic polymorphisms: a) T677C allele for the methylenetetrahydrofolate reductase (MTHFR); b) A1298C allele for the MTHFR gene; c) A66G allele for the methionine synthase reductase gene; and d) A2746G allele for the methionine synthase gene.

Various combinations of genetic and biomarkers were assessed for their effects on the efficacy of the treatment comprising a folate-containing compound (e.g., 6(S)-5-MTHF) and an SSRI in patients with depression. Particularly, specific genetic and biomarkers that were assessed include the following:

(a) BMI calculation of at least about 30 kg/m²;
(b) an expression ratio of SAM/SAH smaller than 2.8 (e.g., 2.71) as measured in a plasma sample;

(c) a level of 4-HNE no less than 3.28 mg/mL (as measured in a plasma sample);
(d) presence of rare variants CT or TT at position 677 of SEQ ID NO: 1 corresponding to a portion of a genomic nucleic acid sequence of methylenetetrahydrofolate reductase(MTHFR) (abbreviated as "MTHFR 677" below);
(e) presence of rare variants AG or GG at position 2756 of SEQ ID NO: 2 corresponding to a portion of genomic nucleic acid sequence of methionine synthase (MTR) (abbreviated as "MTR 2756" below); and
(f) presence of rare variants AG or GG at position 66 of SEQ ID NO: 3 corresponding to a portion of genomic nucleic acid sequence of methionine synthase reductase (MTRR) (abbreviated as "MTRR 66" below).

The results of how various combinations of the above conditions (a)-(f) affect the degree in improvement, as measured by HAMD-17 and HAMD-28 scores, when patients are treated with a folate-containing compound (e.g., 6(S)-5-MTHF) and an SSRI, are shown in Tables 11-36 below. The efficacy effect is determined by measuring the mean change in the HAMD-17 score and HAMD-28 score by the end of Phase I and Phase II, as compared to the baseline.

TABLE 11

Effect of at least one rare variant on both MTHFR 677 and MTR 2756, as opposed to fully normal on both, in MDD patients on the change in HAMD-17 and HAMD-28 scores, when the patients are treated with a folate-containing compound (e.g., 6(S)-5-MTHF) and an SSRI.

| | Phase I | | Phase II | | Pooled phases | | |
|---|---|---|---|---|---|---|---|
| | Effect | p-value | Effect | p-value | Effect | 95% CI | p-value |
| HAMD-17 | | | | | | | |
| MTHFR 677 CC and MTR 2756 AA (29, 13)* | −0.700 | 0.817 | −0.571 | 0.866 | 0.722 | (−2.694, 4.138) | 0.679 |
| MTHFR 677 CT or TT and MTR 2756 AG or GG (8, 4)* | −13.47 | 0.006 | −10.33 | 0.223 | −18.71 | (−24.33, −13.08) | <0.001 |
| HAMD-28 | | | | | | | |
| MTHFR 677 CC and MTR 2756 AA | −0.192 | 0.960 | 0.048 | 0.990 | 0.711 | (−3.121, 4.543) | 0.716 |
| MTHFR 677 CT or TT and MTR 2756 AG or GG | −18.00 | 0.008 | −13.00 | 0.167 | −23.29 | (−32.08, −14.50) | 0.001 |

*The numeric values within the parentheses correspond to the number of patients having the indicated condition

TABLE 12

Effect of at least one rare variant on both MTR 2756 and MTRR 66 and baseline BMI of at least 30 kg/m$^2$, as opposed to fully normal on both genes and baseline BMI less than 30 kg/m$^2$, in MDD patients on the change in HAMD-17 and HAMD-28 scores, when the patients are treated with a folate-containing compound (e.g., 6(S)-5-MTHF) and an SSRI.

| | Phase I | | Phase II | | Pooled phases | | |
|---|---|---|---|---|---|---|---|
| | Effect | p-value | Effect | p-value | Effect | 95% CI | p-value |
| HAMD-17 | | | | | | | |
| MTR 2756 AA and MTRR 66 AA and BMI < 30 kg/m$^2$ (7, 4) | All non-treated | | −4.333 | 0.510 | All non-treated | | |
| MTR 2756 AG or GG and MTRR 66 AG or GG and BMI >= 30 kg/m$^2$ (8, 4) | −13.667 | 0.029 | −11.000 | 0.064 | −10.972 | (−17.377, −4.568) | 0.001 |
| HAMD-28 | | | | | | | |
| MTR 2756 AA and MTRR 66 AA and BMI < 30 kg/m$^2$ | All non-treated | | −4.667 | 0.539 | All non-treated | | |
| MTR 2756 AG or GG and MTRR 66 AG or GG and BMI >= 30 kg/m$^2$ | −18.833 | 0.014 | −12.000 | 0.115 | −15.347 | (−22.967, −7.727) | 0.000 |

TABLE 13

Effect of at least one rare variant on MTR 2756 and baseline BMI of at least 30 kg/m², as opposed to fully normal on the gene and baseline BMI less than 30 kg/m², in MDD patients on the change in HAMD-17 and HAMD-28 scores, when the patients are treated with a folate-containing compound (e.g., 6(S)-5-MTHF) and an SSRI.

| | Phase I | | Phase II | | Pooled phases | | |
|---|---|---|---|---|---|---|---|
| | Effect | p-value | Effect | p-value | Effect | 95% CI | p-value |
| HAMD-17 | | | | | | | |
| MTR 2756 AA and BMI < 30 kg/m² (17, 7) | 4.476 | 0.225 | 1.167 | 0.776 | 3.196 | (−1.906, 8.298) | 0.220 |
| MTR 2756 AG or GG and BMI >= 30 kg/m² (10, 5) | −12.905 | 0.007 | −12.167 | 0.019 | −11.714 | (−15.859, −7.569) | 0.000 |
| HAMD-28 | | | | | | | |
| MTR 2756 AA and BMI < 30 kg/m² | 5.524 | 0.246 | 0.917 | 0.832 | 3.352 | (−2.692, 9.395) | 0.277 |
| MTR 2756 AG or GG and BMI >= 30 kg/m² | −18.762 | 0.002 | −13.000 | 0.036 | −14.433 | (−19.453, −9.414) | 0.000 |

TABLE 14

Effect of at least one rare variant on MTR 2756 and baseline SAM/SAH smaller than a pre-determined reference ratio (e.g., the median ratio of a reference group), as opposed to fully normal on the gene and the baseline SAM/SAH no less than the pre-determined reference ratio, in MDD patients on the change in HAMD-17 and HAMD-28 scores, when the patients are treated with a folate-containing compound (e.g., 6(S)-5-MTHF) and an SSRI.

| | Phase I | | Phase II | | Pooled phases | | |
|---|---|---|---|---|---|---|---|
| | Effect | p-value | Effect | p-value | Effect | 95% CI | p-value |
| HAMD-17 | | | | | | | |
| MTR 2756 AA and SAM/SAH >= median(24, 12) | −1.556 | 0.510 | 1.971 | 0.557 | 0.054 | (−3.764, 3.873) | 0.978 |
| MTR 2756 AG or GG and SAM/SAH < median (10, 4) | −9.800 | 0.007 | −2.500 | 0.598 | −5.583 | (−12.163, 0.998) | 0.096 |
| HAMD-28 | | | | | | | |
| MTR 2756 AA and SAM/SAH >= median | −1.278 | 0.662 | 2.000 | 0.581 | −0.071 | (−3.889, 3.747) | 0.971 |
| MTR 2756 AG or GG and SAM/SAH < median = 2.71 (as measured in a plasma sample) | −14.993 | 0.003 | −7.500 | 0.133 | −11.683 | (−17.836, −5.530) | 0.000 |

TABLE 15

Effect of at least one rare variant on both MTR 2756 and MTRR 66 in combination with baseline SAM/SAH smaller than a pre-determined reference ratio (e.g., the median ratio of a reference group), as opposed to fully normal on both genes in combination with the baseline SAM/SAH no less than the pre-determined reference ratio, in MDD patients on the change in HAMD-17 and HAMD-28 scores, when the patients are treated with a folate-containing compound (e.g., 6(S)-5-MTHF) and an SSRI.

| | Phase I | | Phase II | | Pooled phases | | |
|---|---|---|---|---|---|---|---|
| | Effect | p-value | Effect | p-value | Effect | 95% CI | p-value |
| HAMD-17 | | | | | | | |
| MTR 2756 AA and MTRR 66 AA and SAM/SAH >= median (6, 3) | −0.400 | 0.962 | −7.000 | 0.154 | −3.98* | (−8.03, 0.064) | 0.054 |
| MTR 2756 AG or GG and MTRR 66 AG or GG and SAM/SAH < median (8, 3) | −9.000 | 0.037 | −6.500 | 0.084 | −7.64* | (−11.93, −3.34) | <0.001 |

TABLE 15-continued

Effect of at least one rare variant on both MTR 2756 and MTRR 66 in combination with baseline SAM/SAH smaller than a pre-determined reference ratio (e.g., the median ratio of a reference group), as opposed to fully normal on both genes in combination with the baseline SAM/SAH no less than the pre-determined reference ratio, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
|---|---|---|---|---|---|---|---|
|  | Effect | p-value | Effect | p-value | Effect | 95% CI | p-value |
| HAMD-28 | | | | | | | |
| MTR 2756 AA and MTRR 66 AA and SAM/SAH >= median | −1.000 | 0.916 | −7.500 | 0.333 | −3.74* | (−8.60, 1.12) | 0.131 |
| MTR 2756 AG or GG and MTRR 66 AG or GG and SAM/SAH < median = 2.71 (as measured in a plasma sample) | −12.741 | 0.019 | −10.500 | 0.052 | −11.62* | (−16.14, −7.10) | <0.001 |

TABLE 16

Effect of at least one rare variant on both MTR 2756 and MTRR 66 in combination with baseline HNE-His (or 4-HNE) no less than a predetermined level (e.g., a median level of a reference group), as opposed to fully normal on both genes in combination with the baseline HNE-His smaller than the predetermined level, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
|---|---|---|---|---|---|---|---|
|  | Effect | p-value | Effect | p-value | Effect | 95% CI | p-value |
| HAMD-17 | | | | | | | |
| MTR 2756 AA and MTRR 66 AA and HNE-His < median (6, 4) | 3.000 | 0.750 | −8.667 | 0.532 | 0.466 | (−14.699, 15.630) | 0.952 |
| MTR 2756 AG or GG and MTRR 66 AG or GG and HNE-His >= median (10, 4) | −7.200 | 0.131 | −11.000 | 0.064 | −7.942 | (−14.328, −1.556) | 0.015 |
| HAMD-28 | | | | | | | |
| MTR 2756 AA and MTRR 66 AA and HNE-His < median = 3.28 (as measured in a plasma sample) | 4.200 | 0.735 | −9.000 | 0.500 | −2.221 | (−21.990, 17.549) | 0.826 |
| MTR 2756 AG or GG and MTRR 66 AG or GG and HNE-His >= median | −9.800 | 0.072 | −12.000 | 0.115 | −10.241 | (−17.365, −3.117) | 0.005 |

TABLE 17

Effect of at least one rare variant on both MTHFR 677 and baseline BMI of at least about 30 kg/m$^2$, as opposed to fully normal on the gene and the baseline BMI less than 30 kg/m$^2$, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
|---|---|---|---|---|---|---|---|
|  | Effect | p-value | Effect | p-value | Effect | 95% CI | p-value |
| HAMD-17 | | | | | | | |
| MTHFR 677 CC and BMI < 30 kg/m$^2$ (17, 8) | 4.500 | 0.360 | −2.267 | 0.480 | 1.356 | (−4.388, 7.100) | 0.644 |
| MTHFR 677 CT or TT | −8.738 | 0.009 | −7.333 | 0.129 | −8.090 | (−13.622, −2.558) | 0.004 |

TABLE 17-continued

Effect of at least one rare variant on both MTHFR 677 and baseline BMI of at least about 30 kg/m², as opposed to fully normal on the gene and the baseline BMI less than 30 kg/m², in MDD patients on the change in HAMD-17 and HAMD-28 scores, when the patients are treated with a folate-containing compound (e.g., 6(S)-5-MTHF) and an SSRI.

| | Phase I | | Phase II | | Pooled phases | | |
|---|---|---|---|---|---|---|---|
| | Effect | p-value | Effect | p-value | Effect | 95% CI | p-value |
| and BMI >= 30 kg/m² (13, 6) HAMD-28 | | | | | | | |
| MTHFR 677 CC and BMI < 30 kg/m² | 2.769 | 0.663 | −3.000 | 0.415 | −0.234 | (−7.217, 6.750) | 0.948 |
| MTHFR 677 CT or TT and BMI >= 30 kg/m² | −9.857 | 0.035 | −8.667 | 0.077 | −9.884 | (−15.794, −3.974) | 0.001 |

TABLE 18

Effect of at least one rare variant on both MTHFR 677 and baseline HNE-His (or 4-HNE) no less than a predetermined level (e.g., a median level of a reference group), as opposed to fully normal on the gene and the baseline HNE-His smaller than the predetermined level, in MDD patients on the change in HAMD-17 and HAMD-28 scores, when the patients are treated with a folate-containing compound (e.g., 6(S)-5-MTHF) and an SSRI.

| | Phase I | | Phase II | | Pooled phases | | |
|---|---|---|---|---|---|---|---|
| | Effect | p-value | Effect | p-value | Effect | 95% CI | p-value |
| HAMD-17 | | | | | | | |
| MTHFR 677 CC and HNE-His < median (20, 11) | −1.471 | 0.695 | −0.857 | 0.837 | −1.050 | (−5.914, 3.814) | 0.672 |
| MTHFR 677 CT or TT and HNE-His >= median (11, 6) | −7.143 | 0.050 | −7.500 | 0.215 | −9.446 | (−15.920, −2.972) | 0.004 |
| HAMD-28 | | | | | | | |
| MTHFR 677 CC and HNE-His < median = 3.28 (as measured in a plasma sample) | −2.821 | 0.559 | −0.536 | 0.908 | −1.340 | (−6.933, 4.253) | 0.639 |
| MTHFR 677 CT or TT and HNE-His >= median | −6.929 | 0.090 | −7.500 | 0.223 | −9.865 | (−16.200, −3.529) | 0.002 |

TABLE 19

Effect of at least one rare variant on both MTR 2756 and baseline HNE-His (or 4-HNE) no less than a predetermined level (e.g., a median level of a reference group), as opposed to fully normal on the gene and the baseline HNE-His smaller than the predetermined level, in MDD patients on the change in HAMD-17 and HAMD-28 scores, when the patients are treated with a folate-containing compound (e.g., 6(S)-5-MTHF) and an SSRI.

| | Phase I | | Phase II | | Pooled phases | | |
|---|---|---|---|---|---|---|---|
| | Effect | p-value | Effect | p-value | Effect | 95% CI | p-value |
| HAMD-17 | | | | | | | |
| MTR 2756 AA and HNE-His < median (26, 13) | 0.306 | 0.897 | 0.300 | 0.936 | 1.319 | (−2.257, 4.895) | 0.470 |
| MTR 2756 AG or GG and HNE-His >= median (13, 7) | −7.125 | 0.061 | −8.417 | 0.048 | −8.072 | (−12.314, −3.831) | 0.000 |
| HAMD-28 | | | | | | | |
| MTR 2756 AA and HNE-His < median | 0.639 | 0.835 | −0.125 | 0.975 | 2.085 | (−2.142, 6.312) | 0.334 |

TABLE 19-continued

Effect of at least one rare variant on both MTR 2756 and baseline HNE-His (or 4-HNE) no less than a predetermined level (e.g., a median level of a reference group), as opposed to fully normal on the gene and the baseline HNE-His smaller than the predetermined level, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
| --- | --- | --- | --- | --- | --- | --- | --- |
|  | Effect | p-value | Effect | p-value | Effect | 95% CI | p-value |
| MTR 2756 AG or GG and HNE-His >= median = 3.28 (as measured in a plasma sample) | −9.950 | 0.026 | −9.500 | 0.037 | −9.508 | (−13.855, −5.161) | 0.000 |

TABLE 20

Effect of baseline SAM/SAH ratio smaller than a pre-determined reference ratio (e.g., a median ratio of a reference group) and baseline HNE-His (or 4-HNE) level no less than a predetermined level (e.g., a median level of a reference group), as opposed to the baseline SAM/SAH ratio no less than the pre-determined reference ratio and the baseline HNE-His level smaller than the predetermined level, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
| --- | --- | --- | --- | --- | --- | --- | --- |
|  | Effect | p-value | Effect | p-value | Effect | 95% CI | p-value |
| HAMD-17 | | | | | | | |
| SAM/SAH >= median and HNE-His < median (18, 8) | −0.250 | 0.920 | 4.000 | 0.380 | 2.107 | (−2.851, 7.064) | 0.405 |
| SAM/SAH < median and HNE-His >= median (19, 7) | −3.670 | 0.139 | −9.000 | 0.031 | −9.898 | (−14.436, −5.361) | 0.000 |
| HAMD-28 | | | | | | | |
| SAM/SAH >= median and HNE-His < median | −0.750 | 0.822 | 4.500 | 0.388 | 2.413 | (−3.079, 7.906) | 0.389 |
| SAM/SAH < median and HNE-His >= median | −4.227 | 0.230 | −12.000 | 0.004 | −9.500 | (−13.164, −5.830) | 0.000 |

TABLE 21

Effect of at least one rare variant on MTR 2756 and MTRR 66, as opposed to fully normal on both genes, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
| --- | --- | --- | --- | --- | --- | --- | --- |
|  | Effect | p-value | Effect | p-value | Effect | 95% CI | p-value |
| HAMD-17 | | | | | | | |
| MTR 2756 AA and MTRR 66 AA (11, 5) | 3.125 | 0.555 | −8.000 | 0.451 | −1.373 | (−10.45, 7.705) | 0.767 |
| MTR 2756 AG or GG and MTRR 66 AG or GG (15, 7) | −6.900 | 0.091 | −4.667 | 0.338 | −6.976 | (−11.32, −2.638) | 0.002 |
| HAMD-28 | | | | | | | |
| MTR 2756 AA and MTRR 66 AA | 5.000 | 0.454 | −8.000 | 0.439 | −3.032 | (−13.50, 7.431) | 0.570 |
| MTR 2756 AG or GG and MTRR 66 AG or GG | −9.996 | 0.039 | −6.583 | 0.263 | −9.348 | (−13.01, −5.687) | 0.000 |

TABLE 22

Effect of at least one rare variant on MTR 2756, as opposed to fully normal on the gene, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
| --- | --- | --- | --- | --- | --- | --- | --- |
|  | Effect | p-value | Effect | p-value | Effect | 95% CI | p-value |
| HAMD-17 | | | | | | | |
| MTR 2756 AA (45, 21) | −0.621 | 0.736 | −0.427 | 0.869 | −0.590 | (−3.418, 2.238) | 0.683 |
| MTR 2756 AG/GG (20, 11) | −7.143 | 0.027 | −3.600 | 0.273 | −5.677 | (−9.422, −1.932) | 0.003 |
| HAMD-28 | | | | | | | |
| MTR 2756 AA | 0.409 | 0.859 | −0.446 | 0.869 | −0.047 | (−2.974, 2.879) | 0.975 |
| MTR 2756 AG/GG | −10.926 | 0.007 | −5.300 | 0.160 | −8.243 | (−12.549, −3.938) | 0.000 |

TABLE 23

Effect of baseline BMI of at least 30 kg/m² and baseline SAM/SAH ratio smaller than a pre-determined reference ratio (e.g., a median ratio of a reference group), as opposed to the baseline BMI smaller than 30 kg/m² and the baseline SAM/SAH ratio no less than the pre-determined reference ratio, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
| --- | --- | --- | --- | --- | --- | --- | --- |
|  | Effect | p-value | Effect | p-value | Effect | 95% CI | p-value |
| HAMD-17 | | | | | | | |
| BMI < 30 kg/m² and SAM/SAH >= median (16, 8) | 4.333 | 0.120 | 1.500 | 0.699 | 2.583 | (−2.224, 7.389) | 0.292 |
| BMI >= 30 kg/m² and SAM/SAH < median (21, 9) | −5.611 | 0.011 | −9.200 | 0.005 | −7.302 | (−10.404, −4.201) | 0.000 |
| HAMD-28 | | | | | | | |
| BMI < 30 kg/m² and SAM/SAH >= median | 4.333 | 0.215 | 2.500 | 0.596 | 2.906 | (−3.158, 8.970) | 0.348 |
| BMI >= 30 kg/m² and SAM/SAH < median = 2.71 (as measured in a plasma sample) | −6.306 | 0.049 | −10.350 | 0.005 | −7.572 | (−10.871, −4.274) | 0.000 |

TABLE 24

Effect of at least one rare variant on MTRR 66 and baseline HNE-His (or 4-HNE) level no less than a predetermined level (e.g., a median level of a reference group), as opposed to fully normal on the gene and the baseline HNE-His level smaller than the predetermined level, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
| --- | --- | --- | --- | --- | --- | --- | --- |
|  | Effect | p-value | Effect | p-value | Effect | 95% CI | p-value |
| HAMD-17 | | | | | | | |
| MTRR 66 AA and HNE-His < median (8, 5) | −1.167 | 0.844 | −1.667 | 0.866 | 2.575 | (−11.15, 16.30) | 0.713 |
| MTRR 66 AG or GG and HNE-His >= median (24, 11) | −5.958 | 0.018 | −3.500 | 0.322 | −4.850 | (−9.033, −0.667) | 0.023 |
| HAMD-28 | | | | | | | |
| MTRR 66 AA and HNE-His < median = 3.28 (as measured in a plasma sample) | −4.167 | 0.625 | −2.000 | 0.835 | −2.626 | (−17.80, 12.55) | 0.735 |

TABLE 24-continued

Effect of at least one rare variant on MTRR 66 and baseline HNE-His (or 4-HNE) level no less than a predetermined level (e.g., a median level of a reference group), as opposed to fully normal on the gene and the baseline HNE-His level smaller than the predetermined level, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
| --- | --- | --- | --- | --- | --- | --- | --- |
|  | Effect | p-value | Effect | p-value | Effect | 95% CI | p-value |
| MTRR 66 AG or GG and HNE-His >= median | −6.975 | 0.017 | −4.071 | 0.335 | −6.582 | (−10.895, −2.269) | 0.003 |

TABLE 25

Effect of at least one rare variant on MTRR 66 and baseline SAM/SAH smaller than a pre-determined reference ratio (e.g., a median ratio determined from a reference group), as opposed to fully normal on the gene and the baseline SAM/SAH ratio no less than the pre-determined reference ratio, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
| --- | --- | --- | --- | --- | --- | --- | --- |
|  | Effect | p-value | Effect | p-value | Effect | 95% CI | p-value |
| HAMD-17 | | | | | | | |
| MTRR 66 AA and SAM/SAH >= median (9, 6) | −0.125 | 0.984 | −3.000 | 0.554 | −2.978 | (−8.884, 2.928) | 0.323 |
| MTRR 66 AG or GG and SAM/SAH < median (24, 10) | −5.062 | 0.028 | −6.190 | 0.042 | −5.879 | (−9.272, −2.487) | 0.001 |
| HAMD-28 | | | | | | | |
| MTRR 66 AA and SAM/SAH >= median | 0.500 | 0.945 | −3.333 | 0.523 | −1.221 | (−7.023, 4.581) | 0.680 |
| MTRR 66 AG or GG and SAM/SAH < median = 2.71 (as measured in a plasma sample) | −6.498 | 0.031 | −7.381 | 0.022 | −6.579 | (−10.257, −2.901) | 0.000 |

TABLE 26

Effect of baseline BMI of at least about 30 kg/m$^2$ and baseline HNE-His (or 4-HNE) level no less than a predetermined level (e.g., a median level determined from a reference group), as opposed to the baseline BMI smaller than 30 kg/m$^2$ and the baseline HNE-His level smaller than the predetermined level, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
| --- | --- | --- | --- | --- | --- | --- | --- |
|  | Effect | p-value | Effect | p-value | Effect | 95% CI | p-value |
| HAMD-17 | | | | | | | |
| BMI < 30 kg/m$^2$ and HNE-His < median (19, 9) | 3.771 | 0.307 | 3.667 | 0.382 | 4.738 | (−0.935, 10.412) | 0.102 |
| BMI >= 30 kg/m$^2$ and HNE-His >= median (23, 11) | −6.569 | 0.012 | −4.233 | 0.242 | −5.420 | (−9.107, −1.732) | 0.004 |
| HAMD-28 | | | | | | | |
| BMI < 30 kg/m$^2$ and HNE-His < median | 4.606 | 0.335 | 1.833 | 0.708 | 4.253 | (−2.634, 11.139) | 0.226 |
| BMI >= 30 kg/m$^2$ and HNE-His >= median | −6.510 | 0.055 | −4.933 | 0.253 | −5.996 | (−9.831, −2.160) | 0.002 |

TABLE 27

Effect of baseline BMI of at least about 30 kg/m², as opposed to the baseline BMI smaller than 30 kg/m², in MDD patients on the change in HAMD-17 and HAMD-28 scores, when the patients are treated with a folate-containing compound (e.g., 6(S)-5-MTHF) and an SSRI. The phrase "BMI* treat" as used in Table 27 refers to interaction of BMI with the treatment.

| | Phase I | | Phase II | | Pooled phases | | |
|---|---|---|---|---|---|---|---|
| | Effect | p-value | Effect | p-value | Effect | 95% CI | p-value |
| HAMD-17 | | | | | | | |
| BMI < 25 (14, 7) | 1.576 | 0.666 | −1.400 | 0.761 | −1.248 | (−8.854, 6.359) | 0.748 |
| 25 =< BMI < 30 kg/m² (18, 10) | 2.600 | 0.473 | 2.000 | 0.559 | 3.331 | (−1.345, 8.001) | 0.163 |
| BMI >= 30 kg/m² (40, 21) | −6.414 | 0.000 | −3.009 | 0.231 | −4.600 | (−7.219, −1.981) | 0.001 |
| BMI*treat | −0.567 | 0.005 | 0.113 | 0.619 | −0.233 | (−0.502, 0.036) | 0.090 |
| HAMD-28 | | | | | | | |
| BMI < 25 (14, 7) | 0.909 | 0.857 | −2.300 | 0.681 | −1.018 | (−8.587, 6.552) | 0.792 |
| 25 =< BMI < 30 kg/m² (18, 10) | 2.602 | 0.559 | 0.000 | 1.000 | 2.054 | (−3.884, 7.992) | 0.498 |
| BMI >= 30 kg/m² (40, 21) | −6.677 | 0.005 | −3.245 | 0.262 | −4.660 | (−7.449, −1.871) | 0.001 |
| BMI*treat | −0.668 | 0.013 | 0.082 | 0.757 | −0.270 | (−0.581, 0.040) | 0.088 |

TABLE 28

Effect of baseline SAM/SAH ratio smaller than a pre-determined reference ratio (e.g., a median ratio determined from a reference group), as opposed to the baseline SAM/SAH ratio no less than the pre-determined reference ratio, in MDD patients on the change in HAMD-17 and HAMD-28 scores, when the patients are treated with a folate-containing compound (e.g., 6(S)-5-MTHF) and an SSRI. The phrases "baseHAMD-17* treat" and "SAM/SAH*treat" as used in Table 28 refer to interaction of base HAMD-17 and SAM/SAH, respectively, with the treatment.

| | Phase I | | Phase II | | Pooled phases | | |
|---|---|---|---|---|---|---|---|
| | Effect | p-value | Effect | p-value | Effect | 95% CI | p-value |
| HAMD17 | | | | | | | |
| baseHAMD-17*treat | 0.165 | 0.722 | −0.249 | 0.566 | −0.025 | (−0.553, 0.504) | 0.927 |
| SAM/SAH >= med (36, 21)* | −0.946 | 0.675 | 0.564 | 0.816 | −0.202 | (−3.111, 2.708) | 0.892 |
| SAM/SAH < med (37, 18) | −3.657 | 0.086 | −5.299 | 0.054 | −3.622 | (−6.730, −0.514) | 0.022 |
| SAM/SAH*treat | 0.495 | 0.755 | 1.483 | 0.298 | 0.882 | (−0.913, 2.677) | 0.335 |
| HAMD28 | | | | | | | |
| SAM/SAH*treat | 0.495 | 0.755 | 1.483 | 0.298 | 0.882 | (−0.913, 2.677) | 0.335 |
| SAM/SAH >= med = 2.71 (as measured in a plasma sample) | −1.148 | 0.681 | 1.355 | 0.634 | 0.073 | (−3.333, 3.480) | 0.966 |
| SAM/SAH < med | −4.523 | 0.113 | −7.325 | 0.014 | −4.572 | (−7.732, −1.413) | 0.005 |
| SAM/SAH*treat | 0.972 | 0.636 | 1.806 | 0.271 | 1.112 | (−0.927, 3.151) | 0.285 |

TABLE 29

Effect of baseline HNE-his (or 4-HNE) no less than a predetermined level (e.g., a median level determined from a reference group), as opposed to the baseline HNE-his smaller than the predetermined level, in MDD patients on the change in HAMD-17 and HAMD-28 scores, when the patients are treated with a folate-containing compound (e.g., 6(S)-5-MTHF) and an SSRI. The phrase "HNE-his*treat" as used in Table 29 refers to interaction of HNE-his with the treatment.

| | Phase I | | Phase II | | Pooled phases | | |
|---|---|---|---|---|---|---|---|
| | Effect | p-value | Effect | p-value | Effect | 95% CI | p-value |
| HAMD-17 | | | | | | | |
| HNE-his >= med (37, 20) | −4.349 | 0.048 | −4.030 | 0.086 | −4.175 | (−6.891, −1.459) | 0.003 |
| HNE-his < med (36, 19) | −1.407 | 0.532 | 0.631 | 0.824 | 0.260 | (−2.900, 3.421) | 0.872 |
| HNE-his *treat | −0.465 | 0.754 | 2.027 | 0.188 | 0.626 | (−1.197, 2.449) | 0.501 |

TABLE 29-continued

Effect of baseline HNE-his (or 4-HNE) no less than a predetermined level (e.g., a median level determined from a reference group), as opposed to the baseline HNE-his smaller than the predetermined level, in MDD patients on the change in HAMD-17 and HAMD-28 scores, when the patients are treated with a folate-containing compound (e.g., 6(S)-5-MTHF) and an SSRI. The phrase "HNE-his*treat" as used in Table 29 refers to interaction of HNE-his with the treatment.

| | Phase I | | Phase II | | Pooled phases | | |
|---|---|---|---|---|---|---|---|
| | Effect | p-value | Effect | p-value | Effect | 95% CI | p-value |
| HAMD-28 | | | | | | | |
| HNE-his >= med = 3.28 (as measured in a plasma sample) | −4.825 | 0.086 | −4.455 | 0.118 | −4.554 | (−7.610, −1.499) | 0.003 |
| HNE-his < med | −2.184 | 0.457 | −0.155 | 0.961 | −0.107 | (−3.670, 3.457) | 0.953 |
| HNE-his *treat | −0.133 | 0.945 | 2.362 | 0.184 | 0.685 | (−1.440, 2.810) | 0.527 |

TABLE 30

Effect of at least one rare variant on MTHFR 677 and MTR 2756 in combination with baseline HNE-His (or 4-HNE) no less than a predetermined level (e.g., a median level determined from a reference group), as opposed to fully normal on both genes in combination with the baseline HNE-His smaller than the predetermined level, in MDD patients on the change in HAMD-17 and HAMD-28 scores, when the patients are treated with a folate-containing compound (e.g., 6(S)-5-MTHF) and an SSRI.

| | Phase I | | Phase II | | Pooled phases | | |
|---|---|---|---|---|---|---|---|
| | Effect | p-value | Effect | p-value | Effect | 95% CI | p-value |
| HAMD-17 | | | | | | | |
| MTHFR 677 CC and MTR 2756 AA and HNE-His < median (17, 9) | −1.429 | 0.707 | −2.667 | 0.608 | −0.142 | (−5.972, 5.688) | 0.962 |
| MTHFR 677 CT or TT and MTR 2756 AG or GG and HNE-His > median (4, 2) | −14.500 | 0.066 | −16.0 | NA | | Not enough data | |
| HAMD-28 | | | | | | | |
| MTHFR 677 CC and MTR 2756 AA and HNE-His < median | −2.857 | 0.574 | −2.333 | 0.687 | −0.053 | (−6.980, 6.873) | 0.988 |
| MTHFR 677 CT or TT and MTR 2756 AG or GG and HNE-His > median | −16.000 | 0.084 | −17.0 | NA | | Not enough data | |

TABLE 31

Effect of at least one rare variant on MTHFR 677 and MTR 2756 in combination with baseline SAM/SAH ratio smaller than a pre-determined reference ratio (e.g., a median ratio determined from a reference group), as opposed to fully normal on both genes in combination with the baseline SAM/SAH ratio no less than the pre-determined reference ratio, in MDD patients on the change in HAMD-17 and HAMD-28 scores, when the patients are treated with a folate-containing compound (e.g., 6(S)-5-MTHF) and an SSRI.

| | Phase I | | Phase II | | Pooled phases | | |
|---|---|---|---|---|---|---|---|
| | Effect | p-value | Effect | p-value | Effect | 95% CI | p-value |
| HAMD-17 | | | | | | | |
| MTHFR 677 CC and MTR 2756 AA and SAM/SAH >= median (15, 8) | −6.429 | 0.284 | 4.000 | 0.346 | −0.830 | (−5.190, 3.530) | 0.709 |

TABLE 31-continued

Effect of at least one rare variant on MTHFR 677 and MTR 2756 in combination with baseline SAM/SAH ratio smaller than a pre-determined reference ratio (e.g., a median ratio determined from a reference group), as opposed to fully normal on both genes in combination with the baseline SAM/SAH ratio no less than the pre-determined reference ratio, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
|---|---|---|---|---|---|---|---|
|  | Effect | p-value | Effect | p-value | Effect | 95% CI | p-value |
| MTHFR 677 CT or TT and MTR 2756 AG or GG and SAM/SAH < median (4, 1) HAMD-28 | −12.667 | 0.070 | | | Not enough data | | |
| MTHFR 677 CC and MTR 2756 AA and SAM/SAH >= median | −12.643 | 0.084 | 4.500 | 0.349 | −4.472 | (−10.619, 1.676) | 0.154 |
| MTHFR 677 CT or TT and MTR 2756 AG or GG and SAM/SAH < median | −18.000 | 0.070 | | | Not enough data | | |

TABLE 32

Effect of at least one rare variant on MTHFR 677 and MTR 2756 in combination with baseline BMI of at least about 30 kg/m$^2$, as opposed to fully normal on both genes in combination with the baseline BMI smaller than 30 kg/m$^2$, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
|---|---|---|---|---|---|---|---|
|  | Effect | p-value | Effect | p-value | Effect | 95% CI | p-value |
| HAMD-17 | | | | | | | |
| MTHFR 677 CC and MTR 2756 AA and BMI < 30 kg/m$^2$ (10, 5) | All non-treated | | −4.000 | 0.470 | All non-treated | | |
| MTHFR 677 CT or TT and MTR 2756 AG or GG and BMI >= 30 kg/m$^2$ (5, 2) | −17.333 | 0.014 | −16.0 | NA | Not enough data | | |
| HAMD-28 | | | | | | | |
| MTHFR 677 CC and MTR 2756 AA and BMI < 30 kg/m$^2$ | All non-treated | | −4.000 | 0.544 | All non-treated | | |
| MTHFR 677 CT or TT and MTR 2756 AG or GG and BMI >= 30 kg/m | −23.500 | 0.021 | −17.0 | NA | Not enough data | | |

TABLE 33

Effect of at least one rare variant on MTRR 66 in combination with baseline BMI of at least about 30 kg/m$^2$, as opposed to fully normal on the gene in combination with the baseline BMI smaller than 30 kg/m$^2$, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
|---|---|---|---|---|---|---|---|
|  | Effect | p-value | Effect | p-value | Effect | 95% CI | p-value |
| HAMD-17 | | | | | | | |
| MTRR 66 AA and BMI < 30 kg/m$^2$ (10, 7) | all non-treated | | 0.000 | 1.000 | all non-treated | | |

TABLE 33-continued

Effect of at least one rare variant on MTRR 66 in combination with baseline BMI of at least about 30 kg/m², as opposed to fully normal on the gene in combination with the baseline BMI smaller than 30 kg/m², in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
|---|---|---|---|---|---|---|---|
|  | Effect | p-value | Effect | p-value | Effect | 95% CI | p-value |
| MTRR 66 AG or GG and BMI >= 30 kg/m² (29, 16) HAMD-28 | −7.065 | 0.001 | −2.048 | 0.498 | −4.912 | (−8.151, −1.674) | 0.003 |
| MTRR 66 AA and BMI < 30 kg/m² | all non-treated | | −0.600 | 0.919 | all non-treated | | |
| MTRR 66 AG or GG and BMI >= 30 kg/m² | −7.448 | 0.006 | −2.063 | 0.561 | −4.412 | (−7.852, −0.972) | 0.012 |

TABLE 34

Effect of at least one rare variant on MTHFR 677 and baseline SAM/SAH ratio smaller than a pre-determined reference ratio (e.g., a median ratio determined from a reference group), as opposed to fully normal on the MTHFR 677 and the baseline SAM/SAH ratio no less than the pre-determined reference ratio, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
|---|---|---|---|---|---|---|---|
|  | Effect | p-value | Effect | p-value | Effect | 95% CI | p-value |
| HAMD-17 | | | | | | | |
| MTHFR 677 CC and SAM/SAH >= median (21, 12) | 0.947 | 0.827 | 2.333 | 0.443 | 1.075 | (−3.250, 5.400) | 0.626 |
| MTHFR 677 CT or TT and SAM/SAH < median (11, 5) | −6.233 | 0.059 | 2.333 | 0.751 | −2.041 | (−11.186, 7.104) | 0.662 |
| HAMD-28 | | | | | | | |
| MTHFR 677 CC and SAM/SAH >= median | −2.158 | 0.666 | 2.833 | 0.428 | −0.764 | (−5.320, 3.791) | 0.742 |
| MTHFR 677 CT or TT and SAM/SAH < median | −7.867 | 0.078 | 0.000 | 1.000 | −3.533 | (−11.408, 4.341) | 0.379 |

TABLE 35

Effect of at least one rare variant on both MTHFR 677 and MTRR 66, as opposed to fully normal on both, in MDD patients on the change in HAMD-17 and HAMD-28 scores, when the patients are treated with a folate-containing compound (e.g., 6(S)-5-MTHF) and an SSRI.

|  | Phase I | | Phase II | | Pooled phases | | |
|---|---|---|---|---|---|---|---|
|  | Effect | p-value | Effect | p-value | Effect | 95% CI | p-value |
| HAMD-17 | | | | | | | |
| MTHFR 677 CC and MTRR 66 AA (10, 5) | 3.750 | 0.579 | −12.25 | 0.116 | −8.281 | (−18.82, 2.262) | 0.124 |
| MTHFR 677 CT or TT and MTRR 66 AG or GG (18, 8) | −5.550 | 0.053 | −5.250 | 0.069 | −5.648 | (−9.477, −1.818) | 0.004 |
| HAMD-28 | | | | | | | |
| MTHFR 677 CC and MTRR 66 AA | 5.500 | 0.521 | −13.00 | 0.047 | −9.379 | (−21.55, 2.789) | 0.131 |
| MTHFR 677 CT or TT | −5.275 | 0.141 | −7.500 | 0.025 | −6.264 | (−10.36, −2.167) | 0.003 |

TABLE 35-continued

Effect of at least one rare variant on both MTHFR 677 and MTRR 66, as opposed to fully normal on both, in MDD patients on the change in HAMD-17 and HAMD-28 scores, when the patients are treated with a folate-containing compound (e.g., 6(S)-5-MTHF) and an SSRI.

| | Phase I | | Phase II | | Pooled phases | | |
|---|---|---|---|---|---|---|---|
| | Effect | p-value | Effect | p-value | Effect | 95% CI | p-value |
| and MTRR 66 AG or GG | | | | | | | |

TABLE 36

Overall results combining all conditions from (a)-(f), when patients are treated with a folate-containing compound (e.g., 6(S)-5-MTHF) and an SSRI.

| | Phase I | | Phase II | | Pooled phases | | |
|---|---|---|---|---|---|---|---|
| | Effect | p-value | Effect | p-value | Effect | 95% CI | p-value |
| HAMD-17 | | | | | | | |
| All Patients | −2.978 | 0.056 | −2.111 | 0.235 | −2.264 | (−4.292, −0.236) | 0.029 |
| HAMD-28 | | | | | | | |
| All Patients | −3.632 | 0.069 | −2.706 | 0.187 | −2.738 | (−4.995, −0.482) | 0.017 |

TABLE 37

Summary of results from Tables 11-19 and 36.

| | | | Combinations Of Trial 2 Population Priority Combinations | | | | | | | | | |
|---|---|---|---|---|---|---|---|---|---|---|---|---|
| | | | 0 | 1 | 2 | 3 | 4 | 5 | 6 | 7 | 8 | 9 |
| | | | | | | | Variable Combinations | | | | | |
| Code | Variable | % Trial 2 Population | OVERALL N = 73 | D + E N = 4 | A + E + F N = 4 | A + E N = 5 | B + E N = 6 | B + E + F N = 5 | C + E + F N = 4 | A + D N = 9 | C + D N = 8 | C + E N = 9 |
| A | BMI > 30 | 55% | NA | NA | 55% | 55% | NA | NA | NA | 55% | NA | NA |
| B | LOW SAM/SAH RATIO | 51% | NA | NA | NA | NA | 51% | 51% | NA | NA | NA | NA |
| C | HIGH 4-HNE | 51% | NA | NA | NA | NA | NA | NA | 51% | NA | 51% & | 51% & |
| D | MTHFR 677 CT/TT | 49% | NA | 49% & | NA | NA | NA | NA | NA | 49% | 49% | NA & |
| E | MTR 2756 AG/GG | 34% | NA | 34% | 34% & | 34% | 34% | 34% | 34% & | NA | NA | 34% |
| F | MTRR 66 AG/GG | 74% | NA | NA | 74% | NA | NA | 74% | 74% | NA | NA | NA |
| | COMBINATION % | | 100% | 17% | 14% | 19% | 17% | 13% | 13% | 27% | 25% | 17% |
| | Pooled Effect Size | HAMD-28 | −2.738 | −23.290 | −15.347 | −14.433 | −11.683 | −11.620 | −10.241 | −9.884 | −9.865 | −9.508 |
| | Pooled p-value | HAMD-28 | 0.017 | <0.001 | <0.001 | <0.001 | <0.001 | <0.001 | 0.005 | 0.001 | 0.002 | <0.001 |
| | Pooled Effect Size | HAMD-17 | −2.264 | −18.710 | −10.972 | −11.714 | −5.583 | −7.640 | −7.942 | −8.090 | −9.446 | −8.072 |
| | Pooled p-value | HAMD-17 | 0.029 | <0.001 | 0.001 | <0.001 | 0.096 | <0.001 | 0.015 | 0.004 | 0.004 | <0.001 |

TABLE 38

Summary of results from Tables 20-29.

| | | | Combinations of Trial 2 Population Priority Combinations | | | | | | | | | |
|---|---|---|---|---|---|---|---|---|---|---|---|---|
| | | | 10 | 11 | 12 | 13 | 14 | 15 | 16 | 17 | 18 | 19 |
| | | | | | | | Variable Combinations | | | | | |
| Code | Variable | % Trial 2 Population | B + C N = 11 | E + F N = 8 | E N = 11 | A + B N = 13 | C + F N = 15 | B + F N = 11 | A + C N = 12 | A N = 21 | B N = 18 | C N = 21 |
| A | BMI > 30 | 55% | NA | NA | NA | 55% & | NA | NA | 55% | 55% | NA | NA |
| B | LOW SAM/SAH RATIO | 51% | 51% & | NA | NA | 51% | NA | 51% | NA | NA | 51% | NA |

TABLE 38-continued

Summary of results from Tables 20-29.

| | | | Combinations of Trial 2 Population Priority Combinations | | | | | | | | |
|---|---|---|---|---|---|---|---|---|---|---|---|
| | | | 10 | 11 | 12 | 13 | 14 | 15 | 16 | 17 | 18 | 19 |
| | | | | | | Variable Combinations | | | | | | |
| Code | Variable | % Trial 2 Population | B + C N = 11 | E + F N = 8 | E N = 11 | A + B N = 13 | C + F N = 15 | B + F N = 11 | A + C N = 12 | A N = 21 | B N = 18 | C N = 21 |
| C | HIGH 4-HNE | 51% | 51% | NA | NA | NA | 51% | NA | 51% | NA | NA | 51% |
| D | MTHFR 677 CT/TT | 49% | NA | NA | NA | NA | NA | NA | NA | NA | NA | NA |
| E | MTR 2756 AG/GG | 34% | NA | 34% & | 34% | NA | NA & | NA & | NA | NA | NA | NA |
| F | MTRR 66 AG/GG | 74% | NA | 74% | NA | NA | 74% | 74% | NA | NA | NA | NA |
| | COMBINATION % | | 26% | 25% | 34% | 28% | 38% | 38% | 28% | 55% | 51% | 51% |
| | Pooled Effect Size | HAMD-28 | 9.500 | −9.348 | −8.243 | −7.572 | −6.582 | −6.879 | −5.996 | −4.660 | −4.572 | 4.554 |
| | Pooled p-value | HAMD-28 | <0.001 | <0.001 | <0.001 | <0.001 | 0.003 | <0.001 | 0.002 | 0.001 | 0.005 | 0.003 |
| | Pooled Effect Size | HAMD-17 | −9.898 | −6.976 | −5.677 | −7.302 | −4.850 | −5.879 | −5.420 | −4.600 | −3.622 | −4.175 |
| | Pooled p-value | HAMD-17 | <0.001 | 0.002 | 0.003 | <0.001 | 0.023 | 0.001 | 0.004 | 0.001 | 0.022 | 0.003 |

In addition to using HAMD-17 or HAMD-28 scales to evaluate the effects, other scales such as social functioning questionnaire (SFQ), visual analogue scale (VAS), cognitive and physical function questionnaire (CPFQ), Maier, and HAMD-7 subscales of HAMD were also used to analyze the effects and the results are shown in FIGS. 9A-9C and FIGS. 10A-10E.

Additional SNP biomarkers were also evaluated for their effects on change in HAMD-28 in MDD patients with at least one rare variant as indicated below as opposed to fully normal on the gene, when they were treated with a folate-containing compound (e.g., 6(S)-5-MTHF) and an SSRI. While Table 39 lists individual SNP biomarkers in an order of their decreasing effects in MDD patients (i.e., a SNP marker with a greater reduction in HAMD-28 is listed earlier in the table), it should not be construed as one SNP biomarker is more preferable than another one for use in the assays, methods, systems, and kits described herein, as all these SNP biomarkers have indicated a significant change in HAMD-28 when a MDD patient carrying at least one indicated rare variant was treated with a folate-containing compound, as compared to a MDD patient carrying normal alleles on the gene. In some embodiments, a certain combination of any SNP markers individually with low effect priority can produce a synergistic effect and/or even yield a better predictive power than a single SNP marker with higher effect priority.

Table 39, as shown on the next page, indicates effects of the presence of at least one rare variant in an indicated SNP biomarker, as opposed to fully normal on the gene, in MDD patients on the change in HAMD-28 score, when the patients were treated with a folate-containing compound (e.g., 6(S)-5-MTHF) and an SSRI.

| EFFECT PRIORITY | GENE | HAMD-28 | PHASE I | | PHASE II | | POOLED PHASES | | |
|---|---|---|---|---|---|---|---|---|---|
| | | | EFFECT | p-Value | EFFECT | p-Value | EFFECT | 95% CI | p-Value |
| 1 | COMT (Val 158 Met) rs4680 (GG) | 33 (17, 9) | −12.070 | 0.008 | −10.170 | 0.019 | −10.880 | (−16.700, −4.990) | 0.000 |
| 2 | COMT (Val 158 rs4633 (CC) | 22 (18, 9) | −10.070 | 0.012 | −10.170 | 0.019 | −9.240 | (−14.330, −4.146) | 0.000 |
| 3 | RCF1 (in SLC19A1) rs1051266 (AA) | 44 (11, 6) | −10.000 | 0.081 | −2.750 | 0.316 | −7.673 | (−12.660, −2.090) | 0.003 |
| 4 | DRD2 (H313H) rs6275 (TT) | 11 (10, 5) | −16.560 | 0.144 | 1.667 | 0.728 | −7.627 | (−14.440, −0.814) | 0.028 |
| 5 | DRD2 (Taq1Br) rs1079596 (TC) | 42 (18, 11) 42/44 (18, 11) | −10.640 −10.640 | 0.018 0.018 | −3.893 −3.893 | 0.391 0.391 | −6.903 −6.903 | (−11.260, −2.549) (−11.260, −2.549) | 0.002 0.002 |
| 6 | DNMT3B rs1883729 (AG) | 11 (13, 8) 13 (19, 10) 11/13 (32, 18) | −2.318 −8.097 −6.340 | 0.662 0.038 0.035 | −5.267 −4.667 −4.940 | 0.092 0.335 0.080 | −4.811 −6.748 −5.360 | (−8.908, −0.714) (−10.410, −3.085) (−8.000, −2.720) | 0.021 0.000 0.000 |
| 7 | PCYT1A rs7639752 (AA) | 11 (12, 7) | −10.400 | 0.083 | −3.900 | 0.576 | −6.716 | (−13.770, 0.340) | 0.062 |
| 8 | GCH1 rs8007267 (TC) | 42 (22, 10) | −7.729 | 0.063 | −5.417 | 0.204 | −6.654 | (−10.720, −2.589) | 0.001 |
| 9 | MTHFR G1793A rs2274976 (GA) | 42 (19, 5) | −5.333 | 0.353 | 2.833 | 0.700 | −5.551 | (−11.590, −4.486) | 0.072 |
| 10 | RCF1 A > G rs2297291 (AA) | 11 (12, 7) | −8.778 | 0.049 | −1.400 | 0.667 | −5.458 | (−10.060, −0.857) | 0.020 |
| 11 | GCPH or FOLH1 rs202676 (AG) | 31 (23, 9) | −7.314 | 0.045 | −3.300 | 0.545 | −5.402 | (−9.972, −0.833) | 0.020 |
| 12 | DAT (SLC6A3) rs250682 (CG) | 33 (33, 15) | −5.722 | 0.072 | −5.768 | 0.064 | −4.996 | (−8.003, −1.929) | 0.001 |
| 13 | GCHFR rs7163862 (TA) | 41 (37, 20) | −6.280 | 0.008 | −4.542 | 0.126 | −4.863 | (−7.800, −1.926) | 0.001 |

-continued

| EFFECT PRIORITY | GENE | HAMD-28 | PHASE I EFFFCT | p-Value | PHASE II EFFFCT | p-Value | POOLED PHASES EFFFCT | 95% CI | p-Value |
|---|---|---|---|---|---|---|---|---|---|
| 14 | RCF2 (in SLC19A1) rs12659 (TT) | 11 (10, 7) | −7.571 | 0.110 | −1.400 | 0.667 | −4.860 | (−9.398, −0.857) | 0.036 |
| 15 | CACNA1C rs1006737 (AG) | 13 (30, 16) | −8.006 | 0.007 | −2.467 | 0.505 | −4.633 | (−8.32000, −0.946) | 0.014 |
| 16 | FDRC rs2277820 (TC) | 22 (30, 15) | −2.634 | 0.433 | −6.232 | 0.068 | −4.027 | (−7.718, −0.336) | 0.032 |
| 17 | DRD2 (SLC26A9) rs11240594 (AG) | 33 (36, 20) | −5.018 | 0.109 | −3.424 | 0.238 | −3.758 | (−6.981, −0.535) | 0.022 |
| 18 | MTHFD 1 G1958A (R653Q) rs2236225 (AG) | 33 (28, 16) | −2.742 | 0.322 | −3.762 | 0.262 | −3.496 | (−6.775, −0.217) | 0.037 |

Example 5

Exemplary Methods of Selecting Patients for Folate-Containing Augmentation Therapy (with an SSRI) and Personalized Prognosis of MDD Patients Subjected to Such Therapy Based upon the double-blind placebo controlled multi-site study on augmentation of MDD treatment with a folate-containing compound, e.g., DEPLIN®15, in which 36 patients received a folate-containing compound, e.g., DEPLIN® 15, that had a reduction in their HAMD-28 from the baseline measurement, the patients diagnosed with at least one of the conditions as described in the Panel of Tests (PT) with the corresponding "Values" (as shown in detail later), generally responded in accordance with the expected HAMD-28-reduction as shown in Table 40 below.

Accordingly, methods of treating a MMD patient and/or determining or improving the effectiveness of an anti-depressant drug taken by the MMD patient are also provided herein. For example, in some embodiments, the method can include (1) screening for a treatment resistant MDD patient (see, e.g., Step 1 for details below); and (2) performing the Panel of Tests (PT) on a test sample of the MDD patient (see, e.g., Step 2 for details below). In some embodiments, if the PT results show at least one of the Code grouping as shown in Table 40 below, the patient can be recommended for a treatment regimen comprising an anti-depressant drug and a folate-containing compound (e.g., DEPLIN® 15). In some embodiments, if the PT results show at least one of the Code grouping as shown in Table 40 below, it can be expected that the corresponding reduction in HAMD-28 from the Baseline value (e.g., the value measured at the Baseline visit) would be achievable with a minimum of 4 weeks of treatment with a folate-containing compound (e.g., DEPLIN® 15) in combination with an antidepressant drug (e.g., an SSRI).

Step 1:

Treatment-resistant MDD patients are screened to determine (a) if they meet DSM-IV criteria for MDD; and (b) if they are on an adequate dose of an SSRI and have not adequately responded to one or more courses of an SSRI. Should the patient meet both of the screen criteria (a) and (b) then it is recommended that the physician order the panel of test (PT) as described below.

Step 2:

An example of a panel of test (PT) as shown below can be performed.

| Code | Panel Of Tests | Sample | Value | Decision | |
|---|---|---|---|---|---|
| A | BMI Calculation | Height & Weight | ≥30 kg/m$^2$ | Y | N |
| B | SAM/SAH Ratio | Plasma (nmol/L) | <2.71 | Y | N |
| C | 4-HNE | Plasma | ≥3.28 µg/mL | Y | N |
| D | MTHFR 677 CT/TT | Whole Blood | Yes/No | Y | N |
| E | MTR 2756 AG/GG | Whole Blood | Yes/No | Y | N |
| F | MTRR 66 AG/GG | Whole Blood | Yes/No | Y | N |

The panel of test (PT) as shown above can be modified to delete or add at least one or any combinations of the biomarkers as shown in Tables 41A-41B enclosed herein.

Step 3: Based on the test results of the conditions listed in PT of step (2), any of the PTs (items A through F) tested positive (i.e., with a decision Y) are identified, and then recorded in alphabetical order of the "Codes" the greatest number of Codes that are represented in Table 40 below. Once the Code grouping has been selected for a given patient's PT, the corresponding "95% CI" (95% Confidence Intervals) for that Code grouping can be reviewed from Table 40. In some embodiments, if the upper end of the CI is below zero, the HAMD-28 reduction from the Baseline value is likely to be significant. In other embodiments, if the upper end of the CI is above zero, then the HAMD-28 reduction from the Baseline value should be interpreted with caution.

Step 4:

The expected reduction in HAMD-28 from Baseline can be determined, for example, as follows:

(a) If a patient has only a single hit of the PT (i.e., one condition is positive), then the HAMD-28 reduction from Baseline can be based upon the Code "All"; or (b) If a patient has a double hit of the PT (i.e., two conditions are positive), then the HAMD-28 reduction from Baseline can be based upon the highest response (i.e., greatest change in HAM-D-28) obtained from either A, B, C, E or "ALL" as shown in Table 40. In some embodiments, if the double hit is "D+F," then the reduction can be based upon Code "All";

(c) If a patient has a triple hit of the PT (i.e., three conditions are positive), then the HAMD-28 reduction from Baseline can be based upon the highest response (i.e., greatest change in HAM-D-28) obtained from the best combination (i.e., the best of 2-code combinations) as shown in Table 40. By way of example only, if a patient has a triple hit on A, C and E of the PT, possible 2-code combinations are A+C, A+E and C+E. Among these combinations, as the combination "A+E" corresponds to the greatest HAMD-28 reduction as shown in Table 40, the combination "A+E" is considered as the best combination that corresponds to the greatest HAMD-28 reduction. However, if the triple hit contains "D+F," then the HAM-D-28 reduction should be based upon the highest response obtained from the single Codes of A, B, C, E or "ALL";

(d) The negative HAMDΔ numbers in Table 40 reflect the potential reduction from Trial 2 Baseline HAMD-28 (24.47). The HAMDΔ number represents the expected reduction in a HAMD-28 scale a patient can obtain in response to Deplin® 15 augmentation therapy (with an SSRI) in as little as 4 weeks. In some embodiments, the actual reduction can fall anywhere within the 95% as shown in Table 40 below.

TABLE 40

The expected HAMD-28 reduction based upon Trial 2's mean Baseline of 24.47 per various Code combinations.

| CODE | "N" | 95% CI | HAMDΔ |
|---|---|---|---|
| ALL | 36 | (−20.8, 7.2) | −6.8 |
| A | 21 | (−23.0, 8.2) | −7.4 |
| B | 16 | (−25.3, 6.7) | −9.3 |
| C | 21 | (−20.2, 7.5) | −6.4 |
| E | 11 | (−28.3, 7.6) | −10.3 |
| A + B | 13 | (−27.0, 7.8) | −9.6 |
| A + C | 12 | (−20.3, 7.2) | −6.6 |
| A + D | 9 | (−30.2, 6.9) | −11.7 |
| A + E | 5 | (−35.7, 0.5) | −17.6 |
| B + C | 11 | (−21.3, 5.4) | −7.9 |
| B + E | 6 | (−32.2, −2.1) | −17.2 |
| B + F | 11 | (−24.5, 3.0) | −10.8 |
| C + D | 8 | (−27.2, 9.4) | −8.9 |
| C + E | 9 | (−25.3, 9.3) | −8.0 |
| C + F | 15 | (−23.4, 8.4) | −7.5 |
| D + E | 4 | (−34.3, −10.6) | −22.5 |
| E + F | 8 | (−26.7, 9.2) | −8.7 |

REFERENCES

1. V. Herbert, Experimental nutritional folate deficiency in man. Trans Assoc Am Phys 75 (1961), p. 307.
2. M. W. P. Carney, Serum folate values in 423 psychiatric patients. Br Med J 4 (1967), p. 512.
3. E. H. Reynolds, J. M. Preece, J. Bailey and A. Coppen, Folate deficiency in depressive illness. Br J Psychiatry 117 (1970), p. 287.
4. S. D. Shorvon, M. W. P. Carney, I. Chanarin and E. H. Reynolds, The neuropsychiatry of megaloblastic anaemia. Br Med J 281 (1980), p. 1036.
5. MRC Vitamin Study Research Group, Prevention of neural tube defects: results of the Medical Research Council Vitamin Study. Lancet 338 (1991), p. 131.
6. E. B. Rimm, W. C. Willett, F. B. Hu et al., Folate and vitamin B6 from diet and supplements in relation to risk of coronary heart disease among women. JAMA 279 (1998), p. 359.
7. D. Mischoulon, Herbal remedies for mental illness. Psychiatr Clin North Am Annu Drug Ther 6 (1999), p. 1.
8. A. Fugh-Berman and J. M. Cott, Dietary supplements and natural products as psychotherapeutic agents. Psychosom Med 61 (1999), p. 712.
9. American Psychiatric Association. Diagnostic and statistical manual of mental disorders, 4th ed. Washington, D.C.: American Psychiatric Association, 1994.
10. T. Bottiglieri, Folate, vitamin B12, and neuropsychiatric disorders. Nutr Rev 54 (1997), p. 382.
11. J. E. Alpert and M. Fava, Nutrition and depression: the role of folate. Nutr Rev 55 (1997), p. 145.
12. B. R. Hutto, Folate and cobalamin in psychiatric illness. Compr Psychiatry 38 (1997), p. 305.
13. M. I. Botez, T. Botez, J. Leveille, P. Bielmann and M. Cadotte, Neurological correlates of folic acid deficiency: facts and hypotheses. In: M. I. Botez and E. H. Reynolds, Editors, Folic acid in neurology, psychiatry and internal medicine, Raven Press, New York (1979), p. 435.
14. E. H. Reynolds, Anticonvulsant drugs, folate metabolism and mental symptoms. In: M. Dam, L. Gram and J. K. Penry, Editors, Advances in epileptology. XIIth Epilepsy International Symposium, Raven Press, New York (1981), p. 621.
15. J. Edeh and B. K. Toone, Antiepileptic therapy, folate deficiency, and psychiatric morbidity: a general practice survey. Epilepsia 26 (1985), p. 434.
16. S. D. Shorvon, M. W. P. Carney, I. Chanarin and E. H. Reynolds, The neuropsychiatry of megaloblastic anemia. Br Med J 281 (1980), p. 1036.
17. S. N. Young and M. Ghadirian, Folic acid and psychopathology. Prog Neuropsychopharmacol Biol Psychiatry 13 (1989), p. 841.
18. R. Crellin, T. Bottiglieri and E. H. Reynolds, Folates and psychiatric disorders: clinical potential. Drugs 45 (1993), p. 623.
19. A. M. Ghadirian, J. Anath and F. Engelsmann, Folic acid deficiency in depression. Psychosomatics 21 (1980), p. 926.
20. M. W. P. Carney, T. K. N. Chary, M. Laundy et al., Red cell folate concentrations in psychiatric patients. J Affect Dis 19 (1990), p. 207.
21. T. Bottiglieri, K. Hyland, M. Laundy et al., Folate deficiency, biopterin and monoamine metabolism in depression. Psychol Med 22 (1992), p. 871.
22. A. Wilkinson, D. Anderson, M. Abou-Saleh et al., 5-Methyltetrahydrofolate level in the serum of depressed subjects and its relationship to the outcome of ECT. J Affect Disord 32 (1994), p. 163.
23. M. T. Abou-Saleh and A. Coppen, Serum and red blood cell folate in depression. Acta Psychiatr Scand 80 (1989), p. 78.
24. E. H. Reynolds, J. M. Preece, J. Bailey and A. Coppen, Folate deficiency in depressive illness. Br J Psychiatry 117 (1970), p. 287.
25. V. A. Wesson, A. J. Levitt and R. T. Joffe, Change in folate status with antidepressant treatment. Psychiatry Res 53 (1994), p. 313.
26. A. Levitt and R. Joffee, Folate, B12, and life course of depressive illness. Biol Psychiatry 25 (1989), p. 867.
27. I. R. Bell, J. S. Edman, D. W. Marby et al., Vitamin B12 and folate status in acute geropsychiatric inpatients: affective and cognitive characteristics of a vitamin nondeficient population. Biol Psychiatry 27 (1990), p. 125.
28. M. Fava, J. S. Borus, J. E. Alpert et al., Folate, B12, and homocysteine in major depressive disorder. Am J Psychiatry 154 (1997), p. 426.
29. Alpert M, Silva R, Pouget E. Folate as a predictor of response to sertraline or nortriptyline in geriatric depression. Presented at the 36th Annual Meeting of the NCDEU. Boca Raton, Fla., May 28-31, 1996.
30. M. Fava and K. G. Davidson, Definition and epidemiology of treatment-resistant depression. Psychiatr Clin North Am 119 (1996), p. 176.
31. P. S. A. Godfrey, B. K. Toone, M. W. P. Carney et al., Enhancement of recovery from psychiatric illness by methylfolate. Lancet 336 (1990), p. 392.

32. M. W. P. Carney and B. F. Sheffield, Associations of subnormal serum folate and vitamin B12 values and effects of replacement therapy. J Nerv Ment Dis 150 (1970), p. 404.
33. S. Lee, Y. K. Wing and S. Fong, A controlled study of folate levels in Chinese inpatients with major depression in Hong Kong. J Affect Disord 49 (1998), p. 73.
34. P. F. Jacques, J. Selhub, A. G. Bostom, P. W. F. Wilson and I. H. Rosenberg, The effect of folic acid fortification on plasma folate and total homocysteine concentrations. N Engl J Med 340 (1999), p. 1449.
35. M. T. Abou-Saleh and A. Coppen, The biology of folate in depression: implications for nutritional hypotheses of psychoses. J Psychiatr Res 20 (1986), p. 91.
36. W. E. Thorton and B. P. Thornton, Folic acid, mental function and dietary habits. J Clin Psychiatry 39 (1978), p. 315.
37. A. Coppen, S. Chaudry and C. Swade, Folic acid enhances lithium prophylaxis. J Affect Disord 10 (1986), p. 9.
38. M. Passeri, S. Ventura, G. Abate, D. Cucinotta and P. LaGreca, Oral 5-methyltetrahydrofolate (MTHF) in depression association with Senile Organic Mental Disorders (OMDs): a double-blind, multicenter study vs. trazodone (TRZ). Eur J Clin Invest 21 (1993), p. 24.
39. G. Guaraldi, M. Fava, F. Mazzi and P. LaGreca, An open trial of methyltetrahydrofolate (MTHF) in elderly depressed patients. Ann Clin Psychiatry 5 (1993), p. 101.
40. Alpert J E, Mischoulon D, Rubenstein G E, Bottonari K, Nierenberg A A, Fava M. Folinic acid (Leucovorin) as an adjunctive treatment for SSRI-refractory depression. Ann Clin Psychiatry. 2002 March; 14(1):33-8.
41. M. Spillman and M. Fava, S-adenosyl-methionine in psychiatric disorders: historical perspective and current status. CNS Drugs 6 (1996), p. 416.
42. A. Ruck, S. Kramer, J. Metz and M. Brennan, Methyltetrahydrofolate is a potent and selective agonist for kainic acid receptors. Nature 287 (1980), p. 852.
43. R. A. Schatz, T. E. Wilens and O. Z. Sellinger, Decreased in vivo protein and phospholipid methylation after in vivo elevation of brain S-adenosylhomocysteine. Biochem Biophys Res Commun 98 (1981), p. 1097.
44. P. J. Shaw, Excitatory amino acid receptors, excitotoxicity and the human nervous system. Curr Opin Neurol Neurosurg 6 (1993), p. 414.
45. M. B. Bowers, Jr and E. H. Reynolds, Cerebrospinal fluid folate and acid monoamine metabolites. Lancet 2 (1972), p. 137.
46. M. I. Botez and S. N. Young, Effects of anticonvulsants and low levels of folate and thiamine on amine metabolites in cerebrospinal fluid. Brain 114 (1991), p. 333.
47. M. I. Botez, S. N. Young, J. Bachevalier and S. Gauthier, Folate deficiency and decreased brain 5-hydroxytryptamine synthesis in man and rat. Nature 278 (1979), p. 182.
48. R. Surtees, S. Heales and A. Bowron, Association of cerebrospinal fluid deficiency of 5-methyltetrahydrofolate, but not S-adenosylmethionine, with reduced concentrations of the acid metabolites of 5-hydroxytryptamine and dopamine Clin Sci 986 (1994), p. 697.
49. Alpert J E, Mischoulon D, Nierenberg A A, Fava M. Nutrition and depression: focus on folate. Nutrition. 2000 July-August; 16(7-8):544-6
50. Fava M, Davidson K G. Definition and epidemiology of treatment-resistant depression. Psychiatr Clin North Am. 1996 June; 19(2):179-200.
51. Fava M, Evins A E, Dorer D J, Schoenfeld D A. The problem of the placebo response in clinical trials for psychiatric disorders: culprits, possible remedies, and a novel study design approach. Psychother Psychosom. 2003 May-June; 72(3):115-27.
52. Trivedi M H, Rush A J, Ibrahim H M et al. The Inventory of Depressive Symptomatology, Clinician Rating (IDS-C) and Self-Report (IDS-SR), and the Quick Inventory of Depressive Symptomatology, Clinician Rating (QIDS-C) and Self-Report (QIDS-SR) in public sector patients with mood disorders: a psychometric evaluation. Psychol Med 2004; 34(1):73-82.
53. Fava M. Diagnosis and definition of treatment-resistant depression. Biol Psychiatry. 2003 Apr. 15; 53(8):649-59.
54. Levine J, Schooler N R. General versus specific inquiry with SAFTEE. J Clin Psychopharmacol 1992; 12(6):448.
55. Hamilton M. A rating scale for depression. J Neurol Neurosurg Psychiatry. 1960 February; 23:56-62.
56. Fava M, Rankin M A, Alpert J E, Nierenberg A A, Worthington J J. An open trial of oral sildenafil in antidepressant-induced sexual dysfunction. Psychother Psychosom. 1998; 67(6):328-31.
57. DeLoach L J, Higgins M S, Caplan A B, Stiff J L. The visual analog scale in the immediate postoperative period: intrasubject variability and correlation with a numeric scale. Anesth Analg. 1998; 86(1):102-6.

| SEQUENCE LISTING: |
| --- |

```
SEQ ID NO: 1----human MTHFR (NM_005957.4 CDS plus 12 nucleotides in the
beginning of the sequence) C677T and A1298C
    1 aggaacccag ccatggtgaa cgaagccaga ggaaacagca gcctcaaccc ctgcttggag 61 ggcagtgcca gcagtggcag tgagagctcc aaagatagtt cgagatgttc cacccgggc 121 ctggaccccg agcggcatga gagactccgg gagaagatga ggcggcgatt ggaatctggt 181 gacaagtggt tctccctgga attcttccct cctcgaactg ctgagggagc tgtcaatctc 241 atctcaaggt ttgaccggat ggcagcaggt ggcccctct acatagacgt gacctggcac 301 ccagcaggtg accctggctc agacaaggag acctcctcca tgatgatcgc cagcaccgcc 361 gtgaactact gtggcctgga gaccatcctg cacatgacct gctgccgtca gcgcctggag 421 gagatcacgg gccatctgca caaagctaag cagctgggcc tgaagaacat catggcgctg 481 cggggagacc caataggtga ccagtgggaa gaggaggagg aggcttcaa ctacgcagtg 541 gacctggtga agcacatccg aagtgagttt ggtgactact ttgacatctg tgtggcaggt
```

SEQUENCE LISTING:

```
 601 taccccaaag gccaccccga agcagggagc tttgaggctg acctgaagca cttgaaggag 661 aaggtgtctg cgggagccga tttcatcatc acgcagcttt tctttgaggc tgacacattc 721 ttccgctttg tgaaggcatg caccgacatg ggcatcactt gccccatcgt ccccgggatc 781 tttcccatcc agggctacca ctcccttcgg cagcttgtga agctgtccaa gctggaggtg 841 ccacaggaga tcaaggacgt gattgagcca atcaaagaca acgatgctgc catccgcaac 901 tatggcatcg agctggccgt gagcctgtgc caggagcttc tggccagtgg cttggtgcca 961 ggcctccact tctacacccc caaccgcgag atggctacca cagaggtgct gaagcgcctg 1021 gggatgtgga ctgaggaccc caggcgtccc ctaccctggg ctctcagcgc ccaccccaag 1081 cgccgagagg aagatgtacg tcccatcttc tgggcctcca gaccaaagag ttacatctac 1141 cgtacccagg agtgggacga gttccctaac ggccgctggg gcaattcctc ttcccctgcc 1201 tttggggagc tgaaggacta ctacctcttc tacctgaaga gcaagtcccc caaggaggag 1261 ctgctgaaga tgtgggggga ggagctgacc agtgaagaaa gtgtctttga agtcttcgtt 1321 cttacctct cgggagaacc aaaccggaat ggtcacaaag tgacttgcct gccctggaac 1381 gatgagcccc tggcggctga accagcctg ctgaaggagg agctgctgcg ggtgaaccgc 1441 cagggcatcc tcaccatcaa ctcacagccc aacatcaacg gaagccgtc ctccgacccc 1501 atcgtgggct ggggccccag cggggggctat gtcttccaga aggcctactt agagtttttc 1561 acttcccgcg agacagcgga agcacttctg caagtgctga agaagtacga gctccgggtt 1621 aattaccacc ttgtcaatgt gaagggtgaa acatcacca atgccctga actgcagccg 1681 aatgctgtca cttggggcat cttccctggg cgagagatca tccagcccac cgtagtggat 1741 cccgtcagct tcatgttctg gaaggacgag gcctttgccc tgtggattga gcggtgggga 1801 aagctgtatg aggaggagtc cccgtcccgc accatcatcc agtacatcca cgacaactac 1861 ttcctggtca acctggtgga caatgacttc ccactggaca actgcctctg gcaggtggtg 1921 gaagacacat tggagcttct caacaggccc acccagaatg cgagagaaac ggaggctcca 1981 tga
```

SEQ ID NO 2: ----human MTR (NM_000254.2) CDS A2756G

```
   1 atgtcacccg cgctccaaga cctgtcgcaa cccgaaggtc tgaagaaaac cctgcgggat 61 gagatcaatg ccattctgca agagaggatt atggtgctgg atggagggat ggggaccatg 121 atccagcggg agaagctaaa cgaagaacac ttccgaggtc aggaatttaa agatcatgcc 181 aggccgctga aaggcaacaa tgacattta agtataactc agcctgatgt catttaccaa 241 atccataagg aatacttgct ggctggggca gatatcattg aaacaaatac ttttagcagc 301 actagtattg cccaagctga ctatggcctt gaacacttgg cctaccggat gaacatgtgc 361 tctgcaggag tggccagaaa agctgccgag gaggtaactc tccagacagg aattaagagg 421 tttgtggcag gggctctggg tccgactaat aagacactct ctgtgtcccc atctgtggaa 481 aggccggatt ataggaacat cacatttgat gagcttgttg aagcatacca agagcaggcc 541 aaaggacttc tggatggcgg ggttgatatc ttactcattg aaactatttt tgatactgcc 601 aatgccaagg cagccttgtt tgcactccaa atctttttg aggagaaata tgctccccgg 661 cctatcttta tttcagggac gatcgttgat aaaagtgggc ggactctttc cggacagaca 721 ggagagggat ttgtcatcag cgtgtctcat ggagaaccac tctgcattgg attaaattgt 781 gctttgggtg cagctgaaat gagaccttt attgaaataa ttggaaaatg tacaacagcc
```

SEQUENCE LISTING:

```
 841 tatgtcctct gttatcccaa tgcaggtctt cccaacacct ttggtgacta tgatgaaacg
 901 ccttctatga tggccaagca cctaaaggat tttgctatgg atggcttggt caatatagtt
 961 ggaggatgct gtgggtcaac accagatcat atcagggaaa ttgctgaagc tgtgaaaaat
1021 tgtaagccta gagttccacc tgccactgct tttgaaggac atatgttact gtctggtcta
1081 gagcccttca ggattggacc gtacaccaac tttgttaaca ttggagagcg ctgtaatgtt
1141 gcaggatcaa ggaagtttgc taaactcatc atggcaggaa actatgaaga agccttgtgt
1201 gttgccaaag tgcaggtgga aatgggagcc caggtgttgg atgtcaacat ggatgatggc
1261 atgctagatg gtccaagtgc aatgaccaga ttttgcaact taattgcttc cgagccagac
1321 atcgcaaagg tacctttgtg catcgactcc tccaattttg ctgtgattga agctgggtta
1381 aagtgctgcc aagggaagtg cattgtcaat agcattagtc tgaaggaagg agaggacgac
1441 ttcttggaga aggccaggaa gattaaaaag tatgctgagc tatggtggt catggctttt
1501 gatgaagaag gacaggcaac agaaacagac acaaaaatca gagtgtgcac ccgggcctac
1561 catctgcttg tgaaaaaact gggctttaat ccaaatgaca ttattttga ccctaatatc
1621 ctaaccattg ggactggaat ggaggaacac aacttgtatg ccattaattt tatccatgca
1681 acaaaagtca ttaaagaaac attacctgga gccagaataa gtggaggtct ttccaacttg
1741 tccttctcct tccgaggaat ggaagccatt cgagaagcaa tgcatggggt tttcctttac
1801 catgcaatca agtctggcat ggacatgggg atagtgaatg ctggaaacct ccctgtgtat
1861 gatgatatcc ataaggaact tctgcagctc tgtgaagatc tcatctggaa taaagaccct
1921 gaggccactg agaagctctt acgttatgcc cagactcaag gcacaggagg aagaaagtc
1981 attcagactg atgagtggag aaatggccct gtcgaagaac gccttgagta tgcccttgtg
2041 aagggcattg aaaaacatat tattgaggat actgaggaag ccaggttaaa ccaaaaaaaa
2101 tatccccgac ctctcaatat aattgaagga cccctgatga atggaatgaa aattgttggt
2161 gatcttttg gagctggaaa aatgtttcta cctcaggtta taagtcagc ccgggttatg
2221 aagaaggctg ttggccacct tatccctttc atggaaaaag aaagagaaga aaccagagtg
2281 cttaacggca cagtagaaga agaggaccct taccagggca ccatcgtgct ggccactgtt
2341 aaaggcgacg tgcacgacat aggcaagaac atagttggag tagtccttgg ctgcaataat
2401 ttccgagtta ttgatttagg agtcatgact ccatgtgata agatactgaa agctgctctt
2461 gaccacaaag cagatataat tggcctgtca ggactcatca ctccttccct ggatgaaatg
2521 attttttgttg ccaaggaaat ggagagatta gctataagga ttccattgtt gattggagga
2581 gcaaccactt caaaaaccca cacagcagtt aaaatagctc gagatacag tgcacctgta
2641 atccatgtcc tggacgcgtc caagagtgtg gtggtgtgtt cccagctgtt agatgaaaat
2701 ctaaaggatg aatactttga ggaaatcatg gaagaatatg aagatattag acaggaccat
2761 tatgagtctc tcaaggagag agatactta cccttaagtc aagccagaaa aagtggtttc
2821 caaatggatt ggctgtctga acctcaccca gtgaagccca cgtttattgg acccaggtc
2881 tttgaagact atgacctgca gaagctggtg gactacattg actggaagcc tttctttgat
2941 gtctggcagc tccggggcaa gtacccgaat cgaggctttc ccaagatatt taacgacaaa
3001 acagtaggtg gagaggccag gaaggtctac gatgatgccc acaatatgct gaacacactg
3061 attagtcaaa agaaactccg ggcccggggt gtggttgggt tctggccagc acagagtatc
3121 caagacgaca ttcacctgta cgcagaggct gctgtgcccc aggctgcaga gcccatagcc
```

```
3181  accttctatg ggttaaggca acaggctgag aaggactctg ccagcacgga gccatactac
3241  tgcctctcag acttcatcgc tcccttgcat tctggcatcc gtgactacct gggcctgttt
3301  gccgttgcct gctttgtggt agaagagctg agcaaggcct atgaggatga tggtgacgac
3361  tacagcagca tcatggtcaa ggcgctgggg gaccggctgg cagaggcctt tgcagaagag
3421  ctccatgaaa gagttcgccg agaactgtgg gcctactgtg gcagtgagca gctggacgtc
3481  gcagacctgc gcaggctgcg gtacaagggc atccgcccgg ctcctggcta ccccagccag
3541  cccgaccaca ccgagaagct caccatgtgg agactcgcag acatcgagca gtctacaggc
3601  attaggttaa cagaatcatt agcaatggca cctgcttcag cagtctcagg cctctacttc
3661  tccaatttga agtccaaata ttttgctgtg gggaagattt ccaaggatca ggttgaggat
3721  tatgcattga ggaagaacat atctgtggct gaggttgaga atggcttgg  acccattttg
3781  ggatatgata cagactaa SEQ ID NO: 3-----human MTRR (NM_002454.2) A66G
   1  atgaggaggt tctgttact atatgctaca cagcaggac aggcaaaggc catcgcagaa
  61  gaaatatgtg agcaagctgt ggtacatgga ttttctgcag atcttcactg tattagtgaa
 121  tccgataagt atgacctaaa aaccgaaaca gctcctcttg ttgttgtggt ttctaccacg
 181  ggcaccggag acccacccga cacagcccgc aagttttgtta aggaaataca gaaccaaaca
 241  ctgccggttg atttctttgc tcacctgcgg tatgggttac tgggtctcgg tgattcagaa
 301  tacacctact tttgcaatgg ggggaagata attgataaac gacttcaaga gcttggagcc
 361  cggcatttct atgacactgg acatgcagat gactgtgtag gtttagaact tgtggttgag
 421  ccgtggattg ctggactctg gccagccctc agaaagcatt ttaggtcaag cagaggacaa
 481  gaggagataa gtggcgcact cccggtggca tcacctgcat cctcgaggac agaccttgtg
 541  aagtcagagc tgctacacat tgaatctcaa gtcgagcttc tgagattcga tgattcagga
 601  agaaaggatt ctgaggtttt gaagcaaaat gcagtgaaca gcaaccaatc caatgttgta
 661  attgaagact ttgagtcctc acttacccgt tcggtacccc cactctcaca agcctctctg
 721  aatattcctg gtttacccccc agaatattta caggtacatc tgcaggagtc tcttggccag
 781  gaggaaagcc aagtatctgt gacttcagca gatccagttt ttcaagtgcc aatttcaaag
 841  gcagttcaac ttactacgaa tgatgccata aaaccactc tgctggtaga attggacatt
 901  tcaaatacag acttttccta tcagcctgga gatgccttca gcgtgatctg ccctaacagt
 961  gattctgagg tacaaagcct actccaaaga ctgcagcttg aagataaaag agagcactgc
1021  gtccttttga aaataaaggc agacacaaag aagaaaggag ctaccttacc ccagcatata
1081  cctgcgggat gttctctcca gttcattttt acctggtgtc ttgaaatccg agcaattcct
1141  aaaaaggcat tttgcgagc ccttgtggac tataccagtg acagtgctga aaagcgcagg
1201  ctacaggagc tgtgcagtaa acaaggggca gccgattata gccgctttgt acgagatgcc
1261  tgtgcctgct tgttggatct cctcctcgct ttcccttctt gccagccacc actcagtctc
1321  ctgctcgaac atcttcctaa acttcaaccc agaccatatt cgtgtgcaag ctcaagttta
1381  tttcacccag gaaagctcca ttttgtcttc aacattgtgg aatttctgtc tactgccaca
1441  acagaggttc tgcgaaggg agtatgtaca ggctggctgg ccttgttggt tgcttcagtt
1501  cttcagccaa acatacatgc atcccatgaa gacagcggga aagccctggc tcctaagata
1561  tccatctctc ctcgaacaac aaaattcttc cacttaccag atgacccctc aatccccatc
1621  ataatggtgg gtccaggaac cggcatagcc ccgtttattg ggttcctaca acatagagag
```

-continued

SEQUENCE LISTING:

```
1681  aaactccaag aacaacaccc agatggaaat tttggagcaa tgtggttgtt ttttggctgc 1741  aggcataagg atagggatta tctattcaga aaagagctca gacatttcct taagcatggg 1801  atcttaactc atctaaaggt ttccttctca agagatgctc ctgttgggga ggaggaagcc 1861  ccagcaaagt atgtgcaaga caacatccag cttcatggcc agcaggtggc gagaatcctc 1921  ctccaggaga acggccatat ttatgtgtgt ggagatgcaa agaaatggc caaggatgta 1981  catgatgccc ttgtgcaaat aataagcaaa gaggttggag ttgaaaaact agaagcaatg 2041  aaaaccctgg ccactttaaa agaagaaaaa cgctaccttc aggatatttg gtcataa
```

SEQ ID NO: 4 ---- MTHFR human amino acid sequence (NP_005948.3) A222V & E429A
```
   1  mvneargnss lnpclegsas sgsesskdss rcstpgldpe rherlrekmr rrlesgdkwf 61  sleffpprta egavnlisrf drmaaggply idvtwhpagd pgsdketssm miastavnyc 121  gletilhmtc crqrleeitg hlhkakqlgl knimalrgdp igdqweeeeg gfnyavdlvk 181  hirsefgdyf dicvagypkg hpeagsfead lkhlkekvsa gadfiitqlf feadtffrfv 241  kactdmgitc pivpgifpiq gyhslrqlvk lsklevpqei kdviepikdn daairnygie 301  layslcqell asglvpglhf ytlnremat  evlkrlgmwt edprrplpwa lsahpkrree 361  dvrpifwasr pksyiyrtqe wdefpngrwg nssspafgel kdyylfylks kspkeellkm 421  wgeeltsees vfevfvlyls gepnrnghkv tclpwndepl aaetsllkee llrvnrqgil 481  tinsqpning kpssdpivgw gpsggyvfqk aylefftsre taeallqvlk kyelrvnyhl 541  vnvkgenitn apelqpnavt wgifpgreii qptvvdpvsf mfwkdeafal wierwgklye 601  eespsrtiiq yihdnyflvn lvdndfpldn clwqvvedtl ellnrptqna reteap
```

SEQ ID NO: 5 ---- MTR human amino acid sequence (NP_000245.2) D919G
```
   1  mspalqdlsq peglkktlrd einailqkri mvldggmgtm igreklneeh frgqefkdha 61  rplkgnndil sitqpdviyq ihkeyllaga diietntfss tsiaqadygl ehlayrmnmc 121  sagvarkaae evtlqtgikr fvagalgptn ktlsyspsve rpdyrnitfd elveayqeqa 181  kglldggvdi llietifdta nakaalfalq nlfeekyapr pifisgtivd ksgrtlsgqt 241  gegfvisysh geplciglnc algaaemrpf eiigkctta  yvlcypnagl pntfgdydet 301  psmmakhlkd famdglvniv ggccgstpdh ireiaeavkn ckprvppata feghmllsgl 361  epfrigpytn fvnigercnv agsrkfakli magnyeealc vakvqvemga qvldvnmddg 421  mldgpsamtr fcnliasepd iakvplcids snfavieagl kccqgkcivn sislkegedd 481  flekarkikk ygaamvvmaf deegqatetd tkirvctray hllvkklgfn pndiifdpni 541  ltigtgmeeh nlyainfiha tkviketlpg arisgglsnl sfsfrgmeai reamhgvfly 601  haiksgmdmg ivnagnlpvy ddihkellql cedliwnkdp eateklrya  qtqgtggkkv 661  iqtdewrngp veerleyalv kgiekhiied teearinqkk yprpiniieg plmngmkivg 721  dlfgagkmfl pqviksarvm kkavghlipf mekereetry lngtveeedp yqgtivlatv 781  kgdvhdigkn ivgvvlgcnn frvidlgvmt pcdkilkaal dhkadiigls glitpsldem 841  ifvakemerl airiplligg attskthtav kiaprysapv ihvldasksv vvcsqllden 901  lkdeyfeeim eeyedirqdh yeslkerryl plsgarksgf qmdwlsephp vkptfigtqv 961  fedydlqklv dyidwkpffd vwqlrgkypn rgfpkifndk tvggearkvy ddahnmlntl 1021  isqkklrarg vvgfwpaqsi qddihlyaea avpqaaepia tfyglrqqae kdsastepyy 1081  clsdfiaplh sgirdylglf avacfgveel skayeddgdd yssimvkalg drlaeafaee 1141  lhervrrelw aycgseqldv adlrrlrykg irpapgypsq pdhtekltmw rladieqstg
```

```
1201  irlteslama  pasaysglyf  snlkskyfav  gkiskdqved  yalrknisva  evekwlgpil 1261  gydtd SEQ ID NO: 6 ----MTRR human amino acid sequence (NP_002445.2) I22M
   1  mrrflllyat  qqgqakaiae  excegavvhg  fsadlhcise  sdkydlktet  aplvvvvstt 61  gtgdppdtar  kfvkeiqngt  lpvdffahlr  ygllglgdse  ytyfcnggki  idkrlgelga 121  rhfydtghad  dcvglelvve  pwiaglwpal  rkhfrssrgq  eeisgalpva  spassrtdlv 181  ksellhiesq  vellrfddsg  rkdsevlkqn  avnsnqsnvv  iedfessltr  svpplsgasl 241  nipglppeyl  qvhlgeslgq  eesqvsvtsa  dpvfqvpisk  avqlttndai  kttllveldi 301  sntdfsyqpg  dafsvicpns  dsevqsllqr  lqledkrehc  vllkikadtk  kkgatlpqhi 361  pagcslqfif  twcleiraip  kkaflralvd  ytsdsaekrr  lgelcskqga  adysrfvrda 421  caclldllla  fpscqpplsl  llehlpklqp  rpyscasssl  fhpgklhfvf  niveflstat 481  tevlrkgvct  gwlallvasv  lqpnihashe  dsgkalapki  sisprttnsf  hlpddpsipi 541  imvgpgtgia  pfigflqhre  klgeghpdgn  fgamwlffgc  rhkdrdylfr  kelrhflkhg 601  ilthlkvsfs  rdapvgeeea  pakyvqdniq  lhgqqvaril  lgenghiyvc  gdaknmakdv 661  hdalvqiisk  evgvekleam  ktlatlkeek  rylqdiws SEQ ID NO: 28 ---COMT human amino acid sequence (NP_000745.1) V158M
   1  mpeappllla  avllglvllv  vlllllrhwg  wglcligwne  filqpihnll  mgdtkeqril 61  nhvlqhaepg  naqsvleaid  tycegkewam  nvgdkkgkiv  davigehqps  vllelgaycg 121  ysavrmarll  spgarlitie  inpdcaaitq  rmvdfagvkd  kvtivvgasq  diipqlkkky 181  dvdtldmvfl  dhwkdrylpd  tllleecgll  rkgtvlladn  vicpgapdfl  ahvrgsscfe 241  cthygsfley  revvdgleka  iykgpgseag  p
```

It is understood that the foregoing detailed description and examples are illustrative only and are not to be taken as limitations upon the scope of the invention. Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method for treating at least one symptom of depression in a human subject, said method comprising:
   assaying a biological sample from said human subject who has been diagnosed with depression, and detecting in the biological sample a combination of the following biomarkers:
   i. a SNP at position 27 of SEQ ID NO. 18 (rs8007267) comprising at least one thymine "T" allele or the complement thereof, wherein the SEQ ID NO. 18 is a portion of a genomic nucleic acid sequence of GTP cyclohydrolase 1 (GCH1); and
   ii. a SNP at position 27 of SEQ ID NO. 24 (rs4680) comprising two guanine "G" alleles or the complement thereof, wherein the SEQ ID NO. 24 is a portion of a genomic nucleic acid sequence of catechol-O-methyltransferase (COMT), thereafter,
   administering a composition comprising an effective amount of a folate-containing compound, wherein said folate containing compound is at least 15 mg/day of 6-(S) 5-methyltetrahydrofolate, together with an antidepressant drug, wherein the antidepressant drug is a selective serotonin reuptake inhibitor, to the human subject to treat depression.

2. The method of claim 1, wherein the biological sample comprises a sample selected from a blood sample, a urine sample, a buccal sample, a saliva sample or a cerebrospinal fluid sample.

3. The method of claim 1, wherein the assaying comprises amplifying the biological sample with at least one set of primers flanking any one of the SNPs.

4. The method of claim 3, wherein sets of primers amplifying at least two of the SNPs are used in a multiplex amplification assay.

5. The method of claim 1, further comprising determining a body measurement of the subject.

6. The method of claim 5, wherein the body measurement comprises weight, height, waist circumference, hip circumference, body fat percentage, or any combinations thereof.

7. The method of claim 1, wherein the effective amount of the folate-comprising compound is 15 mg/day to about 50 mg/day.

8. The method of claim 1, wherein the effective amount of the folate-comprising compound is administered as a single daily dose.

9. The method of claim 1, wherein the effective amount of the folate-comprising compound is administered in more than one divided doses per day.

10. The method of claim 1, wherein the administration is oral.

11. The method of claim 1, wherein the composition is formulated to release at least a portion of the folate-comprising compound over a period of at least about 3-6 hours, upon the administration of the composition.

12. The method of claim 11, wherein the release is a steady-state release.

13. The method of claim 1, wherein the administration of the anti-depressant drug in combination with the folate-comprising compound increases the effectiveness of the anti-depressant drug.

14. The method of claim 1, wherein the selective serotonin reuptake inhibitor is selected from the group consisting of fluoxetine, citalopram, paroxetine, eseitalopram, sertraline, and any combinations thereof.

15. The method of claim 1, wherein the depression is major depressive disorder.

16. The method of claim 1, wherein the subject is resistant to at least one antidepressant monotherapy.

17. The method of claim 1, wherein the subject is an adult subject.

18. The method of claim 1, wherein the at least one symptom of depression is selected from low or depressed mood, anhedonia, low energy levels, guilt, decreased work and interests, psychomotor retardation, agitation, psychic anxiety, somatic anxiety, general somatic symptoms, reduced cognition or any combinations thereof.

* * * * *